United States Patent
Jacobsen et al.

(10) Patent No.: US 10,316,038 B2
(45) Date of Patent: Jun. 11, 2019

(54) PYRROLOPYRIMIDINE ITK INHIBITORS FOR TREATING INFLAMMATION AND CANCER

(71) Applicant: ACLARIS THERAPEUTICS, INC., Wayne, PA (US)

(72) Inventors: Eric Jon Jacobsen, Chesterfield, MO (US); James Robert Blinn, O'Fallon, MO (US); John Robert Springer, Wentzville, MO (US); Susan Landis Hockerman, Kirkwood, MO (US); David Randolph Anderson, Salem, CT (US)

(73) Assignee: ACLARIS THERAPEUTICS, INC., Wayne, PA (US)

( * ) Notice: Subject to any disclaimer, the term of this patent is extended or adjusted under 35 U.S.C. 154(b) by 0 days.

(21) Appl. No.: 15/880,385

(22) Filed: Jan. 25, 2018

(65) Prior Publication Data
US 2018/0208594 A1   Jul. 26, 2018

Related U.S. Application Data

(60) Provisional application No. 62/450,450, filed on Jan. 25, 2017.

(51) Int. Cl.
| | | |
|---|---|---|
| C07D 401/10 | (2006.01) | |
| C07D 401/14 | (2006.01) | |
| A61K 31/437 | (2006.01) | |
| A61K 31/4353 | (2006.01) | |
| C07D 471/04 | (2006.01) | |
| A61P 29/00 | (2006.01) | |
| C07D 519/00 | (2006.01) | |

(52) U.S. Cl.
CPC ............ *C07D 471/04* (2013.01); *A61P 29/00* (2018.01); *C07D 519/00* (2013.01)

(58) Field of Classification Search
CPC .. C07D 401/10; C07D 401/02; C07D 401/14; A61K 31/437; A61K 31/4353
USPC .......................... 514/300, 303; 546/119, 121
See application file for complete search history.

(56) References Cited

U.S. PATENT DOCUMENTS

| | | | |
|---|---|---|---|
| 8,518,952 | B2 | 8/2013 | Braganza et al. |
| 9,206,188 | B2 * | 12/2015 | Vankayalapati ..... C07D 471/04 |
| 2007/0179156 | A1 | 8/2007 | Charrier et al. |
| 2008/0280917 | A1 | 11/2008 | Albrecht et al. |
| 2011/0294836 | A1 | 12/2011 | Song et al. |
| 2013/0281432 | A1 | 10/2013 | Currie et al. |
| 2014/0315909 | A1 | 10/2014 | Vankayalapati et al. |
| 2015/0210671 | A1 | 7/2015 | Jacobsen et al. |
| 2016/0213653 | A1 | 7/2016 | Jacobsen et al. |

FOREIGN PATENT DOCUMENTS

| | | | |
|---|---|---|---|
| EP | 2489663 | A1 | 8/2012 |
| WO | 99/65909 | A1 | 12/1999 |
| WO | 00/26211 | A1 | 5/2000 |
| WO | 02/053543 | A1 | 7/2002 |
| WO | 2004/099205 | A1 | 11/2004 |
| WO | 2012/031004 | A1 | 3/2012 |
| WO | 2013/153539 | A1 | 10/2013 |
| WO | 2014/172513 | A2 | 10/2014 |
| WO | 2015/112847 | A1 | 7/2015 |
| WO | 2016000615 | * | 1/2016 |
| WO | 2016/118951 | A2 | 7/2016 |
| WO | 2016118951 | * | 7/2016 |

OTHER PUBLICATIONS

Andreotti et al., T-Cell Signaling Regulated by the Tec Family Kinase, Itk, Jul. 2010, Cold Spring Harb. Perspect. Biol 2(a002287):1-21.
Atherly et al., Tec Kinases Itk and Rlk are Required for CD8+ T Cell Responses to Virus Infection Independent of Their Role in CD4+ T Cell Help, Feb. 1, 2006, The Journal of Immunology, 176(3):1571-1581.
August et al., Regulation of T-cell Responses and Disease by Tec Kinase Itk, 2012, International Reviews of Immunology, 31:155-165.
Auyueng et al., A Key Role for Itk in Both IFNγ and IL-4 Production by NKT Cells, 2007, The Journal of Immunology, 179(1):111-119.
Banker et al., Modern Pharmaceutics, 2002, 4th Ed., Drugs and The Pharmaceutical Sciences, (121) CRC Press. (cover and TOC).
Boucheron et al., The Role of Tec Family Kinases in the Regulation of T-helper-cell Differentiation, 2012, International Reviews of Immunology, 31:133-154.
Dombroski et al., Kinase-Independent Functions for Itk in TCR-Induced Regulation of Vav and the Actin Cytoskeleton, Feb. 1, 2005, The Journal of Immunology, 174(3):1385-1392.
Eliel et al., Stereochemistry of Organic Compounds, Sep. 1994, Wiley, New York, New York. (cover and TOC).
Felices et al., The Tec Kinases Ilk and Rlk Regulate NKT Cell Maturation, Cytokine Production, and Survival, Mar. 1, 2008, The Journal of Immunology, 180(5):3007-3018.
Ferrara et al., Modulation of tracheal smooth muscle responses in inducible T-cell kinase knockout mice, 2004, Pulmonary Pharmacology & Therapeutics, 17(5):301-308.
Ferrara et al., Reduced airway hyperresponsiveness and tracheal responses during allergic asthma in mice lacking tyrosine kinase inducible T-cell kinase, 2006, J. Allergy Clin. Immunol., 117(4):780-786.

(Continued)

*Primary Examiner* — Niloofar Rahmani
(74) *Attorney, Agent, or Firm* — Pepper Hamilton LLP

(57) ABSTRACT

Disclosed herein are arylpyridinone compounds and compositions useful in the treatment of ITK mediated diseases, such as inflammation, having the structure of Formula (I):

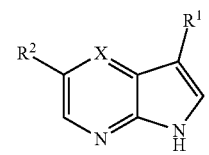

wherein $R^1$, $R^2$, and X are as defined in the detailed description. Methods of inhibition of ITK activity in a human or animal subject are also provided.

27 Claims, No Drawings

(56) References Cited

OTHER PUBLICATIONS

Fowell et al., Impaired NFATc Translocation and Failure of Th2 Development in Itk-Deficient CD4+ T Cells, Oct. 1999, Immunity, 11(4):399-409.
Gomez-Rodriguez et al., Differential Expression of Interleukin-17A and -17F Is Coupled to T Cell Receptor Signaling via Inducible T Cell Kinase, Oct. 16, 2009, Immunity 31(4):587-597.
Goodman et al., The Pharmaceutical Basis of Therapeutics, Twelfth Edition, 2010, McGraw-Hill, New York, New York. (cover and TOC).
Grimstein et al., Alpha-1 antitrypsin protein and gene therapies decrease autoimmunity and delay arthritis development in mouse model, 2011, J. Transl. Med. 9(21):1-13.
Guo et al., Molecular Characteristics of CTA056, a Novel Interleukin-2-Inducible T-Cell Kinase Inhibitor that Selectively Targets Malignant T Cells and Modulates Oncomirs, Nov. 2012, Mol. Pharmacol., 82(5):938-947.
Hao et al., A kinase independent function for Tec kinase ITK in regulating antigen receptor induced serum response factor activation, 2006, FEBS Letters, 580(11):2691-2697.
Higuchi et al., Pro-drugs as Novel Delivery Systems, Pro-drugs: An Overview and Definition, 1975, University of Kansas, Department of Pharmaceutical Chemistry, 14:1-115.
Horna et al., Cellular and Molecular Mechanisms of Tumor-Induced T-Cell Tolerance, 2007, Current Cancer Drug Targets, 7(1):41-53.
Horwood et al., Tec Family Kinases in Inflammation and Disease, 2012, International Reviews of Immunology, 31:87-103.
Huck et al., Girls homozygous for an IL-2-inducible T cell kinase mutation that leads to protein deficiency develop fatal EBV-associated lymphoproliferation, 2009, The Journal of Clinical Investigation, 119(5):1350-1358.
International Preliminary Report on Patentability and Written Opinion for PCT/US2015/012663 dated Jul. 26, 2016.
International Search Report and Written Opinion for PCT/US2015/012663 dated Apr. 21, 2015.
International Search Report and Written Opinion for PCT/US2018/015320 dated Apr. 13, 2018.
Koprulu et al., The role of Tec family kinases in mononuclear phagocytes, 2009, Crit. Rev. Immunol., 29(4):317-333. (abstract only).
Liao et al., Altered T Cell Receptor Signaling and Disrupted T Cell Development in Mice Lacking Itk, Dec. 1995, Immunity, 3(6):757-769.
Mano et al., Tec family of protein-tyrosine kinases: an overview of their structure and function, 1999, Cytokine Growth Factor Rev., 10(3-4):267-280. (abstract only).
Matsumoto et al., Identification of Highly Expressed Genes in Peripheral Blood T Cells from Patients with Atopic Dermatitis, 2002, Int. Arch. Allergy Immunol., 129(4):327-340.
Miller et al., Signaling through Itk Promotes T Helper 2 Differentiation Via Negative Regulation of T-bet, Jul. 2004, Immunity, 21(1):67-80.
Mueller et al., Attenuation of Immunological Symptoms of Allergic Asthma in Mice Lacking the Tyrosine Kinase ITK, 2003, The Journal of Immunology, 170(10):5056-5063.
Readinger et al., Selective targeting of ITK blocks multiple steps of HIV replication, May 6, 2008, PNAS, 105(18):6684-6689.
Roche, Bioreversible Carriers in Drug Design, 1987, University of Nebraska Medical Center, College of Pharmacy, American Pharmaceutical Association, Pergamon Press. (cover and TOC).
Sahu et al., Differential Sensitivity to Itk Kinase Signals for T Helper 2 Cytokine Production and Chemokine-Mediated Migration, 2008, The Journal of Immunology, 180(6):3833-3838.
Schaeffer et al., Mutation of Tec family kinases alters T helper cell differentiation, Dec. 2001, Nature Immunology 2(12):1183-1188.
Schaeffer et al., Requirement for Tec Kinases Rlk and Itk in T Cell Receptor Signaling and Immunity, Apr. 23, 1999, Science 284(5414):638-641.
Smith et al., The Tec family of cytoplasmic tyrosine kinases: mammalian Btk, Bmx, Itk, Tec, Txk and homologs in other species, 2001, BioEssays 23(5):436-446.
Stahl et al., Handbook of pharmaceutical salts: properties, selection, and use, 2002, International Union of Pure and Applied Chemistry, Weinheim; New York, Wiley-VCH, xiv. (abstract only).
Stepensky et al., IL-2-Inducible T-Cell Kinase Deficiency: Clinical Presentation and Therapeutic Approach, Mar. 2011, Haematologica, Journal of the European Hematology Associate, 96(3):472-476.
Takesono et al., Beyond calcium: new signaling pathways for Tec family kinases, 2002, Journal of Cell Science, 115(15):3039-3048.
Testa et al., Hydrolysis in Drug and Prodrug Metabolism: Chemistry, Biochemistry, and Enzymology, 2003, Verlag Helvetica Chimica Acta, Postfach, CH-8042 Zürich, Switzerland. (cover and TOC).
Von Bonin et al., Inhibition of the IL-2-inducible tyrosine kinase (Itk) activity: a new concept for the therapy of Inflammatory skin diseases, 2010, Experimental Dermatology, 20(1):41-47.

* cited by examiner

PYRROLOPYRIMIDINE ITK INHIBITORS FOR TREATING INFLAMMATION AND CANCER

CROSS-REFERENCE TO RELATED APPLICATIONS

This application claims the benefit of U.S. Provisional Application No. 62/450,450 filed Jan. 25, 2017, which is hereby incorporated by reference in its entirety for all purposes.

BRIEF SUMMARY

Some embodiments disclosed herein are directed to a compound of Formula (I):

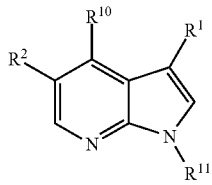

wherein:
- $R^1$ is chosen from aryl and heteroaryl, and may be optionally substituted with one or more $R^3$ substituents;
- $R^2$ is chosen from aryl or heteroaryl, and may be optionally substituted with one or more $R^4$ substituents;
- each $R^3$ is independently chosen from hydrogen, —$C_{1-4}$alkyl, —$OC_{1-4}$alkyl, —$NHC_{1-4}$ alkyl, —$N(C_{1-4}alkyl)_2$, cyano, —$C(O)N(R^6)_2$, —$C(O)C_{1-4}$ alkyl, haloalkyl, oxo, and halo;
- each $R^4$ is independently chosen from hydrogen, —$C_{1-4}$alkyl, —$OC_{1-4}$alkyl, —$OC_{1-6}$ cycloalkyl, —$OC_{1-6}$heterocycloalkyl, aryl, heteroaryl, haloalkyl, haloalkoxy, halo, —$NR^5R^6$, —$(CH_2)_mCR^7$=$CR^9C(O)$Me, —$(CH_2)_mCR^7$=$CR^9C(O)NR^7_2$, and —$(CH_2)_mCR^7$=$CR^9CN$;
- $R^5$ is chosen from hydrogen, cyano, —$C(O)CF_3$, —$C(O)CH$=$CH_2$, —$C(O)CR^7$=$CH_2$, —$C(O)CH$=$CHR^7$, —$C(O)CR^7$=$CHR^7$, —$C(O)CH$=$CR^7_2$, —$C(O)CH$=$CHCH_2R^8$, —$C(O)CH$=$CHC(O)CH_2R^8$, —$COC(CN)$=$CHR^6$, —$C(O)(C(O)NH_2)$=$CHR^6$, —$S(O)_2CH$=$CH_2$, —$(CH_2)_mCR^7$=$CR^9C(O)$Me, —$(CH_2)_mCR^7$=$CR^9C(O)NR^7_2$, and —$(CH_2)_mCR^7$=$CR^9CN$;
- $R^6$ is chosen from hydrogen, —$C_{1-4}$alkyl, and —$(CH_2)_nC_{3-7}$cycloalkyl;
- each $R^7$ is independently chosen from hydrogen, —CN, —$C_{1-4}$alkyl, —$C_{3-7}$cycloalkyl, —$C_{3-7}$ heterocycle, aryl, and heteroaryl where aryl and heteroaryl may be optionally substituted with one or more $R^9$;
- $R^8$ is chosen from hydrogen, —$C_{1-4}$alkyl, —$C_{1-4}$alkylaryl, —$C_{1-4}$alkylheteroaryl, —$C_{3-7}$ cycloalkyl, —$C_{3-7}$heterocycle, —OH, —$OC_{1-4}$alkyl, —$C_{1-4}$alkyl$OC_{1-4}$alkyl, —$NH_2$, —$NHC_{1-4}$ alkyl, —$N(C_{1-4}alkyl)_2$, heterocycle, aryl and heteroaryl;
- $R^9$ is chosen from hydrogen, —$C_{1-4}$ alkyl, —CN, —$CF_3$, —$C(O)$Me, —$C(O)NH_2$, and aryl;
- $R^{10}$ is chosen from H and —$C_{1-4}$alkyl;
- $R^{11}$ is chosen from hydrogen and —$C_{1-4}$alkyl, optionally substituted with —$OPO(OR^{12})_2$, —$OC(O)R^{13}$, or an amino acid;
- $R^{12}$ is chosen from hydrogen and —$C_{1-6}$alkyl;
- $R^{13}$ is —$C_{1-6}$ alkyl;
- m is chosen from 1, 2 and 3; and
- n is chosen from 0, 1, 2, and 3, a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof. Some embodiments also provide pharmaceutical compositions comprising one or more compounds disclosed herein together with a pharmaceutically acceptable carrier.

Some embodiments are directed to making and using the compounds and compositions of embodiments herein.

In some embodiments, the compounds disclosed herein may possess useful ITK inhibiting activity. Some embodiments herein are directed to treatment or prophylaxis of a disease or condition in which ITK plays an active role using the compounds disclosed herein. In some embodiments, a method of treating an ITK mediated disease or disorder in a subject comprises administering to the subject a compound of embodiments herein.

Some embodiments provide methods for treating an ITK-mediated disorder in a subject in need of such treatment comprising administering to the subject a therapeutically effective amount of a compound or composition according to the present disclosure. Also provided is the use of compounds disclosed herein for use in the manufacture of a medicament for the treatment of a disease or condition ameliorated by the inhibition of ITK.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to an "ITK inhibitor" is a reference to one or more ITK inhibitor and equivalents thereof known to those skilled in the art, and so forth.

As used herein, the term "about" means plus or minus 10% of the numerical value of the number with which it is being used. Therefore, about 50% means in the range of 45%-55%.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the formulation or method that treats the specified condition (e.g. alopecia areata) is the specifically recited therapeutic(s) in the particular embodiment or claim.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

As used herein, two embodiments are "mutually exclusive" when one is defined to be something which is different from the other. For example, an embodiment wherein two groups combine to form a cycloalkyl is mutually exclusive with an embodiment in which one group is ethyl the other group is hydrogen. Similarly, an embodiment wherein one group is CH2 is mutually exclusive with an embodiment wherein the same group is NH.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound of embodiments herein, can include, but is not limited to, providing the compound into or onto the target tissue; providing the compound systemically to a patient by, e.g., intravenous injection whereby the therapeutic reaches the target tissue; providing the compound in the form of the encoding sequence thereof to the target tissue (e.g., by so-called gene-therapy techniques). "Administering" a composition may be accomplished by injection, topical administration, orally, or by either method in combination with other known techniques.

The term "subject" or "patient" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The term "improve" is used to convey that the compounds of embodiments herein change either the appearance, form, characteristics and/or the physical attributes of the tissue to which it is being provided, applied or administered.

The term "inhibit" includes the administration of a compound of embodiments herein to prevent the onset of the symptoms, alleviating the symptoms, or eliminating the disease, condition or disorder.

By "pharmaceutically acceptable", it is meant the carrier, diluent or excipient must be compatible with the other ingredients of the pharmaceutical composition and not deleterious to the recipient thereof.

Unless otherwise indicated, the term "skin" means that outer integument or covering of the body, consisting of the dermis and the epidermis and resting upon subcutaneous tissue.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein.

Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH2-). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—).

Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C6H4= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a-OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term, "compound," as used herein is meant to include the structure depicted, a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystalization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

Compounds described herein may contain an asymmetric center and may thus exist as enantiomers. Where the compounds according to embodiments herein possess two or more asymmetric centers, they may additionally exist as diastereomers. Embodiments herein include all such possible stereoisomers as substantially pure resolved enantiomers, racemic mixtures thereof, as well as mixtures of diastereomers. The formulas are shown without a definitive stereochemistry at certain positions. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration. The scope of embodiments herein as described and claimed encompasses the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomic mixture may be separated by chromatography and/or fractional crystallization and one or both of the diastereoisomers converted to the corresponding pure enantiomer(s) by means well known to one skilled in the art. Chiral compounds of embodiments herein (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%0, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of embodiments herein as described and claimed encompasses the racemic forms of the compounds as well as the individual atropisomers (an atropisomer "substantially free" of this corresponding enantiomer) and stereoisomer-enriched mixtures, i.e. mixtures of atropisomers.

Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of kniphologne or by approaches based on thermodynamic equilibration when an isomerization reaction favors one atropisomer over the other.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

Suitable pharmaceutically acceptable acid addition salts of the compounds of embodiments herein may be prepared from an inorganic acid or an organic acid. All of these salts may be prepared by conventional means from the corresponding compound of embodiments herein by treating, for example, the compound with the appropriate acid or base.

Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, chloroprocaine, diethanolamine, N-methylglucamine, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to embodiments herein are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

In some embodiments, the salt is a hydrochloride salt. In some embodiments, the salt is besylate salt. In some embodiments, the salt is a trifluoroacetate salt.

As used herein, an "N-oxide" is formed from the tertiary basic amines or imines present in the molecule, using a convenient oxidizing agent.

The compounds of embodiments herein may exist in both unsolvated and solvated forms. The term solvate is used herein to describe a molecular complex comprising a compound of embodiments herein and an amount of one or more pharmaceutically acceptable solvent molecules. The term hydrate is employed when said solvent is water. Examples of solvate forms include, but are not limited to, compounds of embodiments herein in association with water, acetone, dichloromethane, 2-propanol, ethanol, methanol, dimethylsulfoxide (DMSO), ethyl acetate, acetic acid, ethanolamine, or mixtures thereof. It is specifically contemplated that in embodiments herein one solvent molecule can be associated with one molecule of the compounds of embodiments herein, such as a hydrate.

Furthermore, it is specifically contemplated that in embodiments herein, more than one solvent molecule may be associated with one molecule of the compounds of embodiments herein, such as a dihydrate. Additionally, it is specifically contemplated that in embodiments herein less than one solvent molecule may be associated with one molecule of the compounds of embodiments herein, such as a hemihydrate. Furthermore, solvates of embodiments herein are contemplated as solvates of compounds of embodiments herein that retain the biological effectiveness of the non-solvate form of the compounds.

Embodiments herein also include isotopically-labeled compounds of embodiments herein, wherein one or more atoms is replaced by an atom having the same atomic number, but an atomic mass or mass number different from the atomic mass or mass number usually found in nature. Examples of isotopes suitable for inclusion in the compounds of embodiments herein include isotopes of hydrogen, such as $^2$H and $^3$H, carbon, such as $^{11}$C, $^{13}$C and $^{14}$C, chlorine, such as $^{31}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of embodiments herein, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of embodiments herein can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of embodiments herein. As used herein, the term deuterated derivative embraces compounds of embodiments herein where in a particular position at least one hydrogen atom is replaced by deuterium. Deuterium (D or 2H) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of embodiments herein has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In some embodiments, the isotopic enrichment factor is at least 5000 (75% deuterium). In some embodiments, the isotopic enrichment factor is at least 6333.3 (95% deuterium incorporation). In some embodiments, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known to one of ordinary skilled in the art, including mass spectrometry (MS) and nuclear magnetic resonance (NMR).

The term "prodrug" refers to a compound that is made more active in vivo. Prodrugs of the compounds described herein are also within the scope of embodiments herein. Thus certain derivatives of the compounds of embodiments herein, which derivatives may have little or no pharmacological activity themselves, when administered into or onto the body may be converted into compounds of embodiments herein having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association) or Hydrolysis in Drug and Prodrug Metabolism: Chemistry, Biochemistry, and Enzymology (Testa, Bernard and Mayer, Joachim M. Wiley-VHCA, Zurich, Switzerland 2003).

Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. Prodrugs in accordance with embodiments herein can, for example, be produced by replacing appropriate functionalities present in the compounds of embodiments herein with certain moieties known to those skilled in the art as 'pro-moieties' as described, for example, in Design of Prodrugs by H. Bundgaard (Elsevier, 1985).

In the case of compounds of embodiments herein that are solids, it is understood by those skilled in the art that the inventive compounds and salts may exist in different crystalline or polymorphic forms, or in an amorphous form, all of which are intended to be within the scope of embodiments herein.

The compounds disclosed herein can exist as and therefore include all stereoisomers, conformational isomers and mixtures thereof in all proportions as well as isotopic forms such as deuterated compounds.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more pharmaceutical agents to treat a therapeutic condition or disorder described in the present disclosure. Such administration encompasses co-administration of these pharmaceutical agents in a substantially simultaneous manner, such as in a single capsule having a fixed ratio of active ingredients or in multiple, separate capsules for each active ingredient. In addition, such administration also encompasses use of each type of pharmaceutical agent in a sequential manner. In either case, the treatment regimen will provide beneficial effects of the drug combination in treating the conditions or disorders described herein.

The term "ITK inhibitor" is used herein to refer to a compound that exhibits an IC50 with respect to ITK activity of no more than about 100 µM and more typically not more than about 50 µM, as measured in the ITK enzyme assay described generally herein below. IC50 is that concentration of inhibitor that reduces the activity of an enzyme (e.g., ITK) to half-maximal level. Certain compounds disclosed herein have been discovered to exhibit inhibition against ITK. In certain embodiments, compounds will exhibit an IC50 with respect to ITK of no more than about 10 µM; in further embodiments, compounds will exhibit an IC50 with respect to ITK of no more than about 5 µM; in yet further embodiments, compounds will exhibit an IC50 with respect to ITK of not more than about 1 µM; in yet further embodiments, compounds will exhibit an IC50 with respect to ITK of not more than about 200 nM, as measured in the ITK binding assay described herein.

The term "immune checkpoint inhibitor" means a compound or pharmaceutical composition that inhibit immune checkpoint molecules.

The phrase "therapeutically effective" is intended to qualify the amount of active ingredients used in the treatment of a disease or disorder or on the effecting of a clinical endpoint.

As used herein, the term "therapeutic" means an agent utilized to treat, combat, ameliorate, prevent or improve an unwanted condition or disease of a patient. In part, embodiments of the present invention are directed to the treatment of ITK-mediated diseases.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Also provided is a compound chosen from the Examples disclosed herein. The compounds of embodiments herein may also refer to a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination of the foregoing of the compounds of embodiments herein.

The present disclosure relates to new pyrrolopyrimidine compounds and compositions, and their application as pharmaceuticals for the treatment of disease. Methods of inhibition of ITK activity in a human or animal subject are also provided for the treatment diseases such as those caused by inflammation.

The Tec (tyrosine kinase expressed in hepatocellular carcinoma) family of tyrosine kinases (TFTK) consists of five family members: Tec, BTK (Bruton's tyrosine kinase), BMX (bone marrow kinase on the X chromosome also known as ETK), RLK (resting lymphocyte kinase also known as TXK) and ITK (interleukin-2 inducible T cell kinase, also known as EMT and TSK). These kinases are central to the regulation of hematopoietic cell biology and more specifically the development and activity of lymphocytes and myeloid cells (Horwood et al. (2012) Int. Rev. Immunol. 31, 87-103; Boucheron et al. (2012) Int. Rev. Immunol. 31, 133-154; Koprulu et al. (2009) Crit. Rev. Immunol. 29, 317-333). The TFTK have structural similarities to other non-receptor tyrosine kinases while exhibiting some family specific motifs resulting in a diversity of domain structures associated with complex localization, scaffolding and activation mechanisms. Generally, TFTK contain an amino terminal plekstrin homology domain (PH domain) involved in lipid interactions and membrane targeting followed by a BTK homology domain (BH) that binds $Zn^{2+}$ and an SH3 domain generally involved in proline rich domain binding. A phosphotyrosine binding SH2 domain and a carboxy terminal ATP binding kinase domain complete the TFTK structure (Mano, et al. (1999) Cytokine Growth Factor Rev. 10, 267-280). TFTK expression is generally limited to hematopoietic lineage cells with the exception of ETK and TEC that are expressed in the liver and endothelial cells, respectively (Smith, et al. (2011) Bioessays 23, 436-446). BMX is expressed in monocytes, granulocytes and cardiac endothelium while BTK is expressed in B cells and mast cells but not plasma cells and T cells. TEC, RLK and ITK are all expressed in T cells. To date the TFTK with the most clear biological role in T cells is ITK.

Antigen/MHC dependent activation of the T cell receptor (TCR) has been shown to transduce its signal through ITK. TCR stimulation results in the activation of the kinase LCK and subsequent phosphorylation of the immunoreceptor tyrosine-based activation motifs (ITAMs) on CD3 inducing the binding and activation of the kinase ZAP70. In turn, ZAP70 phosphorylates the adaptor proteins LAT and SLP-76, which together with LCK and other proteins forms a hetermultimeric signaling complex that activates PI3K and generates $PIP_3$ on the plasma membrane. ITK binds to this signaling complex via SH2 and SH3 domains and to $PIP_3$ through its PH domain, resulting in LCK dependent phosphorylation of ITK Y511 and subsequent ITK autophosphorylation of Y180. Activated ITK phosphorylates PLCγ1 that, once activated, hydrolyzes $PIP_2$ to the second messengers IP3 and DAG. The cellular consequences of these sequelae of events include calcium mobilization and flux, PKC and MEK/ERK pathway activation, and transcriptional activation via API, NFκactiv NFAT. As a critical enzyme in the TCR activation pathway ITK impacts T cell function in a number of ways including positive and negative selection, cellular differentiation, and cytokine production and release (Takesono, et al. (2002) J. Cell Science 115, 3039-3048; August, et al. (2012) Int. Rev. Immunol. 31, 155-165; Andreotti, et al. (2010) Cold Spring Harb. Perspect. Biol. 2, a002287 1-21).

The role of ITK in T cell function has been delineated through genetic knockdown/kinase inactivation of the ITK gene in rodents and through characterizing human ITK mutant individuals. Mice with a null mutation of the itk gene expressed a decreased number of mature T cells and a block in thymocyte development as well as a decreased TCR driven T cell proliferative response. Interestingly IL2 and CD28 signaling as well as PMA/ionomycin driven responses remained unchanged, suggesting that the ITK response is membrane proximal and stimuli specific (Liao et al. (1995) Immunity 3, 757-769). It appears that ITK is responsible for amplification of TCR signaling versus an 'on/off' switch, as dual knockdown of the T cell expressing TFTK, ITK and RLK in mice produce a more complete TCR inactivation phenotype compared with ITK genetic deletion alone (Schaeffer et al. (1999) Science 284, 638-641). In contrast to the modulatory effect that ITK appears to have on naïve T cell activation, it plays a more significant role in T helper cell differentiation. Several studies in ITK deficient mice have demonstrated a reduction in the Th2 protective response to parasitic infection (Fowell et al. (1999) Immunity 11, 399-409; Schaeffer et al. (2001) Nat. Immunol. 2, 1183-1188). This reduced Th2 response was linked to a decrease in concentrations of Th2 cytokines IL4, IL5, IL13 and IL10 (Schaeffer et al. (2001) Nat. Immunol. 2, 1183-1188) and to a reduction in RLK expression. In contrast to the ITK requirement for mounting Th2 driven responses, its impact on Th1 responses is modest. For example, IFNg production in ITK knockout cells is partially inhibited while the double ITK/RLK knockout has a more severe phenotype (Fowell et al. (1999) Immunity 11, 399-409; Schaeffer et al. (2001) Nat. Immunol. 2, 1183-1188; Miller et al. (2004) Immunity 21, 67-80). Evaluation of Th17 T helper cells in ITK knockout in vivo and in vitro studies demonstrated a reduction of IL17A mRNA and protein while having little impact on IL17F (Gomez-Rodriguez et al. (2009) Immunity, 31, 587-597). The role of ITK in cytotoxic CD8+ T cells was investigated using ITK knockout mice. Stimulation of CD8+

T cells deficient in ITK results in a reduction in activation of PLCg1, ERK and p38 MAPK and loss of $Ca^{2+}$ response resulting in decreased proliferative response and effector cytokine production (IL2, IL4 and IFNg) while not impacting cytolytic capacity of these cells (Atherly et al. (2006) J. Immunol. 176, 1571-1581). In addition to the defects observed in CD4+ and CD8+ T cells, natural killer T cell development and TCR stimulated response is reduced in ITK knockout cells and animals (Au-Yueng et al. (2007) J. Immunol. 179, 111-119; Felices et al. (2008) J. Immunol. 180, 3007-3018).

Rodent genetic knockout studies reflect the impact of enzyme expression, not necessarily its catalytic activity, on biological responses. As ITK, through its multiple domain structure, has a role in scaffolding, in addition to its catalytic role. It is important to delineate the impact of blocking each of these functions on cellular biology. Kinase activity-independent ITK activities include recruitment of the guanine nucleotide exchange factor VAV to the cell membrane associated with actin polymerization (PH and SH2 domain dependent) (Atherly et al. (2006) J. Immunol. 176, 1571-1581), antigen receptor stimulation, and receptor activation of SRF (Dombroski et al. (2005) J. Immunol., 174, 1385-1392). However, ITK knockout mice expressing an ITK kinase domain deleted transgene demonstrated that the kinase domain is essential for induction of a normal Th2 response (von Bonin et al. (2011) Exp. Dermatol. 20, 41-47).

The relationship between ITK expression and activity and human disease has recently been documented in studies characterizing individuals exhibiting mutations in the gene encoding this protein and or correlation between expression and disease. The ITK gene was found to be elevated in peripheral blood T cells from patients with moderate to severe atopic dermatitis, a Th2 driven chronic inflammatory skin disease (Hao et al. (2006) FEBS Letts., 580, 2691-2697). An investigation of disease-associated single nucleotide polymorphisms (SNP) in seasonal allergic rhinitis identified ITK as a significant risk factor (Matsumoto et al. (2002) Int. Arch. Allergy Immunol. 129, 327-340). A human primary immunodeficiency was uncovered in siblings that died from immune dysregulation resulting in lymphoproliferation following Epstein Barr Virus (EBV) infection. This disorder was linked to a missense (R335W) mutation in the SH2 domain of ITK resulting in structural instability and reduced steady state levels of the enzyme (Felices et al. (2008) J. Immunol., 180, 3007-3018). The finding was confirmed and extended in studies that identified three patients harboring a C1764G nonsense mutation in ITK resulting in a premature stop codon and reduced expression and/or activity of the protein. These patients presented with EBV-positive Hodgkins Lymphoma (Huck et al. (2009) J. Clin. Invest. 119, 1350-1358). These two reports suggest that mutational disruption of the ITK gene in humans results in an autosomal recessive lymphoproliferative disorder and identifies this kinase as a critical modulator in T cell biology.

In addition to the human genetic data summarized above, animal models support ITK as a therapeutic target for autoimmune and inflammatory disease. ITK knockout mice demonstrate reduced airway hypersensitivity and inflammation in models of allergic asthma (Stepensky et al. (2011) Haematologica, 96, 472-476; Mueller et al. (2003) J. Immunol., 170, 5056-5063; Ferrara et al. (2004) Pulm. Pharmacol. Ther. 17, 301-308). In a murine model of atopic dermatitis, ITK deficient mice do not develop inflammation while ITK inhibition reduces the response in wild type mice (Ferrara et al. (2006) J. Allerg. Clin. Immunol. 117, 780-786). The ITK dependent regulation of TCR dependent $Ca^{2+}$ mobilization and transcription factor induction makes it a critical factor in protecting against Influenza A and HIV infection and viral replication. ITK inhibitors have been shown to alter HIV replication at multiple stages and have the potential as effective HIV therapeutics (Sahu et al. (2008) J. Immunol. 180, 3833-3838).

From an oncology perspective, studies have demonstrated that ITK inhibitors selectively target the killing of acute lymphblastic T-cell leukemia and cutaneous T-cell lymphoma while normal T cells are minimally impacted (Readinger et al. (2008) Proc. Nat. Acad. Sci. USA, 105, 6684-6689). ITK is highly expressed in transformed T-cell lines relative to normal T cells and other cancer cell lines. The impact of ITK inhibition on T cell tumors was confirmed in mouse xenograph models. Cancer evasion of the immune system as a result of tumor antigen tolerance induction versus priming is critical for tumor survival. Tumors that develop a microenvironment that induces T cell unresponsiveness demonstrate altered T cell gene expression suggesting skewing to the Th2 phenotype. ITK inhibition will favor Th1 differentiation and could be used to enhance cancer immunotherapy (Gao et al. (2012) Mol. Pharmacol., 82, 938-947; Horna et al. (2007) Curr. Cancer Drug Targ. 7, 41-53).

Compounds useful as dual ITK and JAK3 kinase inhibitors for the treatment of inflammation and immune disorders are reported in WO 2014172513 (pub. 23 Oct. 2014). Compounds described therein include 5-aryl-substituted pyrrolopyridines and pyrrolopyrazines where the 5-aryl group is substituted with acrylamide substituents. Compounds Embodiments of the present disclosure are directed to a compound of structural Formula (I):

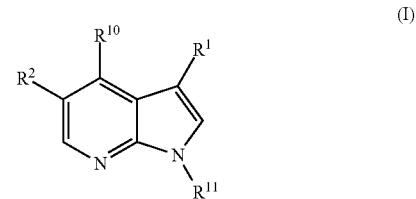

wherein:
$R^1$ is chosen from aryl and heteroaryl, and may be optionally substituted with one or more $R^3$ substituents;
$R^2$ is chosen from aryl or heteroaryl, and may be optionally substituted with one or more $R^4$ substituents;
each $R^3$ is independently chosen from hydrogen, —$C_{1-4}$alkyl, —$OC_{1-4}$alkyl, —$NHC_{1-4}$alkyl, —$N(C_{1-4}$alkyl$)_2$, cyano, —C(O)N($R^6$)$_2$, —C(O)$C_{1-4}$alkyl, haloalkyl, oxo, and halo;
each $R^4$ is independently chosen from hydrogen, —$C_{1-4}$alkyl, —$OC_{1-4}$alkyl, —$OC_{1-6}$cycloalkyl, —$OC_{1-6}$heterocycloalkyl, aryl, heteroaryl, haloalkyl, haloalkoxy, halo, —$NR^5R^6$, —$(CH_2)_mCR^7$=$CR^9C(O)$Me, —$(CH_2)_mCR^7$=$CR^9C(O)NR^7_2$, and —$(CH_2)_m$ $CR^7$=$CR^9CN$;
$R^5$ is chosen from hydrogen, cyano, —C(O)$CF_3$, —C(O) CH=$CH_2$, —C(O)$CR^7$=$CH_2$, —C(O)CH=$CHR^7$, —C(O)$CR^7$=$CHR^7$, —C(O)CH=$CR^7_2$, —C(O) CH=$CHCH_2R^8$, —C(O)CH=CHC(O)$CH_2R^8$, —COC (CN)=$CHR^6$, —C(O)(C(O)$NH_2$)=$CHR^6$, —S(O)$_2$ CH=$CH_2$, —$(CH_2)_mCR^7$=$CR^9C(O)$Me, —$(CH_2)_m$ $CR^7$=$CR^9C(O)NR^7_2$, and —$(CH_2)_mCR^7$=$CR^9CN$;
$R^6$ is chosen from hydrogen, —$C_{1-4}$alkyl, and —$(CH_2)_n$ $C_{3-7}$cycloalkyl;

each $R^7$ is independently chosen from hydrogen, —CN, —$C_{1-4}$alkyl, —$C_{3-7}$cycloalkyl, —$C_{3-7}$ heterocycle, aryl, and heteroaryl where aryl and heteroaryl may be optionally substituted with one or more $R^9$;

$R^8$ is chosen from hydrogen, —$C_{1-4}$alkyl, —$C_{1-4}$alkylaryl, —$C_{1-4}$alkylheteroaryl, —$C_{3-7}$cycloalkyl, —$C_{3-7}$heterocycle, —OH, —$OC_{1-4}$alkyl, —$C_{1-4}$alkyl$OC_{1-4}$alkyl, —$NH_2$, —$NHC_{1-4}$alkyl, —$N(C_{1-4}$ alkyl$)_2$, heterocycle, aryl and heteroaryl;

$R^9$ is chosen from hydrogen, —$C_{1-4}$ alkyl, —CN, —$CF_3$, —C(O)Me, —$C(O)NH_2$, and aryl;

$R^{10}$ is chosen from H and —$C_{1-4}$alkyl;

$R^{11}$ is chosen from hydrogen and —$C_{1-4}$alkyl, optionally substituted with —$OPO(OR^{12})_2$, —$OC(O)R^{13}$, or an amino acid;

$R^{12}$ is chosen from hydrogen and —$C_{1-6}$alkyl;

$R^{13}$ is —$C_{1-6}$ alkyl;

m is chosen from 1, 2 and 3;

n is chosen from 0, 1, 2, and 3; and a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In some embodiments, said compound has structural Formula (II):

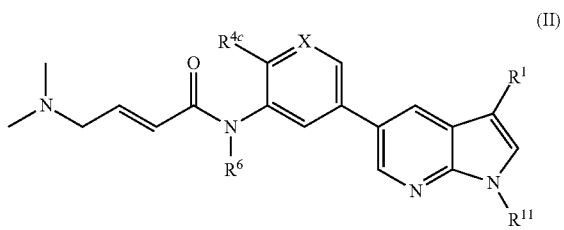

(II)

wherein:

$R^1$ is chosen from aryl and heteroaryl, and may be optionally substituted with one or more $R^3$ substituents;

X is chosen from $CR^{4b}$ and N;

each $R^3$ is independently chosen from hydrogen, —$C_{1-4}$alkyl, —$OC_{1-4}$alkyl, —$NHC_{1-4}$alkyl, —$N(C_{1-4}$ alkyl$)_2$, cyano, —$C(O)N(R^6)_2$, —$C(O)C_{1-4}$alkyl, haloalkyl, oxo, and halo;

$R^{4b}$ is chosen from hydrogen, —$C_{1-4}$alkyl, —$OC_{1-4}$alkyl, aryl, heteroaryl, haloalkyl, haloalkoxy, and halo;

$R^{4c}$ is chosen from hydrogen, —$C_{1-4}$alkyl, —$OC_{1-4}$alkyl, —$OC_{1-6}$cycloalkyl, and —$OC_{1-6}$ heterocycloalkyl;

$R^6$ is chosen from hydrogen and —$C_{1-4}$alkyl;

$R^{11}$ is chosen from hydrogen and —$C_{1-4}$alkyl, optionally substituted with —$OPO(OR^{12})_2$, —$OC(O)R^{13}$, or an amino acid; and $R^{12}$ is chosen from hydrogen and —$C_{1-6}$alkyl;

$R^{13}$ is —$C_{1-6}$ alkyl; and a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (II), $R^1$ is phenyl, optionally substituted with one or more $R^3$ substituents; and each $R^3$ is independently chosen from hydrogen, cyano, —$OC_{1-4}$alkyl, and halo.

In an embodiment of said compound of structural Formula (II), $R^1$ is heteroaryl, and may be optionally substituted with one or more $R^3$ substituents; and each $R^3$ is independently chosen from hydrogen, cyano, —$OC_{1-4}$alkyl, and halo.

In an embodiment of said compound of structural Formula (II), $R^1$ is pyridyl.

In an embodiment of said compound of structural Formula (II), $R^{4b}$ is chosen from hydrogen, —$C_{1-4}$alkyl, heteroaryl, —$OC_{1-4}$alkyl, haloalkyl, haloalkoxy, and halo.

In an embodiment of said compound of structural Formula (II), $R^{4c}$ is hydrogen.

In some embodiments, said compound has structural Formula (III):

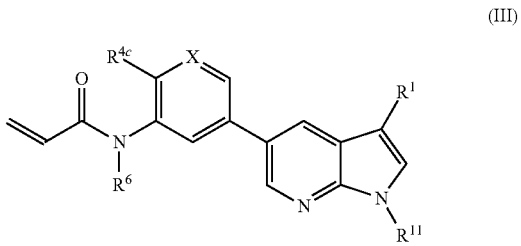

(III)

wherein:

$R^1$ is chosen from aryl and heteroaryl, and may be optionally substituted with one or more $R^3$ substituents;

X is chosen from $CR^{4b}$ and N;

each $R^3$ is independently chosen from hydrogen, —$C_{1-4}$alkyl, —$OC_{1-4}$alkyl, —$NHC_{1-4}$alkyl, —$N(C_{1-4}$ alkyl$)_2$, cyano, —$C(O)N(R^6)_2$, —$C(O)C_{1-4}$alkyl, haloalkyl, oxo, and halo;

$R^{4b}$ is chosen from hydrogen, —$C_{1-4}$alkyl, —$OC_{1-4}$alkyl, aryl, heteroaryl, haloalkyl, haloalkoxy, and halo;

$R^4$ is chosen from hydrogen, —$C_{1-4}$alkyl, —$OC_{1-4}$alkyl, —$OC_{1-6}$cycloalkyl, and —$OC_{1-6}$heterocycloalkyl;

$R^6$ is chosen from hydrogen and —$C_{1-4}$alkyl;

$R^{11}$ is chosen from hydrogen and —$C_{1-4}$alkyl, optionally substituted with —$OPO(OR^{12})_2$, —$OC(O)R^{13}$, or an amino acid; and $R^{12}$ is chosen from hydrogen and —$C_{1-6}$alkyl;

$R^{13}$ is $C_{1-6}$ alkyl; and a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (III), $R^1$ is phenyl, optionally substituted with one or more $R^3$ substituents; and each $R^3$ is independently chosen from hydrogen, cyano, —$OC_{1-4}$alkyl, and halo.

In an embodiment of said compound of structural Formula (III), $R^1$ is heteroaryl, and may be optionally substituted with one or more $R^3$ substituents; and each $R^3$ is independently chosen from hydrogen, cyano, —$OC_{1-4}$alkyl, and halo.

In an embodiment of said compound of structural Formula (III), $R^1$ is pyridyl.

In an embodiment of said compound of structural Formula (III), $R^{4b}$ is chosen from hydrogen, —$C_{1-4}$alkyl, heteroaryl, —$OC_{1-4}$alkyl, haloalkyl, haloalkoxy, and halo.

In an embodiment of said compound of structural Formula (III), $R^4$ is hydrogen.

In an embodiment of said compound of structural Formula (III), a compound of the present disclosure is administered with a pharmaceutically acceptable carrier, adjuvant, or vehicle.

Embodiments of the present disclosure are directed to a compound of structural Formula (IV):

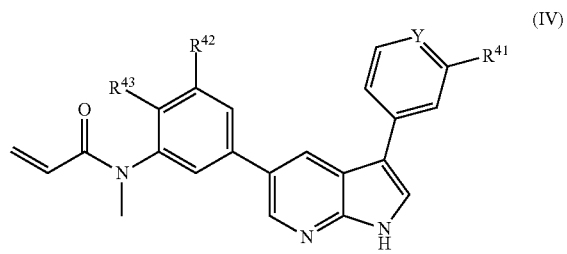

(IV)

wherein:
Y is chosen from CH and N;
$R^{41}$ is chosen from —$C_{1-4}$alkyl, —$OC_{1-4}$alkyl, cyano, and halo;
$R^{42}$ is chosen from hydrogen and —$OC_{1-4}$alkyl;
$R^{43}$ is chosen from hydrogen and halo; and
a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (IV), a compound of the present disclosure is administered with a pharmaceutically acceptable carrier, adjuvant, or vehicle.

Embodiments of the present disclosure are directed to a compound of structural Formula (V):

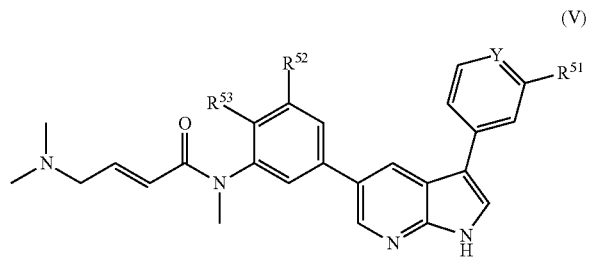

(V)

wherein:
Y is chosen from CH and N;
$R^{51}$ is chosen from —$C_{1-4}$alkyl, —$OC_{1-4}$alkyl, cyano, and halo;
$R^{52}$ is chosen from hydrogen and —$OC_{1-4}$alkyl;
$R^{53}$ is chosen from hydrogen and halo; and
a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (V), a compound of the present disclosure is administered with a pharmaceutically acceptable carrier, adjuvant, or vehicle.

Embodiments of the present disclosure are directed to a compound of structural Formula (VI):

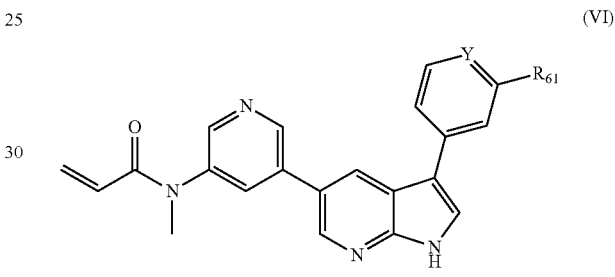

(VI)

wherein:
Y is chosen from CH and N;
$R^{61}$ is chosen from —$OC_{1-4}$alkyl, cyano, and halo; and
a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (VI), a compound of the present disclosure is administered with a pharmaceutically acceptable carrier, adjuvant, or vehicle.

Embodiments of the present disclosure are directed to a compound of structural Formula (VII):

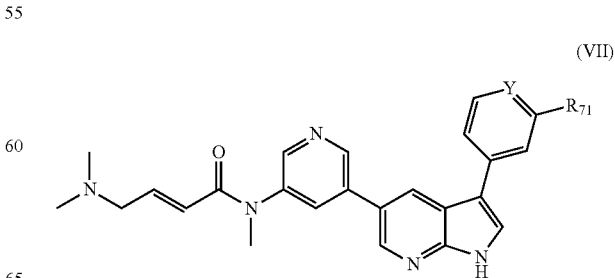

(VII)

wherein:
Y is chosen from CH and N;
$R^{71}$ is chosen from —$OC_{1-4}$alkyl, cyano, and halo; and
a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (VII), a compound of the present disclosure is administered with a pharmaceutically acceptable carrier, adjuvant, or vehicle.

Embodiments of the present disclosure are directed to a compound of structural Formula (VIII):

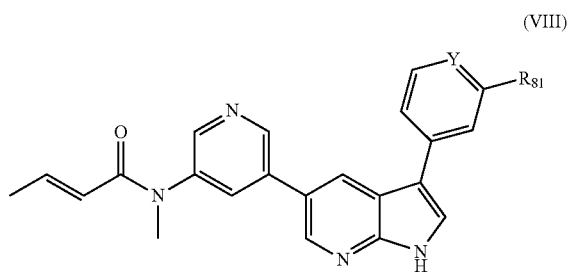

(VIII)

wherein:
Y is chosen from CH and N;
$R^{81}$ is chosen from —$OC_{1-4}$alkyl, cyano, and halo; and
a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (VIII), a compound of the present disclosure is administered with a pharmaceutically acceptable carrier, adjuvant, or vehicle.

Embodiments of the present disclosure are directed to a compound of structural Formula (IX):

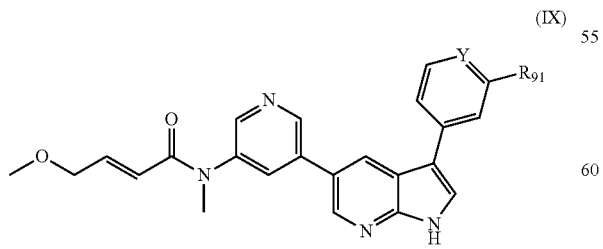

(IX)

wherein:
Y is chosen from CH and N;
$R^{91}$ is chosen from —$OC_{1-4}$alkyl, cyano, and halo; and
a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In an embodiment of said compound of structural Formula (IX), a compound of the present disclosure is administered with a pharmaceutically acceptable carrier, adjuvant, or vehicle.

In some embodiments, the compound of Formula I may be selected from:

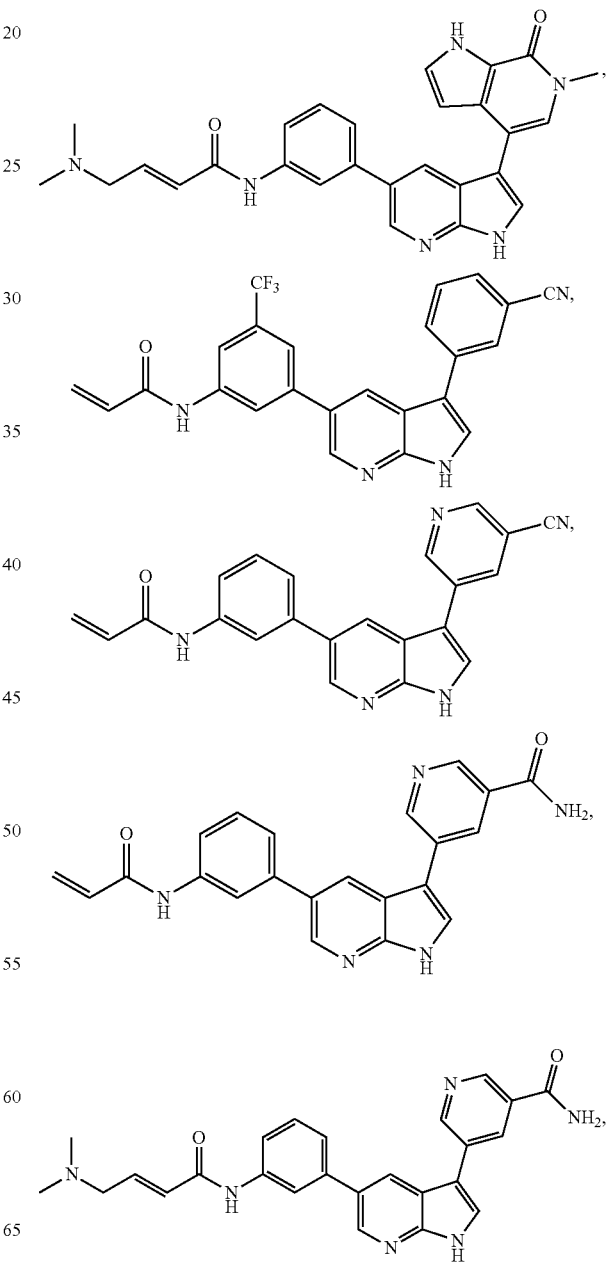

27
-continued
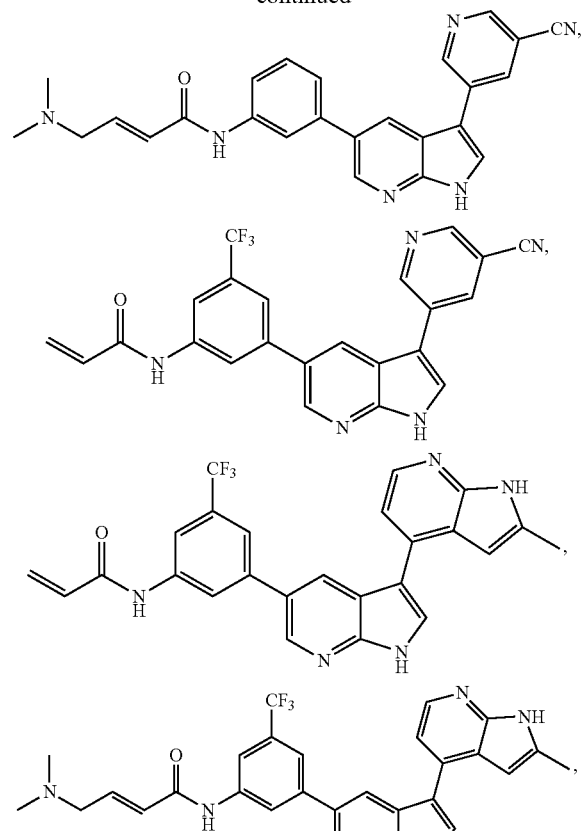
28
-continued
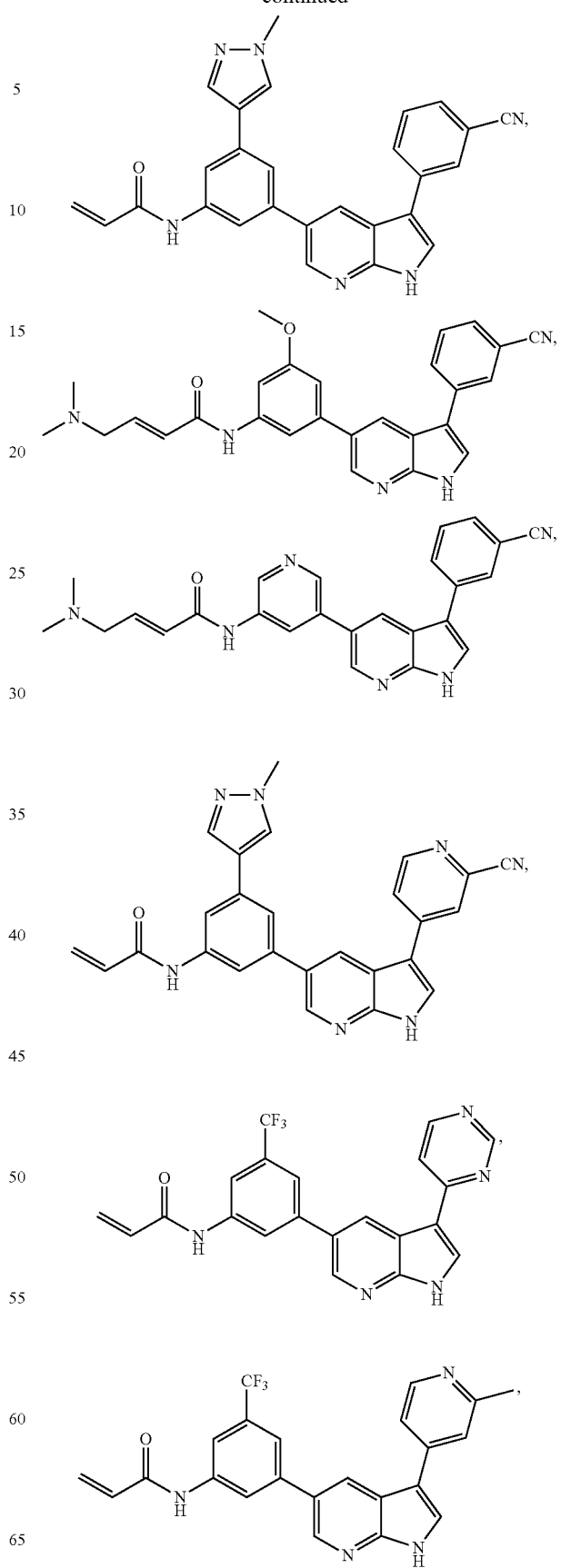

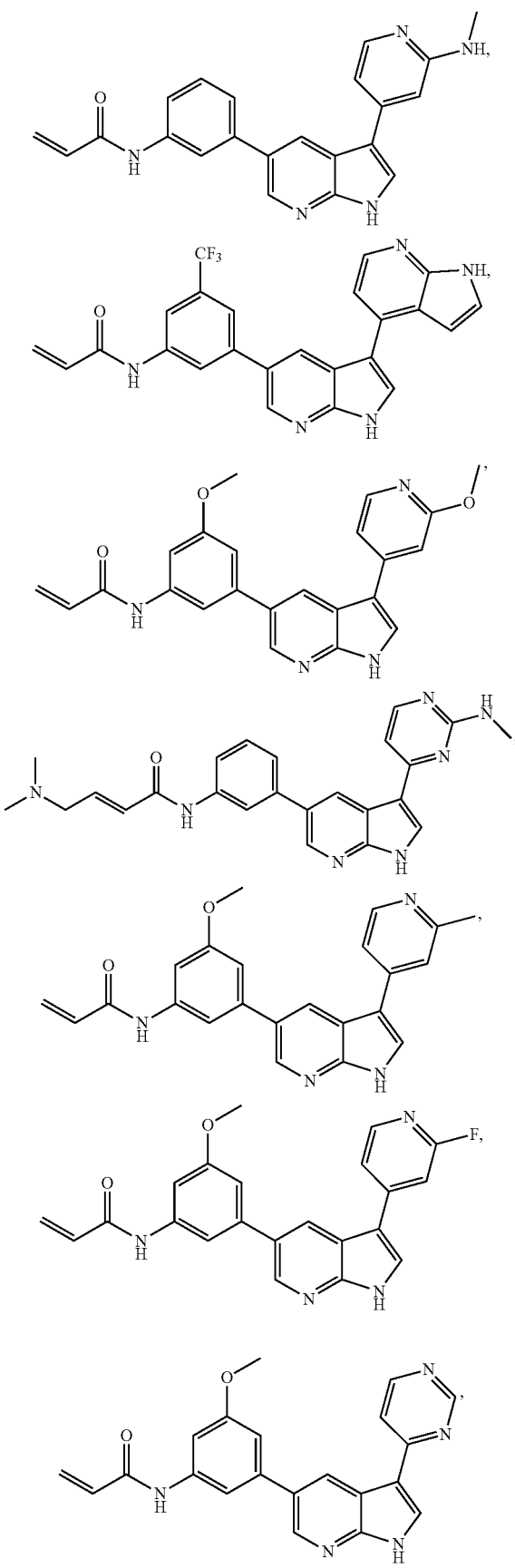
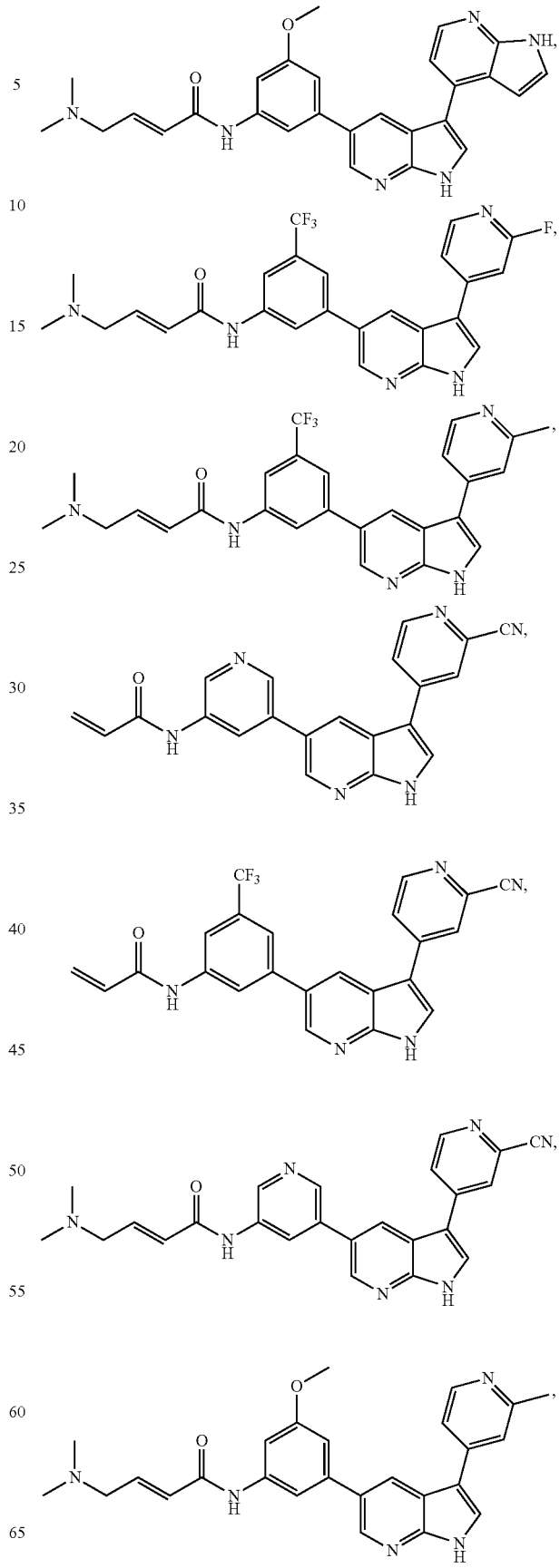

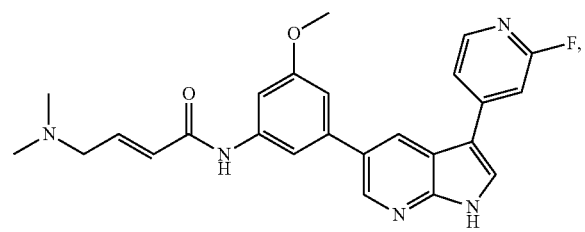
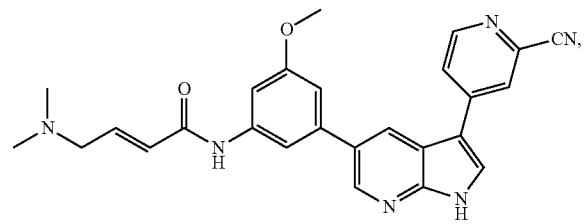
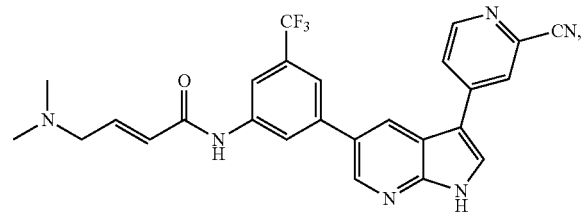
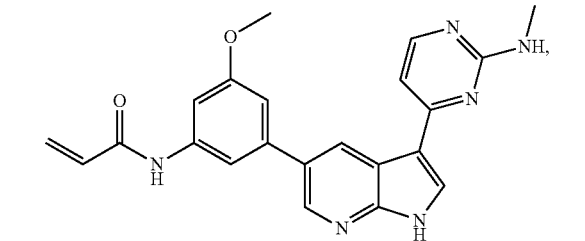
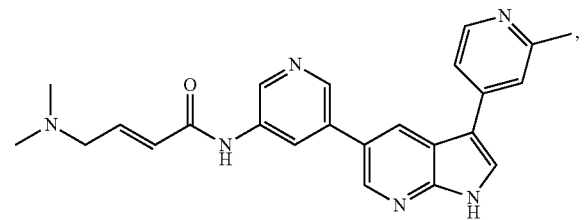
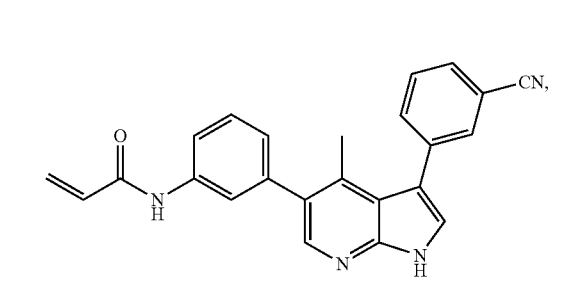
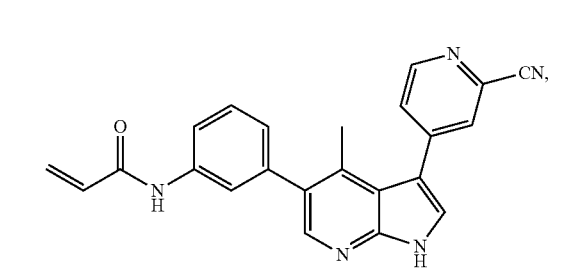
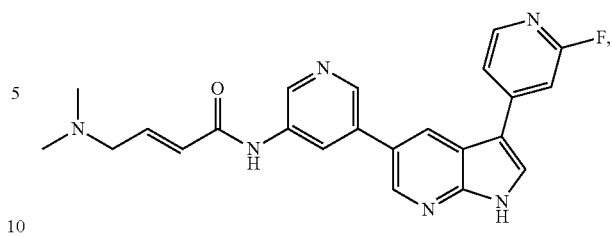
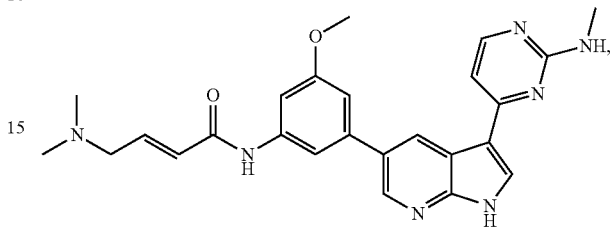
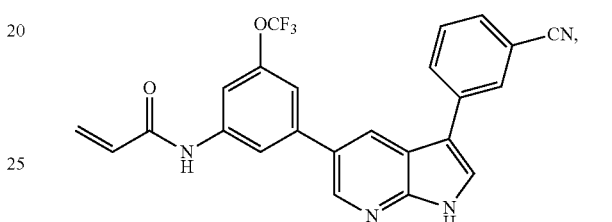
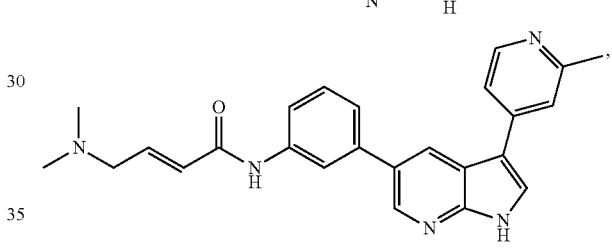
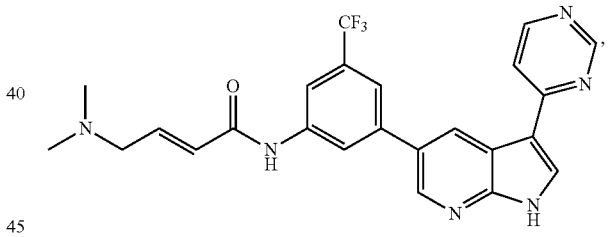
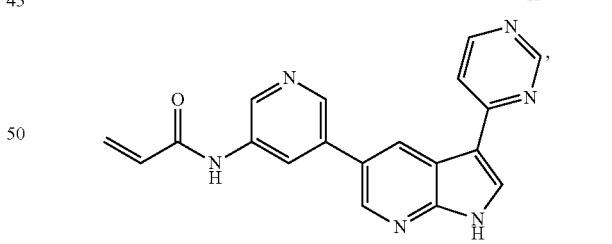
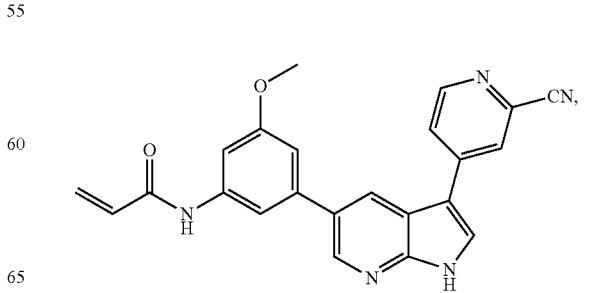

-continued
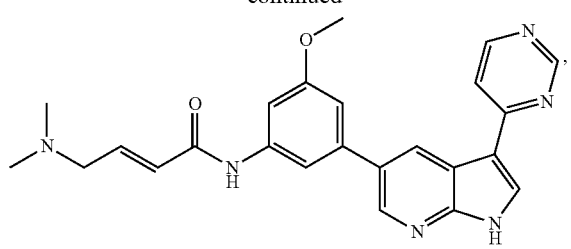
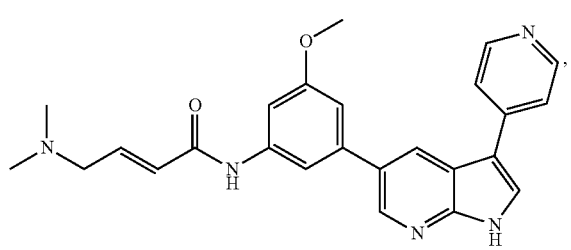
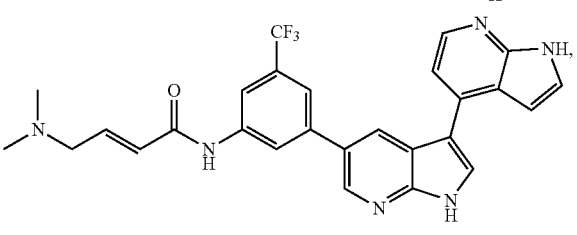
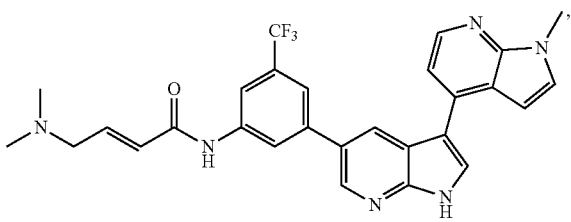
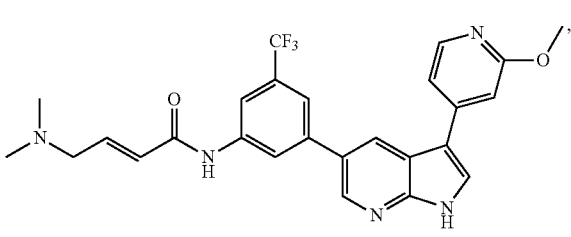
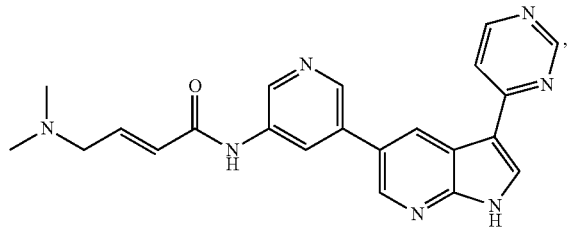
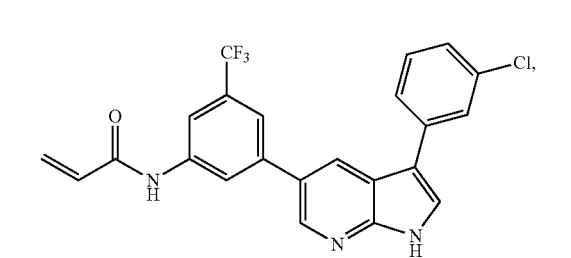
-continued
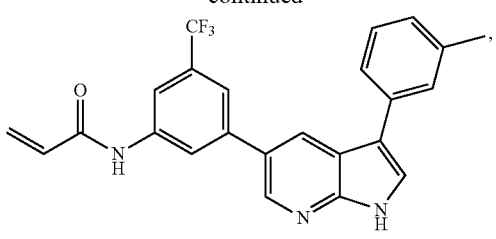
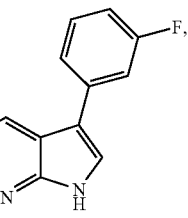
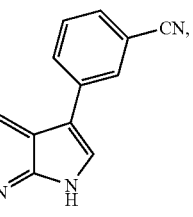
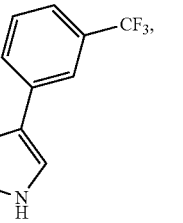
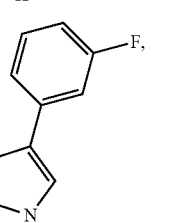
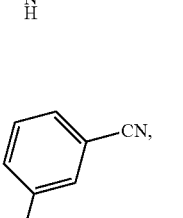
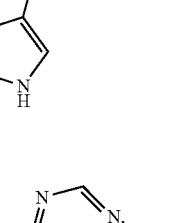
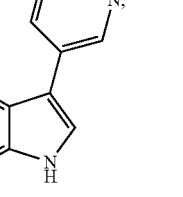

35
-continued
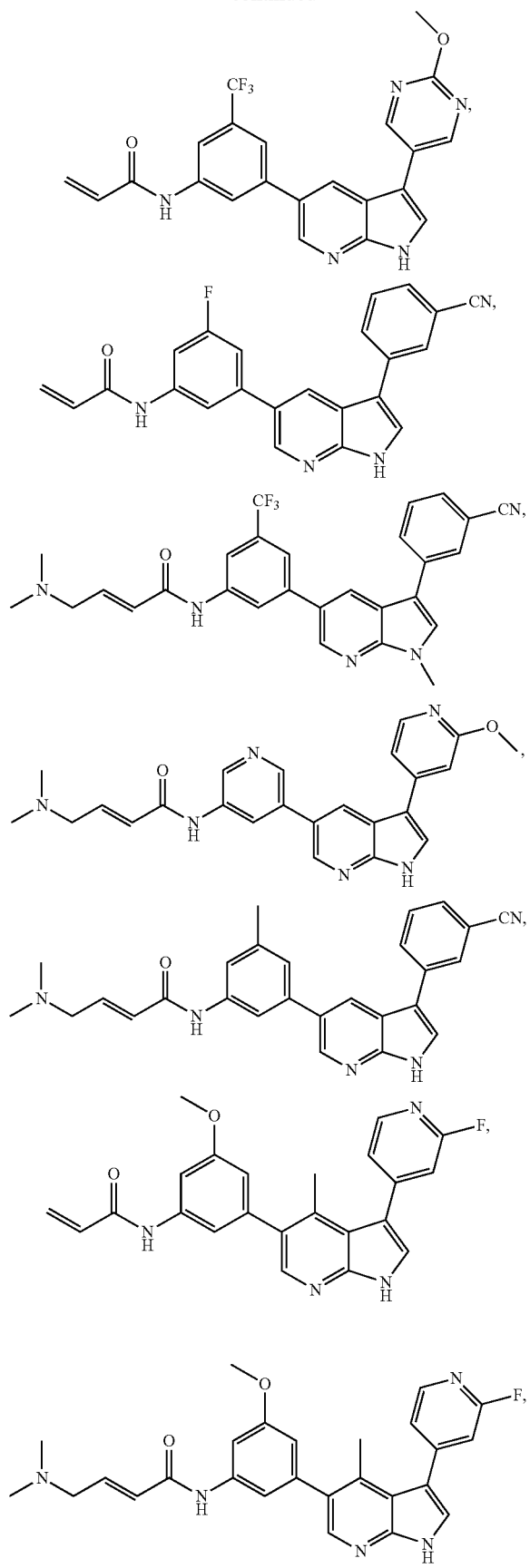
36
-continued
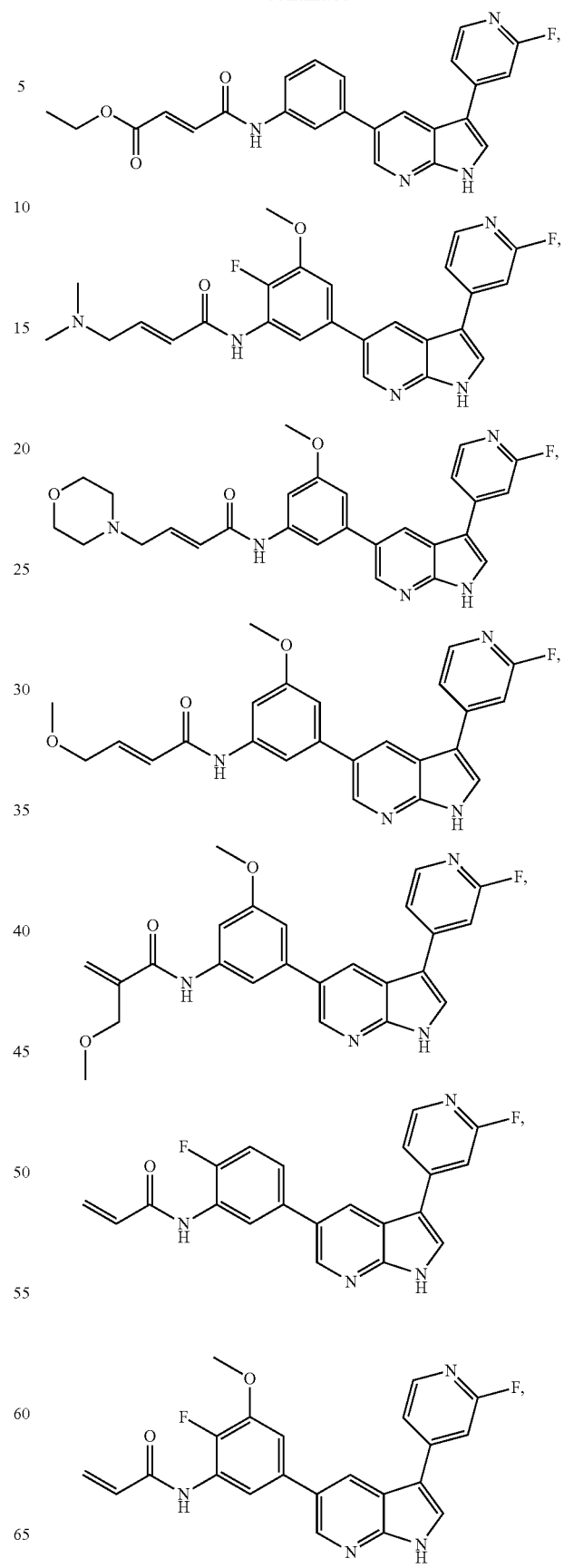

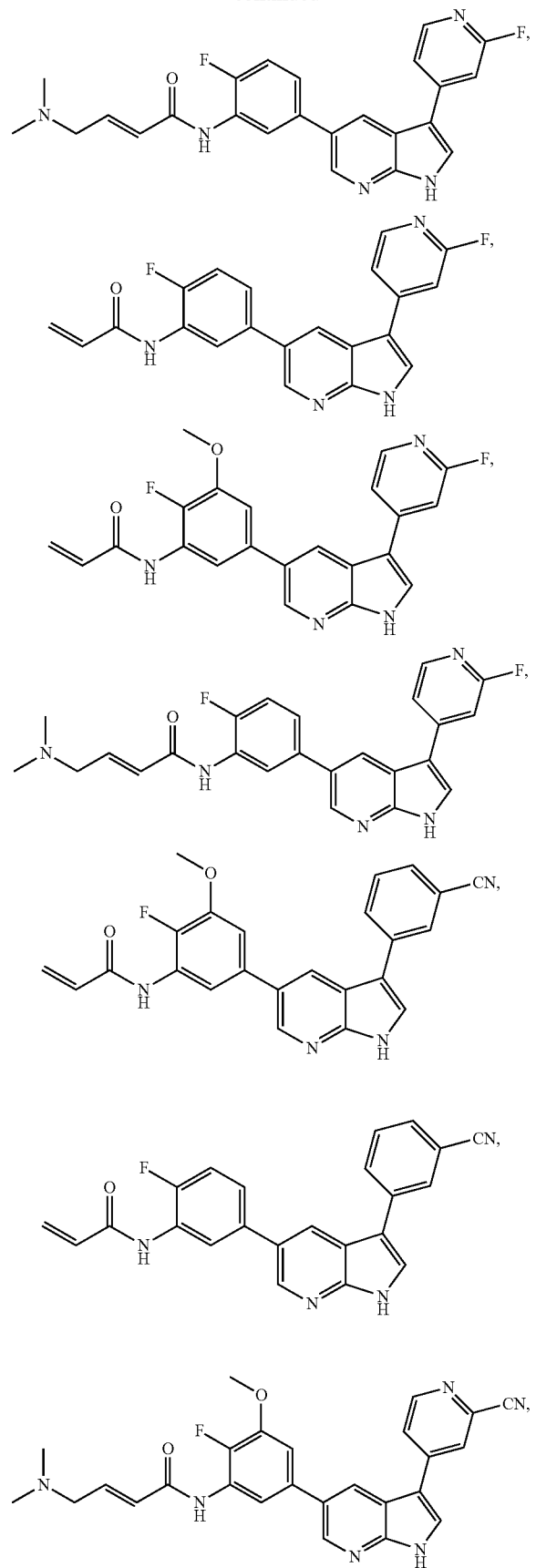
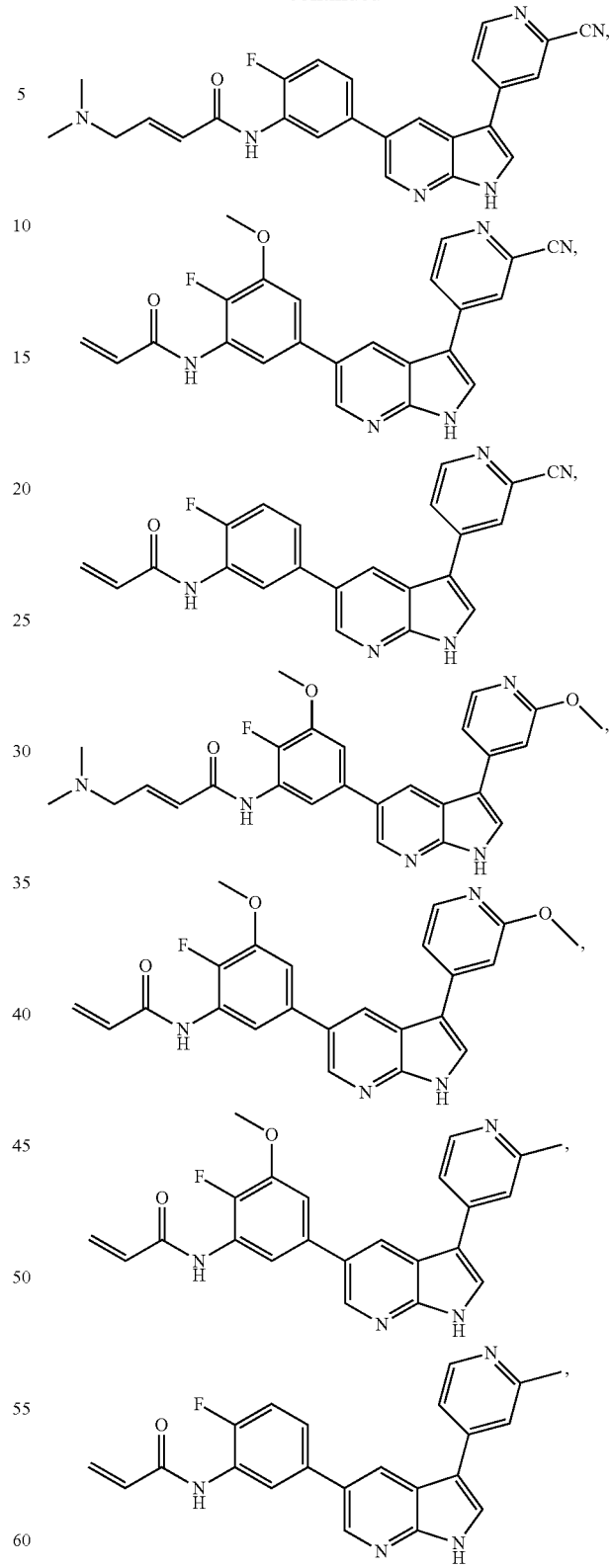
a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.
In some embodiments, the compound of Formula IV may be selected from:
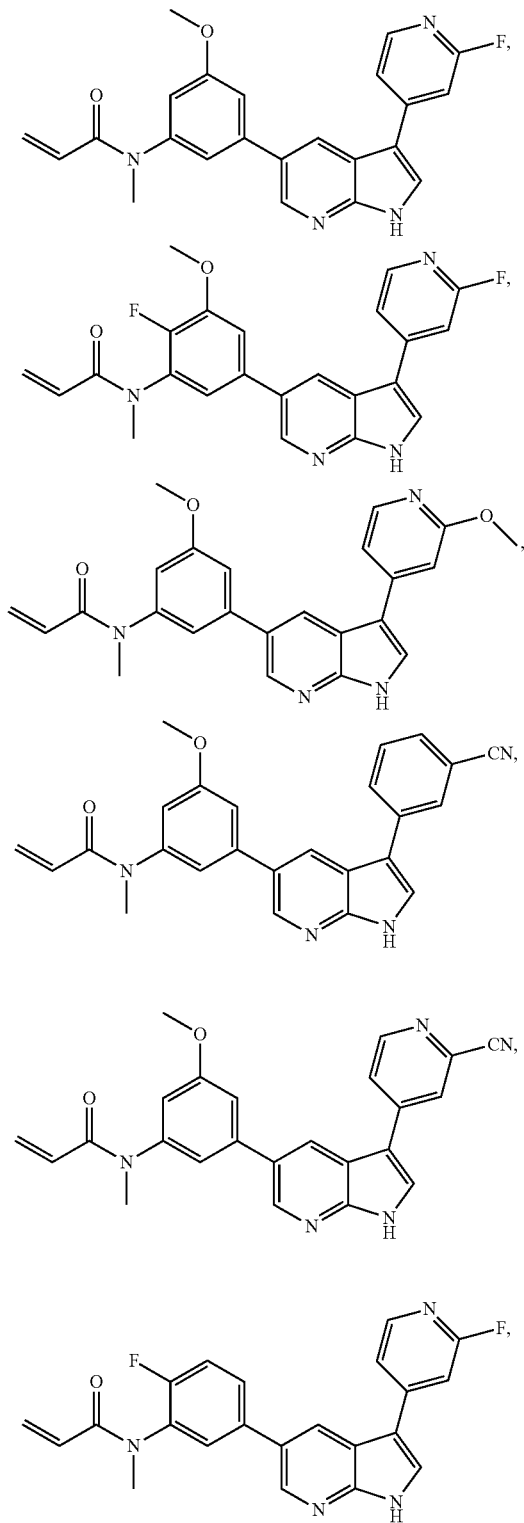
-continued
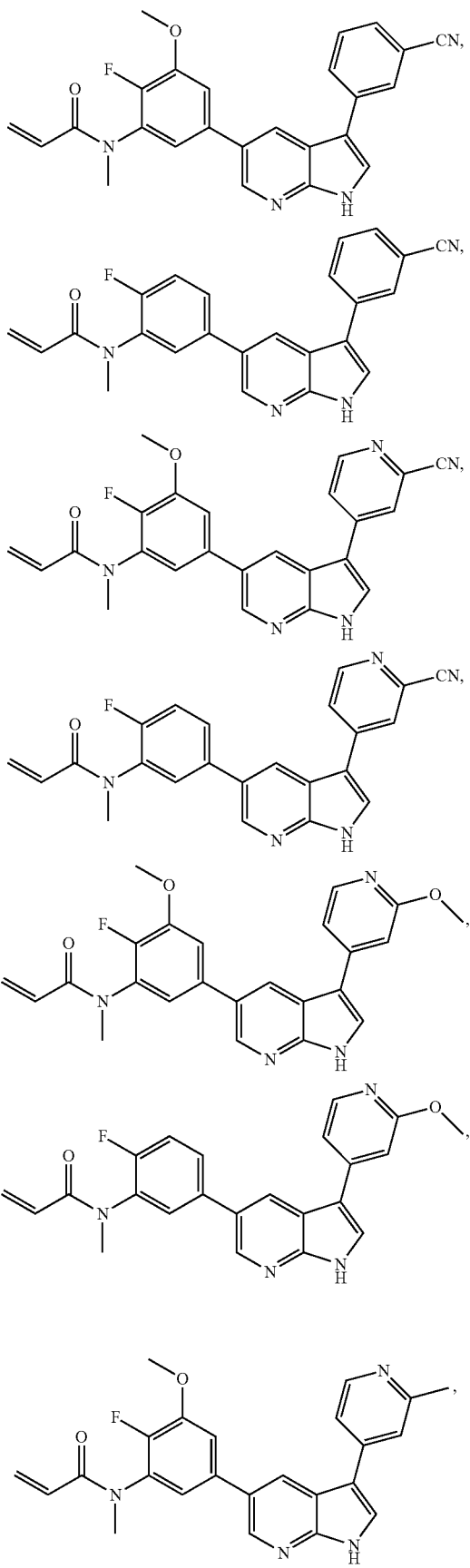

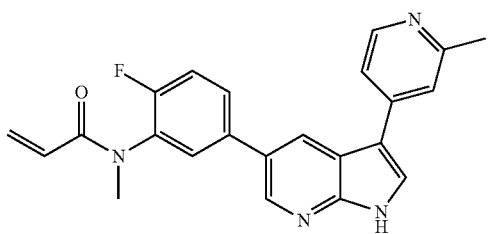

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In some embodiments, the compound of Formula V may be selected from:

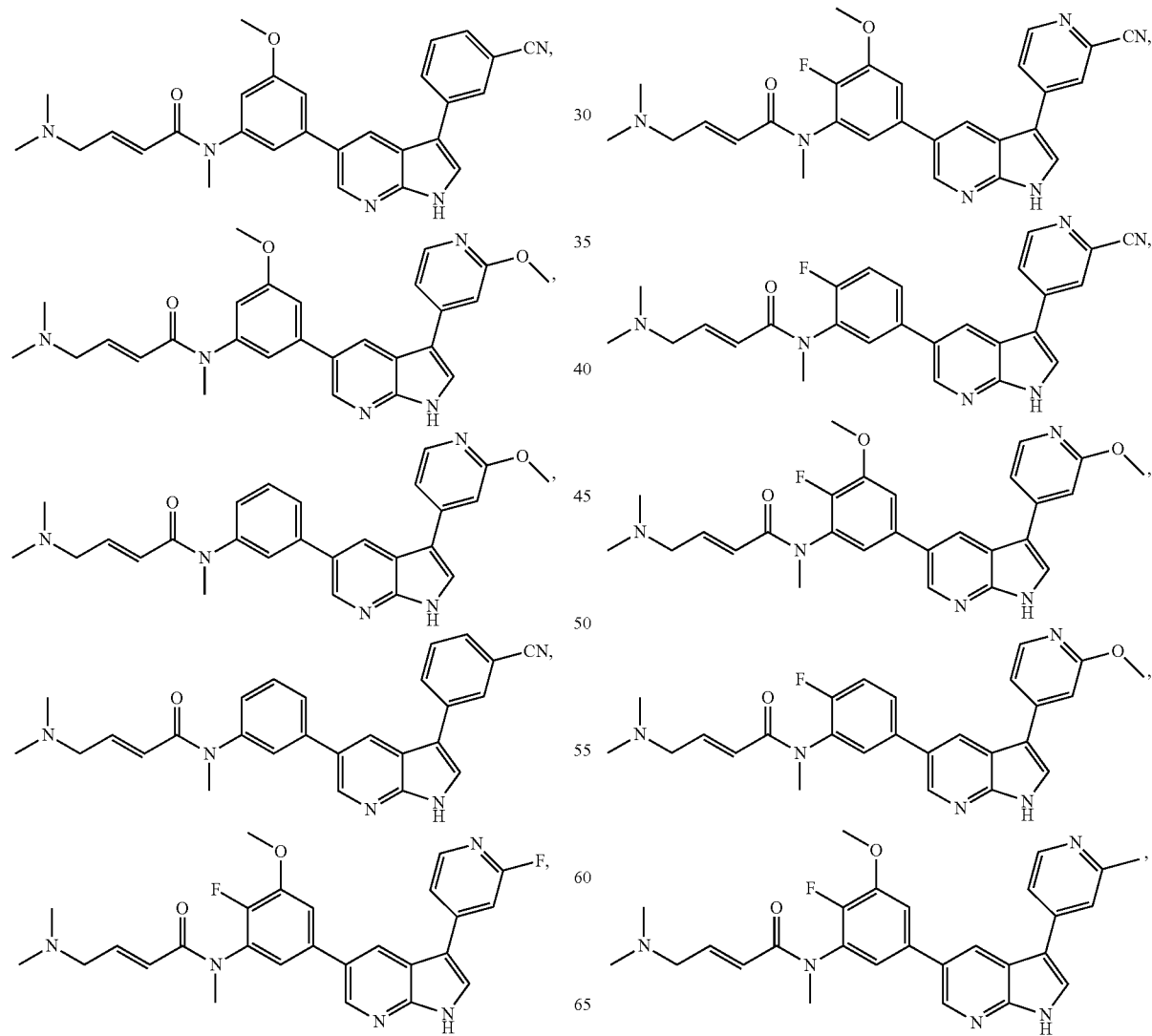

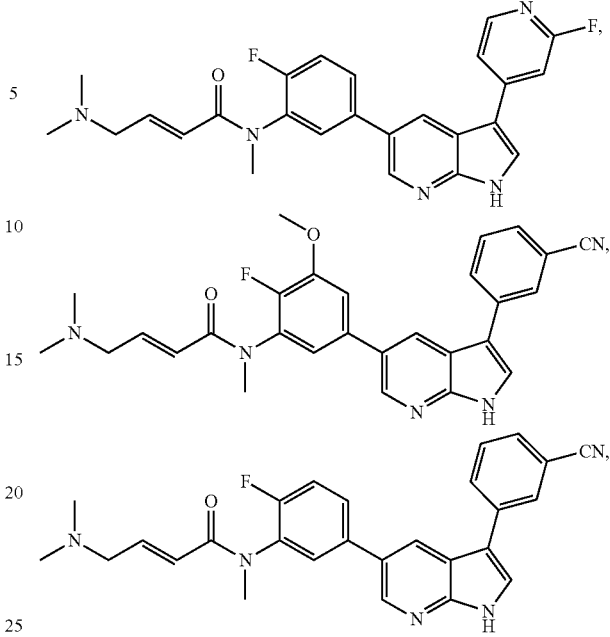

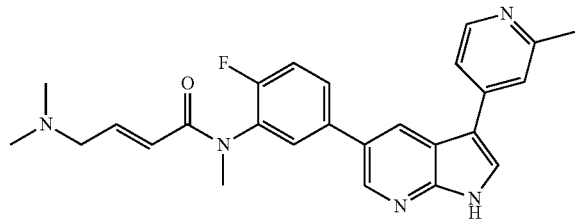

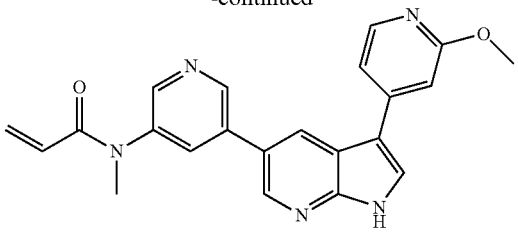

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In some embodiments, the compound of Formula VI may be selected from:

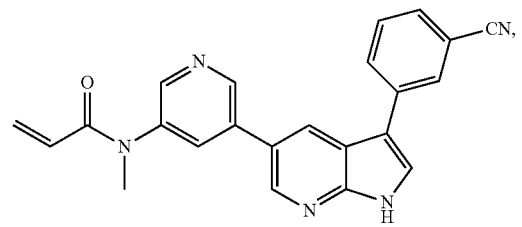

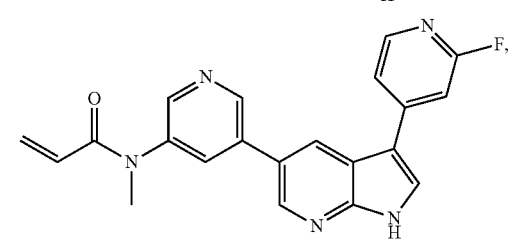

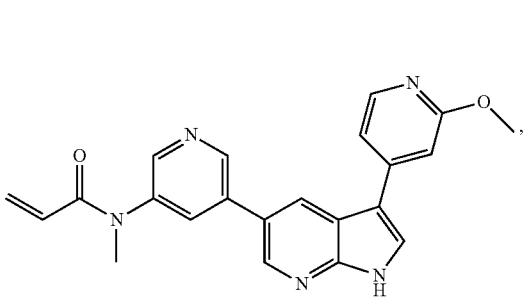

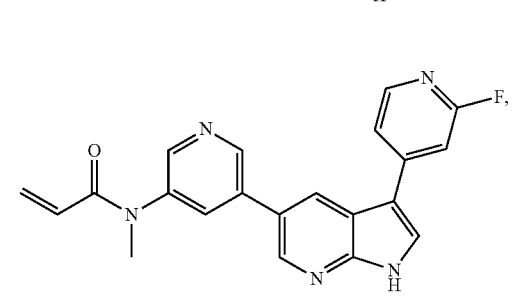

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In some embodiments, the compound of Formula VII may be selected from:

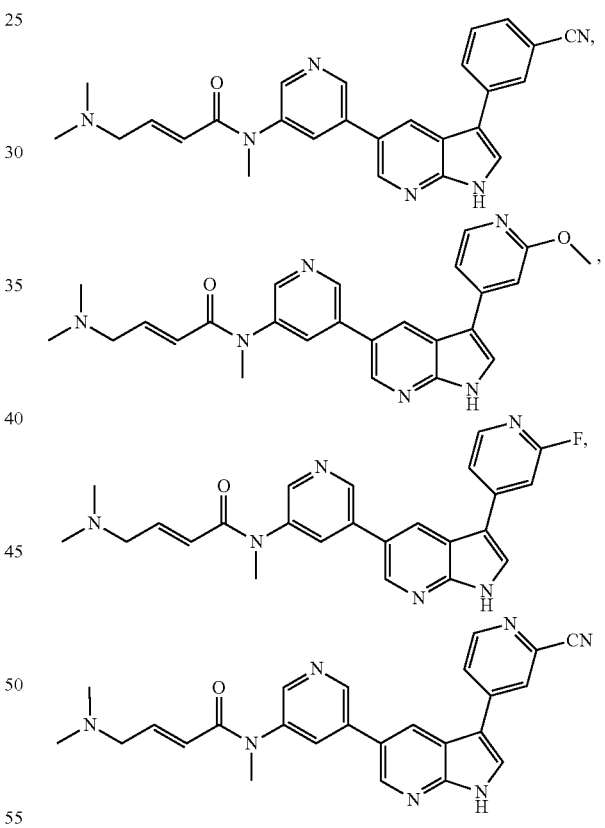

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In some embodiments, the compound of Formula VIII may be selected from:

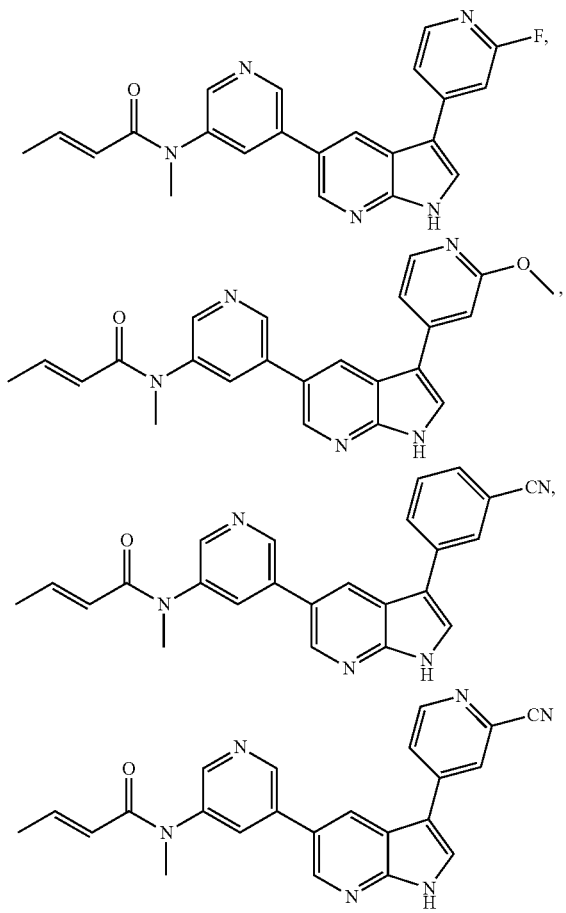

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

In some embodiments, the compound of Formula IX may be selected from:

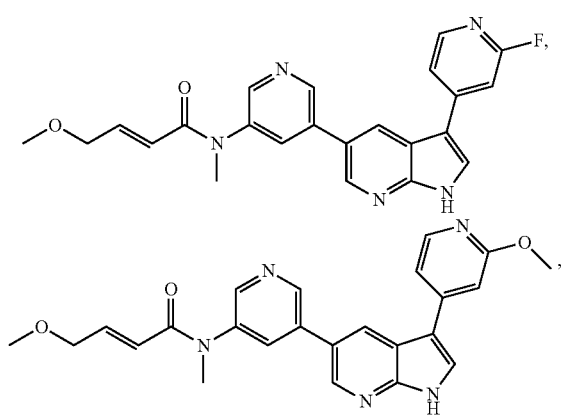

a salt thereof, an ester thereof a free acid form thereof, a free base form thereof a solvate thereof, a deuterated derivative thereof, a hydrate thereof an N-oxide thereof a clathrate thereof, a prodrug thereof, a polymorph thereof, a stereoisomer thereof, a geometric isomer thereof, a tautomer thereof, a mixture of tautomers thereof an enantiomer thereof, a diastereomer thereof, a racemate thereof a mixture of stereoisomers thereof, an isotope thereof (e.g., tritium, deuterium), or a combination thereof.

In some embodiments, the compound of embodiments herein is in a pharmaceutical composition, wherein the pharmaceutical composition may comprise about 0.01% to about 50% of one or more compounds disclosed herein. In some embodiments, the one or more compounds is in an amount of about 0.01% to about 50%, about 0.01% to about 45%, about 0.01% to about 40%, about 0.01% to about 30%, about 0.01% to about 20%, about 0.01% to about 10%, about 0,01% to about 5%, about 0,05% to about 50%, about 0.05% to about 45%, about 0.05% to about 40%, about 0.05% to about 30%, about 0.05% to about 20%, about 0,05% to about 10%, about 0.1% to about 50%, about 0.1% to about 45%, about 0.1% to about 40%, about 0.1% to about 30%, about 0.1% to about 20%, about 0.1% to about 10%, about 0,1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.10%, about 0.25%, about 0.5%, about 0.75%, about 1%, about 5%, about 10%, about 15%, about 20%, about 25%, about 300/%, about 35%, about 40%, about 45%, about 50%, about 60%, about 70%, about 80%, about 90%, or a range between any two of these values. The foregoing all representing weight percentages of the composition.

In some embodiments, the compound is in a therapeutically effective amount. In some embodiments, the therapeutically effective amount may be about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

Pharmaceutical Compositions

Some embodiments herein are directed to a pharmaceutical composition comprising a compound of embodiments herein and a pharmaceutically acceptable carrier or diluent.

Also provided is a pharmaceutical composition comprising a compound as disclosed herein, together with a pharmaceutically acceptable carrier.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

In some embodiments, the pharmaceutical compositions for use in accordance with embodiments herein can be formulated in conventional manner using one or more physiologically acceptable carriers or excipients.

When employed as pharmaceuticals, the compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be oral, parenteral (including subcutaneous, intradermal, intramuscular, intravenous, intraarticular, and intramedullary), pulmonary (e.g., by inhalation or insufflation of powders or aerosols, including by nebulizer; intratracheal or intranasal), intraperitoneal, transmucosal, transdermal, rectal, topical (including dermal, buccal, sublingual and intraocular), or intravaginal administration). Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions for topical administration may include foams, transdermal patches, ointments, lotions, creams, gels, solutions, fluid emulsions, fluid suspensions, semi-solids, pastes, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance. For example, Modern Pharmaceutics, 4th Edition, Banker & Rhodes, CRC Press (2002); and Goodman & Gilman's The Pharmaceutical Basis of Therapeutics, 12th Edition, McGraw Hill, New York (2011) can be consulted.

In some embodiments, a method of treating an ITK mediated disease comprises administering a compound or a pharmaceutical composition of embodiments disclosed herein. In some embodiments, the compound is in a therapeutically effective amount. In some embodiments, the therapeutically effective amount is an amount disclosed herein.

Some embodiments disclosed herein also include pharmaceutical compositions which contain, as the active ingredient, one or more of the compounds disclosed herein in combination with one or more pharmaceutically acceptable carriers (excipients).

In some embodiments, a method of making a pharmaceutical composition comprises mixing the active ingredient with an excipient, diluting the active ingredient using an excipient, or enclosing the active ingredient within a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions can be formulated so as to provide quick, sustained or delayed release of the active ingredient after administration to the patient by employing procedures known in the art.

The compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

Compositions of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All compositions for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally therapeutically effective unit dosage forms such as tablets, pills and capsules. This solid pre-formulation is then subdivided into unit dosage forms of the type described above containing from, for example, about 0.1 to about 1000 mg of the active ingredient.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The compounds may be formulated for parenteral administration by injection, e.g., by bolus injection or continuous infusion. Compositions for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Compositions for parenteral administration include aqueous and non-aqueous (oily) sterile injection solutions of the active compounds which may contain antioxidants, buffers, bacteriostats and solutes which render the composition isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In addition to the compositions described previously, the compounds may also be formulated as a depot preparation. Such long acting compositions may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

In some embodiments, the composition is suitable for topical administration. In some embodiments, the composition is suitable for oral administration. In some embodiments, the composition is suitable for oral, parenteral (including subcutaneous, intradermal, intramuscular, intravenous, intraarticular, and intramedullary), intraperitoneal, transmucosal, transdermal, rectal, intranasal, topical (including dermal, buccal, sublingual and intraocular), or intravaginal administration.

Compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.0010% to 10% w/w (by weight) of the composition. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the composition.

Gels for topical or transdermal administration may comprise, generally, a mixture of volatile solvents, nonvolatile solvents, and water. In certain embodiments, the volatile solvent component of the buffered solvent system may include lower ($C_1$-$C_6$) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. Several optional ingredients can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

In some embodiments, the compositions administered to a patient can be in the form of pharmaceutical compositions described above. In some embodiments, these compositions can be sterilized by conventional sterilization techniques, or may be sterile filtered. Aqueous solutions can be packaged for use as is, or lyophilized, the lyophilized preparation being combined with a sterile aqueous carrier prior to administration. In some embodiments, the pH of the compound preparations is about 3 to about 11, about 5 to about 9, about 5.5 to about 6.5, or about 5.5 to about 7.5. It will be understood that use of certain of the foregoing excipients, carriers, or stabilizers will result in the formation of pharmaceutical salts.

Preferred unit dosage compositions are those containing an effective dose, as herein below recited, or an appropriate fraction thereof, of the active ingredient.

It should be understood that in addition to the ingredients particularly mentioned above, the compositions described above may include other agents conventional in the art having regard to the type of composition in question, for example those suitable for oral administration may include flavoring agents.

In some embodiments, the therapeutically effective amount can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges for the compounds are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. In addition, the route of administration may vary depending on the condition and its severity.

The compositions can further include one or more additional pharmaceutical agents such as a chemotherapeutic, steroid, anti-inflammatory compound, or immunosuppressant.

Methods of Treatment

Some embodiments herein are directed to a method of modulation of an ITK-mediated function in a subject comprising the administration of a therapeutically effective amount of a compound as disclosed herein. In some embodiments, a method of inhibiting ITK in a subject comprises administering to the subject a compound of embodiments herein.

The present invention also relates to a method of inhibiting at least one ITK function comprising the step of contacting ITK with a compound as described herein. The cell phenotype, cell proliferation, activity of ITK, change in biochemical output produced by active ITK, expression of ITK, or binding of ITK with a natural binding partner may be monitored. Such methods may be modes of treatment of disease, biological assays, cellular assays, biochemical assays, or the like.

Also provided herein is a method of treating an ITK-mediated disease comprising administering to a patient in need thereof a therapeutically effective amount of a compound as disclosed herein. In certain embodiments, the therapeutically effective amount of a compound as disclosed herein may be in the form of a pharmaceutical composition. In embodiments, the pharmaceutical composition may further include a pharmaceutically acceptable excipient.

In some embodiments, a method for treating a ITK mediated disease or disorder in a patient in need thereof comprises administering to said patient a therapeutically effective amount of a compound of embodiments herein, or composition thereof. Such ITK-mediated diseases or disorders include, but are not limited to, those described herein.

In some embodiments, diseases or disorders associated with a ITK kinase that are treated by compounds of the present disclosure include autoimmune disorders, chronic inflammatory disorders, acute inflammatory disorders, auto-inflammatory disorders, fibrotic disorders, metabolic disorders, neoplasias, cardiovascular or cerebrovascular disorders, respiratory diseases, allergy and allergic diseases and allergic hypersensitivity disorders, immunological disorders, proliferative disorders, transplant rejection, graft versus host disease, HIV, aplastic anemia, pain including inflammatory pain and other diseases and disorders associated with ITK.

In some embodiments, said ITK-mediated disease or disorder is chosen from a skin disorder, pruritus, a hair loss disorder, a cancer, a neoplasm, Alzheimer's disease, an inflammatory condition, connective tissue diseases, an autoimmune condition, asthma, rheumatoid arthritis, juvenile idiopathic arthritis, psoriatic arthritis, ankylosing spondylitis, contact hypersensitivity and inflammatory bowel disease.

In some embodiments, the compounds and pharmaceutical compositions of the present disclosure may be administered in therapeutically effective amounts to prevent or treat HIV.

In certain embodiments, said ITK-mediated disease or disorder is a neoplasm, a malignancy, a myeloproliferative disorder, a hematopoietic neoplasm, a myeloid neoplasm, a lymphoid neoplasm, including myelofibrosis, primary myelofibrosis, polycythemia vera, essential thrombocythemia, leukemias, childhood leukemias, acute leukemias, acute lymphoblastic T-cell leukemia, chronic leukemias, lymphomas, including systemic lymphomas, T-cell lymphomas, B-cell lymphomas, Hodgkins lymphoma, non-Hodgkins lymphomas, cutaneous lymphomas including but not limited to cutaneous T-cell lymphoma (CTCL), mucosis fungoides, and cutaneous B-cell lymphoma, other myeloid malignancies, and myelodysplastic syndrome. In certain embodiments the ITK-mediated disease or disorder is resistant to prior therapy (e.g. a cancer that is resistant to or has failed chemotherapy).

In some embodiments, the ITK-mediated disease or disorder is an autoimmune disorder, a chronic and/or acute inflammatory disorder, and/or auto-inflammatory disorder. Exemplary autoimmune and/or inflammatory and/or auto-inflammatory disorders include: arthritis, juvenile rheumatoid arthritis, systemic-onset juvenile rheumatoid arthritis, osteoarthritis, infectious arthritis, Lyme disease, inflammatory arthritis, inflammatory bowel disease-associated arthritis, myositis, autoimmune myositis, carditis, myocarditis, dermatomyositis, juvenile dermatomyositis, idiopathic arthritis, juvenile idiopathic arthritis, systemic juvenile idiopathic arthritis, ankylosing spondylitis, gout, scleroderma, juvenile scleroderma, Reiter's syndrome, spondylitis, spondyloarthritis, spondyloarthropathy, lupus, systemic lupus erythematosus (SLE), pediatric systemic lupus erythematosus, cutaneous lupus, subacute cutaneous lupus, chronic cutaneous lupus, discoid lupus, psoriatic arthritis, reactive arthritis, Sjogren's syndrome, polymyositis, polymyalgia rheumatica, mixed connective tissue disease, vasculitis, large vessel vasculitis, small vessel vasculitis, vasculitis syndromes including Takayasu's arteritis, Wegener's granulomatosis, Behcet's Disease, giant-cell arteritis, polyarteritis nodosa, sarcoidosis, familial Mediterranean fever, a Cryopyrin associated periodic syndrome (e.g.), Muckle-Wells syndrome, familial cold auto-inflammatory syndrome, neonatal-onset multisystem inflammatory disease, TNF receptor associated periodic syndrome; gastrointestinal disorders (e.g.) inflammatory bowel disease, irritable bowel syndrome, spastic colon, Crohn's disease, ulcerative colitis, acute and chronic pancreatitis, celiac disease, primary biliary cirrhosis, primary sclerosing cholangitis, periodontitis, gingivitis, esophagitis, gastritis, gastric and duodenal ulcers, peritonitis, periodontitis, enteritis, colitis; pulmonary-respiratory disorders (e.g.) pulmonary inflammation, sinusitis, pneumonia, bronchitis, pulmonary fibrosis, idiopathic pulmonary fibrosis, asthma, bronchial asthma, Churg-Strauss syndrome, bronchiolitis, bronchiolitis obliterans, chronic obstructive pulmonary disease (COPD), interstitial lung disease; endocrinologic disorders (e.g.) diabetes, Type I diabetes Hashimoto's thyroiditis, Graves' disease, Addison's disease; autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia; neurological/neuromuscular disorders (e.g.), neurodegenerative disorders, multiple sclerosis Parkinson's disease, Huntington's disease, amyotrophic lateral sclerosis (ALS), familial ALS, Alzheimer's disease, myasthenia gravis (Lambert-Eaton myasthenic syndrome (LEMS)), Guillain-Barret syndrome, meningitis, encephalitis, traumatic brain injury; nephropathies including (e.g.) immunologically mediated glomerulonephropathy, autoimmune nephropathy, membranous glomerulopathy, chronic progressive nephropathies, diabetic nephropathy, renal fibrosis, ischemic/reperfusion injury associated, HIV associated nephropathy, ureteral obstructive nephropathy, glomerulosclerosis, proteinuria, nephrotic syndrome, polycystic kidney disease, autosomal dominant polycystic kidney disease, diabetic kidney disease; ocular disorders including, (e.g.), dry eye, uveitis, keratoconjunctivitis sicca, scleritis, episcleritis, keratitis, keratopathy, chorditis, retinal vasculitis, optic neuritis, retinopathy, diabetic retinopathy, immune mediated retinopathy, macular degeneration, wet macular degeneration, dry (age related) macular degeneration, and ocular malignancies; allergy and allergic reactions including hypersensitivity reactions such as Type I hypersensitivity reactions, (e.g. including anaphylaxis), Type II hypersensitivity reactions (e.g. Goodpasture's Disease, autoimmune hemolytic anemia), Type III hypersensitivity reaction diseases (e.g. the Arthus reaction, serum sickness), and Type IV hypersensitivity reactions (e.g. contact dermatitis, allograft rejection); disorders of fibrosis and scarring (e.g.), hepatic fibrosis, pulmonary fibrosis, idiopathic pulmonary fibrosis, low grade scarring such as, scleroderma, increased fibrosis, keloids, post-surgical scars; dermatologic disorders (e.g.), psoriasis, atopy, atopic dermatitis, alopecia, nonscarring alopecia, alopecia areata (AA), including patchy AA, alopecia totalis (AT), alopecia universalis (AU), androgenetic alopecia (AGA), male and female pattern AGA, ophiasis pattern alopecia areata, sisaihpo pattern alopecia areata, telogen effluvium, tinea capitis, hypotrichosis, hereditary hypotrichosis simplex, scarring alopecia, lichen planopilaris, central centrifugal cicatricial alopecia, frontal fibrosing alopecia; vitiligo including segmental vitiligo, unisegmental, bisegmental or multisegmental vitiligo, non-segmental vitiligo including acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo (nonsegmental associated with segmental vitiligo), focal vitiligo, solitary mucosal vitiligo or vitiligo with or without leukotricia (involvement of body hair); immunobullous diseases such as (e.g.), bullous pemphigoid, cicatricial pemphigoid, pemphigus vulgaris, linear IgA disease; dermatologic drug reactions, and pruritus (itch) including (e.g.), atopic pruritus, xerotic pruritus, pruritus associated with psoriasis ("psoriatic itch"), acute pruritus, chronic pruritus, idiopathic pruritus, chronic idiopathic itch, hepatobiliary-associated itch, renal associated itch, lichen simplex chronicus associated pruritus, prurigo nodularis).

In some embodiments, additional exemplary disorders include, but are not limited to: complications from organ transplants (including xenotransplantation) such as graft vs. host reaction (for example, graft vs. host disease), allograft rejections (for example, acute allograft rejection or chronic allograft rejection), early transplantation, diabetes, a myeloproliferative disorder, a rejection (for example, acute allograft rejection); bone resorption diseases, asthma (e.g., bronchial asthma), atopy, autoimmune thyroid disorders, chronic atypical neutrophilic dermatosis with lipodystrophy, elevated temperature syndrome, SAVI (stimulator of interferon genes (STING) associated vasculopathy with onset in infancy), ulcerative colitis, inflammatory bowel disease, Crohn's disease, celiac disease, ulcerative colitis, Behcet's disease, myasthenia gravis, nephropathies, and myocarditis, secondary hematologic manifestations of autoimmune diseases (for example, anemias), autoimmune hemolytic syndromes, autoimmune and inflammatory hepatitis, autoimmune ovarian failure, autoimmune orchitis, autoimmune thrombocytopenia, silicone implant associated autoimmune disease, drug-induced autoimmunity, HIV-related autoimmune syndromes; acute and chronic infection, sepsis syndromes (e.g.) sepsis, septic shock, endotoxic shock, exotoxin-induced toxic shock, gram negative sepsis, gram positive sepsis, fungal sepsis, toxic shock syndrome; hyperoxia induced inflammations, reperfusion injury, post-surgical trauma, tissue injury, pain (e.g.) acute pain, chronic pain, neuropathic pain, or fibromyalgia.

In an embodiment, said vitiligo is segmental vitiligo including unisegmental, bisegmental or multisegmental vitiligo, non-segmental vitiligo including acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo (nonsegmental associated with segmental vitiligo), focal vitiligo, solitary mucosal vitiligo or vitiligo with or without leukotricia (involvement of body hair) or any type of vitiligo set forth in Table 1 below:

TABLE 1

Classification of vitiligo.

| NOMENCLATURE | SUBSET | NOTES |
| --- | --- | --- |
| Non-segmental vitiligo | Acrofacial | Usually limited to face, head, hands, and feet |
| | Generalized | Symmetrical macules, mainly hands, fingers, face, and trauma-exposed areas |
| | Mucosal (at least two sites involved) | Involvement of the oral and/or genital mucosae with other sites of skin involvement |
| | Universal | Depigmentation affects 80%-90% of body surface. |
| Segmental vitiligo | Unisegmental | One or more depigmented macules distributed on one side of the body |
| | Bisegmental | Two segmental lesions distributed either unilaterally or bilaterally |
| | Plurisegmental | Multiple segmental lesions distributed either unilaterally or bi-laterally |
| Mixed vitiligo | Occurrence of SV and NSV | SV followed by NSV with a delay of at least 6 months. At least 20% of a dermatomal segment affected by SV. |
| Unclassified vitiligo | Focal vitiligo | Isolated macules that do not have a segmental distribution. No evolution into NSV after at least 2 years |
| | Mucosal vitiligo (only one site involved) | Exclusive involvement of the oral or genital mucosae |

In an embodiment, said skin disorder is atopic dermatitis, psoriasis, psoriasis vulgaris, skin sensitization, skin irritation, skin rash, contact dermatitis, allergic contact sensitization, allergic dermatitis, inflammatory dermatoses, or neutrophilic dermatoses.

"Pruritus", as used herein, is interchangeable with "itch." In some embodiments, pruritus includes chronic idiopathic pruritus, as well as pruritic components of other pruritic disorders. In some embodiments, pruritus may be a symptom of a disease or condition selected from the group consisting of: allergic reaction, arthropod bites, athlete's foot, atopic dermatitis (AD), atopic itch, atopic dermatitis-associated itch, autoimmune responses, autoimmune connective tissue disease, bacterial infection, biliary itch, broad activation of the immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma-associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, popular urticaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uremia, pruritus or uremic itch, urticaria, urticarial itch, varicella, viral infection, wound or scab healing, and xerosis.

In an embodiment, said hair loss disorder is alopecia, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, tinea capitis, hypotrichosis, hereditary hypotrichosis simplex, scarring alopecia, lichen planopilaris, central centrifugal cicatricial alopecia, or frontal fibrosing alopecia.

In an embodiment, a connective tissue disease is SLE (systemic lupus erythematosus), cutaneous lupus (e.g. SCLE, discoid lupus), chilblain lupus erythematosus, myositis, polymyositis, dermatomyositis, scleroderma, Sjogren's syndrome, polychondritis (relapsing polychondritis), vasculitis, or large vessel vasculitis.

In an embodiment, a nephropathy is an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulosclerosis, proteinuria, nephrotic syndrome, polycystic kidney disease, autosomal dominant polycystic kidney disease or diabetic kidney disease.

In an embodiment, said cancer is a solid tumor.

In an embodiment, said cancer is prostate cancer, a genitourinary cancer, renal cancer, hepatic cancer, breast cancer, lung cancer, thyroid cancer, Kaposi's sarcoma, Castleman's disease, pancreatic cancer, skin cancer, bone cancer, ovarian cancer, liver cancer, non-small cell lung cancer, brain cancer, cancer of the larynx, gall bladder, pancreas, rectum, parathyroid, adrenal, neural tissue, head and neck, colon, stomach, bronchi, kidney cancer, basal cell carcinoma, squamous cell carcinoma, metastatic skin carcinoma, osteo sarcoma, Ewing's sarcoma, myeloma, giant cell tumor, small-cell lung tumor, islet cell tumor, primary brain tumor, lymphocytic and granulocytic tumors, hairy-cell tumor, adenoma, hyperplasia, medullary carcinoma, pheochromocytoma, mucosal neuromas, intestinal ganglioneuromas, ovarian tumor, cervical dysplasia, neuroblastoma, retinoblastoma, soft tissue sarcoma, malignant carcinoid, topical skin lesion, rhabdomyosarcoma, Kaposi's sarcoma, osteogenic sarcoma, malignant hypercalcemia, adenocarcinoma, glioblastoma multiforma, leukemias, lymphomas, malignant melanomas, and epidermoid carcinomas.

In an embodiment, said cancer is lymphoma, leukemia, or multiple myeloma.

In an embodiment, said myeloproliferative disorder (MPD) is polycythemia vera (PV), essential thrombocythemia (ET), myeloid metaplasia with myelofibrosis (MMM), primary myelofibrosis (PMF), chronic myelogenous leukemia (CML), chronic myelomonocytic leukemia (CMML), hypereosinophilic syndrome (HES), idiopathic myelofibrosis (IMF), or systemic mast cell disease (SMCD).

In an embodiment, said myeloproliferative disorder is myelofibrosis.

In an embodiment, said myeloproliferative disorder is primary myelofibrosis (PMF).

In an embodiment, said bone resorption disease is osteoporosis, osteoarthritis, bone resorption associated with hormonal imbalance, bone resorption associated with hormonal therapy, bone resorption associated with autoimmune disease, or bone resorption associated with cancer.

In some embodiments, the ITK-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the ITK-mediated disease or disorder is a metabolic disorder. Exemplary metabolic disorders include obesity, steroid-resistance, glucose intolerance, and metabolic syndrome. In some embodiments, the ITK-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xeroderma pigmentosum, keratoacanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the ITK-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

Also provided herein is a compound as disclosed herein for use as a medicament. Also provided herein is a compound as disclosed herein for use as a medicament for the treatment of a ITK-mediated disease. Also provided is the use of a compound as disclosed herein as a medicament. Also provided is the use of a compound as disclosed herein as a medicament for the treatment of a ITK-mediated disease. Also provided is a compound as disclosed herein for use in the manufacture of a medicament for the treatment of a ITK-mediated disease. Also provided is the use of a compound as disclosed herein for the treatment of a ITK-mediated disease. Also provided herein is a method of inhibiting ITK comprising contacting ITK with a compound as disclosed herein.

Also provided herein is a method for achieving an effect in a patient comprising the administration of a therapeutically effective amount of a compound as disclosed hereinto a patient, wherein the effect is chosen from cognition enhancement.

In certain embodiments, the ITK-mediated disease is chosen from pruritus, alopecia, alopecia areata, vitiligo, male pattern androgenetic alopecia, female pattern androgenetic alopecia, atopic dermatitis, rheumatoid arthritis, psoriatic arthritis, and psoriasis.

Some embodiments are directed to a method of inhibiting ITK activity in a biological sample comprising contacting the biological sample with a compound or pharmaceutical composition as described herein.

Combination Therapy

In an embodiment, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, an agent for treating immunodeficiency disorders, and immune checkpoint inhibitors. Compounds and pharmaceutically acceptable compositions of the present disclosure can be employed in combination therapies, that is, the compounds and pharmaceutically acceptable compositions may have potential utility in combination with other therapies for the treatment of immune, inflammatory, proliferative, and allergic disorders. Examples include, but not limited, to co-administration with steroids, leukotriene antagonists, anti-histamines, anti-cancer agents, protein kinase inhibitors, cyclosporine, rapamycin, or immune checkpoint inhibitors.

Cancer cells often use immune checkpoint molecules to evade or suppress attack by the immune system. Thus, expression of immune checkpoint molecules on the surface of cancers cells prevents immune cells such as T cells from recognizing them as "foreign" or "abnormal." Consequently, immune checkpoint inhibitors are compounds which block inhibitory immune checkpoint molecules leading to the activation of the immune system via T cell recognition.

Inhibitory checkpoint molecules have been increasingly considered as new targets for cancer immunotherapies due to the effectiveness of two checkpoint inhibitor drugs that were initially indicated for advanced melanoma—ipilimumab (YERVOY™; a monoclonal antibody that works to activate the immune system by targeting CTLA-4), and pembrolizumab (KEYTRUDA™; a humanized antibody that targets the programmed cell death 1 (PD-1) receptor). Another checkpoint inhibitor known as nivolumab (OPDIVO™) blocks the interaction between PD-1 and programmed cell death ligand 1 (PD-L1) which prevents inhibition of an immune.

Any molecule capable of inhibiting one or more immune checkpoint molecules can be used in the methods disclosed herein as an additional pharmaceutical agent. Such immune checkpoint inhibitors include, without limitation, antibodies or functional fragments thereof, inhibitory polypeptides, small molecule chemical compounds, and/or inhibitory nucleic acids (such as, but not limited to, antisense oligonucleotides, small inhibitory RNAs (siRNAs), small hairpin RNAs (shRNAs), and/or catalytic nucleic acids such as ribozymes). Immune checkpoint molecules suitable for targeting by checkpoint inhibitors for use in any of the methods disclosed herein include, without limitation, one or more of the adenosine $A_{2A}$ receptor (A2AR), B7-H3 (a.k.a. CD276; e.g., MGA271), cytotoxic T-lymphocyte-associated protein 4 (CTLA4; a.k.a. CD152; e.g., ipilimumab; AGEN-1884 (Agenus)), programmed cell death ligand 1 (PD-L1; a.k.a. CD274; e.g., MDX-1105 (Bristol Myers Squibb), WBP-3155 (C-stone), LY3300054 (Eli Lilly)), programmed cell death protein 1 (PD-1; a.k.a. CD279; e.g., pembrolizumab, SHR-1210 (Incyte), STI-A1110 (Sorrento), REGN2810 (Regeneron), CT-011 (pidilizumab; Curetech), PDR-001 (Novartis), BGB-A317 (BeiGene), TSR-042 (Tesaro), ENUMC-8 (Enumeral), MGD-013 (Macrogenics; bispecific antibody for PDI and Lag3), B7-H4 (a.k.a. VTCN1), T-cell immunoglobulin and mucin-domain containing-3 (TIM3; a.k.a. HAVCR2), B and T Lymphocyte Attenuator (BTLA; a.k.a. CD272), indoleamine-pyrrole 2,3-dioxygenase (IDO), killer-cell immunoglobulin-like receptors (KIRs; e.g., lirilumab), lymphocyte-activation gene 3 (LAG-3; e.g., BMS-986016), T cell immunoreceptor with Ig and ITIM domains (TIGIT; a.k.a. WUCAM and Vstm3), ILT-3, ILT-4, and/or V-domain Ig suppressor of T cell activation (VISTA).

In some embodiments, the immune checkpoint inhibitor is an antagonistic antibody, such as, but not limited to, one or more of ipilimumab (Bristol-Myers Squibb), nivolumab (Bristol-Myers Squibb), Pembrolizumab (Merck) durvalumab (Medimmune), atezolizumab (Genentech/Roche), tremelimumab (Medimmune), and/or avelumab (Pfizer).

The compounds and pharmaceutical composition of the present disclosure may be used to prevent or treat an ITK-mediated disorder by the sequential or co-administration of another pharmaceutical agent.

In certain instances, it may be appropriate to administer at least one of the compounds described herein in combination with another pharmaceutical agent. By way of example only, if one of the side effects experienced by a patient upon receiving one of the compounds herein is hypertension, then it may be appropriate to administer an anti-hypertensive agent in combination with the initial pharmaceutical agent. Or, by way of example only, the therapeutic effectiveness of one of the compounds described herein may be enhanced by administration of an adjuvant (i.e., by itself the adjuvant may only have minimal therapeutic benefit, but in combination with another pharmaceutical agent, the overall therapeutic benefit to the patient is enhanced). Or, by way of example only, the benefit of experienced by a patient may be increased by administering one of the compounds described herein with another pharmaceutical agent (which also includes a therapeutic regimen) that also has therapeutic benefit. By way of example only, in a treatment for diabetes involving administration of one of the compounds described herein, increased therapeutic benefit may result by also providing the patient with another pharmaceutical agent for diabetes. In any case, regardless of the disease, disorder or condition being treated, the overall benefit experienced by the patient may simply be additive of the two pharmaceutical agents or the patient may experience a synergistic benefit.

Specific, non-limiting examples of possible combination therapies include use of compounds of embodiments herein with: chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

Specific, non-limiting examples of possible combination therapies for inflammation include use of certain compounds of the disclosure with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON™), flurbiprofen (ANSAID™), ketoprofen, oxaprozin (DAYPRO™), diclofenac sodium (VOLTAREN™), diclofenac potassium (CATAFLAM™), etodolac (LODINE™), indomethacin (INDOCIN™), ketorolac (TORADOL™), sulindac (CLINORIL™), tolmetin (TOLECTIN™), meclofenamate (MECLOMEN™), mefenamic acid (PONSTEL™), nabumetone (RELAFEN™) and piroxicam (FELDENE™); (3) immunosuppressants, including but not limited to methotrexate (RHEUMATREX™), leflunomide (ARAVA™), azathioprine (IMURAN™), cyclosporine (NEORAL™, SANDIMMUNE™), tacrolimus and cyclophosphamide (CYTOXAN™); (4) CD20 blockers, including but not limited to rituximab (RITUXAN™); (5) Tumor Necrosis Factor (TNF) blockers, including but not limited to etanercept (ENBREL™), infliximab (REMICADE™) and adalimumab (HUMIRA™); (6) interleukin-1 receptor antagonists, including but not limited to anakinra (KINERET™); (7) interleukin-6 inhibitors, including but not limited to tocilizumab (ACTEMRA™); (8) interleukin-17 inhibitors, including but not limited to AIN457; (9) Janus kinase inhibitors, including but not limited to tasocitinib; and (10) syk inhibitors, including but not limited to fostamatinib.

Specific, non-limiting examples of possible combination therapies for the treatment of cancer include use of certain compounds of the disclosure with: (1) alkylating agents, including but not limited to cisplatin (PLATIN™), carboplatin (PARAPLATIN™), oxaliplatin (ELOXATIN™), streptozocin (ZANOSAR™), busulfan (MYLERAN™) and cyclophosphamide (ENDOXAN™); (2) anti-metabolites, including but not limited to mercaptopurine (PURINETHOL™), thioguanine, pentostatin (NIPENT™), cytosine arabinoside (ARA-C™), gemcitabine (GEMZAR™), fluorouracil (CARAC™), leucovorin (FUSILEV™) and methotrexate (RHEUMATREX™); (3) plant alkaloids and terpenoids, including but not limited to vincristine (ONCOVIN™), vinblastine and paclitaxel (TAXOL™); (4) topoisomerase inhibitors, including but not limited to irinotecan (CAMPTOSAR™), topotecan (HYCAMTIN™) and etoposide (EPOSIN™); (5) cytotoxic antibiotics, including but not limited to actinomycin D (COSMEGEN™), doxorubicin (ADRIAMYCIN™), bleomycin (BLENOXANE™) and mitomycin (MITOSOL™); (6) angiogenesis inhibitors, including but not limited to sunitinib (SUTENT™) and bevacizumab (AVASTIN™); (7) tyrosine kinase inhibitors, including but not limited to imatinib (GLEEVEC™), erlotinib (TARCEVA™), lapatininb (TYKERB™) and axitinib (INLYTA™); and (8) immune checkpoint inhibitors, including but not limited to atezolizumab (TECENTRIQ™), avelumab (BAVENCIO™), durvalumab (IMFINZI™), ipilimumab (YERVOY™), pembrolizumab (KEYTRUDA™), nivolumab (OPDIVO™), and tremelimumab.

In some embodiments, the compounds disclosed in embodiments herein can also be co-administered (concurrently or sequentially) with a variety of other pharmaceutical agents or treatments, for example, pharmaceutical agents or treatments that are administered systemically, such as orally or parenterally. Examples of such systemic treatments include topical or systemic corticosteroids (such as prednisone), antibiotics (such as erythromycin, tetracycline, and dicloxacillin), antifungal agents (such as ketoconazole and fluconazole sold under the tradename Diflucan™), antiviral agents (such as valacyclovir sold under the tradename Valtrex™, acyclovir, and famciclovir sold under the tradename Famvir™), corticosteroids, immunosuppressants (such as cyclophosphamide sold under the tradename Cytoxan™, azathioprine, methotrexate, mycophenolate), biologics (such as rituximab sold under the tradename Rituxan™, etanercept sold under the tradename Enbrel™, adalimumab sold under the tradename Humira™, infliximab sold under the tradename Remicade™, ustenkinumab sold under the tradename Stelara™, and alefacept sold under the tradename Amevive™), and/or thyroid hormone replacement.

In some embodiments, other therapies that can be used in combination with the compounds disclosed herein include, for example, mercaptopurine, topical or systemic corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil, azathioprine, various antibodies, for example, anti-lymphocyte globulin (ALG), antithymocyte globulin (ATG), monoclonal anti-T-cell antibodies (OKT3), and irradiation. These various agents can be used in accordance with their standard or common dosages, as specified in the prescribing information accompanying commercially available forms of the drugs (see also, the prescribing information in the 2006 Edition of The Physician's Desk Reference). In some embodiments, standard dosages of these agents may be reduced when used in combination with the compounds of embodiments herein. Without limiting the scope of this disclosure, it is believed the such combination may result in synergistic results with better efficacy, less toxicity, longer duration of action, or quicker response to therapy. In some embodiments, the combination therapies in embodiments herein may be administered in sub-therapeutic amounts of either the compounds of embodiments herein or the additional pharmaceutical agents, or both. Azathioprine is currently available from Salix Pharmaceuticals, Inc. under the brand name Azasan™; mercaptopurine is currently available from Gate Pharmaceuticals, Inc. under the brand name Purinethol™; prednisone and prednisolone are currently available from Roxane Laboratories, Inc.; methyl prednisolone is currently available from Pfizer; sirolimus (rapamycin) is currently available from Wyeth-Ayerst under the brand name Rapamune™; tacrolimus is currently available from Fujisawa under the brand name Prografr™; cyclosporine is current available from Novartis under the brand name Sandimmune™ and Abbott under the brand name Gengraf™; IMPDH inhibitors such as mycophenolate mofetil and mycophenolic acid are currently available from Roche under the brand name Cellcept™ and Novartis under the brand name Myfortic™; azathioprine is currently available from Glaxo Smith Kline under the brand name Imuran™; and antibodies are currently available from Ortho Biotech under the brand name Orthoclone™, Novartis under the brand name Simulect™ (basiliximab) and Roche under the brand name Zenapax™ (daclizumab).

In some embodiments, the compounds of embodiments herein is administered in conjunction, concomitantly or adjunctively, with the pharmaceutical agents or therapies above and/or with a pharmaceutical agent or therapy for another disease. For example, the compounds of embodiments herein may be combined with thyroid hormone replacement therapy or with anti-inflammatory or immunomodulatory therapies.

In any case, the multiple pharmaceutical agents (at least one of which is a compound disclosed herein) may be administered in any order or even simultaneously. If simultaneously, the multiple pharmaceutical agents may be provided in a single, unified form, or in multiple forms (by way of example only, either as a single pill or as two separate pills). One of the pharmaceutical agents may be given in multiple doses, or both may be given as multiple doses. If not simultaneous, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

Thus, in another aspect, certain embodiments provide methods for treating ITK-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of ITK-mediated disorders.

One or more additional pharmaceutical agents such as, for example, anti-inflammatory agents, steroids, immunosuppressants, as well as one or more other ITK kinase inhibitors and/or other kinase inhibitors, such as JAK3 kinase, JAK1 kinase, JAK1/2 kinase, or JAK2 kinase inhibitors, such as, for example, those described in WO 99/65909, WO 00/00202, and/or WO/2004/099205, or other agents can be used in combination with the compounds of the present invention for treatment of ITK-associated diseases, disorders or conditions.

In certain embodiments, the additional pharmaceutical agent is selected from taxanes, inhibitors of bcr-abl, inhibitors of EGFR, DNA damaging agents, antimetabolites, paclitaxel, imatinib, dasatinib, nilotinib, erlotinib, gefitinib, cisplatin, oxaliplatin, carboplatin, anthracyclines, AraC, 5-FU, camptothecin, doxorubicin, idarubicin, paclitaxel, docetaxel, vincristine, a MEK inhibitor, U0126, a KSP inhibitor, vorinostat, pembrolizumab, nivolumab, atezolizumab, avelumab, tremelimumab, and durvalumab.

In some embodiments, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, and an agent for treating immunodeficiency disorders.

In some embodiments, one or more compounds of the embodiments herein can be used in combination with one or more other therapeutics used in the treatment of ITK-mediated disorders, and may improve the treatment response as compared to the response to the other therapeutics alone, without exacerbation of its toxic effects. In some embodiments, compounds of embodiments herein can be used in combination with one or more other ITK inhibitors, and/or JAK 1 and/or JAK3 inhibitors and/or JAK2 inhibitors and/or TYK2 inhibitors for the treatment of ITK-mediated disorders. Additive or synergistic effects are desirable outcomes of such combinations. The additional agents can be combined with the present compounds in a single or continuous dosage form, or the agents can be administered simultaneously or sequentially as separate dosage forms. In some embodiments, one or more additional agents can be administered to a patient in combination with at least one JAK3 inhibitor/antagonist described herein where the additional agents are administered intermittently as opposed to continuously.

For example, in certain embodiments, a topically or orally administered ITK inhibitor/antagonist described herein can be used for the treatment of alopecia areata (e.g. patchy alopecia areata, alopecia totalis, alopecia universalis) alone or in combination with topical or intralesional corticosteroids, topical minoxidil, oral finasteride, oral dutasteride, contact sensitization therapy such as with squaric acid dibutyl ester, dinitrochlorobenzene, diphencyprone, topical or oral methoxalen and ultraviolet a (PUVA), topical anthralin, hair transplantation procedures, or other therapies known to have beneficial effects in the condition.

For example, in certain embodiments, a topically or orally administered ITK inhibitor/antagonist disclosed herein can be used for the treatment of male or female-pattern baldness (androgenetic alopecia) alone or in combination with topical minoxidil, oral finasteride (in male), oral dutasteride (in male), topical antiandrogens, hair transplantation procedures, or other therapies known to have beneficial effects in the condition.

For example, in certain embodiments, the compounds can be used for the treatment of vitiligo (e.g. localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin mini-grafting, transplantation of autologous epidermal suspension, camouflage such as with make-up or dihydroxyacetone and such, or other therapies known to have beneficial effects in the condition.

Besides being useful for human treatment, the compounds and compositions disclosed herein may also be useful for veterinary treatment of companion animals, exotic animals and farm animals, including mammals, rodents, and the like. More preferred animals include horses, dogs, and cats.

General Synthetic Methods for Preparing Compounds

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1 and 2 below. Solvents and reagents, whose synthetic preparations are not described below, can be purchased at Sigma-Aldrich or Fisher Scientific.

Scheme 1 highlights the general synthesis of the 3,5-disubstituted pyrrolopyridines. Aryl analogs of 1b ($R^{200}$=aryl) may be prepared by the reaction of 1a with an aryl or heteroaryl boronic acid using a palladium catalyst under Suzuki conditions. In some cases 1a may need to be protected as the tosylate (at N1) for the coupling to occur to provide 1b (as the tosyl intermediate). In this case after coupling, deprotection using lithium hydroxide or cesium carbonate in a solvent such as THF or ethanol provides 1b. Iodination of 1b with a halogenating agent such as NIS furnishes 1c. Protection of the indole nitrogen of 1c using tosyl chloride and NaH in a solvent such as THF or DMF provides 1d. Coupling of 1d with the desired boronic acid in the presence of a palladium catalyst such as bis(diphenylphosphino)ferrocene]dichloropalladium(II) (Pd(dppf)Cl$_2$) in dioxane or DMF gives 1e. Often the protecting group is cleaved in this step. If not the desired final compounds may then be obtained by treating the intermediate with lithium hydroxide in dioxane to give 1e. In most cases $R^{200}$ may be manipulated to add an electrophile as detailed in schemes 2-5, following methods common to those skilled in the art.

Scheme 1. Preparation of 3,5-Disubstituted Pyrrolopyridines

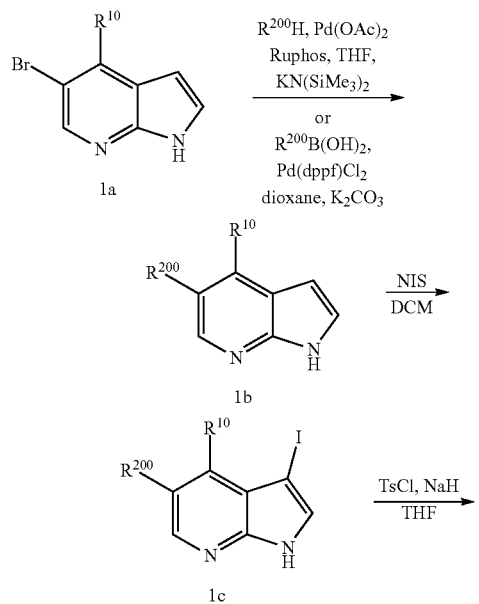

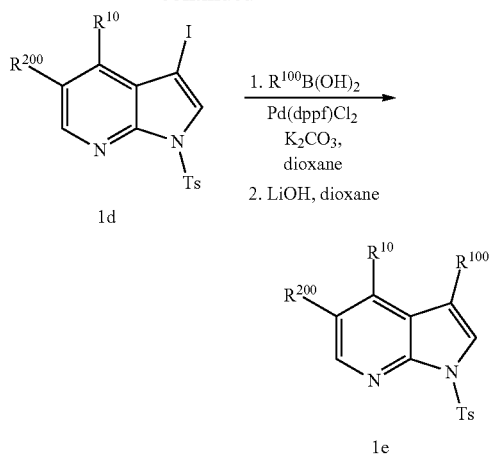

Scheme 2 highlights the synthesis of the 5-aryl substituted pyrrolopyridines. Reaction of 1a with an aryl or heteroaryl boronic acid using a palladium catalyst such as bis(diphenylphosphino)ferrocene]dichloropalladium(II) (Pd(dppf)Cl$_2$) under Suzuki conditions provides 2a. Iodination of 2a with a halogenating agent such as NIS furnishes 2b. Protection of the indole nitrogen on 2b using tosyl chloride and NaH in a solvent such as THF or DMF provides 2c. Coupling of 2c with the desired boronic acid in the presence of a palladium catalyst such as bis(diphenylphosphino)ferrocene]dichloropalladium(II) (Pd(dppf)Cl$_2$) in dioxane or DMF gives 2d. Deprotection of the Boc carbamate of 2d using an acid such as HCl or TFA provides 2e. Reaction of 2e with the desired electrophile can then take place through amide coupling conditions such as using O-(benzotriazol-1-yl)-N,N,N',N'-tetramethyluronium tetrafluoroborate (HTBU) and triethylamine as a base in a solvent such as THF to provide 2f. The tosyl group may be removed by treating 2f with lithium hydroxide in dioxane to give 2g. In certain cases $R^{100}$ or $R^{500}$ may be manipulated to a different substituent following methods common to those skilled in the art.

Scheme 2. Preparation of 5-(3-Aminoaryl)-Substituted Pyrrolopyridines

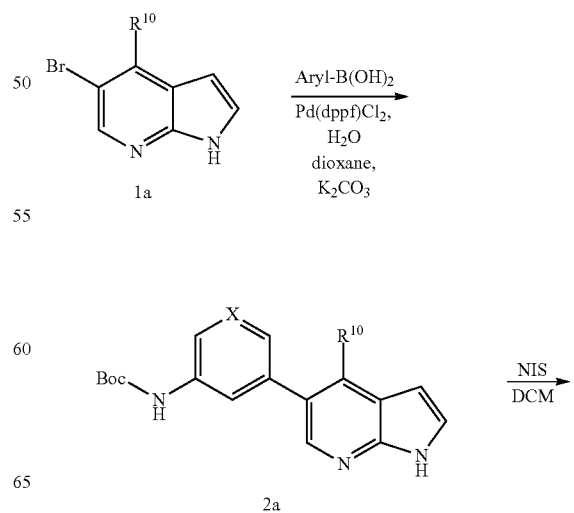

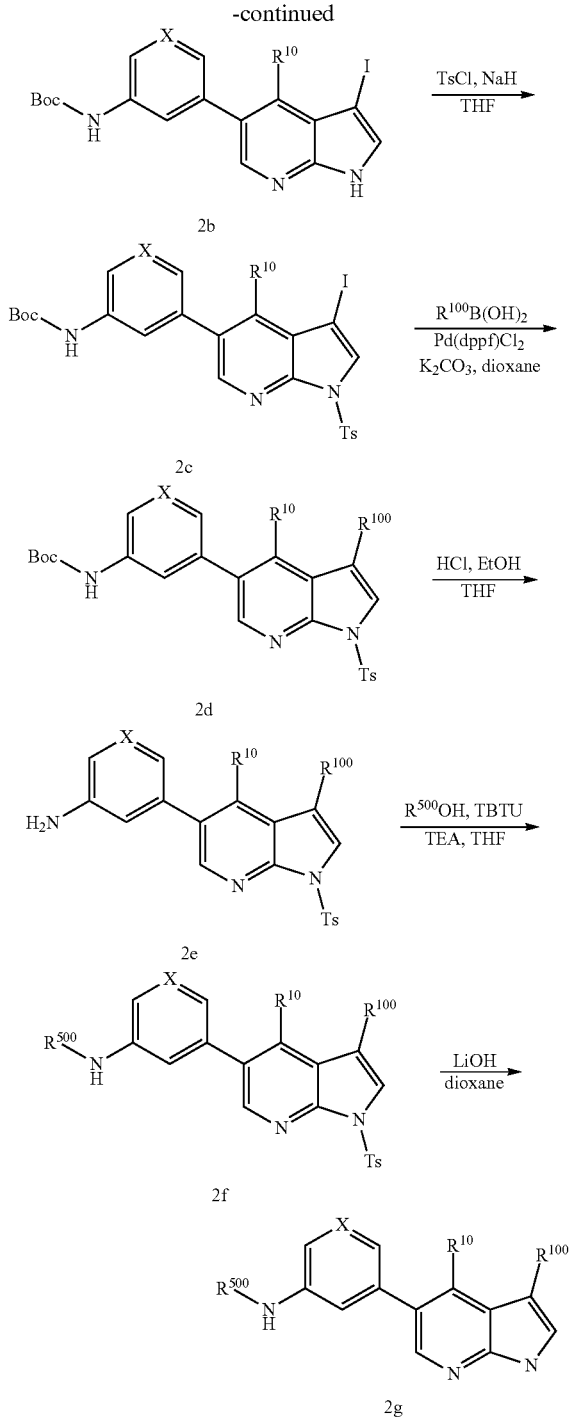

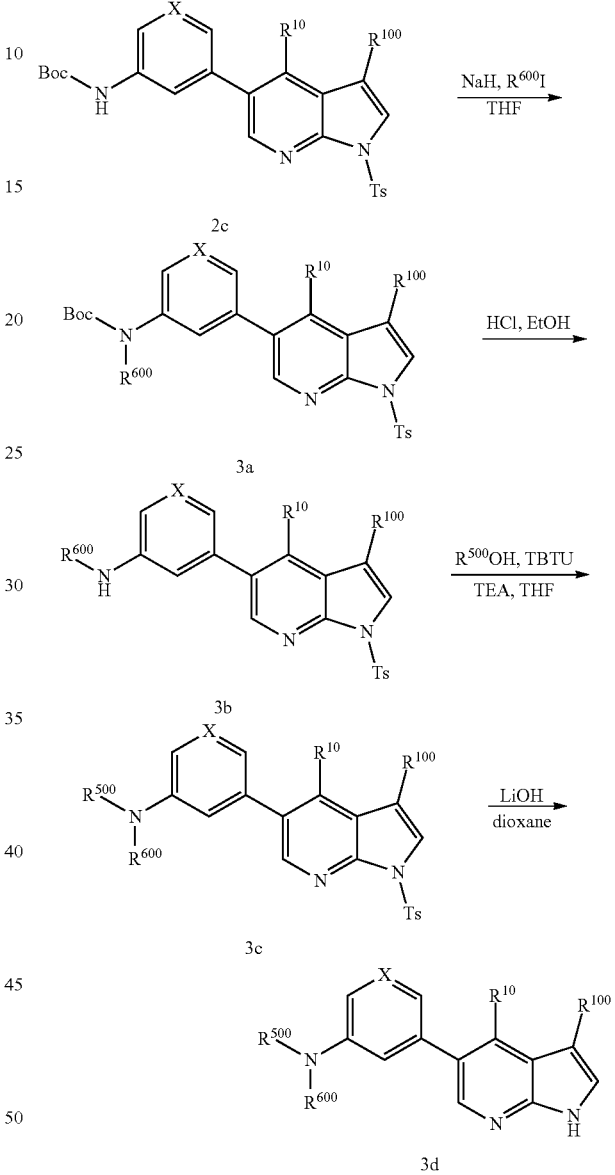

certain cases $R^{100}$ or $R^{500}$ may be manipulated to a different substituent following methods common to those skilled in the art.

Scheme 3 highlights the synthesis of the 5-(3-aminoalkyl)-3-aryl substituted pyrrolopyridines. Reaction of 2d with NaH and an alkyl halide ($R^{600}$—X) in a solvent such as THF provides 3a. Deprotection of the Boc carbamate of 3a using an acid such as HCl or TFA provides 3b. Reaction of 3b with the desired electrophile can then take place through amide coupling conditions such as using O-(benzotriazol-1-yl)-N,N,N',N'-tetramethyluronium tetrafluoroborate (HTBU) and triethylamine as a base in a solvent such as THF to provide 3c. The tosyl group may be removed by treating 3c with lithium hydroxide in dioxane to give 3d. In Scheme 4 highlights the synthesis of the 5-aryl substituted pyrrolopyridines via aryl coupling starting with a pyrrolopyridine-5-boronic acid pinacol ester. Reaction of boronic acid pinacol ester 4a with an aryl or heteroaryl halide using a palladium catalyst such as bis(diphenylphosphino)ferrocene]dichloropalladium(II) (Pd(dppf)Cl$_2$) under Suzuki conditions provides 4b. Iodination of 4b with a halogenating agent such as NIS furnishes 4c. Protection of the indole nitrogen on 4c using tosyl chloride and NaH in a solvent such as THF or DMF provides 4d. Coupling of 4d with the desired boronic acid in the presence of a palladium catalyst such as bis(diphenylphosphino)ferrocene]dichloropalladium (II) (Pd(dppf)Cl$_2$) in dioxane or DMF gives 4e. Deprotection of the Boc carbamate of 4e using an acid such as HCl or TFA provides 4f. Reaction of 4f with the desired electrophile can then take place through amide coupling conditions such as using O-(benzotriazol-1-yl)-N,N,N',N'-tetramethyluronium tetrafluoroborate (HTBU) and triethylamine as a base in a solvent such as THF to provide 4g. The tosyl group may be removed by treating 4g with lithium hydroxide in dioxane to give 4h. In certain cases $R^{100}$ or $R^{500}$ may be manipulated to a different substituent following methods common to those skilled in the art.

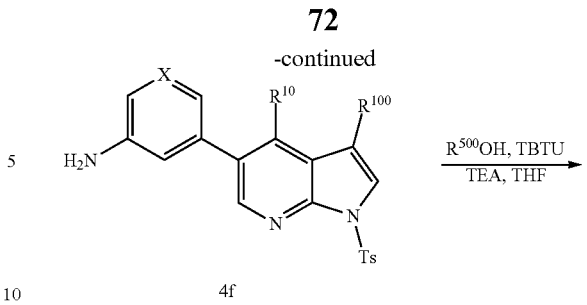
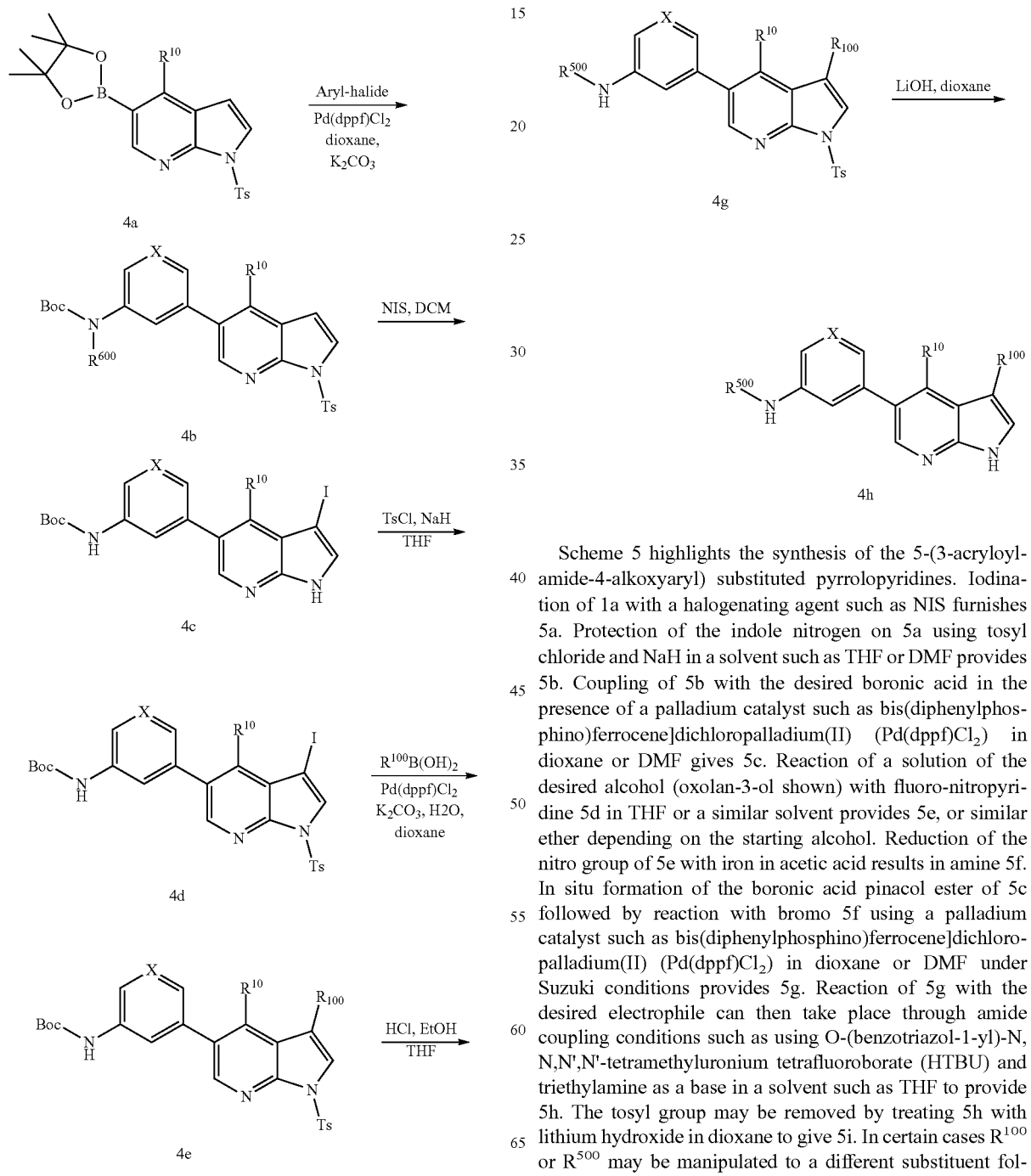

Scheme 5 highlights the synthesis of the 5-(3-acryloyl-amide-4-alkoxyaryl) substituted pyrrolopyridines. Iodination of 1a with a halogenating agent such as NIS furnishes 5a. Protection of the indole nitrogen on 5a using tosyl chloride and NaH in a solvent such as THF or DMF provides 5b. Coupling of 5b with the desired boronic acid in the presence of a palladium catalyst such as bis(diphenylphosphino)ferrocene]dichloropalladium(II) (Pd(dppf)Cl$_2$) in dioxane or DMF gives 5c. Reaction of a solution of the desired alcohol (oxolan-3-ol shown) with fluoro-nitropyridine 5d in THF or a similar solvent provides 5e, or similar ether depending on the starting alcohol. Reduction of the nitro group of 5e with iron in acetic acid results in amine 5f. In situ formation of the boronic acid pinacol ester of 5c followed by reaction with bromo 5f using a palladium catalyst such as bis(diphenylphosphino)ferrocene]dichloropalladium(II) (Pd(dppf)Cl$_2$) in dioxane or DMF under Suzuki conditions provides 5g. Reaction of 5g with the desired electrophile can then take place through amide coupling conditions such as using O-(benzotriazol-1-yl)-N,N,N',N'-tetramethyluronium tetrafluoroborate (HTBU) and triethylamine as a base in a solvent such as THF to provide 5h. The tosyl group may be removed by treating 5h with lithium hydroxide in dioxane to give 5i. In certain cases $R^{100}$ or $R^{500}$ may be manipulated to a different substituent following methods common to those skilled in the art.

Scheme 5. Preparation of 5-(3-Amino-4-etheraryl) Substituted Pyrrolopyridines

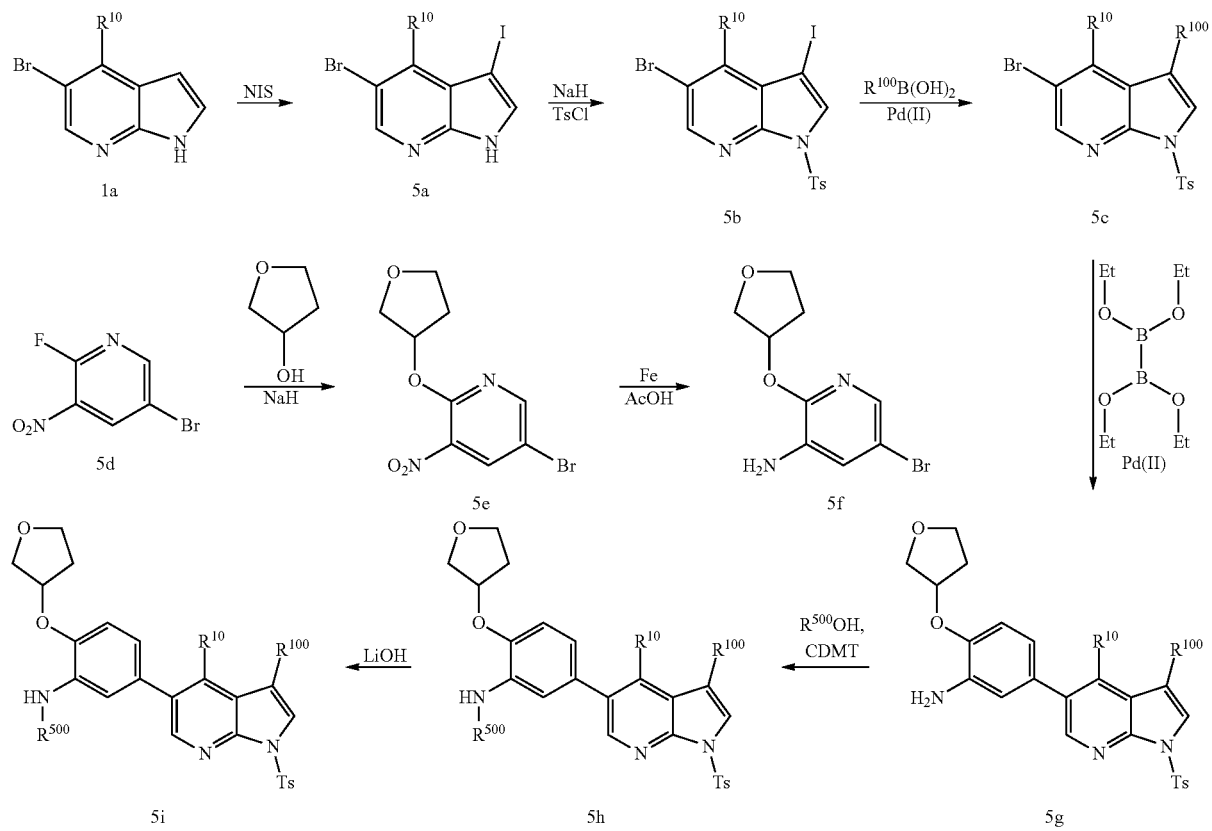

Scheme 6 highlights the synthesis of prodrugs of the substituted pyrrolopyridines. Reaction of 3d with $K_2CO_3$ or potassium hydroxide or an amine base such as diisopropylethylamine with the desired chloromethyl prodrug moiety (several options shown in Scheme 6) in a solvent such as dioxane, THF or DMF provides 6a. In certain cases the prodrug may be further manipulated to a different substituent following methods common to those skilled in the art.

Scheme 6. Preparation of Prodrugs of the Substituted Pyrrolopyridines

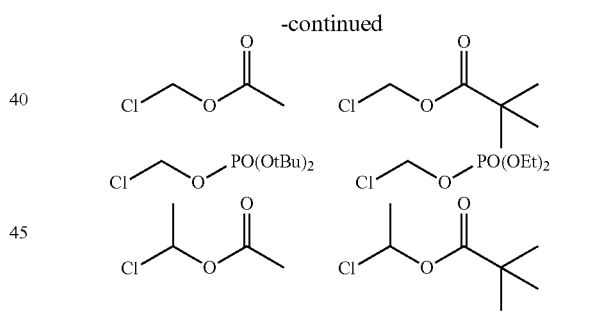

-continued

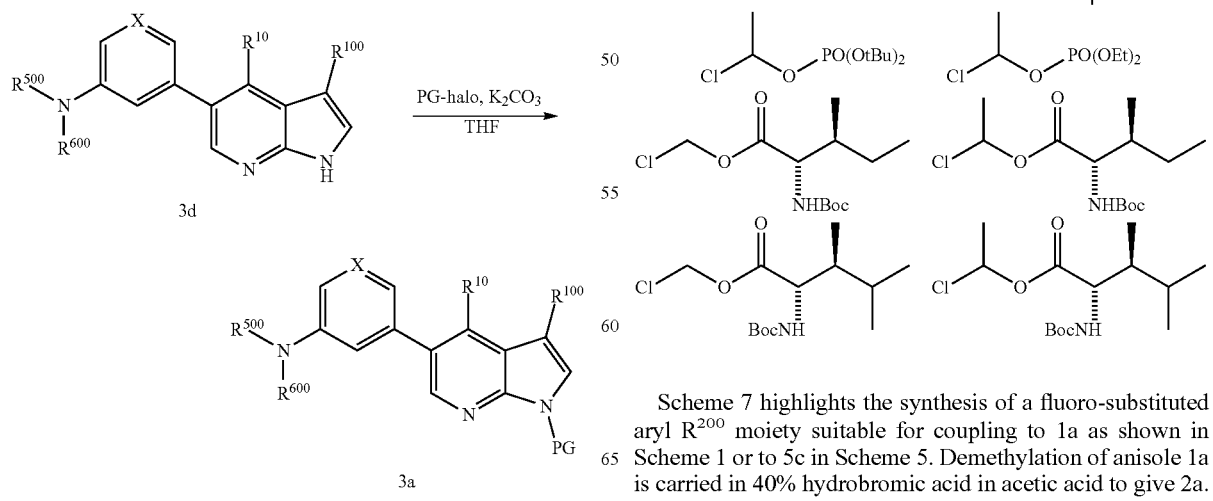

Scheme 7 highlights the synthesis of a fluoro-substituted aryl $R^{200}$ moiety suitable for coupling to 1a as shown in Scheme 1 or to 5c in Scheme 5. Demethylation of anisole 1a is carried in 40% hydrobromic acid in acetic acid to give 2a. Treating 2a with bromine in methylene chloride provides dibromo 3a. Methylation of 3a using iodomethane in DMF in the presence of a weak base such as potassium carbonate provides ester 4a. Nitration of 4a can be achieved by using nitric acid in sulfuric acid to give 5a. The nitro and bromo groups of 5a are then reduced using hydrogen in the presence of palladium on carbon to give aniline 6a. Nitrosylation of the aniline of 6 followed by bromo displacement of the diazo intermediate in acetylnitrile provides 7a. Hydrolysis of the ester of 7a using lithium hydroxide in aqueous methanol gives 8a. Curtius rearrangement of acid 8a using diphenylphosphoryl azide (DPPA) in t-butyl alcohol in the presence of trimethylamine furnishes Boc-carbamate 9a. The boronate ester of 9a is formed using bis(pinacolato)diboron (B$_2$pin$_2$) and [1,1'-bis(diphenylphosphino)ferrocene]dichloropalladium(II) (Pd(dppf)Cl$_2$) in dioxane and sodium acetate to give 10a. Intermediate 10a may then be coupled and further manipulated as shown in Schemes 1-5.

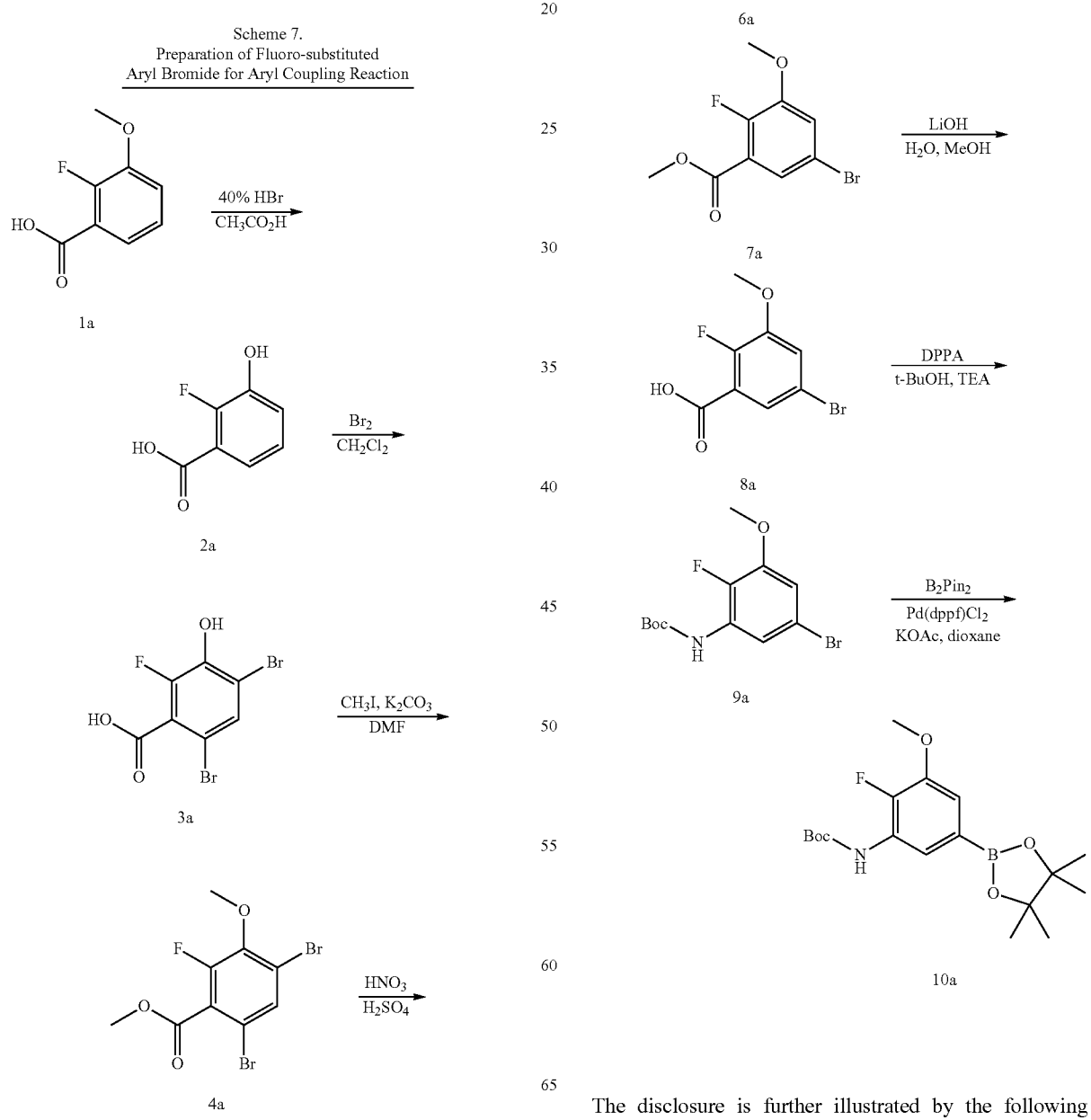

The disclosure is further illustrated by the following examples.

EXAMPLES

Example 1

Preparation of (E)-N-(3-(3-(3-Cyanophenyl)-1H-pyrrolo[2,3-b]pyridin-5-yl)-5-(trifluoromethyl)phenyl)-4-(dimethylamino)but-2-enamide

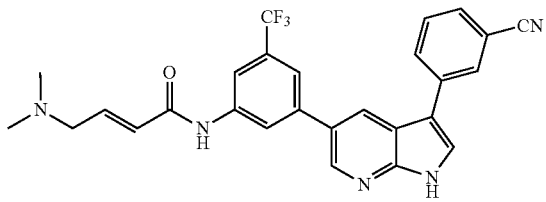 [SMILES: CN(C)C/C=C/C(=O)Nc1cc(-c2cnc3[nH]cc(-c4cccc(C#N)c4)c3c2)cc(C(F)(F)F)c1]

Step 1: Preparation of tert-Butyl (3-(1H-pyrrolo[2,3-b]pyridin-5-yl)-5-(trifluoromethyl)-phenyl)carbamate

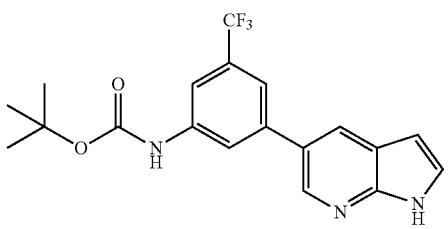 [SMILES: CC(C)(C)OC(=O)Nc1cc(-c2cnc3[nH]ccc3c2)cc(C(F)(F)F)c1]

To a solution of pyrrolo[2,3-b]pyridine-5-boronic acid, pinacol ester (976 mg, 4.0 mmol), in 1,4-dioxane (15 mL) and water (5 mL), was added N-boc-3-bromo-5-trifluoromethylaniline (1.36 g, 4.0 mmol), potassium carbonate (1.65 g, 12 mmol) and [1,1'-bis(diphenylphosphino)ferrocene]dichloropalladium(II).DCM (164 mg, 0.20 mmol). The solution was treated with microwave radiation at 120° C. for one hour. After cooling the resulting mixture was partitioned between ethyl acetate and water. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (3-(1H-pyrrolo[2,3-b]pyridin-5-yl)-5-(trifluoromethyl)phenyl)carbamate (1.06 g, 70%): MS (ES) m/z 378 (M+H).

Step 2: Preparation of tert-Butyl (3-(3-iodo-1H-pyrrolo[2,3-b]pyridin-5-yl)-5-(trifluoromethyl)phenyl)carbamate

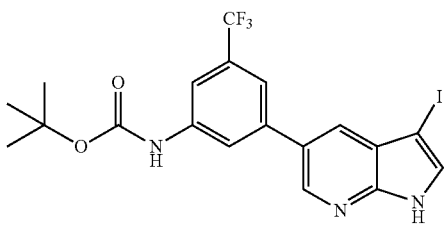 [SMILES: CC(C)(C)OC(=O)Nc1cc(-c2cnc3[nH]cc(I)c3c2)cc(C(F)(F)F)c1]

To a solution of tert-butyl (3-(1H-pyrrolo[2,3-b]pyridin-5-yl)-5-(trifluoromethyl)phenyl)carbamate from step 1 (1.06 g, 2.8 mmol) in dichloromethane (10 mL) was added N-iodosuccinimide (632 mg, 2.8 mmol) and the solution was stirred for 1.5 hours at ambient temperature. The resulting beige solid was collected by vacuum filtration to provide tert-butyl (3-(3-iodo-1H-pyrrolo[2,3-b]pyridin-5-yl)-5-(trifluoromethyl)phenyl)carbamate (1.05 g, 74% yield): MS (ES) m/z 504 (M+H).

Step 3: Preparation of tert-Butyl (3-(3-iodo-1-tosyl-1H-pyrrolo[2,3-b]pyridin-5-yl)-5-(trifluoromethyl)phenyl)carbamate

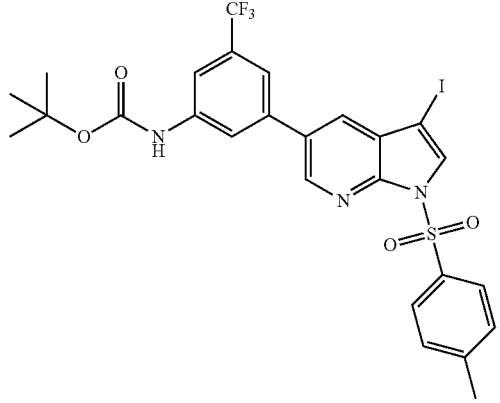 [SMILES: Cc1ccc(S(=O)(=O)n2cc(I)c3cc(-c4cc(NC(=O)OC(C)(C)C)cc(C(F)(F)F)c4)cnc32)cc1]

To a solution of tert-butyl (3-(3-iodo-1H-pyrrolo[2,3-b]pyridin-5-yl)-5-(trifluoromethyl)phenyl)carbamate from step 2 (1.05 g, 2.1 mmol) in tetrahydrofuran (10 mL) was added sodium hydride (60% mineral oil dispersion, 126 mg, 3.1 mmol) followed by p-toluenesulfonyl chloride (400 mg, 2.1 mmol) and the solution was stirred for 2 hours at ambient temperature. The reaction mixture was quenched with water and extracted with ethyl acetate. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (3-(3-iodo-1-tosyl-1H-pyrrolo[2,3-b]pyridin-5-yl)-5-(trifluoromethyl)phenyl)carbamate (1.26 g, 91% yield): MS (ES) m/z 658 (M+H).

Step 4: Preparation of tert-Butyl (3-(3-(3-cyanophenyl)-1-tosyl-1H-pyrrolo[2,3-b]pyridin-5-yl)-5-(trifluoromethyl)phenyl)carbamate

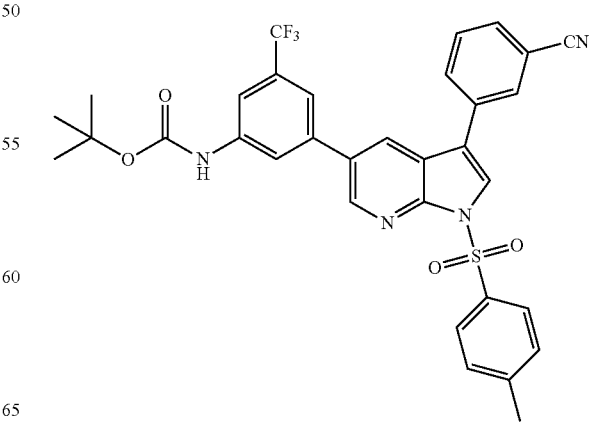

To a solution of tert-butyl (3-(3-iodo-1-tosyl-1H-pyrrolo[2,3-b]pyridin-5-yl)-5-(trifluoromethyl)phenyl)carbamate from step 3 (728 mg, 1.1 mmol) in 1,4-dioxane (7 mL) and water (3 mL) was added 3-cyanophenylboronic acid (162 mg, 1.1 mmol), potassium carbonate (455 mg, 3.3 mmol) and [1,1'-bis(diphenylphosphino)ferrocene]dichloropalladium(II).DCM (45 mg, 0.055 mmol) and the solution was treated with microwave radiation at 120° C. for thirty minutes. After cooling the resulting solution was partitioned between ethyl acetate and water. The organic layer was washed with water, brine and dried over magnesium sulfate. The mixture was filtered and concentrated in vacuo. The crude material was purified using normal phase chromatography (ethyl acetate/heptane) to provide tert-butyl (3-(3-(3-cyanophenyl)-1-tosyl-1H-pyrrolo[2,3-b]pyridin-5-yl)-5-(trifluoromethyl)phenyl)carbamate as a tan oil (567 mg, 82% yield): MS (ES) m/z 633 (M+H).

Step 5: Preparation of (E)-N-(3-(3-(3-Cyanophenyl)-1-tosyl-1H-pyrrolo[2,3-b]pyridin-5-yl)-5-(trifluoromethyl)phenyl)-4-(dimethylamino)but-2-enamide

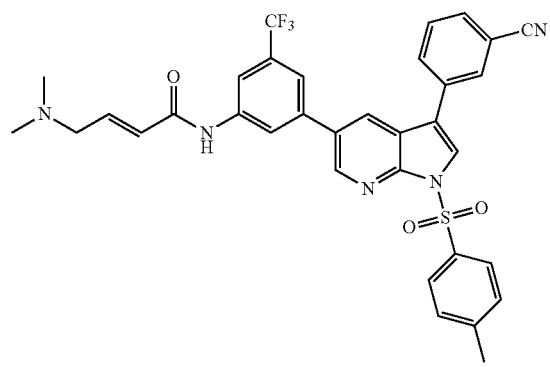 [SMILES: Cc1ccc(S(=O)(=O)n2cc(-c3cccc(C#N)c3)c3cc(-c4cc(NC(=O)/C=C/CN(C)C)cc(C(F)(F)F)c4)cnc32)cc1]

To a solution of tert-butyl (3-(3-(3-cyanophenyl)-1-tosyl-1H-pyrrolo[2,3-b]pyridin-5-yl)-5-(trifluoromethyl)phenyl)carbamate from step 4 (567 mg, 0.90 mmol) in dichloromethane (3 mL) was added trifluoroacetic acid (1 mL) and the solution was stirred for 2 hours at ambient temperature. The solution was concentrated in vacuo. The residue was dissolved into ethyl acetate and washed with saturated sodium bicarbonate solution. The organic layer was dried over magnesium sulfate, filtered and concentrated. To a solution of the free-based aniline in THF (4 mL) was added a solution of 2-chloro-4,6-dimethoxy-1,3,5-triazine (189 mg, 1.1 mmol), 4-methylmorpholine (0.3 mL, 2.7 mmol) and trans-4-dimethylaminocrotonic acid HCl (149 mg, 0.90 mmol). The solution was stirred at ambient temperature for 48 hours. The reaction mixture was quenched with water and extracted with ethyl acetate. The organic layer was washed with water, brine and dried over magnesium sulfate. The mixture was filtered and concentrated in vacuo to provide the crude coupled product. The material was purified using normal phase chromatography (dichloromethane/methanol) to provide (E)-N-(3-(3-(3-cyanophenyl)-1-tosyl-1H-pyrrolo[2,3-b]pyridin-5-yl)-5-(trifluoromethyl)phenyl)-4-(dimethylamino)but-2-enamide (78 mg, 13% yield): MS (ES) m/z 644 (M+H).

Step 6: Preparation of (E)-N-(3-(3-(3-Cyanophenyl)-1H-pyrrolo[2,3-b]pyridin-5-yl)-5-(trifluoromethyl)phenyl)-4-(dimethyl amino)but-2-enamide

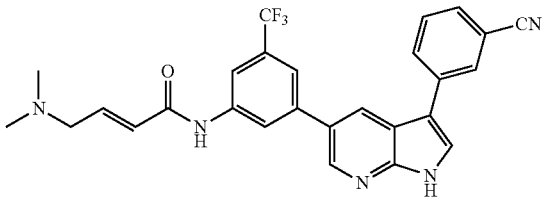 [SMILES: CN(C)C/C=C/C(=O)Nc1cc(-c2cnc3[nH]cc(-c4cccc(C#N)c4)c3c2)cc(C(F)(F)F)c1]

To a solution of (E)-N-(3-(3-(3-cyanophenyl)-1-tosyl-1H-pyrrolo[2,3-b]pyridin-5-yl)-5-(trifluoromethyl)phenyl)-4-(dimethylamino)but-2-enamide from step 5 (78 mg, 0.12 mmol) in 1,4-dioxane (1 mL) was added 1.5 M lithium hydroxide (1 mL) and the solution was stirred for 6 hours at ambient temperature. The reaction mixture was partitioned between ethyl acetate and water. The organic layer was washed with water, brine, dried over magnesium sulfate and concentrated. The residue was purified using reverse phase chromatography (acetonitrile/water/TFA) to provide (E)-N-(3-(3-(3-cyanophenyl)-1H-pyrrolo[2,3-b]pyridin-5-yl)-5-(trifluoromethyl)phenyl)-4-(dimethylamino)but-2-enamide as a white solid (15 mg, 25% yield): $^1$H NMR (400 MHz, DMSO-$d_6$) δ ppm, 12.28 (s, 1H), 10.50 (s, 1H), 8.58 (s, 1H), 8.58 (s, 1H), 8.26 (s, 1H), 8.23 (s, 1H), 8.19 (d, J=7.83 Hz, 1H), 8.15 (s, 1H), 8.10 (s, 1H), 7.82 (s, 1H), 7.72-7.64 (m, 2H), 6.85-6.78 (m, 1H), 6.30 (d, J=15.65 Hz, 1H), 3.32 (s, 6H), 3.09 (d, J=5.86 Hz, 2H); MS (ES) m/z 490 (M+H).

Example 2: Preparation of N-(3-(3-(2-Methoxypyridin-4-yl)-1H-pyrrolo[2,3-b]pyridin-5-yl)phenyl)-N-methylacrylamide

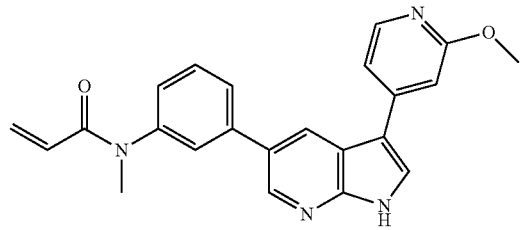 [SMILES: C=CC(=O)N(C)c1cccc(-c2cnc3[nH]cc(-c4ccnc(OC)c4)c3c2)c1]

Step 1: Preparation of tert-Butyl (3-(1H-pyrrolo[2,3-b]pyridin-5-yl)phenyl)carbamate

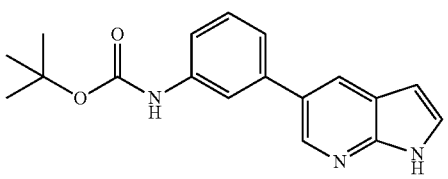 [SMILES: CC(C)(C)OC(=O)Nc1cccc(-c2cnc3[nH]ccc3c2)c1]

To a solution of 5-bromo-1H-pyrrolo[2,3-b]pyridine (196 mg, 1.00 mmol) in 1,4-dioxane (7 mL) and H$_2$O (3 mL) was added 3-Boc-aminophenylboronic acid (237 mg, 1.00 mmol), K$_2$CO$_3$ (414 mg, 3.00 mmol) and [1,1'-bis(diphenylphosphino)ferrocene]-dichloropalladium(II).DCM (36 mg, 0.05 mmol). The solution was treated with microwave radiation at 120° C. for one hour. After cooling the resulting mixture was partitioned between EtOAc and H$_2$O. The organic layer was washed with H$_2$O, brine and dried over MgSO$_4$. The solution was filtered and concentrated in vacuo to provide the crude coupled product. The material was purified using normal phase chromatography (EtOAc/heptane) to provide the title compound as a white solid (113 mg, 37% yield): MS (ES) m/z 310 (M+H).

Step 2: Preparation of tert-Butyl (3-(3-iodo-1H-pyrrolo[2,3-b]pyridin-5-yl)phenyl)carbamate

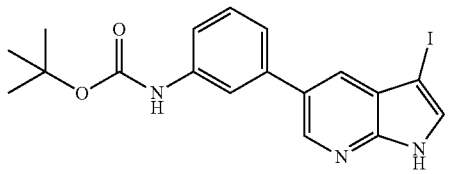 [SMILES: CC(C)(C)OC(=O)Nc1cccc(-c2cnc3[nH]cc(I)c3c2)c1]

To a solution of tert-butyl (3-(1H-pyrrolo[2,3-b]pyridin-5-yl)phenyl)carbamate from step 1 (309 mg, 1.00 mmol) in CH$_2$Cl$_2$ (5 mL) was added N-iodosuccinimide (225 mg, 1.00 mmol) and the solution was stirred for 2 hours at ambient temperature. The resulting white solid was collected by vacuum filtration to provide the title compound (246 mg, 56% yield): MS (ES) m/z 436 (M+H).

Step 3: Preparation of tert-Butyl (3-(3-iodo-1-tosyl-1H-pyrrolo[2,3-b]pyridin-5-yl)phenyl)carbamate

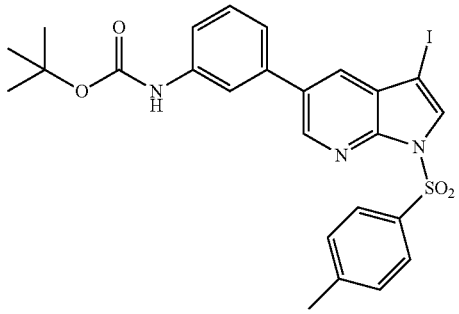 [SMILES: Cc1ccc(S(=O)(=O)n2cc(I)c3cc(-c4cccc(NC(=O)OC(C)(C)C)c4)cnc32)cc1]

To a solution of tert-butyl (3-(3-iodo-1H-pyrrolo[2,3-b]pyridin-5-yl)phenyl)-carbamate from step 2 (246 mg, 0.560 mmol) in THF (3 mL) was added NaH (60% mineral oil dispersion, 34 mg, 0.84 mmol) followed by p-toluenesulfonyl chloride (108 mg, 0.560 mmol) and the solution was stirred for 18 hours at ambient temperature. The reaction mixture was quenched with H$_2$O and extracted with EtOAc. The organic layer was washed with H$_2$O, brine and dried over MgSO$_4$. The solution was filtered and concentrated in vacuo to provide the crude coupled product. The material was purified using normal phase chromatography (EtOAc/heptane) to provide the title compound (325 mg, 98% yield): MS (ES) m/z 590 (M+H).

Step 4: Preparation of tert-Butyl (3-(3-(2-methoxypyridin-4-yl)-1-tosyl-1H-pyrrolo[2,3-b]pyridin-5-yl)phenyl)carbamate

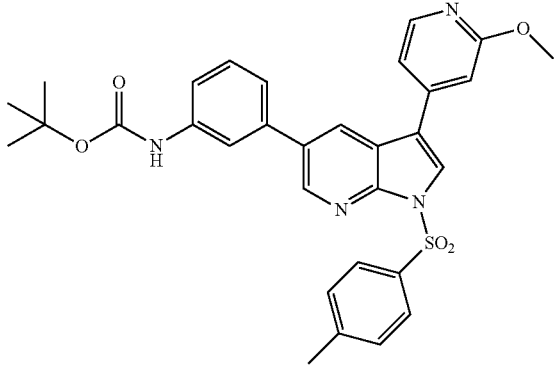 [SMILES: COc1cc(-c2cn(S(=O)(=O)c3ccc(C)cc3)c3ncc(-c4cccc(NC(=O)OC(C)(C)C)c4)cc23)ccn1]

To a solution of tert-butyl (3-(3-iodo-1-tosyl-1H-pyrrolo[2,3-b]pyridin-5-yl)phenyl)-carbamate from step 3 (125 mg, 0.21 mmol) in 1,4-dioxane (2 mL) and H$_2$O (0.5 mL) was added 2-methoxy-4-pyridine boronic acid (32 mg, 0.21 mmol), K$_2$CO$_3$ (87 mg, 0.63 mmol) and [1,1'-bis(diphenylphosphino)ferrocene]dichloropalladium(II).DCM (8 mg, 0.01 mmol) and the solution was treated with microwave radiation at 120° C. for one hour. After cooling the resulting solution was partitioned between EtOAc and H$_2$O. The organic layer was washed with H$_2$O, brine and dried over MgSO$_4$. The mixture was filtered and concentrated in vacuo. The crude material was purified using normal phase chromatography (EtOAc/heptane) to provide the title compound as a white solid (96 mg, 53% yield): MS (ES) m/z 571 (M+H).

Step 5: Preparation of tert-Butyl (3-(3-(2-methoxypyridin-4-yl)-1-tosyl-1H-pyrrolo[2,3-b]pyridin-5-yl)phenyl)(methyl)carbamate

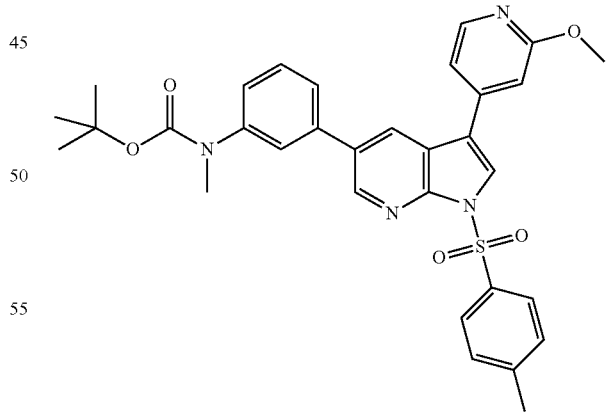

To a solution of tert-butyl (3-(3-(2-methoxypyridin-4-yl)-1-tosyl-1H-pyrrolo[2,3-b]pyridin-5-yl)phenyl)carbamate from step 4 (188 mg, 0.33 mmol) in THF (2 mL) was added NaH (60% mineral oil dispersion, 20 mg, 0.49 mmol) followed by CH$_3$I (0.02 mL, 0.33 mmol). The solution was stirred at ambient temperature. After 1.5 hours the reaction was quenched with H$_2$O and extracted into EtOAc. The organic layer was washed with H$_2$O and brine, dried over MgSO$_4$, filtered and concentrated. The crude material was purified using normal phase chromatography (EtOAc/heptane) to provide the title compound as a colorless oil (120 mg, 62% yield): MS (ES) m/z 585 (M+H).

Step 6: Preparation of N-(3-(3-(2-Methoxypyridin-4-yl)-1-tosyl-1H-pyrrolo[2,3-b]pyridin-5-yl)phenyl)-N-methylacrylamide

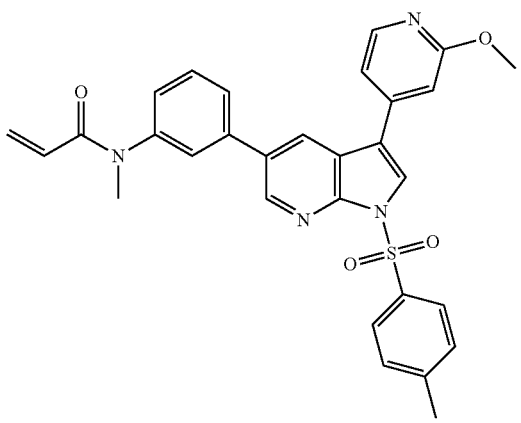 [SMILES: C=CC(=O)N(C)c1cccc(-c2cnc3c(c2)c(-c2ccnc(OC)c2)cn3S(=O)(=O)c2ccc(C)cc2)c1]

To a solution of tert-butyl (3-(3-(2-methoxypyridin-4-yl)-1-tosyl-1H-pyrrolo[2,3-b]pyridin-5-yl)phenyl)(methyl)carbamate from step 5 (120 mg, 0.20 mmol) in CH$_2$Cl$_2$ (2 mL) was added trifluoroacetic acid (1 mL) and the solution was stirred for 1 hour at ambient temperature. The solution was concentrated in vacuo to provide the amine salt. The crude amine was dissolved into DMF (2 mL) and Et$_3$N (0.08 mL, 0.60 mmol) was added followed by O-(benzotriazol-1-yl)-N,N,N',N'-tetramethyluronium tetrafluoroborate (96 mg, 0.30 mmol) and acrylic acid (0.014 mL, 0.20 mmol). The solution was stirred at ambient temperature for 18 hours. The reaction mixture was quenched with H$_2$O and extracted with EtOAc. The organic layer was washed with H$_2$O, brine and dried over MgSO$_4$. The mixture was filtered and concentrated in vacuo to provide the crude coupled product. The material was purified using normal phase chromatography (EtOAc/heptane) to provide the title compound (81 mg, 75% yield): MS (ES) m/z 539 (M+H).

Step 7: Preparation of N-(3-(3-(2-Methoxypyridin-4-yl)-1H-pyrrolo[2,3-b]pyridin-5-yl)phenyl)-N-methylacrylamide

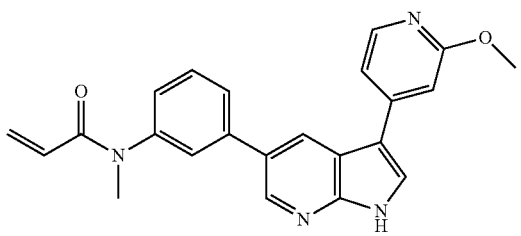 [SMILES: C=CC(=O)N(C)c1cccc(-c2cnc3[nH]cc(-c4ccnc(OC)c4)c3c2)c1]

To a solution of N-(3-(3-(2-methoxypyridin-4-yl)-1-tosyl-1H-pyrrolo[2,3-b]pyridin-5-yl)phenyl)-N-methylacrylamide from step 6 (81 mg, 0.15 mmol) in 1,4-dioxane (1 mL) was added 1.5 M LiOH (1 mL) and the solution was stirred for 18 hours at ambient temperature. The reaction mixture was partitioned between EtOAc and H$_2$O. The organic layer was washed with H$_2$O, brine, dried over MgSO$_4$ and concentrated. The residue was purified using normal phase chromatography (CH$_2$Cl$_2$/methanol) to provide the title compound as a white solid (8 mg, 14% yield): $^1$H NMR (400 MHz, DMSO-d$_6$) δ ppm, 12.31 (s, 1H), 8.63 (s, 1H), 8.54 (s, 1H), 8.27 (s, 1H), 8.17 (s, 1H), 7.79 (br. s, 2H), 7.59-7.59 (m, 1H), 7.47 (s, 1H), 7.29 (d, J=6.65 Hz, 1H), 7.22 (s, 1H), 6.19 (br. s, 2H), 5.60 (br. s, 1H), 3.89 (s, 3H), 3.34 (s, 3H); MS (ES) m/z 385 (M+H).

Example 3: Preparation of N-(3-(3-(2-(Methylamino)pyrimidin-4-yl)-1H-pyrrolo[2,3-b]pyridin-5-yl)-5-(trifluoromethyl)phenyl)acrylamide

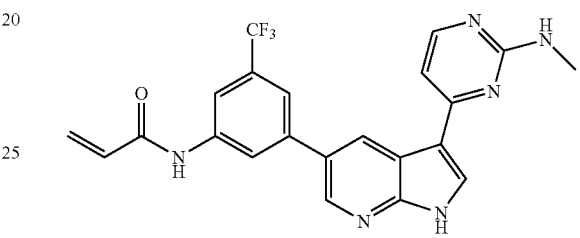

Step 1: Preparation of tert-Butyl (3-(3-(2-(methylamino)pyrimidin-4-yl)-1-tosyl-1H-pyrrolo[2,3-b]pyridin-5-yl)-5-(trifluoromethyl)phenyl)carbamate

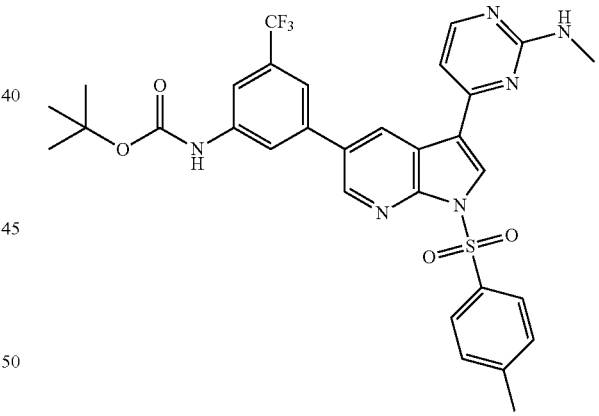

To a solution of tert-butyl (3-(3-iodo-1-tosyl-1H-pyrrolo[2,3-b]pyridin-5-yl)-5-(trifluoromethyl)phenyl)carbamate from Example 1, step 3 (657 mg, 1.0 mmol) in 1,4-dioxane (7 mL) was added potassium acetate (294 mg, 3.0 mmol), bis(pinacolato)diboron (1.02 g, 4.0 mmol) and [1,1'-bis(diphenylphosphino)ferrocene]dichloropalladium(II).DCM (41 mg, 0.05 mmol) and was treated with microwave radiation at 130° C. for 90 minutes. To the resulting slurry was added 4-bromo-N-methylpyrimidine-2-amine (188 mg, 1.0 mmol), potassium carbonate (414 mg, 3.0 mmol) and [1,1'-bis(diphenylphosphino)ferrocene]dichloropalladium (II).DCM (41 mg, 0.05 mmol) along with 3 mL of water and the solution was treated with microwave radiation at 120° C. for one hour. The resulting solution was partitioned between ethyl acetate and water. The organic layer was washed with brine and concentrated in vacuo. The crude material was purified using normal phase chromatography (ethyl acetate/heptane) to provide tert-butyl (3-(3-(2-(methylamino)pyrimidin-4-yl)-1-tosyl-1H-pyrrolo[2,3-b]pyridin-5-yl)-5-(trifluoromethyl)phenyl)carbamate (310 mg, 48% yield): MS (ES) m/z 639 (M+H).

Step 2: Preparation of N-(3-(3-(2-(Methylamino)pyrimidin-4-yl)-1-tosyl-1H-pyrrolo[2,3-b]pyridin-5-yl)-5-(trifluoromethyl)phenyl)acrylamide

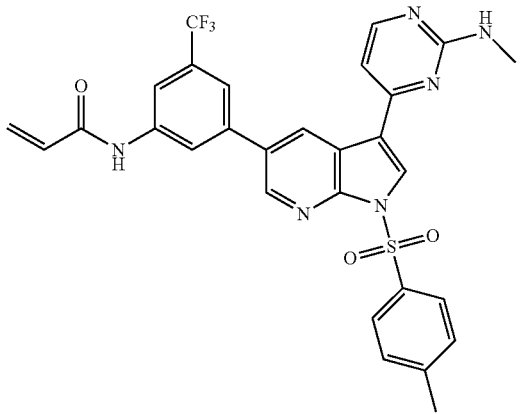 [SMILES: C=CC(=O)Nc1cc(-c2cnc3c(c2)c(-c2ccnc(NC)n2)cn3S(=O)(=O)c2ccc(C)cc2)cc(C(F)(F)F)c1]

To a solution of tert-butyl (3-(3-(2-(methylamino)pyrimidin-4-yl)-1-tosyl-1H-pyrrolo[2,3-b]pyridin-5-yl)-5-(trifluoromethyl)phenyl)carbamate from step 1 (310 mg, 0.48 mmol) in dichloromethane (3 mL) was added trifluoroacetic acid (1 mL) and the solution was stirred for 3 hours at ambient temperature. The solution was concentrated in vacuo. To a solution of the crude aniline in tetrahydrofuran (2 mL) was added a solution of 2-chloro-4,6-dimethoxy-1,3,5-triazine (101 mg, 0.58 mmol), 4-methylmorpholine (0.16 mL, 1.44 mmol) and acrylic acid (0.033 mL, 0.48 mmol). The solution was stirred at ambient temperature for 3 hours. The reaction mixture was quenched with water and extracted with ethyl acetate. The organic layer was washed with water, brine and dried over magnesium sulfate. The mixture was filtered and concentrated in vacuo to provide the crude coupled product. The material was purified using normal phase chromatography (ethyl acetate/heptane) to provide N-(3-(3-(2-(methylamino)pyrimidin-4-yl)-1-tosyl-1H-pyrrolo[2,3-b]pyridin-5-yl)-5-(trifluoromethyl)phenyl)acrylamide (87 mg, 31% yield): MS (ES) m/z 593 (M+H).

Step 3: Preparation of N-(3-(3-(2-(Methylamino)pyrimidin-4-yl)-1H-pyrrolo[2,3-b]pyridin-5-yl)-5-(trifluoromethyl)phenyl)acrylamide

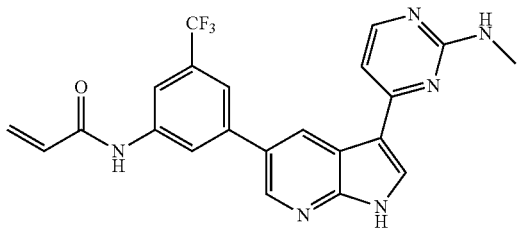 [SMILES: C=CC(=O)Nc1cc(-c2cnc3[nH]cc(-c4ccnc(NC)n4)c3c2)cc(C(F)(F)F)c1]

To a solution of N-(3-(3-(2-(methylamino)pyrimidin-4-yl)-1-tosyl-1H-pyrrolo[2,3-b]pyridin-5-yl)-5-(trifluoromethyl)phenyl)acrylamide from step 2 (87 mg, 0.15 mmol) in 1,4-dioxane (2 mL) was added 1.5 M lithium hydroxide (1 mL) and the solution was stirred for 18 hours at ambient temperature. The reaction mixture was partitioned between ethyl acetate and water. The organic layer was washed with water, brine, dried over magnesium sulfate and concentrated. The residue was purified using normal phase chromatography (dichloromethane/methanol) to provide N-(3-(3-(2-(methylamino)pyrimidin-4-yl)-1H-pyrrolo[2,3-b]pyridin-5-yl)-5-(trifluoromethyl)phenyl)acrylamide as a white solid (20 mg, 30% yield): $^1$H NMR (400 MHz, DMSO-$d_6$) δ ppm, 13.65 (s, 1H), 12.95 (s, 1H), 10.65 (s, 1H), 9.09 (s, 1H), 8.78 (s, 1H), 8.68 (s, 1H), 8.46 (s, 1H), 8.14-8.02 (m, 1H), 7.80 (s, 1H), 6.57 (d, J=5.2 Hz, 1H), 6.50-6.44 (m, 1H), 6.37 (d, J=1.6 Hz, 1H), 6.33 (d, J=2.0 Hz, 1H), 5.87 (dd, J=2.0 Hz, 7.6 Hz, 1H), 2.98 (d, J=11.2 Hz, 3H): MS (ES) m/z 439 (M+H).

Example 4: Preparation of (E)-N-(5-(3-(2-Cyanopyridin-4-yl)-1H-pyrrolo[2,3-b]pyridin-5-yl)pyridin-3-yl)-4-(dimethylamino)but-2-enamide

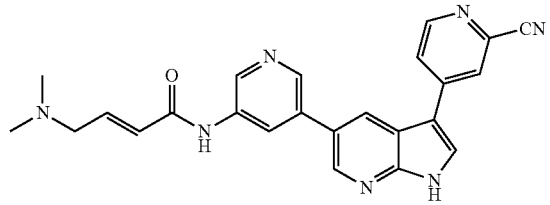 [SMILES: CN(C)C/C=C/C(=O)Nc1cncc(-c2cnc3[nH]cc(-c4ccnc(C#N)c4)c3c2)c1]

Step 1: Preparation of tert-Butyl (5-(1H-pyrrolo[2,3-b]pyridin-5-yl)pyridin-3-yl)carbamate

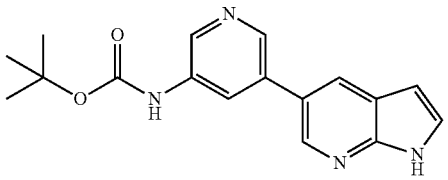 [SMILES: CC(C)(C)OC(=O)Nc1cncc(-c2cnc3[nH]ccc3c2)c1]

To a solution of pyrrolo[2,3-b]pyridine-5-boronic acid, pinacol ester (976 mg, 4.0 mmol), in 1,4-dioxane (20 mL) and water (8 mL), was added tert-butyl-N-(5-bromopyridin-3yl)carbamate (1.1 g, 4.0 mmol), potassium carbonate (1.65 g, 12 mmol) and [1,1'-bis(diphenylphosphino)ferrocene]dichloropalladium(II).DCM (164 mg, 0.20 mmol). The solution was treated with microwave radiation at 120° C. for one hour. After cooling the resulting mixture was partitioned between ethyl acetate and water. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (5-(1H-pyrrolo[2,3-b]pyridin-5-yl)pyridin-3-yl)carbamate (515 mg, 42%): MS (ES) m/z 311 (M+H).

Step 2: Preparation of tert-Butyl (5-(3-iodo-1H-pyrrolo[2,3-b]pyridin-5-yl)pyridin-3-yl)carbamate

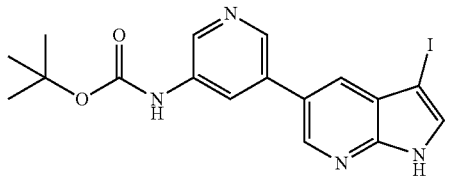 [SMILES: CC(C)(C)OC(=O)Nc1cncc(-c2cnc3[nH]cc(I)c3c2)c1]

To a solution of tert-butyl (5-(1H-pyrrolo[2,3-b]pyridin-5-yl)pyridin-3-yl)carbamate from step 1 (515 mg, 1.7 mmol) in dichloromethane (5 mL) was added N-iodosuccinimide (373 mg, 1.7 mmol) and the solution was stirred for 1 hour at ambient temperature. The resulting beige solid was collected by vacuum filtration to provide tert-butyl (5-(3-iodo-1H-pyrrolo[2,3-b]pyridin-5-yl)pyridin-3-yl)carbamate (715 mg, 99% yield): MS (ES) m/z 437 (M+H).

Step 3: Preparation of tert-Butyl (5-(3-iodo-1-tosyl-1H-pyrrolo[2,3-b]pyridin-5-yl)pyridin-3-yl)carbamate

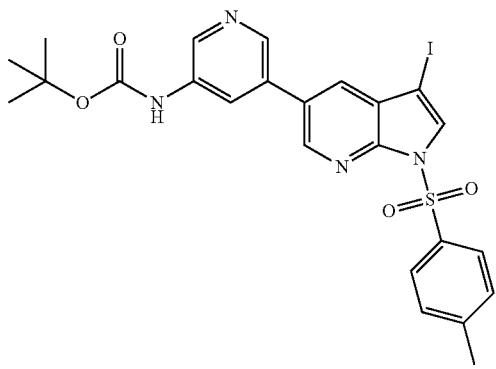 [SMILES: Cc1ccc(S(=O)(=O)n2cc(I)c3cc(-c4cncc(NC(=O)OC(C)(C)C)c4)cnc32)cc1]

To a solution tert-butyl (5-(3-iodo-1H-pyrrolo[2,3-b]pyridin-5-yl)pyridin-3-yl)carbamate from step 2 (715 g, 1.6 mmol) in tetrahydrofuran (8 mL) was added sodium hydride (60% mineral oil dispersion, 100 mg, 2.5 mmol) followed by p-toluenesulfonyl chloride (315 mg, 1.6 mmol) and the solution was stirred for 30 minutes at ambient temperature. The reaction mixture was quenched with water and extracted with ethyl acetate. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (5-(3-iodo-1-tosyl-1H-pyrrolo[2,3-b]pyridin-5-yl)pyridin-3-yl)carbamate (987 mg, 99% yield): MS (ES) m/z 591 (M+H).

Step 4: Preparation of tert-Butyl (5-(3-(2-cyanopyridin-4-yl)-1-tosyl-1H-pyrrolo[2,3-b]pyridin-5-yl)pyridin-3-yl)carbamate

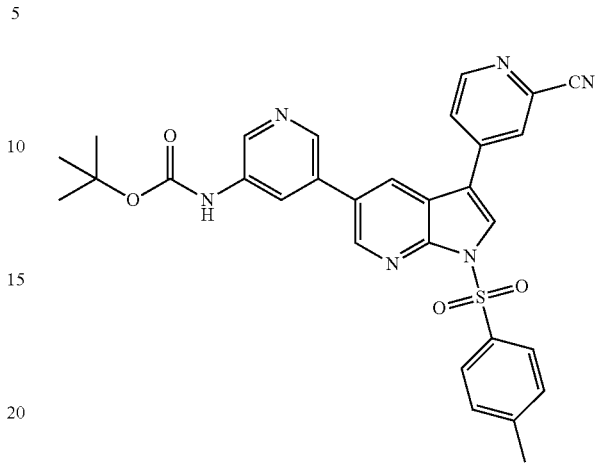

To a solution of tert-butyl (5-(3-iodo-1-tosyl-1H-pyrrolo[2,3-b]pyridin-5-yl)pyridin-3-yl)carbamate from step 3 (500 mg, 0.85 mmol) in 1,4-dioxane (7 mL) and water (3 mL) was added 2-cyanopyridine-4-boronic acid, pinacol ester (195 mg, 0.85 mmol), potassium carbonate (352 mg, 2.5 mmol) and [1,1'-bis(diphenylphosphino)ferrocene]dichloropalladium(II).DCM (35 mg, 0.042 mmol) and the solution was treated with microwave radiation at 120° C. for one hour. After cooling the resulting solution was partitioned between ethyl acetate and water. The organic layer was washed with water, brine and dried over magnesium sulfate. The mixture was filtered and concentrated in vacuo. The crude material was purified using normal phase chromatography (ethyl acetate/heptane) to provide tert-butyl (5-(3-(2-cyanopyridin-4-yl)-1-tosyl-1H-pyrrolo[2,3-b]pyridin-5-yl)pyridin-3-yl)carbamate (51 mg, 11% yield): MS (ES) m/z 567 (M+H).

Step 5: Preparation of (E)-N-(5-(3-(2-Cyanopyridin-4-yl)-1-tosyl-1H-pyrrolo[2,3-b]pyridin-5-yl)pyridin-3-yl)-4-(dimethylamino)but-2-enamide

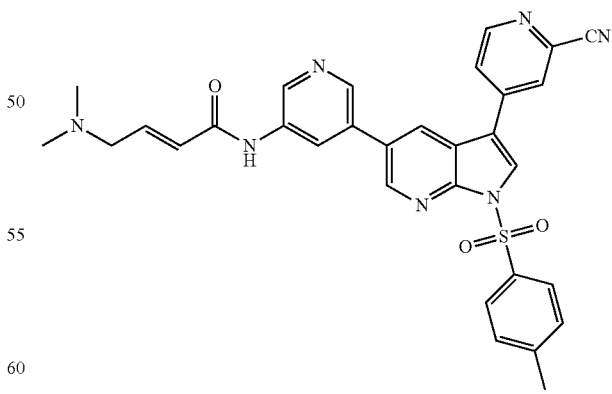

To a solution of tert-butyl (5-(3-(2-cyanopyridin-4-yl)-1-tosyl-1H-pyrrolo[2,3-b]pyridin-5-yl)pyridin-3-yl)carbamate from step 4 (51 mg, 0.09 mmol) in dichloromethane (2 mL) was added trifluoroacetic acid (1 mL) and the solution was stirred for 2 hours at ambient temperature. The solution was concentrated in vacuo. The residue was dissolved into ethyl acetate and washed with saturated sodium bicarbonate solution. The organic layer was dried over magnesium sulfate, filtered and concentrated. To a solution of the free-based aniline dissolved into THF (1 mL) was added a solution of 2-chloro-4,6-dimethoxy-1,3,5-triazine (17 mg, 0.097 mmol), 4-methylmorpholine (0.03 mL, 0.27 mmol) and trans-4-dimethylaminocrotonic acid HCl (15 mg, 0.090 mmol). The solution was stirred at ambient temperature for 6 days. The reaction mixture was quenched with water and extracted with ethyl acetate. The organic layer was washed with water, brine and dried over magnesium sulfate. The mixture was filtered and concentrated in vacuo to provide the crude coupled product. The material was purified using normal phase chromatography (dichloromethane/methanol) to provide (E)-N-(5-(3-(2-cyanopyridin-4-yl)-1-tosyl-1H-pyrrolo[2,3-b]pyridin-5-yl)pyridin-3-yl)-4-(dimethylamino)but-2-enamide (10 mg, 19% yield): MS (ES) m/z 578 (M+H).

Step 6: Preparation of (E)-N-(5-(3-(2-Cyanopyridin-4-yl)-1H-pyrrolo[2,3-b]pyridin-5-yl)pyridin-3-yl)-4-(dimethylamino)but-2-enamide

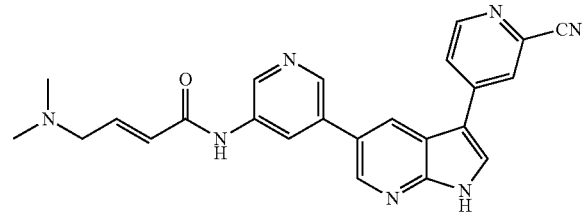 [SMILES: CN(C)C/C=C/C(=O)Nc1cncc(-c2cnc3[nH]cc(-c4ccnc(C#N)c4)c3c2)c1]

To a solution of (E)-N-(5-(3-(2-cyanopyridin-4-yl)-1-tosyl-1H-pyrrolo[2,3-b]pyridin-5-yl)pyridin-3-yl)-4-(dimethylamino)but-2-enamide from step 5 (10 mg, 0.017 mmol) in 1,4-dioxane (0.5 mL) was added 1.5 M lithium hydroxide (0.5 mL) and the solution was stirred for 1 hour at ambient temperature. The reaction mixture was partitioned between ethyl acetate and water. The organic layer was washed with water, brine, dried over magnesium sulfate and concentrated. The residue was purified using reverse phase chromatography (acetonitrile/water/TFA) to provide (E)-N-(5-(3-(2-cyanopyridin-4-yl)-1H-pyrrolo[2,3-b]pyridin-5-yl)pyridin-3-yl)-4-(dimethylamino)but-2-enamide as a white solid (5 mg, 55% yield): $^1$H NMR (400 MHz, DMSO-d$_6$) δ ppm, 12.62 (s, 1H), 10.71 (s, 1H), 8.90 (s, 1H), 8.82 (s, 1H), 8.78 (s, 1H), 8.70 (d, J=5.47 Hz, 1H), 8.62 (s, 1H), 8.52 (s, 2H), 8.41 (s, 1H), 8.23 (d, 0.1=3.91 Hz, 1H), 6.86-6.78 (m, 1H), 6.52 (d, 0.1=15.65 Hz, 1H), 3.99 (d, 0.1-7.04 Hz, 2H), 2.82 (s, 6H); MS (ES) m/z 424 (M+H).

Example 5: Preparation of N-(5-(3-(3-Cyanophenyl)-1H-pyrrolo[2,3-b]pyridin-5-yl)-2-((tetrahydrofuran-3-yl)oxy)pyridin-3-yl)acrylamide

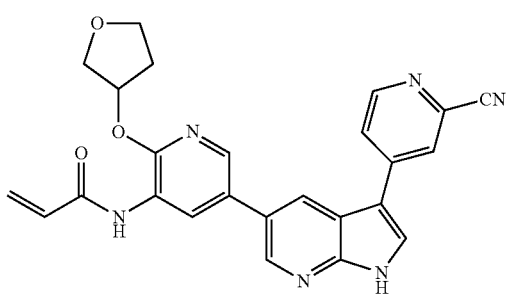 [SMILES: C=CC(=O)Nc1cc(-c2cnc3[nH]cc(-c4ccnc(C#N)c4)c3c2)cnc1OC1CCOC1]

Step 1: Preparation of 5-Bromo-3-nitro-2-((tetrahydrofuran-3-yl)oxy)pyridine

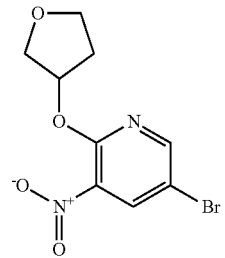

To a solution of oxolan-3-ol (398 mg, 4.92 mmol) in THF (3 mL) was added NaH (60% mineral oil dispersion, 87 mg, 3.6 mmol) and the mixture stirred at ambient temperature for 30 min. To the resultant mixture was added 5-bromo-2-fluoro-3-nitropyridine (500 mg, 2.26 mmol) and the solution was stirred for 18 hours at ambient temperature. The reaction mixture was quenched with H$_2$O and extracted with EtOAc. The organic layer was washed with H$_2$O, brine and dried over MgSO$_4$. The solution was filtered and concentrated in vacuo to provide the crude desired product. The material was purified using normal phase chromatography (EtOAc/heptane) to provide the title compound as a light tan solid (0.5 g, 76% yield): MS (ES) m/z 290 (M+H).

Step 2: Preparation of 5-Bromo-2-((tetrahydrofuran-3-yl)oxy)pyridin-3-amine

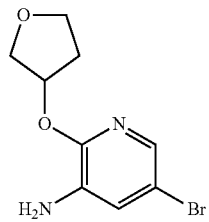 [SMILES: Nc1cc(Br)cnc1OC1CCOC1]

To a solution of 5-bromo-3-nitro-2-((tetrahydrofuran-3-yl)oxy)pyridine from step 1 (500 mg, 2.26 mmol) and acetic acid (1 mL) in ethanol (5 mL) was added iron powder (96 mg, 1.72 mmol) and the mixture was heated to 85° C. for 2 hours. The mixture was allowed to cool to ambient temperature, filtered through celite, and concentrated in vacuo to provide a resin. The resin was partitioned between EtOAc and H$_2$O. The organic layer was washed with H$_2$O, brine and dried over MgSO$_4$. The solution was filtered and concentrated in vacuo to provide the title compound as a brown solid which was used without further purification (350 mg, 78% yield): MS (ES) m/z 260 (M+H).

Step 3: Preparation of 5-Bromo-3-iodo-1H-pyrrolo[2,3-b]pyridine

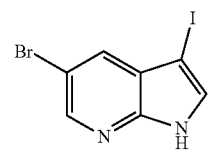 [SMILES: Brc1cnc2[nH]cc(I)c2c1]

To a solution of commercially available 5-bromo-1H-pyrrolo[2,3-b]pyridine (5.60 g, 28.4 mmol) in CH$_2$Cl$_2$ (25 mL) was added N-iodosuccinimide (7.67 g, 34.1 mmol). The reaction mixture was stirred at ambient temperature for 2 h. The precipitate was filtered and washed with cold CH$_2$Cl$_2$ (2×5 mL) to provide the title compound as a light tan solid (7.17 g, 78% yield) which was used as is in the next step without further purification: MS (ES) m/z 323 (M+H).

Step 4: Preparation of 5-Bromo-3-iodo-1-tosyl-1H-pyrrolo[2,3-b]pyridine

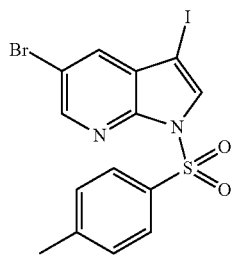 [SMILES: Cc1ccc(S(=O)(=O)n2cc(I)c3cc(Br)cnc32)cc1]

To a solution of 5-bromo-3-iodo-1H-pyrrolo[2,3-b]pyridine from step 3 (5.60 g, 17.4 mmol) in THF (20 mL) was added NaH (60% mineral oil dispersion, 666 mg, 27.8 mmol) followed by p-toluenesulfonyl chloride 3.97 g, 20.8 mmol) and the solution was stirred for 18 hours at ambient temperature. The reaction mixture was quenched with H$_2$O and extracted with EtOAc. The organic layer was washed with H$_2$O, brine and dried over MgSO$_4$. The solution was filtered and concentrated in vacuo to provide the crude coupled product. The material was purified using normal phase chromatography (EtOAc/heptane) to provide the title compound (6.75 g, 82% yield): MS (ES) m/z 478 (M+H).

Step 5: Preparation of 3-(5-Bromo-1-tosyl-1H-pyrrolo[2,3-b]pyridin-3-yl)benzonitrile

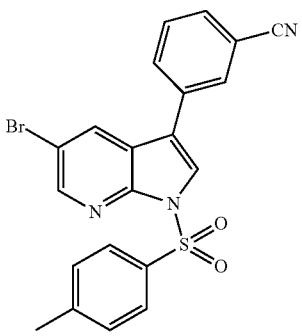 [SMILES: Cc1ccc(S(=O)(=O)n2cc(-c3cccc(C#N)c3)c3cc(Br)cnc32)cc1]

To a solution of 5-bromo-3-iodo-1-tosyl-1H-pyrrolo[2,3-b]pyridine from step 4 (500 mg, 1.05 mmol) in 1,4-dioxane (2 mL) and H$_2$O (0.5 mL) was added (3-cyanophenyl)-boronic acid (154 mg, 1.05 mmol), K$_2$CO$_3$ (434 mg, 3.14 mmol) and [1,1'-bis(diphenyl-phosphino)ferrocene]dichloropalladium(II) (43 mg, 0.053 mmol). The solution was treated with microwave radiation at 100° C. for one hour, cooled to ambient temperature, then quenched with H$_2$O and extracted with EtOAc. The organic layer was washed with H$_2$O, brine, and dried over MgSO$_4$. The solution was filtered and concentrated in vacuo. The crude material was purified using normal phase chromatography (EtOAc/heptane) to provide the title compound as a tan solid (400 mg, 84% yield): MS (ES) m/z 453 (M+H).

Step 6: Preparation of 3-(5-(5-Amino-6-((tetrahydrofuran-3-yl)oxy)pyridin-3-yl)-1-tosyl-1H-pyrrolo[2,3-b]pyridin-3-yl)benzonitrile

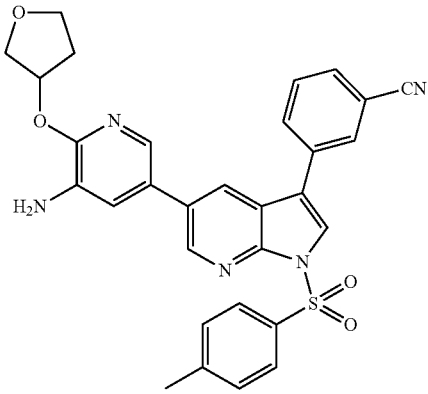 [SMILES: Cc1ccc(S(=O)(=O)n2cc(-c3cccc(C#N)c3)c3cc(-c4cnc(OC5CCOC5)c(N)c4)cnc32)cc1]

To a solution of 3-(5-bromo-1-tosyl-1H-pyrrolo[2,3-b]pyridin-3-yl)benzonitrile from step 5 (384 mg, 0.849 mmol) and bis(pinacolato)diboron (862 mg, 3.40 mmol) in dioxane (15 mL) was added potassium acetate (250 mg, 2.55 mmol) and PdCl$_2$(dppf)$_2$ (35 mg, 0.043 mmol). The mixture was heated in a microwave to 90° C. for 1 hour. The reaction was monitored by LCMS and after 1 hour at 90° C. all of the N-(1-(3-phenyl-1-tosyl-1H-pyrrolo[2,3-b]pyridin-5-yl)azetidin-3-yl)acrylamide had been consumed. To the reaction was added 5-bromo-2-((tetrahydrofuran-3-yl)oxy)pyridin-3-amine from step 2 (220 mg, 0.849 mmol), additional PdCl$_2$(dppf)$_2$ (35 mg, 0.043 mmol) and H$_2$O (3 mL). The resulting solution was heated in a microwave to 120° C. for 1 hour, cooled to ambient temperature, quenched with H$_2$O and extracted with EtOAc. The organic layer was washed with H$_2$O, brine and dried over MgSO$_4$. The solution was filtered and concentrated in vacuo to afford the crude desired product. The crude product was purified by silica gel chromatography (5-95% EtOAc-hexane) to provide the title compound as a tan solid (105 mg, 22% yield): MS (ES) m/z 552 (M+H).

Step 7: Preparation of N-{5-[3-(3-Cyanophenyl)-1-(4-methylbenzenesulfonyl)-1H-pyrrolo[2,3-b]pyridin-5-yl]-2-(oxolan-3-yloxy)pyridin-3-yl}prop-2-enamide

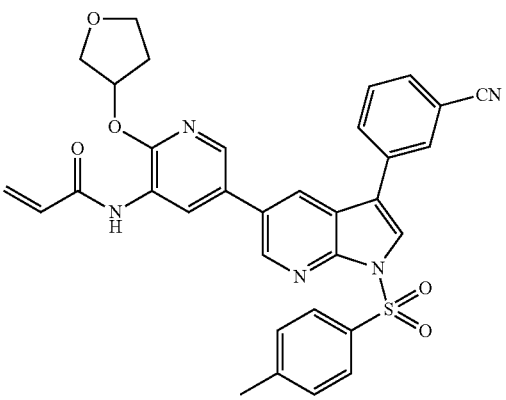 [SMILES: C=CC(=O)Nc1cc(-c2cnc3c(c2)c(-c2cccc(C#N)c2)cn3S(=O)(=O)c2ccc(C)cc2)cnc1OC1CCOC1]

To a solution of acrylic acid (13.0 mg, 0.178 mmol) in THF (2 mL) was added 2-chloro-4,6-dimethoxy-1,3,5-triazine (35 mg, 0.090 mmol), and N-methylmorpholine (107 mg, 1.06 mmol). The resulting solution was allowed to stir at ambient temperature for 15 minutes by which time a white precipitate formed. To this was added 3-(5-(5-amino-6-((tetrahydrofuran-3-yl)oxy)pyridin-3-yl)-1-tosyl-1H-pyrrolo[2,3-b]pyridin-3-yl)benzonitrile from step 6 (98.0 mg, 0.178 mmol) in THF (2 mL) and the resulting solution was stirred at ambient temperature for 2 hours, cooled to ambient temperature, quenched with H₂O and extracted with EtOAc. The organic layer was washed with H₂O, brine and dried over MgSO₄. The mixture was filtered and concentrated in vacuo to provide the crude coupled product. The material was purified using normal phase chromatography (EtOAc/heptane) to provide the title compound as an off white solid (23 mg, 22% yield): MS (ES) m/z 606 (M+H).

Step 8: Preparation of N-(5-(3-(3-Cyanophenyl)-1H-pyrrolo[2,3-b]pyridin-5-yl)-2-((tetrahydrofuran-3-yl)oxy)pyridin-3-yl)acrylamide

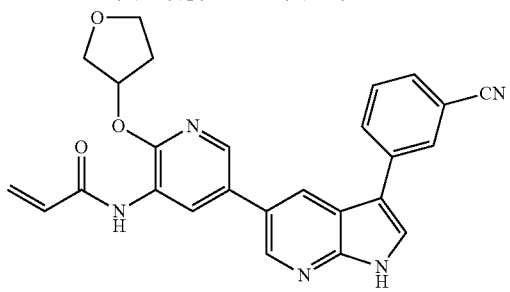 [SMILES: C=CC(=O)Nc1cc(-c2cnc3[nH]cc(-c4cccc(C#N)c4)c3c2)cnc1OC1CCOC1]

To a solution of N-{5-[3-(3-cyanophenyl)-1-(4-methylbenzenesulfonyl)-1H-pyrrolo-[2,3-b]pyridin-5-yl]-2-(oxolan-3-yloxy)pyridin-3-yl}prop-2-enamide from step 7 (23 mg, 0.037 mmol) in 1,4-dioxane (1 mL) was added 1.5 M LiOH (1 mL) and the solution was stirred for 18 hours at ambient temperature. The reaction mixture was extracted with EtOAc. The organic layer was washed with H₂O, brine and dried over MgSO₄. The solution was filtered and concentrated in vacuo to provide the crude coupled product. The material was purified using normal phase chromatography (CH₂Cl₂/methanol) to provide the title compound as a white solid (7.0 mg, 41% yield): $^1$H NMR (400 MHz, DMSO-d₆) δ ppm, 12.22 (s, 1H), 9.50 (s, 1H), 8.75 (s, 1H), 8.51 (s, 1H), 8.34 (d, J=1.96 Hz, 1H), 8.25 (s, 1H), 8.18 (d, J=7.82 Hz, 1H), 8.13 (s, 1H), 6.79-6.72 (m, 1H), 6.29 (d, J=16.43 Hz, 1H), 5.80 (d, J=11.34 Hz, 1H), 5.58 (s, 1H), 4.02-3.90 (m, 4H), 3.80-3.75 (m, 1H), 2.30-2.26 (m, 1H), 2.20-2.18 (m, 1H); MS (ES) m/z 452 (M+H).

Example 6: Preparation of N-(3-(3-(2-fluoropyridin-4-yl)-4-methyl-1H-pyrrolo[2,3-b]pyridin-5-yl)-5-methoxyphenyl)acrylamid

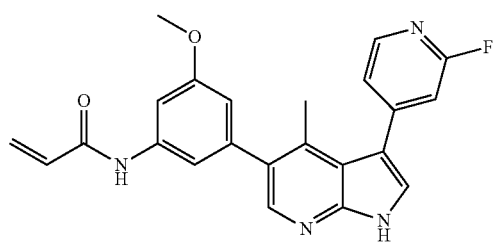 [SMILES: C=CC(=O)Nc1cc(OC)cc(-c2cnc3[nH]cc(-c4ccnc(F)c4)c3c2C)c1]

Step 1: Preparation of 5-bromo-3-iodo-4-methyl-1H-pyrrolo[2,3-b]pyridine

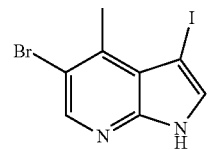

To a solution of 5-bromo-4-methyl-1H-pyrrolo[2,3-b]pyridine (1.5 g, 7.1 mmol) in dichloromethane (10 mL) was added N-iodosuccinimide (1.6 g, 7.1 mmol) and the solution was stirred for one hour at ambient temperature. The resulting yellow solid was collected by vacuum filtration to provide 5-bromo-3-iodo-4-methyl-1H-pyrrolo[2,3-b]pyridine (2.35 g, 98% yield): MS (ES) m/z 337 (M+H).

Step 2: Preparation of 5-bromo-3-iodo-4-methyl-1-tosyl-1H-pyrrolo[2,3-b]pyridine

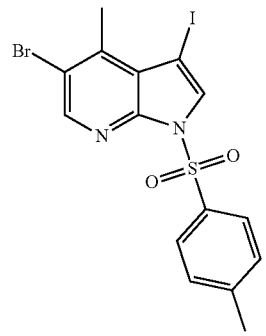 [SMILES: Cc1ccc(S(=O)(=O)n2cc(I)c3c(C)c(Br)cnc32)cc1]

To an ice cold solution of 5-bromo-3-iodo-4-methyl-1H-pyrrolo[2,3-b]pyridine from step 1 (2.35 g, 7.0 mmol) in tetrahydrofuran (15 mL) was added sodium hydride (60% mineral oil dispersion, 426 mg, 10.6 mmol) followed by p-toluenesulfonyl chloride (1.35 g, 7.1 mmol). The solution was stirred for 4 hours at ambient temperature. The reaction mixture was quenched with water and diluted with ethyl acetate. The resulting beige solid was collected by vacuum filtration to provide 5-bromo-3-iodo-4-methyl-1-tosyl-1H-pyrrolo[2,3-b]pyridine (2.47 g, 71% yield): MS (ES) m/z 491 (M+H).

Step 3: Preparation of 5-bromo-3-(2-fluoropyridin-4-yl)-4-methyl-1-tosyl-1H-pyrrolo[2,3-b]pyridine

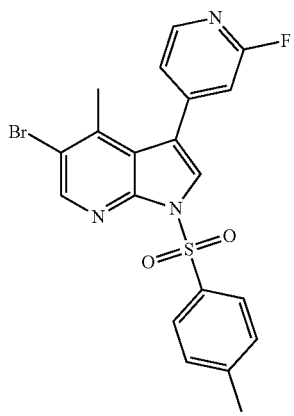 [SMILES: Cc1ccc(S(=O)(=O)n2cc(-c3ccnc(F)c3)c3c(C)c(Br)cnc32)cc1]

To a solution of 5-bromo-3-iodo-4-methyl-1-tosyl-1H-pyrrolo[2,3-b]pyridine from step 2 (750 mg, 1.53 mmol) in 1,4-dioxane (10 mL) and water (4 mL) was added 2-fluoropyridine-4-boronic acid (215 mg, 1.53 mmol), potassium carbonate (633 mg, 4.59 mmol) and [1,1'-bis(diphenylphosphino)ferrocene]dichloropalladium(II).DCM (62 mg, 0.08 mmol) and the solution was treated with microwave radiation at 120° C. for thirty minutes. After cooling the resulting solution was partitioned between ethyl acetate and water. The organic layer was washed with water, brine and dried over magnesium sulfate. The mixture was filtered and concentrated in vacuo. The crude material was purified using normal phase chromatography (ethyl acetate/heptane) to provide 5-bromo-3-(2-fluoropyridin-4-yl)-4-methyl-1-tosyl-1H-pyrrolo[2,3-h]pyridine (258 mg, 37% yield): MS (ES) m/z 460 (M+H).

Step 4: Preparation of 3-(3-(2-fluoropyridin-4-yl)-4-methyl-1-tosyl-1H-pyrrolo[2,3-b]pyridin-5-yl)-5-methoxyaniline

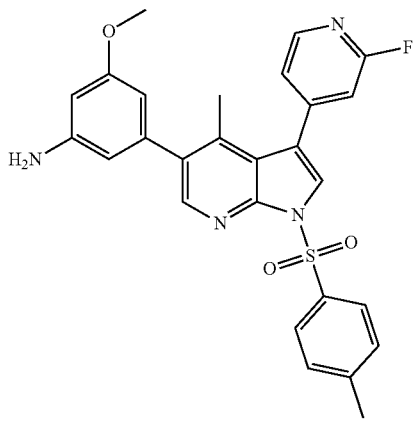 [SMILES: COc1cc(N)cc(-c2cnc3c(c(-c4ccnc(F)c4)cn3S(=O)(=O)c3ccc(C)cc3)c2C)c1]

To a solution of 5-bromo-3-(2-fluoropyridin-4-yl)-4-methyl-1-tosyl-1H-pyrrolo[2,3-b]pyridine from step 3 (258 mg, 0.56 mmol) in 1,4-dioxane (5 mL) was added potassium acetate (165 mg, 1.68 mmol), bis(pinacolato) diboron (569 mg, 2.24 mmol) and bis(diphenylphosphino)ferrocene]dichloropalladium(II).DCM (23 mg, 0.028 mmol). The solution was treated with microwave radiation at 130° C. for 3.5 hours. To this solution was added 3-bromo-5-methoxyaniline (113 mg, 0.56 mmol), potassium carbonate (232 mg, 1.68 mmol) and bis(diphenylphosphino)ferrocene]dichloropalladium(II).DCM (23 mg, 0.028 mmol). The solution was treated with microwave radiation at 120° C. for one hour. After cooling the resulting solution was partitioned between ethyl acetate and water. The organic layer was washed with water, brine and dried over magnesium sulfate. The mixture was filtered and concentrated in vacuo. The crude material was purified using normal phase chromatography (ethyl acetate/heptane) to provide 3-(3-(2-fluoropyridin-4-yl)-4-methyl-1-tosyl-1H-pyrrolo[2,3-b]pyridin-5-yl)-5-methoxyaniline (154 mg, 55% yield): MS (ES) m/z 503 (M+H).

Step 5: Preparation of N-(3-(3-(2-fluoropyridin-4-yl)-4-methyl-1-tosyl-1H-pyrrolo[2,3-b]pyridin-5-yl)-5-methoxyphenyl)acrylamide

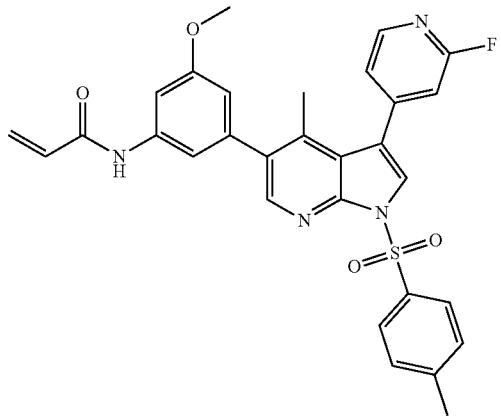 [SMILES: C=CC(=O)Nc1cc(OC)cc(-c2cnc3c(c(-c4ccnc(F)c4)cn3S(=O)(=O)c3ccc(C)cc3)c2C)c1]

To a solution of 3-(3-(2-fluoropyridin-4-yl)-4-methyl-1-tosyl-1H-pyrrolo[2,3-b]pyridin-5-yl)-5-methoxyaniline from step 4 (54 mg, 0.11 mmol) in tetrahydrofuran (2 mL) was added a solution of 2-chloro-4,6-dimethoxy-1,3,5-triazine (23 mg, 0.13 mmol), 4-methylmorpholine (0.036 mL, 0.33 mmol) and acrylic acid (0.007 mL, 0.11 mmol). The solution was stirred at ambient temperature for 1 hour. The reaction mixture was quenched with water and extracted with ethyl acetate. The organic layer was washed with water, brine and dried over magnesium sulfate. The mixture was filtered and concentrated in vacuo to provide the crude coupled product. The material was purified using normal phase chromatography (ethyl acetate/heptane) to provide N-(3-(3-(2-fluoropyridin-4-yl)-4-methyl-1-tosyl-1H-pyrrolo[2,3-b]pyridin-5-yl)-5-methoxyphenyl)acrylamide (22 mg, 36% yield): MS (ES) m/z 557 (M+H).

Step 6: Preparation of N-(3-(3-(2-fluoropyridin-4-yl)-4-methyl-1H-pyrrolo[2,3-b]pyridin-5-yl)-5-methoxyphenyl)acrylamide

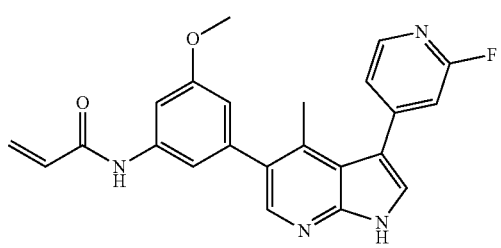 [SMILES: C=CC(=O)Nc1cc(OC)cc(-c2cnc3[nH]cc(-c4ccnc(F)c4)c3c2C)c1]

To a solution of N-(3-(3-(2-fluoropyridin-4-yl)-4-methyl-1-tosyl-1H-pyrrolo[2,3-b]pyridin-5-yl)-5-methoxyphenyl)acrylamide from step 5 (22 mg, 0.04 mmol) in 1,4-dioxane (1 mL) was added 1.5 M lithium hydroxide (1 mL) and the solution was stirred for 7 hours at ambient temperature. The reaction mixture was partitioned between ethyl acetate and water. The organic layer was washed with water, brine, dried over magnesium sulfate and concentrated. The residue was purified using normal phase chromatography (dichloromethane/methanol) to provide N-(3-(3-(2-fluoropyridin-4-yl)-4-methyl-1H-pyrrolo[2,3-b]pyridin-5-yl)-5-methoxyphenyl)

acrylamide (5.3 mg, 33% yield): $^1$H NMR (400 MHz, DMSO-d$_6$) δ ppm, 12.23 (s, 1H), 10.23 (s, 1H), 8.23 (d, J=5.48 Hz, 1H), 8.15 (s, 1H), 7.80 (s, 1H), 7.51 (d, J=5.48 Hz, 1H), 7.39 (s, 1H), 7.31 (s, 1H), 7.27 (s, 1H), 6.72 (s, 1H), 6.47-6.41 (m, 1H), 6.27 (d, 0.1-16.83 Hz, 1H), 5.77 (d, J=11.73 Hz, 1H), 3.79 (s, 3H), 2.30 (s, 3H); MS (ES) m/z 403 (M+H).

Example 7: Preparation of (E)-4-(dimethylamino)-N-(3-(3-(2-fluoropyridin-4-yl)-4-methyl-1H-pyrrolo[2,3-b]pyridin-5-yl)-5-methoxyphenyl)but-2-enamide

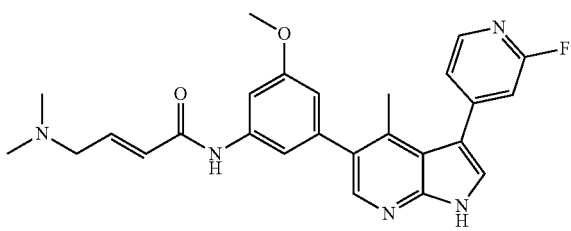 [SMILES: COc1cc(NC(=O)/C=C/CN(C)C)cc(-c2cnc3[nH]cc(-c4ccnc(F)c4)c3c2C)c1]

Step 1: Preparation of (E)-4-(dimethylamino)-N-(3-(3-(2-fluoropyridin-4-yl)-4-methyl-1-tosyl-1H-pyrrolo[2,3-b]pyridin-5-yl)-5-methoxyphenyl)but-2-enamide

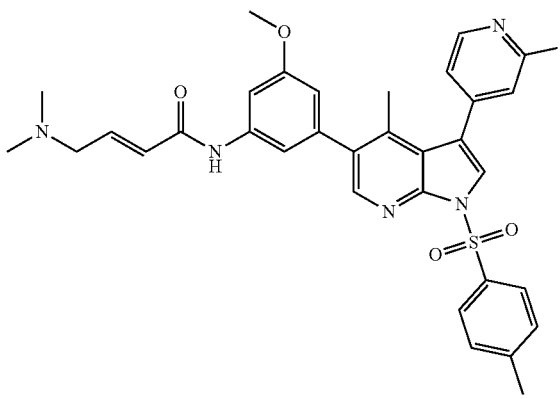

To a solution of 3-(3-(2-fluoropyridin-4-yl)-4-methyl-1-tosyl-1H-pyrrolo[2,3-b]pyridin-5-yl)-5-methoxyaniline from example 6, step 4 (100 mg, 0.20 mmol) in tetrahydrofuran (1.5 mL) was added a solution of 2-chloro-4,6-dimethoxy-1,3,5-triazine (42 mg, 0.24 mmol), 4-methylmorpholine (0.066 mL, 0.60 mmol) and trans-4-dimethylaminocrotonic acid HCl (33 mg, 0.20 mmol). The solution was stirred at ambient temperature for 18 hours. The reaction mixture was quenched with water and extracted with ethyl acetate. The organic layer was washed with water, brine and dried over magnesium sulfate. The mixture was filtered and concentrated in vacuo to provide the crude coupled product. The material was purified using normal phase chromatography (dichloromethane/methanol) to provide (E)-4-(dimethylamino)-N-(3-(3-(2-fluoropyridin-4-yl)-4-methyl-1-tosyl-1H-pyrrolo[2,3-b]pyridin-5-yl)-5-methoxyphenyl)but-2-enamide (33 mg, 27% yield): MS (ES) m/z 614 (M+H).

Step 2: Preparation of (E)-4-(dimethylamino)-N-(3-(3-(2-fluoropyridin-4-yl)-4-methyl-1H-pyrrolo[2,3-b]pyridin-5-yl)-5-methoxyphenyl)but-2-enamide

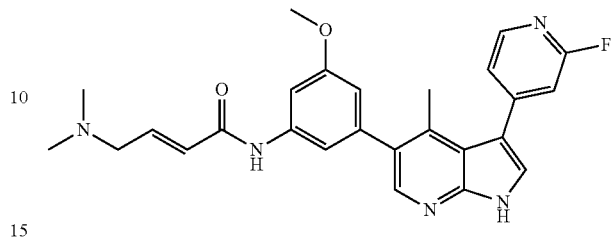

To a solution of (E)-4-(dimethylamino)-N-(3-(3-(2-fluoropyridin-4-yl)-4-methyl-1-tosyl-1H-pyrrolo[2,3-b]pyridin-5-yl)-5-methoxyphenyl)but-2-enamide from step 1 (33 mg, 0.05 mmol) in 1,4-dioxane (1 mL) was added 1.5 M lithium hydroxide (1 mL) and the solution was stirred for 6 hours at ambient temperature. The reaction mixture was partitioned between ethyl acetate and water. The organic layer was washed with water, brine, dried over magnesium sulfate and concentrated to provide (E)-4-(dimethylamino)-N-(3-(3-(2-fluoropyridin-4-yl)-4-methyl-1H-pyrrolo[2,3-b]pyridin-5-yl)-5-methoxyphenyl)but-2-enamide (15 mg, 60% yield): $^1$H NMR (400 MHz, DMSO-d$_6$) δ ppm, 12.23 (s, 1H), 10.13 (s, 1H), 8.23 (d, J=5.09 Hz, 1H), 8.14 (s, 1H), 7.80 (s, 2H), 7.51 (d, J=5.08 Hz, 1H), 7.39 (s, 1H), 7.31 (s, 1H), 7.25 (s, 1H), 6.70 (br. s, 1H), 6.27 (d, J=15.65 Hz, 1H), 3.79 (s, 3H), 3.06 (d, J=6.26 Hz, 2H), 2.30 (s, 3H), 2.17 (s, 6H); MS (ES) m/z 460 (M+H).

Example 8. Preparation of N-(2-fluoro-5-(3-(2-fluoropyridin-4-yl)-1H-pyrrolo[2,3-b]pyridin-5-yl)-3-methoxyphenyl)acrylamide

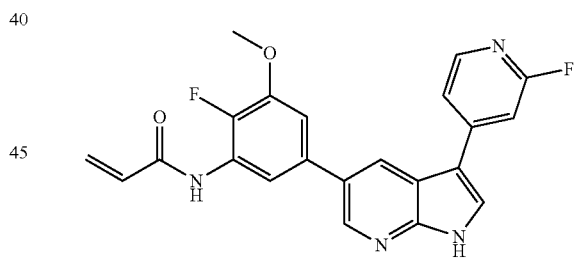

Step 1: Preparation of 2-fluoro-3-hydroxybenzoic acid

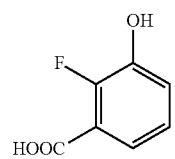 [SMILES: O=C(O)c1cccc(O)c1F]

To the solution of hydrobromic acid in acetic acid (40%, 250 ml) was added 2-fluoro-3-methoxybenzoic acid (25 g, 147 mmol). The mixture was heated at 110° C. overnight. After cooling, acetic acid was removed under reduced pressure. The residue was added water, and extracted with ethyl acetate. The combined extracts were washed with water, brine, and concentrated in vacuo to give the title compound 2-fluoro-3-hydroxybenzoic acid (47.8 g, yield=99%) as a yellow solid, which was used in the next step without further purification: MS (ES) m/z=157 (M+H).

Step 2: Preparation of 4,6-dibromo-2-fluoro-3-hydroxybenzoic acid

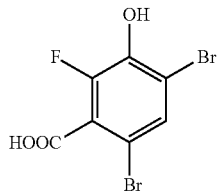 [SMILES: O=C(O)c1c(Br)cc(Br)c(O)c1F]

To a solution of 2-fluoro-3-hydroxybenzoic acid (47.8 g, 0.31 mol) in $CH_2Cl_2$ (950 mL) and acetic acid (150 mL) was added dropwise a solution of bromine (108 g, 0.67 mol) in $CH_2Cl_2$ (350 mL) over 30 min at 0° C. The mixture was then stirred for 30 min at 0° C. The mixture was poured into water (500 mL), and extracted with $CH_2Cl_2$/i-PrOH (10/1). The combined extracts were washed brine, dried over anhydrous $Na_2SO_4$, and concentrated in vacuo to give 4,6-dibromo-2-fluoro-3-hydroxybenzoic acid (92.8 g, yield=97%) as a beige solid which was carried on crude.

Step 3: Preparation of methyl 4,6-dibromo-2-fluoro-3-methoxybenzoate

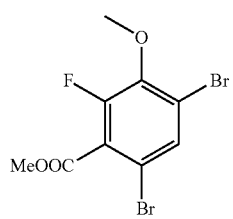

To a solution of 4,6-dibromo-2-fluoro-3-hydroxybenzoic acid (92.8 g, 0.300 mol) in DMF (900 mL) was added $K_2CO_3$ (124 g, 0.9 mol) and iodomethane (136 g, 0.96 mol), and then the mixture was heated at 60° C. overnight. The mixture was partitioned between ethyl acetate and water. The organic layer was concentrate in vacuo. The residue was purified by flash chromatography on silica gel (eluting with 10% EtOAc in petroleum ether) to give 4,6-dibromo-2-fluoro-3-methoxybenzoate (93.4 g, yield=91%) as light brown oil: MS (ES) m/z=341 (M+H).

Step 4: Preparation of methyl 2,4-dibromo-6-fluoro-5-methoxy-3-nitrobenzoate

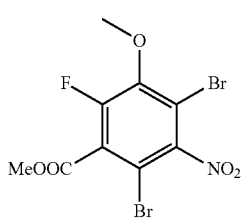 [SMILES: COC(=O)c1c(F)c(OC)c(Br)c([N+](=O)[O-])c1Br]

To a solution of methyl 4,6-dibromo-2-fluoro-3-methoxybenzoate (93.4 g, 0.275 mol) in concentrated $H_2SO_4$ (180 mL) was added $HNO_3$ (20.8 g, 0.33 mmol) dropwise while the temperature was kept at 0-5° C. over 20 min. The mixture was stirred for another 30 min. The mixture was poured into crushed ice and extracted with ethyl acetate. The organic layer was concentrated in vacuo, and the residue was purified by flash chromatography on silica gel (eluting with 10% of EtOAc in petroleum ether) to give methyl 2,4-dibromo-6-fluoro-5-methoxy-3-nitrobenzoate (80 g, yield=75%) as a light yellow solid: MS (ES) m/z=386 (M+H).

Step 5: Preparation of methyl 5-amino-2-fluoro-3-methoxybenzoate

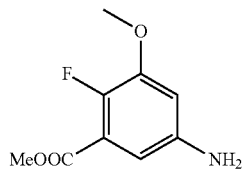

To a solution of methyl 2,4-dibromo-6-fluoro-5-methoxy-3-nitrobenzoate (80 g, 0.21 mol) in MeOH (500 mL) was added Na2CO3 (24 g, 0.23 mol), followed by Pd/C (5 g). The mixture was stirred under 2.5 MPa of hydrogen for 2 h. The mixture was filtered, and the filtrate was concentrated in vacuo. The residue was purified by flash chromatography on silica gel (eluting with 20% of EtOAc in petroleum ether) to give methyl 5-amino-2-fluoro-3-methoxybenzoate (27.5 g, yield=67%) as a beige solid: MS (ES) m/z=200 (M+H).

Step 6: Preparation of methyl 5-bromo-2-fluoro-3-methoxybenzoate

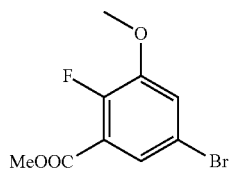

To a solution of $CuBr_2$ (11.2 g, 0.05 mol) in acetonitrile (120 mL) was added t-BuONO (7.7 g, 0.075 mol) at 0° C., followed by methyl 5-amino-2-fluoro-3-methoxybenzoate (10 g, 0.05 mol). The mixture was stirred for 1 h at 0° C. The reaction was quenched with dilute ammonium hydroxide and extracted with ethyl acetate. The combined extracts were washed with water, brine, and concentrated in vacuo. The residue was purified by flash chromatography on silica gel (eluting with 10% EtOAc in petroleum ether) to give methyl 5-bromo-2-fluoro-3-methoxybenzoate (4.6 g, yield=35%) as a yellow oil: MS (ES) m/z=263 (M+H).

Step 7: Preparation of
5-bromo-2-fluoro-3-methoxybenzoic acid

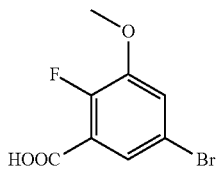

To a solution of methyl 5-bromo-2-fluoro-3-methoxybenzoate (4.6 g, 17.6 mmol) in MeOH (40 mL) was added a solution of lithium hydroxide (3.69 g, 87.8 mmol) in water (10 mL). The mixture was stirred for 2 h at room temperature, and then concentrated to dryness. The residue was dissolved in water, and adjusted to pH=3 with dilute HCl. The white precipitate was extracted with ethyl acetate. The combined extracts were washed with water, and concentrated to dryness. The residue was purified by flash chromatography on silica gel (eluting with 20-50% of EtOAc in petroleum ether) to give 5-bromo-2-fluoro-3-methoxybenzoic acid (3.6 g, yield=82%) as white solid: MS (ES) m/z=249 (M+H).

Step 8: Preparation of tert-butyl
5-bromo-2-fluoro-3-methoxyphenylcarbamate

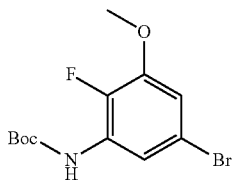 [SMILES: COc1cc(Br)cc(NC(=O)OC(C)(C)C)c1F]

A mixture of 5-bromo-2-fluoro-3-methoxybenzoic acid (3.57 g, 14.4 mmol), triethylamine (2.4 ml, 17 mmol) and diphenylphosphoryl azide (4.75 g, 17 mmol) in t-butyl alcohol (60 mL) was heated at reflux overnight. After cooling to ambient temperature, the solvent was removed. The residue was partitioned between ethyl acetate and aqueous NaOH (1 M). The organic layer was concentrated in vacuo. The residue was purified by flash chromatography on silica gel (eluting with 10% of EtOAc in petroleum ether) to give tert-butyl 5-bromo-2-fluoro-3-methoxyphenylcarbamate (3.2 g, yield=85%) as a white solid: MS (ES) m/z=342 (M+Na).

Step 9: Preparation of tert-butyl 2-fluoro-3-methoxy-5-(4,4,5,5-tetramethyl-1,3,2-dioxaborolan-2-yl)phenylcarbamate

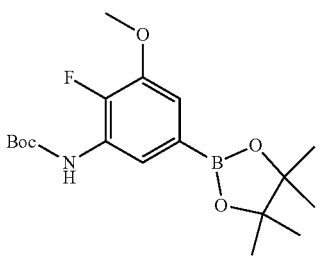 [SMILES: COc1cc(B2OC(C)(C)C(C)(C)O2)cc(NC(=O)OC(C)(C)C)c1F]

A mixture of tert-butyl 5-bromo-2-fluoro-3-methoxyphenylcarbamate (2.80 g, 8.78 mmol), bis(pinacolato)diboron (B$_2$pin$_2$, 2.68 g, 10.54 mmol), potassium acetate (2.58 g, 26.3 mmol), and [1,1'-bis(diphenylphosphino)ferrocene]dichloropalladium(II) (Pd(dppf)Cl$_2$, 643 mg, 0.88 mmol) in dioxane (100 mL) was stirred at 90° C. under nitrogen overnight. After cooling the mixture was filtered through a pad of celite, and the filtrate was concentrated in vacuo. The residue was purified by flash chromatography on silica gel (eluting with 10% of EtOAc in petroleum ether) to give tert-butyl 2-fluoro-3-methoxy-5-(4,4,5,5-tetramethyl-1,3,2-dioxaborolan-2-yl)phenylcarbamate (2.7 g, yield=83%) as white solid: $^1$H NMR (400 MHz, DMSO-d$_6$) δ 8.98 (s, 1H), 7.56 (d, J=6.6 Hz, 1H), 7.03 (d, J=7.0 Hz, 1H), 3.84 (s, 3H), 1.46 (s, 9H), 1.29 (s, 12H); MS (ES) m/z=390 (M+Na)

Step 10: Preparation of tert-butyl (2-fluoro-5-(3-(2-fluoropyridin-4-yl)-1-tosyl-1H-pyrrolo[2,3-b]pyridin-5-yl)-3-methoxyphenyl)carbamate

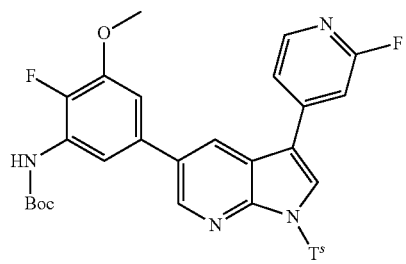 [SMILES: COc1cc(-c2cnc3c(c2)c(-c2ccnc(F)c2)cn3S(=O)(=O)c2ccc(C)cc2)cc(NC(=O)OC(C)(C)C)c1F]

A mixture of tert-butyl (2-fluoro-3-methoxy-5-(4,4,5,5-tetramethyl-1,3,2-dioxaborolan-2-yl)phenyl)carbamate (200 mg, 0.54 mmol), 5-bromo-3-(2-fluoropyridin-4-yl)-1-tosyl-1H-pyrrolo[2,3-b]pyridine (243 mg, 0.54 mmol), K$_2$CO$_3$ (224 mg, 1.62 mmol), and Pd(dppf)Cl$_2$ (37 mg, 0.05 mmol) in 1,4-dioxane (2 mL) and H$_2$O (0.5 mL) was stirred for 2 h at 100° C. under a nitrogen atmosphere. After cooling the solvent was removed under reduced pressure, and the residue purified by flash chromatography on silica gel (eluting with 10-60% of EtOAc in petroleum ether) to give the desired product (115 mg, yield=35%) as an off-white solid: MS (ES) m/z=608 (M+H).

Step 11: Preparation of 2-fluoro-5-(3-(2-fluoropyridin-4-yl)-1-tosyl-1H-pyrrolo[2,3-b]pyridin-5-yl)-3-methoxyaniline

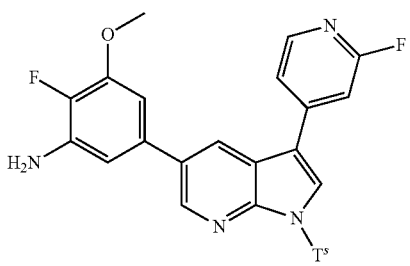 [SMILES: COc1cc(-c2cnc3c(c2)c(-c2ccnc(F)c2)cn3S(=O)(=O)c2ccc(C)cc2)cc(N)c1F]

Trifluoroacetic acid (1.0 mL) was added to a solution of 2-fluoro-5-(3-(2-fluoropyridin-4-yl)-1-tosyl-1H-pyrrolo[2,3-b]pyridin-5-yl)-3-methoxyaniline (115 mg, 0.19 mmol) in dichloromethane (4 mL) and the mixture stirred for 2 h at room temperature. The solvent was removed under reduced pressure to give the product (85 mg, yield=88%) as a light yellow oil, which was used in the next step without further purification: MS (ES) m/z=507 (M+H).

Step 12: Preparation of N-(2-fluoro-5-(3-(2-fluoro-pyridin-4-yl)-1-tosyl-1H-pyrrolo[2,3-b]pyridin-5-yl)-3-methoxyphenyl)acrylamide

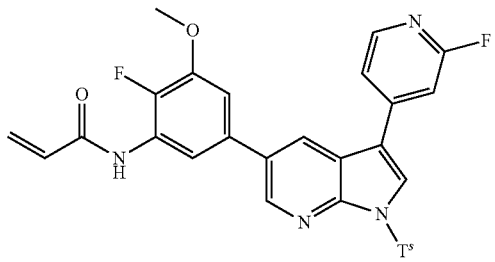 [SMILES: C=CC(=O)Nc1cc(-c2cnc3c(c2)c(-c2ccnc(F)c2)cn3S(=O)(=O)c2ccc(C)cc2)cc(OC)c1F]

To a solution of N-(2-fluoro-5-(3-(2-fluoropyridin-4-yl)-1-tosyl-1H-pyrrolo[2,3-b]pyridin-5-yl)-3-methoxyphenyl)acrylamide (85 mg, 0.17 mmol) and diisopropyethylamine (0.1 mL, 0.5 mmol) in dry dichloromethane (3 mL) was added acryloyl chloride (0.05 mL, 0.25 mmol) at 0° C., and the mixture stirred for 30 min. The mixture was poured into water (30 mL) and extracted with EtOAc (50 mL×3). The combined organic layers were washed with brine, and concentrated in vacuo. The residue was purified by flash chromatography on silica gel (eluting with 55% of EtOAc in petroleum ether) to give the product (80 mg, yield=85%) as a light yellow solid: MS (ES) m/z=561 (M+H).

Step 14: Preparation of N-(2-fluoro-5-(3-(2-fluoropyridin-4-yl)-1H-pyrrolo[2,3-b]pyridin-5-yl)-3-methoxyphenyl)acrylamide

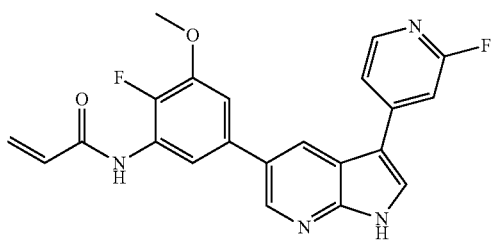 [SMILES: C=CC(=O)Nc1cc(-c2cnc3[nH]cc(-c4ccnc(F)c4)c3c2)cc(OC)c1F]

To a solution of N-(2-fluoro-5-(3-(2-fluoropyridin-4-yl)-1-tosyl-1H-pyrrolo[2,3-b]pyridin-5-yl)-3-methoxyphenyl)-N-methylacrylamide (80 mg, 0.14 mmol) in dry THF (2 mL) was added tetra-n-butylammonium fluoride solution (1.0 M in THF, 0.3 mL, 0.3 mmol), and the mixture stirred at room temperature for 8 h. The mixture was purified by prep-HPLC to give the product (12 mg, yield=21%) as a white solid: $^1$H NMR (400 MHz, DMSO-$d_6$) δ 12.48 (narrow m, 1H), 10.07 (s, 1H), 8.60-8.55 (m, 1H), 8.39 (d, J=2.8 Hz, 1H), 8.23 (d, J=5.3 Hz, 1H), 7.86-7.83 (m, 1H), 7.60 (s, 1H), 7.35 (dd, J=7.4, 1.8 Hz, 1H), 6.64 (dd, J=17.0, 10.2 Hz, 1H), 6.29 (dd, J=17.0, 1.8 Hz, 1H), 5.80 (dd, J=10.2, 1.8 Hz, 1H), 3.99 (s, 3H); MS (ES) m/z=407 (M+H).

Example 9: Preparation of N-(3-(3-(2-methoxypyridin-4-yl)-1H-pyrrolo[2,3-b]pyridin-5-yl)phenyl)-N-methylacrylamide

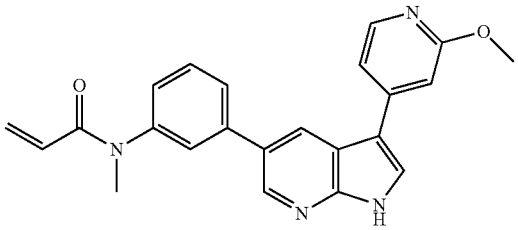 [SMILES: C=CC(=O)N(C)c1cccc(-c2cnc3[nH]cc(-c4ccnc(OC)c4)c3c2)c1]

Step 1: Preparation of tert-butyl (3-(1H-pyrrolo[2,3-b]pyridin-5-yl)phenyl)carbamate

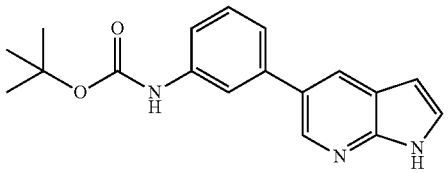 [SMILES: CC(C)(C)OC(=O)Nc1cccc(-c2cnc3[nH]ccc3c2)c1]

To a solution of 5-bromo-1H-pyrrolo[2,3-b]pyridine (196 mg, 1.00 mmol) in 1,4-dioxane (7 mL) and water (3 mL) was added 3-boc-aminophenylboronic acid (237 mg, 1.00 mmol), potassium carbonate (414 mg, 3.00 mmol) and [1,1'-bis(diphenylphosphino)ferrocene]dichloropalladium (II) (36 mg, 0.05 mmol). The solution was treated with microwave radiation at 120° C. for one hour. After cooling the resulting mixture was partitioned between ethyl acetate and water. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (3-(1H-pyrrolo[2,3-b]pyridin-5-yl)phenyl)carbamate as a white solid (113 mg, 37% yield): MS (ES) m/z 310 (M+H).

Step 2: Preparation of tert-butyl (3-(3-iodo-1H-pyrrolo[2,3-b]pyridin-5-yl)phenyl)carbamate

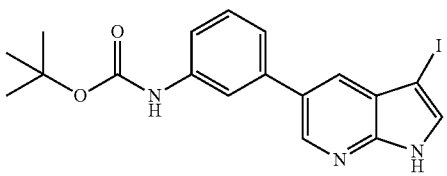 [SMILES: CC(C)(C)OC(=O)Nc1cccc(-c2cnc3[nH]cc(I)c3c2)c1]

To a solution of tert-butyl (3-(1H-pyrrolo[2,3-b]pyridin-5-yl)phenyl)carbamate from step 1 (309 mg, 1.00 mmol) in dichloromethane (5 mL) was added N-iodosuccinimide (225 mg, 1.00 mmol) and the solution was stirred for 2 hours at ambient temperature. The resulting white solid was collected by vacuum filtration to provide tert-butyl (3-(3-iodo-1H-pyrrolo[2,3-b]pyridin-5-yl)phenyl)carbamate (246 mg, 56% yield): MS (ES) m/z 436 (M+H).

Step 3: Preparation of tert-butyl (3-(3-iodo-1-tosyl-1H-pyrrolo[2,3-b]pyridin-5-yl)phenyl)carbamate

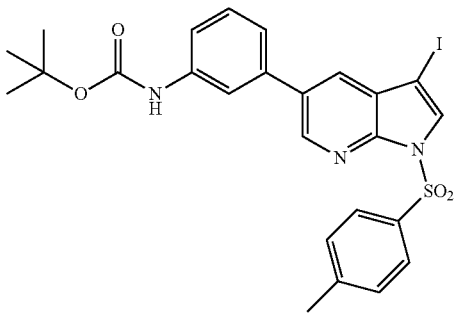 [SMILES: Cc1ccc(S(=O)(=O)n2cc(I)c3cc(-c4cccc(NC(=O)OC(C)(C)C)c4)cnc32)cc1]

To a solution of tert-butyl (3-(3-iodo-1H-pyrrolo[2,3-b]pyridin-5-yl)phenyl)carbamate from step 2 (246 mg, 0.560 mmol) in tetrahydrofuran (3 mL) was added sodium hydride (60% mineral oil dispersion, 34 mg, 0.84 mmol) followed by p-toluenesulfonyl chloride (108 mg, 0.560 mmol) and the solution was stirred for 18 hours at ambient temperature. The reaction mixture was quenched with water and extracted with ethyl acetate. The organic layer was washed with water, brine and dried over magnesium sulfate. The solution was filtered and concentrated in vacuo to provide the crude coupled product. The material was purified using normal phase chromatography (ethyl acetate/heptane) to provide tert-butyl (3-(3-iodo-1-tosyl-1H-pyrrolo[2,3-b]pyridin-5-yl)phenyl)carbamate (325 mg, 98% yield): MS (ES) m/z 590 (M+H).

Step 4: Preparation of tert-butyl (3-(3-(2-methoxypyridin-4-yl)-1-tosyl-1H-pyrrolo[2,3-b]pyridin-5-yl)phenyl)carbamate

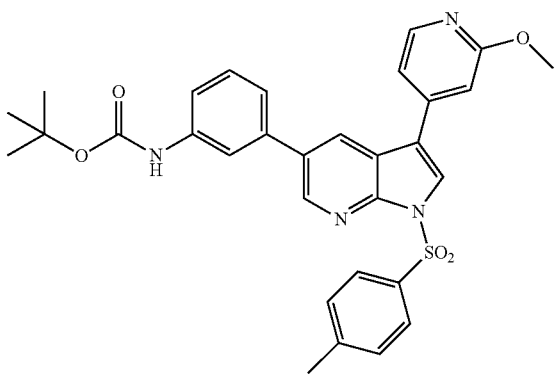 [SMILES: COc1cc(-c2cn(S(=O)(=O)c3ccc(C)cc3)c3ncc(-c4cccc(NC(=O)OC(C)(C)C)c4)cc23)ccn1]

To a solution of tert-butyl (3-(3-iodo-1-tosyl-1H-pyrrolo[2,3-b]pyridin-5-yl)phenyl)carbamate from step 3 (125 mg, 0.21 mmol) in 1,4-dioxane (2 mL) and water (0.5 mL) was added 2-methoxy-4-pyridine boronic acid (32 mg, 0.21 mmol), potassium carbonate (87 mg, 0.63 mmol) and [1,1'-bis(diphenylphosphino)ferrocene]dichloropalladium(II) .DCM (8 mg, 0.01 mmol) and the solution was treated with microwave radiation at 120° C. for one hour. After cooling the resulting solution was partitioned between ethyl acetate and water. The organic layer was washed with water, brine and dried over magnesium sulfate. The mixture was filtered and concentrated in vacuo. The crude material was purified using normal phase chromatography (ethyl acetate/heptane) to provide tert-butyl (3-(3-(2-methoxypyridin-4-yl)-1-tosyl-1H-pyrrolo[2,3-b]pyridin-5-yl)phenyl)carbamate as a white solid (96 mg, 53% yield): MS (ES) m/z 571 (M+H).

Step 5: Preparation of tert-butyl (3-(3-(2-methoxypyridin-4-yl)-1-tosyl-1H-pyrrolo[2,3-b]pyridin-5-yl)phenyl)(methyl)carbamate

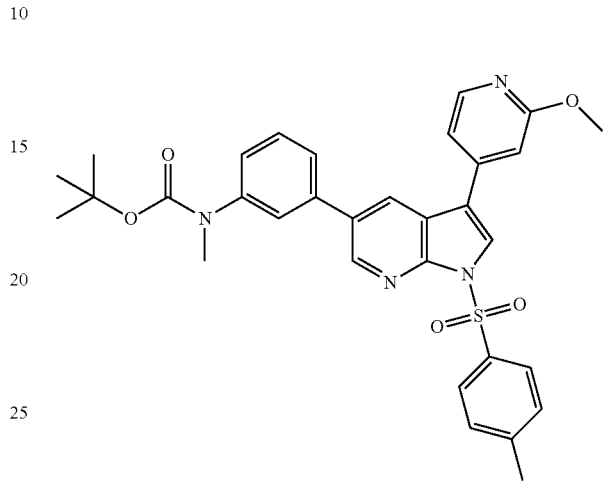

To a solution of tert-butyl (3-(3-(2-methoxypyridin-4-yl)-1-tosyl-1H-pyrrolo[2,3-b]pyridin-5-yl)phenyl)carbamate from step 4 (188 mg, 0.33 mmol) in tetrahydrofuran (2 mL) was added sodium hydride (60% mineral oil dispersion, 20 mg, 0.49 mmol) followed by methyl iodide (0.02 mL, 0.33 mmol). The solution was stirred at ambient temperature. After 1.5 hours the reaction was quenched with water and extracted into ethyl acetate. The organic layer was washed with water and brine, dried over magnesium sulfate, filtered and concentrated. The crude material was purified using normal phase chromatography (ethyl acetate/heptane) to provide tert-butyl (3-(3-(2-methoxypyridin-4-yl)-1-tosyl-1H-pyrrolo[2,3-b]pyridin-5-yl)phenyl)(methyl)carbamate as a colorless oil (120 mg, 62% yield): MS (ES) m/z 585 (M+H).

Step 6: Preparation of N-(3-(3-(2-methoxypyridin-4-yl)-1-tosyl-1H-pyrrolo[2,3-b]pyridin-5-yl)phenyl)-N-methylacrylamide

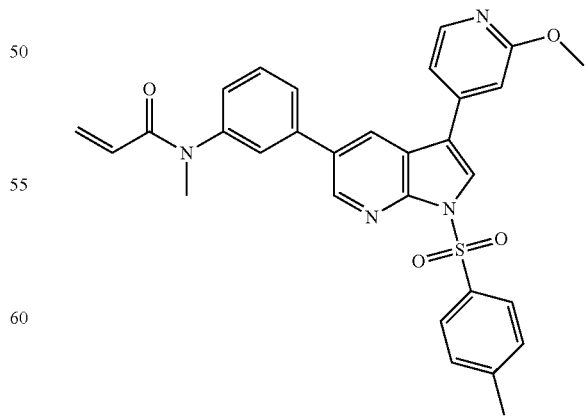

To a solution of tert-butyl (3-(3-(2-methoxypyridin-4-yl)-1-tosyl-1H-pyrrolo[2,3-b]pyridin-5-yl)phenyl)(methyl)carbamate from step 5 (120 mg, 0.20 mmol) in dichloromethane (2 mL) was added trifluoroacetic acid (1 mL) and the solution was stirred for 1 hour at ambient temperature. The solution was concentrated in vacuo to provide the amine salt. The crude amine was dissolved into N,N-dimethylformamide (2 mL) and triethylamine (0.08 mL, 0.60 mmol) was added followed by O-(benzotriazol-1-yl)-N,N,N',N'-tetramethyluronium tetrafluoroborate (96 mg, 0.30 mmol) and acrylic acid (0.014 mL, 0.20 mmol). The solution was stirred at ambient temperature for 18 hours. The reaction mixture was quenched with water and extracted with ethyl acetate. The organic layer was washed with water, brine and dried over magnesium sulfate. The mixture was filtered and concentrated in vacuo to provide the crude coupled product. The material was purified using normal phase chromatography (ethyl acetate/heptane) to provide N-(3-(3-(2-methoxypyridin-4-yl)-1-tosyl-1H-pyrrolo[2,3-b]pyridin-5-yl)phenyl)-N-methylacrylamide (81 mg, 75% yield): MS (ES) m/z 539 (M+H).

Step 7: Preparation of N-(3-(3-(2-methoxypyridin-4-yl)-1H-pyrrolo[2,3-b]pyridin-5-yl)phenyl)-N-methylacrylamide

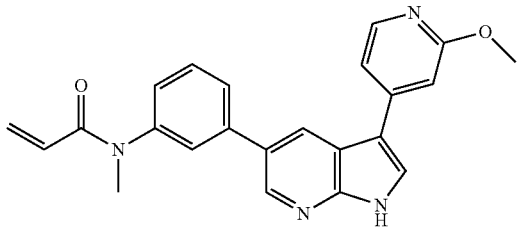 [SMILES: C=CC(=O)N(C)c1cccc(-c2cnc3[nH]cc(-c4ccnc(OC)c4)c3c2)c1]

To a solution of N-(3-(3-(2-methoxypyridin-4-yl)-1-tosyl-1H-pyrrolo[2,3-b]pyridin-5-yl)phenyl)-N-methylacrylamide from step 6 (81 mg, 0.15 mmol) in 1,4-dioxane (1 mL) was added 1.5 M lithium hydroxide (1 mL) and the solution was stirred for 18 hours at ambient temperature. The reaction mixture was partitioned between ethyl acetate and water. The organic layer was washed with water, brine, dried over magnesium sulfate and concentrated. The residue was purified using normal phase chromatography (dichloromethane/methanol) to provide N-(3-(3-(2-methoxypyridin-4-yl)-1H-pyrrolo[2,3-b]pyridin-5-yl)phenyl)-N-methylacrylamide as a white solid (8 mg, 14% yield): $^1$H NMR (400 MHz, DMSO-$d_6$) δ ppm, 12.31 (s, 1H), 8.63 (s, 1H), 8.54 (s, 1H), 8.27 (s, 1H), 8.17 (s, 1H), 7.79 (br. s, 2H), 7.59-7.59 (m, 1H), 7.47 (s, 1H), 7.29 (d, J=6.65 Hz, 1H), 7.22 (s, 1H), 6.19 (br. s, 2H), 5.60 (br. s, 1H). 3.89 (s, 3H), 3.34 (s, 3H). MS (ES) m/z 385 (M+H).

Embodiments include the compounds in Table 2. The following compounds in Table 2 were made using the methods described above. Mass spectroscopic analysis is expected to yield m/z values within 1 D of the calculated value.

TABLE 2

| | | | |
|---|---|---|---|
| | | Compound Examples | |
| Ex. # | Structure | Name | Spectral Data |
| 6 | | (E)-4-(dimethylamino)-N-(3-(3-(6-methyl-7-oxo-6,7-dihydro-1H-pyrrolo[2,3-c]-pyridin-4-yl)-1H-pyrrolo[2,3-b]-pyridin-5-yl)-phenyl)but-2-enamide | $^1$H NMR (400 MHz, DMSO-$d_6$) δ ppm, 12.11 (s, 1H), 11.96 (s, 1H), 10.40 (s, 1H), 8.54 (s, 1H), 8.20 (s, 1H), 7.95 (s, 1H), 7.75 (s, 1H), 7.70-7.68 (m, 1H), 7.48-7.44 (m, 4H), 7.33 (br. s, 1H), 6.78-6.74 (m, 1H), 6.48-6.44 (m, 1H), 6.40 (s, 1H), 3.99-3.92 (m, 2H), 3.61 (s, 3H), 2.80 (s, 6H). MS (ES) m/z 467 (M + H). |
| 7 | | N-(3-(3-(3-cyanophenyl)-1H-pyrrolo[2,3-b]-pyridin-5-yl)-5-(trifluoromethyl)-phenyl)acrylamide | $^1$H NMR (400 MHz, DMSO-$d_6$) δ ppm, 12.28 (s, 1H), 10.59 (s, 1H), 8.59 (s, 2H), 8.27 (s, 1H), 8.24 (s, 1H), 8.19 (d, J = 7.83 Hz, 1H), 8.15 (s, 1H), 8.11 (s, 1H), 7.84 (s, 1H), 7.72-7.64 (m, 2H), 6.50-6.43 (m, 1H), 6.33 (d, J = 16.82 Hz, 1H), 5.85 (d, J = 11.34 Hz, 1H). MS (ES) m/z 433 (M + H). |

TABLE 2-continued

Compound Examples

| Ex. # | Structure | Name | Spectral Data |
|---|---|---|---|
| 8 | 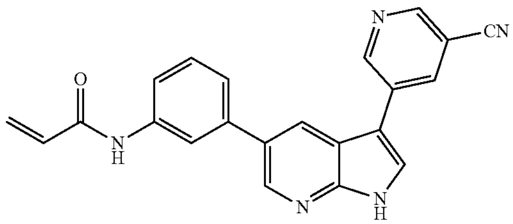 [SMILES: C=CC(=O)Nc1cccc(-c2cnc3[nH]cc(-c4cncc(C#N)c4)c3c2)c1] | N-(3-(3-(5-cyano-pyridin-3-yl)-1H-pyrrolo[2,3-b]-pyridin-5-yl)-phenyl)acrylamide | $^1$H NMR (400 MHz, DMSO-d$_6$) δ ppm, 12.35 (s, 1H), 10.27 (s, 1H), 9.33 (s, 1H), 8.88 (s, 1H), 8.74 (s, 1H), 8.58 (s, 1H), 8.57 (s, 1H), 8.25 (s, 1H), 7.98 (s, 1H), 7.76 (d, J = 8.22 Hz, 1H), 7.54 (d, J = 7.82 Hz, 1H), 7.46 (t, J = 7.82 Hz, 1H), 6.51-6.44 (m, 1H), 6.29 (d, J = 16.83 Hz, 1H), 5.78 (d, J = 10.17 Hz, 1H). MS (ES) m/z 366. (M + H). |
| 9 | 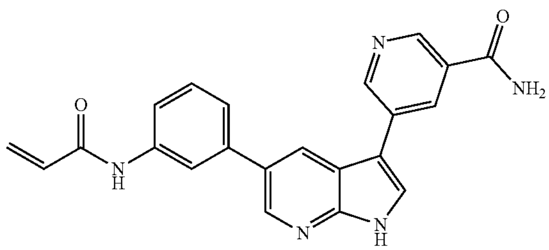 [SMILES: C=CC(=O)Nc1cccc(-c2cnc3[nH]cc(-c4cncc(C(N)=O)c4)c3c2)c1] | 5-(5-(3-acryl-amidophenyl)-1H-pyrrolo[2,3-b]-pyridin-3-yl)-nicotinamide | $^1$H NMR (400 MHz, DMSO-d$_6$) δ ppm, 12.25 (s, 1H), 10.27 (s, 1H), 9.15 (s, 1H), 8.91 (s, 1H), 8.57 (s, 1H), 8.52 (s, 1H), 8.48 (s, 1H), 8.26 (br. s, 1H), 8.15 (s, 1H), 7.97 (s, 1H), 7.76 (d, J = 8.22 Hz, 1H), 7.65 (br. s, 1H), 7.52-7.46 (m, 2H), 6.50-6.47 (m, 1H), 6.28 (d, J = 16.83 Hz, 1H), 5.78 (d, J = 10.18 Hz, 1H). MS (ES) m/z 384 (M + H). |
| 10 | 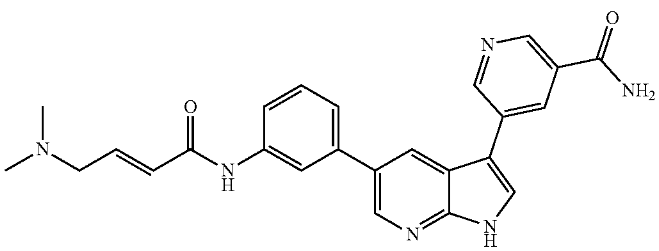 [SMILES: CN(C)C/C=C/C(=O)Nc1cccc(-c2cnc3[nH]cc(-c4cncc(C(N)=O)c4)c3c2)c1] | (E)-5-(5-(3-(4-(dimethylamino)-but-2-enamido)-phenyl)-1H-pyrrolo[2,3-b]-pyridin-3-yl)-nicotinamide | $^1$H NMR (400 MHz, DMSO-d$_6$) δ ppm, 12.26 (s, 1H), 10.44 (s, 1H), 9.15 (s, 1H), 8.91 (s, 1H), 8.57 (s, 1H), 8.52 (s, 1H), 8.46 (s, 1H), 8.26 (br. s, 1H), 8.15 (s, 1H), 7.98 (s, 1H), 7.74 (d, J = 7.44 Hz, 1H), 7.65 (s, 1H), 7.55-7.46 (m, 2H), 6.79-6.75 (m, 1H), 6.48 (d, J = 15.65 Hz, 1H), 3.98-3.91 (m, 2H), 2.81 (s, 6H). MS (ES) m/z 441 (M + H). |
| 11 | 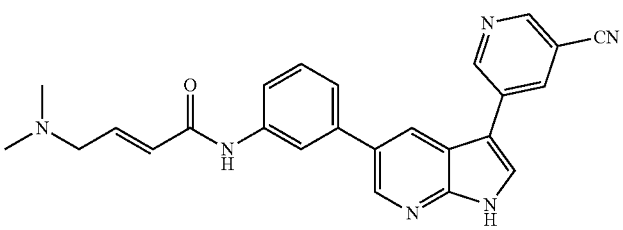 [SMILES: CN(C)C/C=C/C(=O)Nc1cccc(-c2cnc3[nH]cc(-c4cncc(C#N)c4)c3c2)c1] | (E)-N-(3-(3-(5-cyanopyridin-3-yl)-1H-pyrrolo-[2,3-b]pyridin-5-yl)phenyl)-4-(dimethylamino)-but-2-enamide | MS (ES) m/z 423 (M + H). |
| 12 | 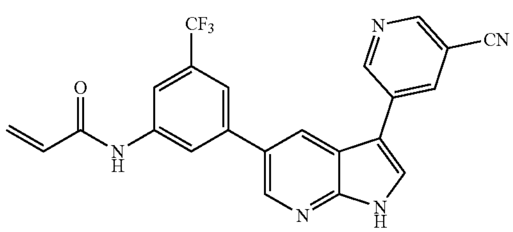 [SMILES: C=CC(=O)Nc1cc(-c2cnc3[nH]cc(-c4cncc(C#N)c4)c3c2)cc(C(F)(F)F)c1] | N-(3-(3-(5-cyano-pyridin-3-yl)-1H-pyrrolo[2,3-b]-pyridin-5-yl)-5-(trifluoromethyl)-phenyl)acrylamide | $^1$H NMR (400 MHz, DMSO-d$_6$) δ ppm, 12.41 (s, 1H), 10.61 (s, 1H), 9.37 (s, 1H), 8.89 (s, 1H), 8.75 (s, 1H), 8.69 (s, 1H), 8.62 (s, 1H), 8.28 (s, 1H), 8.24 (s, 1H), 8.13 (s, 1H), 7.88 (s, 1H), 6.51-6.44 (m, 1H), 6.33 (d, J = 16.04 Hz, 1H), 5.85 (d, J = 9.39 Hz, 1H). MS (ES) m/z 434 (M + H). |
| 13 | 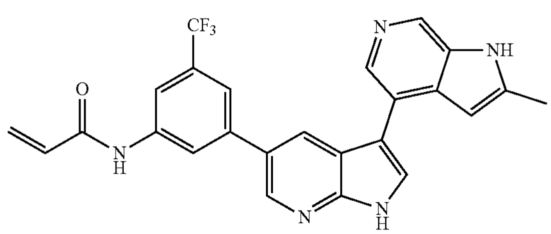 [SMILES: C=CC(=O)Nc1cc(-c2cnc3[nH]cc(-c4cncc5[nH]c(C)cc45)c3c2)cc(C(F)(F)F)c1] | N-(3-(2'-methyl-1H,1'H-[3,4'-bipyrrolo[2,3-b]-pyridin]-5-yl)-5-(trifluoro-methyl)phenyl)-acrylamide | MS (ES) m/z 462 (M + H). |

TABLE 2-continued

Compound Examples

| Ex. # | Structure | Name | Spectral Data |
|---|---|---|---|
| 14 | 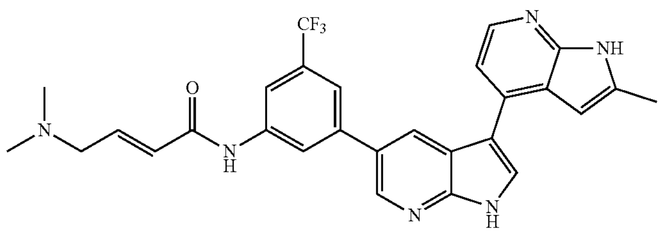 | (E)-4-(dimethyl-amino)-N-(3-(2'-methyl-1H,1'H-[3,4'-bipyrrolo-[2,3-b]pyridin]-5-yl)-5-(trifluoro-methyl)phenyl)-but-2-enamide | MS (ES) m/z 519 (M + H). |
| 15 | 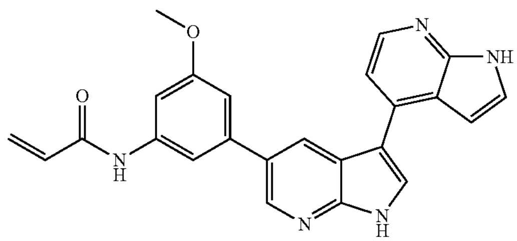 [SMILES: C=CC(=O)Nc1cc(OC)cc(-c2cnc3[nH]cc(-c4ccnc5[nH]ccc45)c3c2)c1] | N-(3-(1H,1'H-[3,4'-bipyrrolo-[2,3-b]pyridin]-5-yl)-5-methoxy-phenyl)acrylamide | $^1$H NMR (400 MHz, DMSO-d$_6$) δ ppm, 12.25 (s, 1H), 11.70 (s, 1H), 10.25 (s, 1H), 8.59 (d, J = 2.0 Hz, 1H), 8.37 (d, J = 2.0 Hz, 1H), 8.29 (d, J = 4.8 Hz, 1H), 8.11 (s, 1H), 7.47-7.50 (m, 3H), 7.41 (d, J = 4.8 Hz, 1H), 7.03 (t, J = 1.6 Hz, 1H), 6.69 (d, J = 3.6 Hz, 1H), 6.43-6.41 (m, 1H), 6.31-6.30 (m, 1H), 5.78 (dd, J = 2.0 Hz, 8.0 Hz, 1H), 3.83 (d, J = 6.8 Hz, 3H). MS (ES) m/z 410 (M + H). |
| 16 | 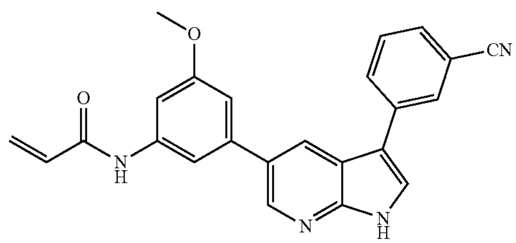 [SMILES: C=CC(=O)Nc1cc(OC)cc(-c2cnc3[nH]cc(-c4cccc(C#N)c4)c3c2)c1] | N-(3-(3-(3-cyano-phenyl)-1H-pyrrolo[2,3-b]-pyridin-5-yl)-5-methoxyphenyl)-acrylamide | $^1$H NMR (400 MHz, DMSO-d$_6$) δ ppm, 12.21 (s, 1H), 10.25 (s, 1H), 8.54 (s, 1H), 8.47 (s, 1H), 8.24 (s, 1H), 8.16 (d, J = 7.83 Hz, 1H), 8.13 (s, 1H), 7.71-7.63 (m, 2H), 7.48 (s, 2H), 7.06 (s, 1H), 6.49-6.42 (m, 1H), 6.28 (d, J = 15.26 Hz, 1H), 5.78 (d, J = 12.13 Hz, 1H), 3.84 (s, 3H). MS (ES) m/z 395 (M + H). |
| 17 | 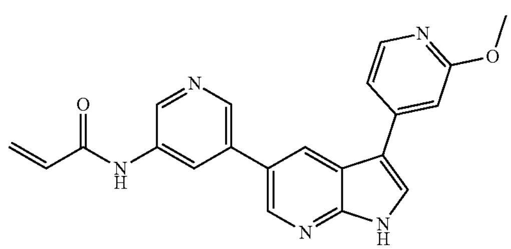 [SMILES: C=CC(=O)Nc1cncc(-c2cnc3[nH]cc(-c4ccnc(OC)c4)c3c2)c1] | N-(5-(3-(2-methoxypyridin-4-yl)-1H-pyrrolo-[2,3-b]pyridin-5-yl)pyridin-3-yl)-acrylamide | $^1$H NMR (400 MHz, DMSO-d$_6$) δ ppm, 12.39 (s, 1H), 10.50 (s, 1H), 8.88 (s, 1H), 8.75 (s, 1H), 8.59 (s, 1H), 8.57 (s, 1H), 8.39 (s, 1H), 8.28 (s, 1H), 8.18 (d, J = 5.48 HZ, 1H), 7.48 (d, J = 5.48 Hz, 1H), 7.23 (s, 1H), 6.53-6.46 (m, 1H), 6.33 (d, J = 16.82 Hz, 1H), 5.85 (d, J = 9.39 Hz, 1H), 3.90 (s, 3H). MS (ES) m/z 372 (M + H). |
| 18 | 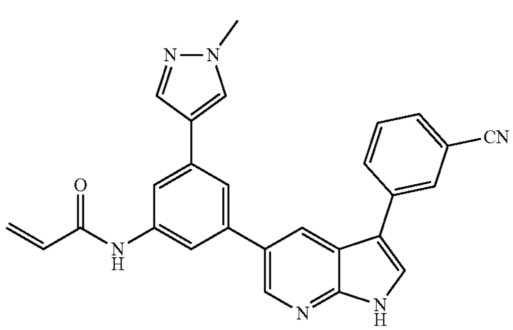 [SMILES: C=CC(=O)Nc1cc(-c2cnc3[nH]cc(-c4cccc(C#N)c4)c3c2)cc(-c2cnn(C)c2)c1] | N-(3-(3-(3-cyano-phenyl)-1H-pyrrolo[2,3-b]-pyridin-5-yl)-5-(1-methyl-1H-pyrazol-4-yl)-phenyl)acrylamide | $^1$H NMR (400 MHz, DMSO-d6) δ ppm, 12.24 (s, 1H), 10.29 (s, 1H), 8.60 (s, 1H), 8.53 (s, 1H), 8.19 (m, 4H), 7.93 (d, J = 10.4 Hz, 2H), 7.70 (m, 4H), 6.48 (s, 1H), 6.30 (d, J = 16 Hz, 1H), 5.80 (m, 1H).3.88 (d, J = 6 Hz, 3H). MS (ES) m/z 445 (M + H). |

TABLE 2-continued

| Ex. # | Structure | Name | Spectral Data |
|---|---|---|---|
| 19 | 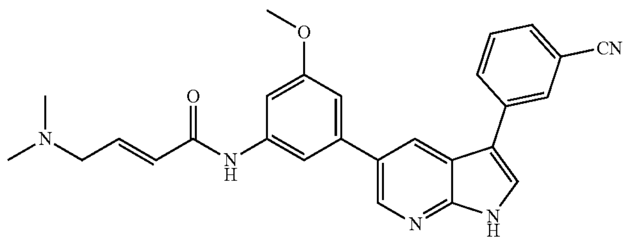 [SMILES: COc1cc(NC(=O)/C=C/CN(C)C)cc(-c2cnc3[nH]cc(-c4cccc(C#N)c4)c3c2)c1] | (E)-N-(3-(3-(3-cyanophenyl)-1H-pyrrolo[2,3-b]-pyridin-5-yl)-5-methoxyphenyl)-4-(dimethyl-amino)but-2-enamide | $^1$H NMR (400 MHz, DMSO-d$_6$) δ ppm, 12.21 (s, 1H), 10.16 (s, 1H), 8.54 (s, 1H), 8.47 (s, 1H), 8.24 (s, 1H), 8.16 (d, J = 7.44 Hz, 1H), 8.13 (d, J = 2.35, 1H), 7.72-7.64 (m, 2H), 7.48 (s, 1H), 7.46 (s, 1H), 7.04 (s, 1H), 6.79-6.72 (m, 1H), 6.28 (d, J = 14.87 Hz, 1H), 3.83 (s, 3H), 3.08 (d, J = 5.09 Hz, 2H), 2.19 (s, 6H). MS (ES) m/z 452 (M + H). |
| 20 | 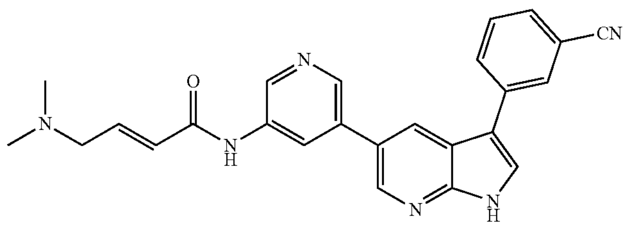 | (E)-N-(5-(3-(3-cyanophenyl)-1H-pyrrolo[2,3-b]pyridin-5-yl)pyridin-3-yl)-4-(dimethyl-amino)but-2-enamide | $^1$H NMR (400 MHz, DMSO-d$_6$) δ ppm, 12.28 (s, 1H), 10.49 (s, 1H), 8.87 (s, 1H), 8.76 (s, 1H), 8.60 (s, 1H), 8.58 (s, 1H), 8.39 (s, 1H), 8.27 (s, 1H), 8.19 (d, J = 7.43 Hz, 1H), 8.16 (s, 1H), 7.71 (d, J = 8.22 Hz, 1H), 7.65 (t, J = 7.43 Hz, 1H), 6.52-6.46 (m, 1H), 6.32 (d, J = 15.26 Hz, 1H), 5.84 (d, J = 11.34 Hz, 1H). MS (ES) m/z 366 (M + H). |
| 21 | 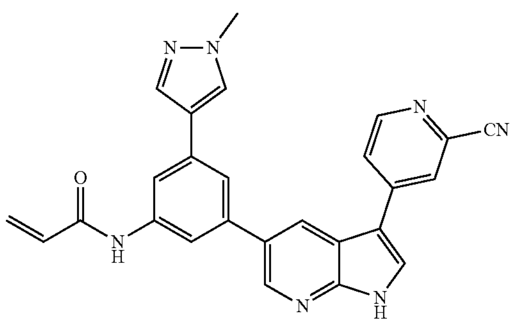 [SMILES: C=CC(=O)Nc1cc(-c2cnc3[nH]cc(-c4ccnc(C#N)c4)c3c2)cc(-c2cnn(C)c2)c1] | N-(3-(3-(2-cyano-pyridin-4-yl)-1H-pyrrolo[2,3-b]pyridin-5-yl)-5-(1-methyl-1H-pyrazol-4-yl)-phenyl)acrylamide | $^1$H NMR (400 MHz, DMSO-d6) δ ppm, 12.21 (s, 1H), 8.70 (m, 2H), 8.63 (d, J = 2.0 Hz, 1H), 8.51 (m, 2H), 8.23 (m, 2H), 7.94 (m, 2H), 7.77 (s, 1H), 7.70 (s, 1H), 6.50 (m, 1H), 6.29 (dd, J = 1.6 Hz, 15.2 Hz, 1H), 5.80 (dd, J = 2.0 Hz, 8.6 Hz, 1H), 3.90 (s, 3H). MS (ES) m/z 446 (M + H). |
| 22 | 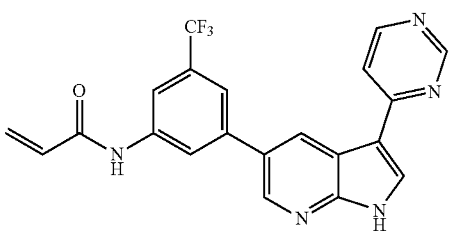 [SMILES: C=CC(=O)Nc1cc(-c2cnc3[nH]cc(-c4ccncn4)c3c2)cc(C(F)(F)F)c1] | N-(3-(3-(pyrimidin-4-yl)-1H-pyrrolo[2,3-b]pyridin-5-yl)-5-(trifluoro-methyl)phenyl)-acrylamide | $^1$H NMR (400 MHz, DMSO-d$_6$) δ ppm, 12.60 (s, 1H), 10.66 (s, 1H), 9.17 (s, 1H), 9.04 (s, 1H), 8.70 (d, J = 5.48 Hz, 1H), 8.67-8.64 (m, 2H), 8.28 (s, 1H), 8.14 (s, 1H), 8.03 (d, J = 5.48 Hz, 1H), 7.76 (s, 1H), 6.52-6.45 (m, 1H), 6.35 (d, J = 15.26 Hz, 1H), 5.86 (d, J = 11.74 Hz, 1H). MS (ES) m/z 410 (M + H). |
| 23 | 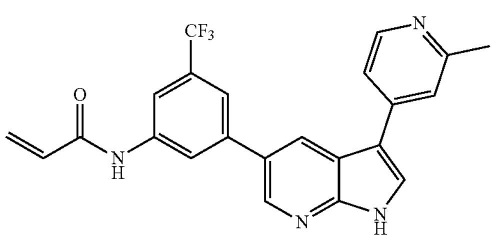 [SMILES: C=CC(=O)Nc1cc(-c2cnc3[nH]cc(-c4ccnc(C)c4)c3c2)cc(C(F)(F)F)c1] | N-(3-(3-(2-methyl-pyridin-4-yl)-1H-pyrrolo[2,3-b]-pyridin-5-yl)-5-(trifluoromethyl)-phenyl)acrylamide | $^1$H NMR (400 MHz, DMSO-d6) δ ppm, 12.37 (s, 1H), 10.60 (s, 1H), 8.60 (dd, J = 2.0 Hz, 5.6 Hz, 2H), 8.45 (d, J = 5.6 Hz, 1H), 8.26 (s, 2H), 8.12 (s, 1H), 7.84 (s, 1H), 7.69 (s, 1H), 7.66 (m, 2H), 6.48 (m, 1H), 6.34 (m, 1H), 5.85 (dd, J = 1.6 Hz, 8.0 Hz, 1H), 2.51 (m, 3H). MS (ES) m/z 423 (M + H). |

TABLE 2-continued

Compound Examples

| Ex. # | Structure | Name | Spectral Data |
|---|---|---|---|
| 24 | 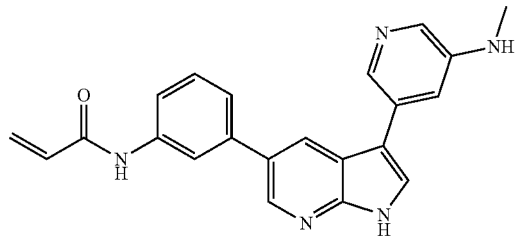 [SMILES: C=CC(=O)Nc1cccc(-c2cnc3[nH]cc(-c4cncc(NC)c4)c3c2)c1] | N-(3-(3-(5-(methylamino)-pyridin-3-yl)-1H-pyrrolo[2,3-b]-pyridin-5-yl)-phenyl)acrylamide | $^1$H NMR (400 MHz, DMSO-d6) δ ppm, 12.12 (s, 1H), 10.29 (s, 1H), 8.56 (d, J = 2.0 Hz, 1H), 8.37 (d, J = 2.0 Hz, 1H), 8.21 (d, J = 2.0 Hz, 1H), 7.98 (m, 2H), 7.86 (d, J = 2.8 Hz, 1H), 7.74 (d, J = 7.6 Hz, 1H), 7.48 (m, 2H), 7.22 (t, J = 2.0 Hz, 2H), 6.47 (m, 1H), 6.29 (m, 1H), 5.96 (m, 1H), 5.79 (dd, J = 2.0 Hz, J = 8.0 Hz, 1H), 2.78 (d, J = 5.2 Hz, 3H). MS (ES) m/z 370 (M + H). |
| 25 | 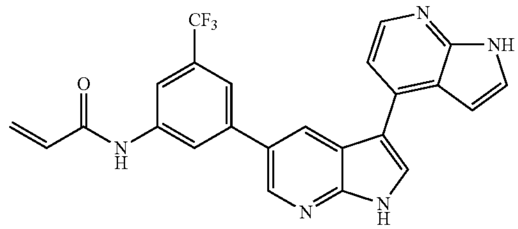 [SMILES: C=CC(=O)Nc1cc(-c2cnc3[nH]cc(-c4ccnc5[nH]ccc45)c3c2)cc(C(F)(F)F)c1] | N-(3-(1H,1'H-[3,4'-bipyrrolo-[2,3-b]pyridin]-5-yl)-5-(trifluoro-methyl)phenyl)-acrylamide | MS (ES) m/z 448 (M + H). |
| 26 | 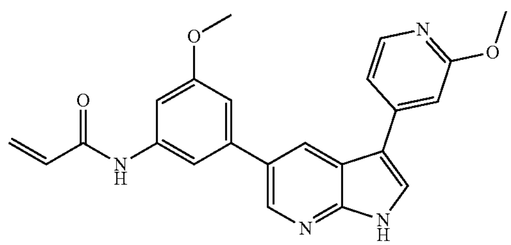 [SMILES: C=CC(=O)Nc1cc(OC)cc(-c2cnc3[nH]cc(-c4ccnc(OC)c4)c3c2)c1] | N-(3-methoxy-5-(3-(2-methoxy-pyridin-4-yl)-1H-pyrrolo[2,3-b]-pyridin-5-yl)-phenyl)acrylamide | $^1$H NMR (400 MHz, DMSO-d6) δ ppm, 12.33 (s, 1H), 10.28 (s, 1H), 8.56 (d, J = 2.0 Hz, 1H), 8.45 (d, J = 2.0 Hz, 1H), 5.28 (s, 1H), 8.18 (d, J = 5.6 Hz, 1H), 7.46 (m, 3H), 7.2 (d, J = 0.4 Hz, 1H), 7.06 (t, J = 2.0 Hz, 1H), 6.45 (m, 1H), 6.31 (m, 1H), 5.79 (dd, J = 2.0 Hz, 8.0 Hz, 1H), 3.90 (s, 3H), 3.85 (s, 3H). MS (ES) m/z 400 (M + H). |
| 27 | 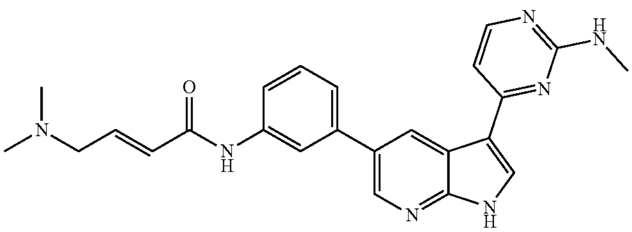 | (E)-4-(dimethyl-amino)-N-(3-(3-(2-(methylamino)-pyrimidin-4-yl)-1H-pyrrolo[2,3-b]pyridin-5-yl)phenyl)but-2-enamide | $^1$H NMR (400 MHz, DMSO-d6) δ ppm, 12.15 (s, 1H), 10.20 (s, 1H), 9.08 (d, J = 2.0 Hz, 1H), 8.52 (d, J = 2.4 Hz, 1H), 8.21 (s, 1H), 8.09 (s, 1H), 7.66 (d, J = 2.4 Hz, 1H), 7.43 (m, 2H), 7.26 (d, J = 4.4 Hz, 1H), 6.77 (m, 1H), 6.28 (m, 2H), 3.07 (m, 2H), 2.97 (s, 3H), 2.25 (s, 6H). MS (ES) m/z 428 (M + H). |
| 28 | 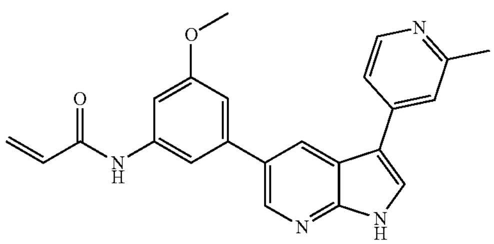 [SMILES: C=CC(=O)Nc1cc(OC)cc(-c2cnc3[nH]cc(-c4ccnc(C)c4)c3c2)c1] | N-(3-methoxy-5-(3-(2-methyl-pyridin-4-yl)-1H-pyrrolo[2,3-b]-pyridin-5-yl)-phenyl)acrylamide | $^1$H NMR (400 MHz, DMSO-d6) δ ppm, 12.29 (s, 1H), 10.25 (s, 1H), 8.52 (dd, J = 13.3 Hz, 1.57 Hz, 2H), 8.43 (d, J = 5.10 Hz, 1H), 8.29 (s, 1H), 7.67 (s, 1H), 7.62 (d, J = 5.09 Hz, 1H), 7.48 (s, 3H), 7.05 (s, 1H), 6.49-6.42 (m, 2H), 6.30 (d, J = 1.56 Hz, 1H), 6.26 (J = 1.96 Hz, 1H), 5.78 (dd, J = 8.22 Hz, 1.95 Hz, 1H), 3.84 (s, 3H). MS (ES) m/z 385 (M + H). |
| 29 | 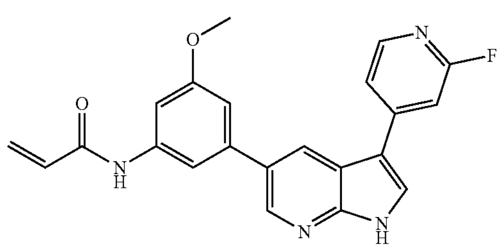 [SMILES: C=CC(=O)Nc1cc(OC)cc(-c2cnc3[nH]cc(-c4ccnc(F)c4)c3c2)c1] | N-(3-(3-(2-fluoro-pyridin-4-yl)-1H-pyrrolo[2,3-b]-pyridin-5-yl)-5-methoxyphenyl)-acrylamide | $^1$H NMR (400 MHz, DMSO-d6) δ ppm, 12.46 (s, 1H), 10.25 (s, 1H), 8.56 (d, J = 3.52 Hz, 2H), 8.38 (d, J = 2.27 Hz, 1H), 8.22 (d, J = 5.48 Hz, 1H), 7.82 (d, J = 4.31 Hz, 1H), 7.59 (s, 1H), 7.49 (d, J = 1.56 Hz, 2H), 7.08 (s, 1H), 6.49-6.42 (m, 1H), 6.30 (s, 1H), 5.77 (d, J = 10.17 Hz, 1H), 3.84 (s, 3H). MS (ES) m/z 389 (M + H). |

TABLE 2-continued

Compound Examples

| Ex. # | Structure | Name | Spectral Data |
|---|---|---|---|
| 30 | 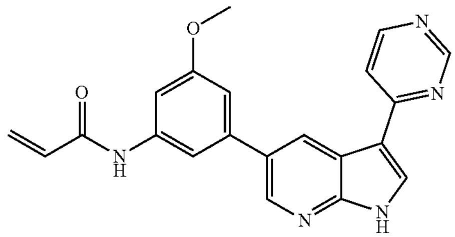 [SMILES: C=CC(=O)Nc1cc(OC)cc(-c2cnc3[nH]cc(-c4ccncn4)c3c2)c1] | N-(3-methoxy-5-(3-(pyrimidin-4-yl)-1H-pyrrolo-[2,3-b]pyridin-5-yl)phenyl)-acrylamide | MS (ES) m/z 372 (M + H). |
| 21 | 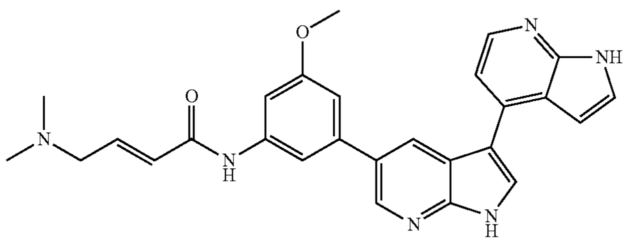 [SMILES: COc1cc(NC(=O)/C=C/CN(C)C)cc(-c2cnc3[nH]cc(-c4ccnc5[nH]ccc45)c3c2)c1] | (E)-N-(3-(1H,1'H-[3,4'-bipyrrolo[2,3-b]pyridin]-5-yl)-5-methoxyphenyl)-4-(dimethylamino)-but-2-enamide | $^1$H NMR (400 MHz, DMSO-d6) δ ppm, 12.31 (s, 1H), 11.71 (s, 1H), 10.79 (s, 1H), 8.59 (s, 1H), 8.37 (s, 1H), 8.28 (s, 1H), 8.10 (s, 1H), 7.46 (m, 4H). MS (ES) m/z 467 (M + H). |
| 32 | 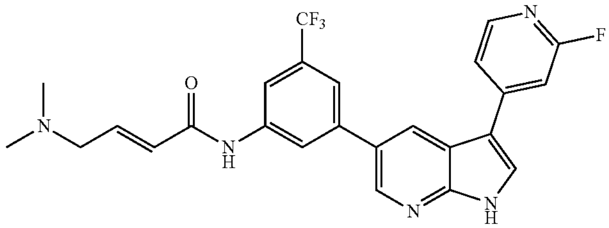 [SMILES: CN(C)C/C=C/C(=O)Nc1cc(-c2cnc3[nH]cc(-c4ccnc(F)c4)c3c2)cc(C(F)(F)F)c1] | (E)-4-(dimethyl-amino)-N-(3-(3-(2-fluoropyridin-4-yl)-1H-pyrrolo-[2,3-b]pyridin-5-yl)-5-(trifluoro-methyl)phenyl)-but-2-enamide | $^1$H NMR (400 MHz, DMSO-d$_6$) δ ppm, 12.54 (s, 1H), 10.78 (s, 1H), 9.77 (br. s, 1H), 8.67 (s, 1H), 8.63 (s, 1H), 8.43 (d, J = 2.74 Hz, 1H), 8.25 (s, 1H), 8.24 (s, 1H), 8.14 (s, 1H), 7.91 (s, 1H), 7.86 (d, J = 5.09 Hz, 1H), 7.63 (s, 1H), 6.86-6.78 (m, 1H), 6.49 (d, J = 15.65 Hz, 1H), 4.03-3.96 (m, 2H), 2.82 (s, 6H). MS (ES) m/z 484 (M + H). |
| 33 | 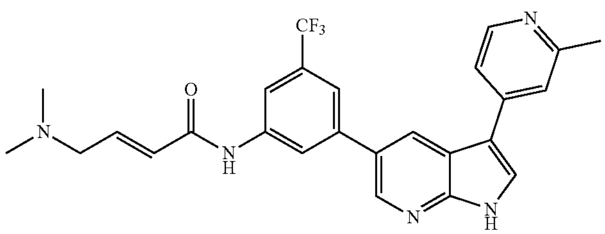 | (E)-4-(dimethyl-amino)-N-(3-(3-(2-methylpyridin-4-yl)-1H-pyrrolo-[2,3-b]-pyridin-5-yl)-5-(trifluoro-methyl)phenyl)-but-2-enamide | $^1$H NMR (400 MHz, DMSO-d$_6$) δ ppm, 13.03 (s, 1H), 10.86 (s, 1H), 9.91 (s, 1H), 8.84 (s, 1H), 8.79 (s, 1H), 8.68 (s, 1H), 8.66 (s, 1H), 8.34 (s, 1H), 8.31 (d, J = 5.87 Hz, 1H), 8.25 (s, 1H), 7.90 (s, 1H), 6.86-6.78 (m, 1H), 6.50 (d, J = 14.87 Hz, 1H), 4.03-3.94 (m, 2H), 2.82 (s, 6H), 2.74 (s, 3H). MS (ES) m/z 480 (M + H). |
| 34 | 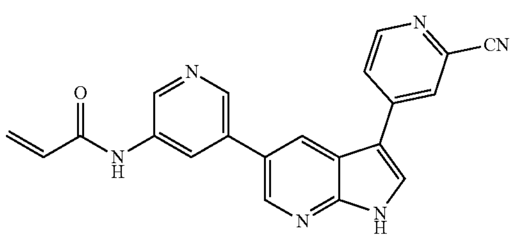 | N-(5-(3-(2-cyano-pyridin-4-yl)-1H-pyrrolo[2,3-b]-pyridin-5-yl)-pyridin-3-yl)-acrylamide | $^1$H NMR (400 MHz, DMSO-d$_6$) δ ppm, 12.62 (s, 1H), 10.57 (s, 1H), 8.93 (s, 1H), 8.81 (s, 1H), 8.80 (s, 1H), 8.70 (d, J = 5.09 Hz, 1H), 8.63 (s, 1H), 8.52 (s, 2H), 8.44 (s, 1H), 8.23 (d, J = 3.91 Hz, 1H), 6.54-6.47 (m, 1H), 6.34 (d, J = 16.43 Hz, 1H), 5.56 (d, J = 11.35, 1H). MS (ES) m/z 367 (M + H). |
| 35 | 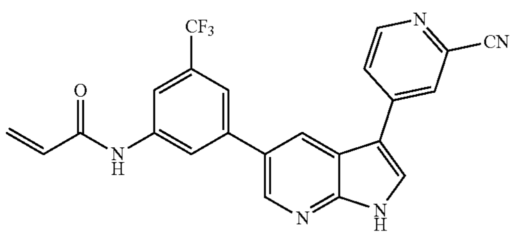 [SMILES: C=CC(=O)Nc1cc(-c2cnc3[nH]cc(-c4ccnc(C#N)c4)c3c2)cc(C(F)(F)F)c1] | N-(3-(3-(2-cyano-pyridin-4-yl)-1H-pyrrolo[2,3-b]-pyridin-5-yl)-5-(trifluoromethyl)-phenyl)acrylamide | $^1$H NMR (400 MHz, DMSO-d$_6$) δ ppm, 12.60 (s, 1H), 10.61 (s, 1H), 8.76 (s, 1H), 8.71 (d, J = 5.08 Hz, 1H), 8.62 (s, 1H), 8.52 (s, 1H), 8.50 (s, 1H), 8.26 (s, 1H), 8.23 (d, J = 5.48 Hz, 1H), 8.13 (s, 1H), 7.87 (s, 1H), 6.51-6.44 (m, 1H), 6.34 (d, J = 16.82 Hz, 1H), 5.85 (d, J = 11.35 Hz, 1H). MS (ES) m/z 434 (M + H). |

TABLE 2-continued

Compound Examples

| Ex. # | Structure | Name | Spectral Data |
|---|---|---|---|
| 36 | 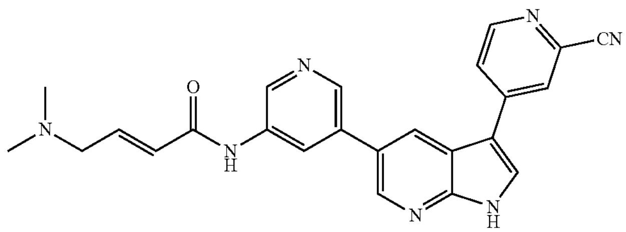 [SMILES: CN(C)C/C=C/C(=O)Nc1cncc(-c2cnc3[nH]cc(-c4ccnc(C#N)c4)c3c2)c1] | (E)-N-(5-(3-(2-cyanopyridin-4-yl)-1H-pyrrolo[2,3-b]pyridin-5-yl)pyridin-3-yl)-4-(dimethylamino)but-2-enamide | $^1$H NMR (400 MHz, DMSO-d$_6$) δ ppm, 12.30 (s, 1H), 10.75 (s, 1H), 8.91 (s, 1H), 8.81 (s, 1H), 8.61 (s, 1H), 8.59 (s, 1H), 8.42 (s, 1H), 8.27 (s, 1H), 8.20 (s, 1H0, 8.18 (br. s, 1H), 7.72 (d, J = 7.43 Hz, 1H), 7.67-7.63 (m, 1H), 6.87-6.79 (m, 1H), 6.52 (d, J = 15.65 Hz, 1H), 4.01-3.95 (m, 2H), 2.82 (s, 3H), 2.81 (s, 3H). MS (ES) m/z 423 (M + H). |
| 37 | 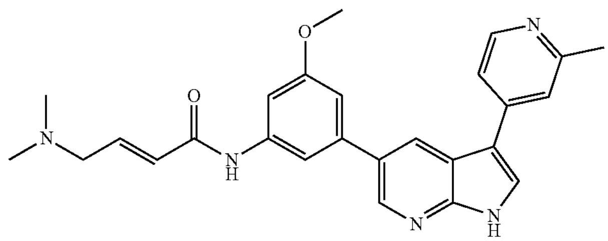 | (E)-4-(dimethylamino)-N-(3-methoxy-5-(3-(2-methylpyridin-4-yl)-1H-pyrrolo[2,3-b]pyridin-5-yl)phenyl)but-2-enamide | $^1$H NMR (400 MHz, DMSO-d6) δ ppm, 12.91 (s, 1H), 10.55 (s, 1H), 8.70 (d, J = 4.70 Hz, 2H), 8.62-8.60 (m, 2H), 8.25-8.20 (m, 2H), 7.56 (s, 1H), 7.48 (s, 1H), 7.11 (s, 1H), 6.81-6.74 (m, 1H), 6.52-6.49 (m, 1H), 3.98 (d, J = 7.05 Hz, 2H), 3.85 (s, 3H), 2.81 (s, 6H), 2.71 (s, 3H). MS (ES) m/z 442 (M + H). |
| 38 | 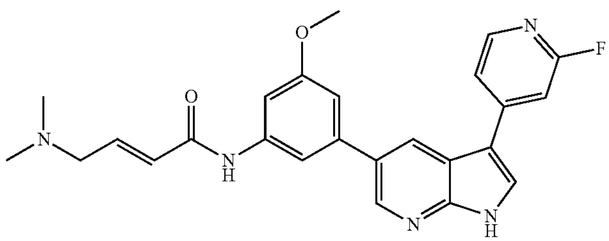 [SMILES: COc1cc(NC(=O)/C=C/CN(C)C)cc(-c2cnc3[nH]cc(-c4ccnc(F)c4)c3c2)c1] | (E)-4-(dimethylamino)-N-(3-(3-(2-fluoropyridin-4-yl)-1H-pyrrolo[2,3-b]pyridin-5-yl)-5-methoxyphenyl)but-2-enamide | $^1$H NMR (400 MHz, DMSO-d6) δ ppm, 12.47 (s, 1H), 10.44 (s, 1H), 8.56 (d, J = 6.26 Hz, 2H), 8.40 (d, J = 2.74 Hz, 1H), 8.23 (J = 5.48 Hz, 1H), 7.83 (d, J = 5.48 Hz, 1H), 7.59 (s, 1H), 7.51-7.46 (m, 3H), 7.11 (d, J = 7.83 Hz, 1H), 6.80-6.73 (m, 1H), 6.50-6.46 (m, 1H), 3.96 (s, 1H), 3.85 (s, 3H), 2.81 (d, J = 5.0 Hz, 6H). MS (ES) m/z 446 (M + H). |
| 39 | 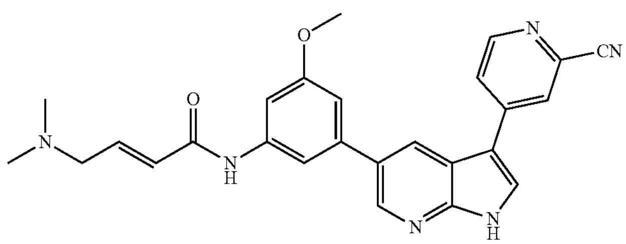 [SMILES: COc1cc(NC(=O)/C=C/CN(C)C)cc(-c2cnc3[nH]cc(-c4ccnc(C#N)c4)c3c2)c1] | (E)-N-(3-(3-(2-cyanopyridin-4-yl)-1H-pyrrolo[2,3-b]pyridin-5-yl)-5-methoxyphenyl)-4-(dimethylamino)-but-2-enamide | MS (ES) m/z 453 (M + H). |
| 40 | 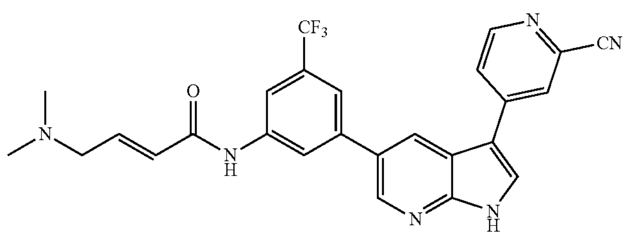 [SMILES: CN(C)C/C=C/C(=O)Nc1cc(-c2cnc3[nH]cc(-c4ccnc(C#N)c4)c3c2)cc(C(F)(F)F)c1] | (E)-N-(3-(3-(2-cyanopyridin-4-yl)-1H-pyrrolo[2,3-b]pyridin-5-yl)-5-(trifluoromethyl)phenyl)-4-(dimethylamino)but-2-enamide | $^1$H NMR (400 MHz, DMSO-d$_6$) δ ppm, 12.62 (s, 1H), 10.80 (s, 1H), 8.76 (s, 1H), 8.71 (d, J = 5.09 Hz, 1H), 8.62 (s, 1H), 8.52 (s, 2H), 8.25-8.22 (m, 2H), 8.14 (s, 1H), 6.86-6.78 (m, 1H), 6.49 (d, J = 15.65 Hz, 1H), 3.99 (d, J = 6.65 Hz, 2H), 2.82 (s, 6H). MS (ES) m/z 491 (M + H). |
| 41 | 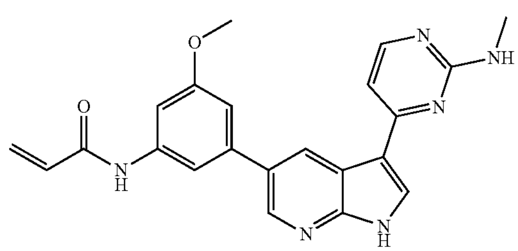 [SMILES: C=CC(=O)Nc1cc(OC)cc(-c2cnc3[nH]cc(-c4ccnc(NC)n4)c3c2)c1] | N-(3-methoxy-5-(3-(2-(methylamino)pyrimidin-4-yl)-1H-pyrrolo[2,3-b]pyridin-5-yl)phenyl)acrylamide | $^1$H NMR (400 MHz, DMSO-d6) δ ppm, 13.72 (s, 1H), 12.97 (s, 1H), 10.29 (s, 1H), 9.25 (d, J = 5.6 Hz, 1H), 9.02 (s, 1H), 8.70 (d, J = 7.76 Hz, 2H), 8.12 (d, J = 6.8 Hz, 1H), 7.83 (s, 1H), 7.24 (s, 1H), 7.05 (s, 1H), 6.58 (d, J = 7.2 Hz, 1H), 6.46 (m, 1H), 6.31 (d, J = 1.6 Hz, 1H), 6.27 (d, J = 2.0 Hz, 1H), 5.80 (dd, J = 1.6 Hz, 8.4 Hz, 1H), 3.84 (s, 3H), 3.77 (s, 3H). MS (ES) m/z 401 (M + H). |

TABLE 2-continued

Compound Examples

| Ex. # | Structure | Name | Spectral Data |
|---|---|---|---|
| 42 | 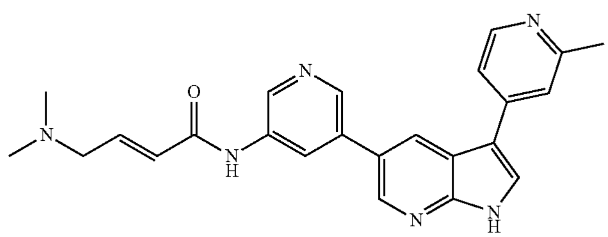 | (E)-4-(dimethylamino)-N-(5-(3-(2-methylpyridin-4-yl)-1H-pyrrolo[2,3-b]pyridin-5-yl)pyridin-3-yl)but-2-enamide | $^1$H NMR (400 MHz, DMSO-d6) δ ppm, 12.37 (s, 1H), 10.42 (s, 1H), 8.86 (d, J = 2.14 Hz, 1H), 8.73 (d, J = 2.0 Hz, 1H), 8.58 (dd, J = 1.6 Hz, 15.2 Hz, 1H), 8.44 (d, J = 5.2 Hz, 1H), 8.39 (t, J = 2.0 Hz, 1H), 8.26 (s, 1H), 7.70 (s, 1H), 7.65 (m, 1H), 6.80 (m, 1H), 6.32 (d, J = 15.2 Hz, 1H), 3.10 (dd, J = 1.2 Hz, 4.4 Hz, 2H), 2.51 (s, 3H), 2.20 (s, 6H). MS (ES) m/z 413 (M + H). |
| 43 | 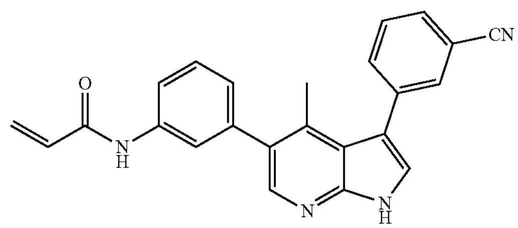 [SMILES: C=CC(=O)Nc1cccc(-c2cnc3[nH]cc(-c4cccc(C#N)c4)c3c2C)c1] | N-(3-(3-(3-cyanophenyl)-4-methyl-1H-pyrrolo[2,3-b]pyridin-5-yl)-phenyl)acrylamide | $^1$H NMR (400 MHz, DMSO-d$_6$) δ ppm, 12.02 (s, 1H), 10.23 (s, 1H), 8.12 (s, 1H), 7.96 (s, 1H), 7.85 (d, J = 7.83 Hz, 1H), 7.78 (d, J = 7.43 Hz, 1H), 7.72 (s, 1H), 7.68 (d, J = 8.61 Hz, 1H), 7.64-7.60 (m, 2H), 7.43-7.39 (m, 1H), 6.49-6.42 (m, 1H), 6.27 (d, J = 17.22 Hz, 1H), 5.77 (d, J = 9.78 Hz, 1H). 2.20 (s, 3H). MS (ES) m/z 379 (M + H). |
| 44 | 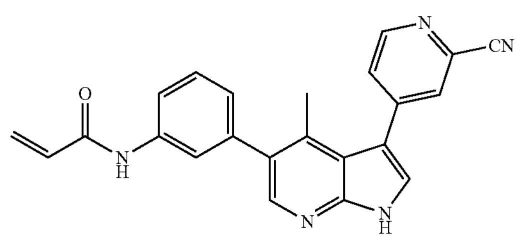 [SMILES: C=CC(=O)Nc1cccc(-c2cnc3[nH]cc(-c4ccnc(C#N)c4)c3c2C)c1] | N-(3-(3-(2-cyanopyridin-4-yl)-4-methyl-1H-pyrrolo[2,3-b]-pyridin-5-yl)-phenyl)acrylamide | $^1$H NMR (400 MHz, DMSO-d$_6$) δ ppm, 12.32 (s, 1H), 10.25 (s, 1H), 8.72 (d, J = 5.09 Hz, 1H), 8.22 (s, 1H), 8.16 (s, 1H), 7.88 (s, 2H), 7.76 (s, 1H), 7.68 (d, J = 8.21 Hz, 1H), 7.45-7.41 (m, 1H), 7.14 (d, J = 7.83 Hz, 1H), 6.49-6.43 (m, 1H), 6.27 (d, J = 16.82 Hz, 1H), 5.77 (d, J = 11.34 Hz, 1H), 2.29 (s, 3H). MS (ES) m/z 380 (M + H). |
| 45 | 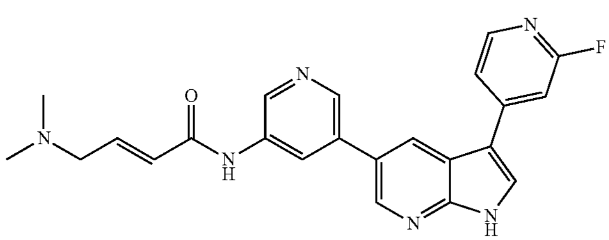 [SMILES: CN(C)C/C=C/C(=O)Nc1cncc(-c2cnc3[nH]cc(-c4ccnc(F)c4)c3c2)c1] | (E)-4-(dimethylamino)-N-(5-(3-(2-fluoropyridin-4-yl)-1H-pyrrolo[2,3-b]pyridin-5-yl)pyridin-3-yl)but-2-enamide | $^1$H NMR (400 MHz, DMSO-d6) δ ppm, 12.45 (s, 1H), 10.43 (s, 1H), 8.86 (d, J = 2.4 Hz, 1H), 8.75 (d, J = 2.0 Hz, 1H), 8.68 (d, J = 2.0 Hz, 1H), 8.61 (d, J = 2.0 Hz, 1H), 8.41 (m, 2H), 8.22 (d, J = 5.2 Hz, 1H), 7.86 (d, J = 5.2 Hz, 1H), 7.63 (s, 1H), 6.81 (m, 1H), 6.32 (d, J = 15.6 Hz, 1H), 3.10 (dd, J = 1.2 Hz, 4.4 Hz, 2H), 2.19 (s, 6H). MS (ES) m/z 417 (M + H). |
| 46 | 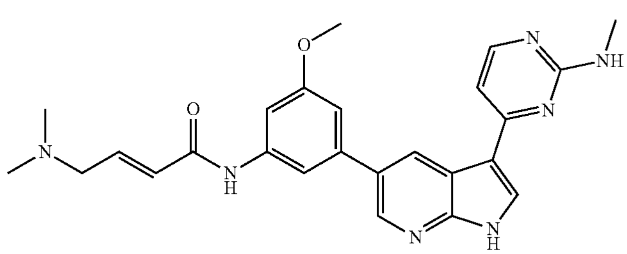 | (E)-4-(dimethylamino)-N-(3-methoxy-5-(3-(2-(methylamino)-pyrimidin-4-yl)-1H-pyrrolo[2,3-b]-pyridin-5-yl)-phenyl)but-2-enamide | $^1$H NMR (400 MHz, DMSO-d6) δ ppm, 12.96 (t, J = 4.0 Hz, 1H), 10.47 (s, 1H), 9.90 (s, 1H), 9.26 (s, 1H), 9.02 (d, J = 2.0 Hz, 1H), 8.69 (s, 2H), 8.13 (d, J = 7.2 Hz, 1H), 7.76 (s, 1H), 7.29 (s, 1H), 7.06 (s, 1H), 6.77 (m, 1H), 6.59 (d, J = 2.4 Hz, 1H), 6.47 (d, J = 7.2 Hz, 1H), 3.97 (d, J = 6.8 Hz, 2H), 3.85 (d, J = 12.0 Hz, 3H), 3.19 (d, J = 3.2 Hz, 3H), 2.82 (s, 6H). MS (ES) m/z 457 (M + H). |

TABLE 2-continued

Compound Examples

| Ex. # | Structure | Name | Spectral Data |
|---|---|---|---|
| 47 | 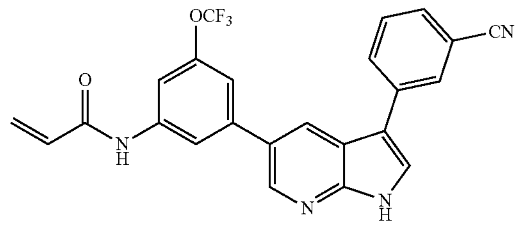 [SMILES: C=CC(=O)Nc1cc(OC(F)(F)F)cc(-c2cnc3[nH]cc(-c4cccc(C#N)c4)c3c2)c1] | N-(3-(3-(3-cyano-phenyl)-1H-pyrrolo[2,3-b]-pyridin-5-yl)-5-(trifluoromethoxy)-phenyl)acrylamide | ¹H NMR (400 MHz, DMSO-d₆) δ ppm, 12.27 (s, 1H), 10.54 (s, 1H), 8.56 (s, 1H), 8.55 (s, 1H), 8.27 (s, 1H), 8.19 (d, J = 7.44 Hz, 1H), 8.15 (s, 1H), 7.96 (s, 1H), 7.85 (s, 1H), 7.72-7.64 (m, 2H), 7.54 (s, 1H), 6.49-6.42 (m, 1H), 6.32 (d, J = 16.82 Hz, 1H), 5.84 (d, J = 10.18 Hz, 1H). MS (ES) m/z 449 (M + H). |
| 48 | 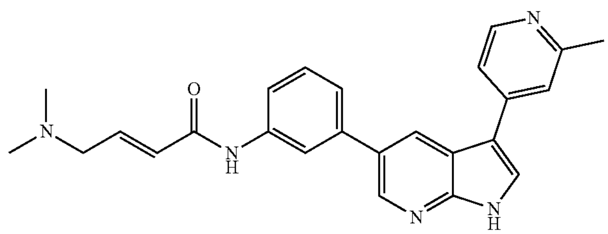 | (E)-4-(dimethyl-amino)-N-(3-(3-(2-methylpyridin-4-yl)-1H-pyrrolo-[2,3-b]pyridin-5-yl)phenyl)but-2-enamide | ¹H NMR (400 MHz, DMSO-d6) δ ppm, 12.92 (s, 1H), 10.56 (s, 1H), 8.73 (d, J = 5.6 Hz, 2H), 8.62 (m, 2H), 8.23 (m, 2H), 8.03 (s, 1H), 7.77 (d, J = 7.6 Hz, 1H), 7.54 (m, 2H), 6.71 (m, 1H), 6.52 (d, J = 15.2 Hz, 1H), 3.98 (d, J = 6.8 Hz, 2H), 2.82 (s, 6H), 2.72 (s, 3H). MS (ES) m/z 412 (M + H). |
| 49 | 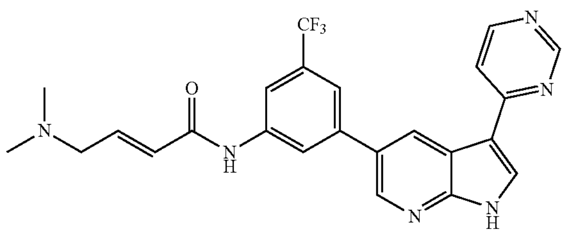 [SMILES: CN(C)C/C=C/C(=O)Nc1cc(-c2cnc3[nH]cc(-c4ccncn4)c3c2)cc(C(F)(F)F)c1] | (E)-4-(dimethyl-amino)-N-(3-(3-(pyrimidin-4-yl)-1H-pyrrolo[2,3-b]pyridin-5-yl)-5-(trifluoro-methyl)phenyl)-but-2-enamide | ¹H NMR (400 MHz, DMSO-d₆) δ ppm, 12.60 (s, 1H), 10.56 (s, 1H), 9.16 (s, 1H), 9.03 (s, 1H), 8.70 (d, J = 5.47 Hz, 1H), 8.66 (s, 1H), 8.64 (s, 1H), 8.27 (s, 1H), 8.13 (s, 1H), 8.03 (d, J = 5.87 Hz, 1H), 7.74 (s, 1H), 6.86-6.79 (m, 1H), 6.31 (d, J = 15.26 Hz, 1H), 3.10 (d, J = 5.48 Hz, 2H), 2.20 (s, 6H). MS (ES) m/z 467 (M + H). |
| 50 | 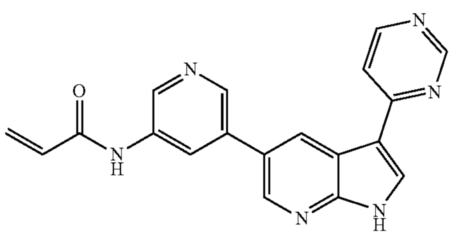 [SMILES: C=CC(=O)Nc1cncc(-c2cnc3[nH]cc(-c4ccncn4)c3c2)c1] | N-(5-(3-(pyrimidin-4-yl)-1H-pyrrolo-[2,3-b]pyridin-5-yl)pyridin-3-yl)acrylamide | MS (ES) m/z 343 (M + H). |
| 51 | 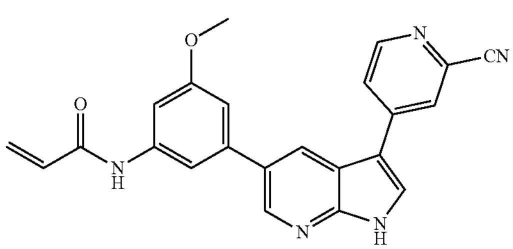 [SMILES: C=CC(=O)Nc1cc(OC)cc(-c2cnc3[nH]cc(-c4ccnc(C#N)c4)c3c2)c1] | N-(3-(3-(2-cyano-pyridin-4-yl)-1H-pyrrolo[2,3-b]-pyridin-5-yl)-5-methoxyphenyl)-acrylamide | ¹H NMR (400 MHz, DMSO-d6) δ ppm, 12.35 (s, 1H), 10.25 (s, 1H), 9.33 (d, J = 1.96 Hz, 1H), 8.87 (s, 1H), 8.73 (s, 1H), 8.57 (s, 2H), 8.25 (s, 1H), 7.49 (d, J = 7.04 Hz, 2H), 7.10 (s, 1H), 6.52-6.42 (m, 1H), 6.30-6.26 (m, 1H), 5.78 (d, J = 9.39 Hz, 1H), 3.84 (s, 3H). MS (ES) m/z 396 (M + H). |
| 52 | 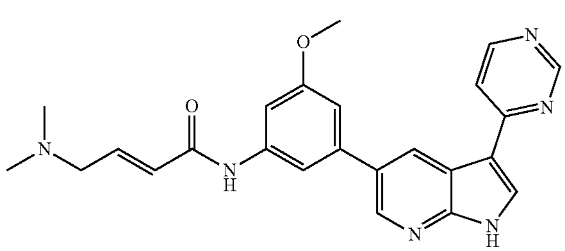 [SMILES: COc1cc(NC(=O)/C=C/CN(C)C)cc(-c2cnc3[nH]cc(-c4ccncn4)c3c2)c1] | (E)-4-(dimethyl-amino)-N-(3-methoxy-5-(3-(pyrimidin-4-yl)-1H-pyrrolo-[2,3-b]pyridin-5-yl)phenyl)but-2-enamide | MS (ES) m/z 429 (M + H). |

TABLE 2-continued

Compound Examples

| Ex. # | Structure | Name | Spectral Data |
|---|---|---|---|
| 53 | 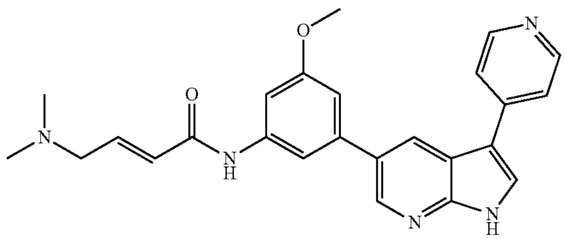 [SMILES: COc1cc(NC(=O)/C=C/CN(C)C)cc(-c2cnc3[nH]cc(-c4ccncc4)c3c2)c1] | (E)-4-(dimethylamino)-N-(3-methoxy-5-(3-(pyridin-4-yl)-1H-pyrrolo[2,3-b]pyridin-5-yl)phenyl)but-2-enamide | MS (ES) m/z 428 (M + H). |
| 54 | 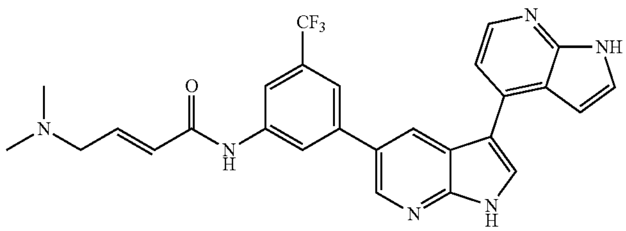 [SMILES: CN(C)C/C=C/C(=O)Nc1cc(-c2cnc3[nH]cc(-c4ccnc5[nH]ccc45)c3c2)cc(C(F)(F)F)c1] | (E)-N-(3-(1H,1'H-[3,4'-bipyrrolo[2,3-b]pyridin]-5-yl)-5-(trifluoromethyl)phenyl)-4-(dimethylamino)-but-2-enamide | MS (ES) m/z 505 (M + H). |
| 55 | 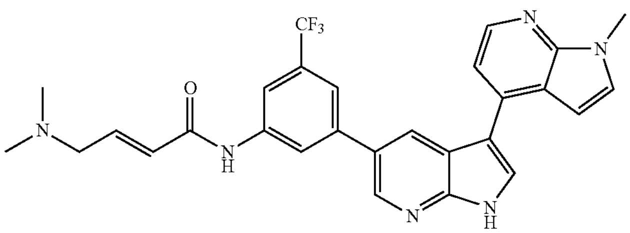 | (E)-4-(dimethylamino)-N-(3-(1'-methyl-1H,1'H-[3,4'-bipyrrolo[2,3-b]pyridin]-5-yl)-5-(trifluoromethyl)phenyl)-but-2-enamide | $^1$H NMR (400 MHz, DMSO-d6) δ ppm, 12.48 (s, 1H), 11.80 (s, 1H), 10.77 (s, 1H), 8.65 (s, 1H), 8.47 (d, J = 1.56 Hz, 1H), 8.30 (d, J = 5.09 Hz, 1H), 8.21-8.14 (m, 4H), 7.84 (s, 1H), 7.53 (s, 1H), 7.49 (d, J = 5.09 Hz, 1H), 6.83-6.78 (m, 1H), 6.73 (s, 1H), 6.47 (d, J = 15.65 Hz, 1H), 3.98 (s, 3H), 2.80 (s, 6H). MS (ES) m/z 520 (M + H). |
| 56 | 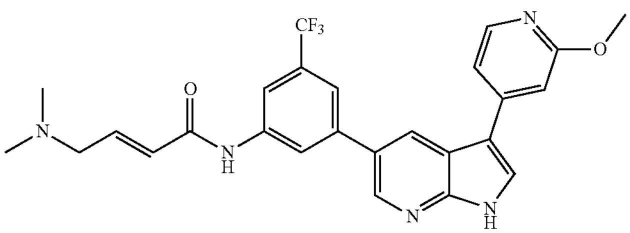 | (E)-4-(dimethylamino)-N-(3-(3-(2-methoxypyridin-4-yl)-1H-pyrrolo[2,3-b]pyridin-5-yl)-5-(trifluoromethyl)phenyl)but-2-enamide | $^1$H NMR (400 MHz, DMSO-d6) δ ppm, 12.41 (d, J = 2.0 Hz, 1H), 10.79 (s, 1H), 8.58 (d, J = 2.0 Hz, 1H), 8.56 (d, J = 1.6 Hz, 1H), 8 29 (d, J = 2.8 Hz, 1H), 8.24 (s, 1H), 8.19 (d, J = 5.6 Hz, 1H), 8.14 (s, 1H), 7.95 (s, 1H), 7.48 (dd, J = 1.2 Hz, 4.4 Hz, 1H), 7.24 (s, 1H), 6.83 (m, 1H), 6.48 (m, 1H), 4.00 (t, J = 5.2 Hz, 2H), 3.88 (m, 3H), 2.8 (d, J = 4.4 Hz, 6H). MS (ES) m/z 496 (M + H). |
| 57 | 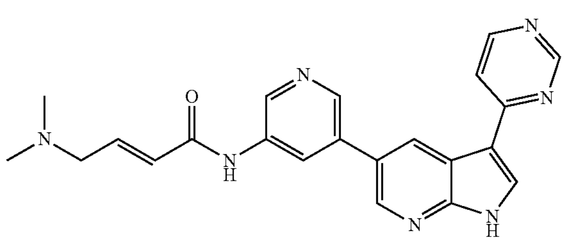 [SMILES: CN(C)C/C=C/C(=O)Nc1cncc(-c2cnc3[nH]cc(-c4ccncn4)c3c2)c1] | (E)-4-(dimethylamino)-N-(5-(3-(pyrimidin-4-yl)-1H-pyrrolo[2,3-b]pyridin-5-yl)pyridin-3-yl)but-2-enamide | $^1$H NMR (400 MHz, DMSO-d$_6$) δ ppm, 12.65 (s, 1H), 10.80 (s, 1H), 9.16 (s, 1H), 9.05 (s, 1H), 8.94 (s, 1H), 8.74 (s, 1H), 8.71-8.69 (m, 2H), 8.65 (s, 1H), 8.44 (s, 1H), 8.05 (d, J = 5.48 Hz, 1H), 6.87-6.80 (m, 1H), 6.53 (d, J = 15.26 Hz, 1H), 4.00 (d, J = 6.26 Hz, 2H), 2.83 (s, 6H). MS (ES) m/z 400 (M + H). |
| 58 | 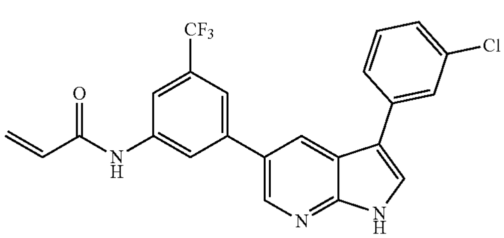 [SMILES: C=CC(=O)Nc1cc(-c2cnc3[nH]cc(-c4cccc(Cl)c4)c3c2)cc(C(F)(F)F)c1] | N-(3-(3-(3-chlorophenyl)-1H-pyrrolo[2,3-b]pyridin-5-yl)-5-(trifluoromethyl)phenyl)acrylamide | $^1$H NMR (400 MHz, DMSO-d$_6$) δ ppm, 12.22 (s, 1H), 10.58 (s, 1H), 8.59 (s, 1H), 8.49 (s, 1H), 8.24 (s, 1H), 8.12 (s, 1H), 8.09 (s, 1H), 7.82 (s, 2H), 7.80 (s, 1H), 7.51-7.48 (m, 1H), 7.33 (d, J = 7.44 Hz, 1H), 6.50-6.43 (m, 1H), 6.33 (d, J = 16.82 Hz, 1H), 5.85 (d, J = 9.78 Hz, 1H). MS (ES) m/z 442 (M + H). |

TABLE 2-continued

Compound Examples

| Ex. # | Name | Spectral Data |
|---|---|---|
| 59 | N-(3-(3-(m-tolyl)-1H-pyrrolo[2,3-b]-pyridin-5-yl)-5-(trifluoromethyl)phenyl)acrylamide | $^1$H NMR (400 MHz, DMSO-d$_6$) δ ppm, 12.07 (s, 1H), 10.57 (s, 1H), 8.58 (s, 1H), 8.46 (s, 1H), 8.23 (s, 1H), 8.12 (s, 1H), 7.92 (s, 1H), 7.80 (s, 1H), 7.58 (s, 2H), 7.38-7.35 (m, 1H), 7.14-7.11 (m, 1H), 6.49-6.42 (m, 1H), 6.33 (d, J = 17.60 Hz, 1H), 5.84 (d, J = 11.74 Hz, 1H), 3.32 (s, 3H). MS (ES) m/z 422 (M + H). |
| 60 | (E)-4-(dimethylamino)-N-(5-(3-(2-fluoropyridin-4-yl)-1H-pyrrolo-[2,3-b]pyridin-5-yl)pyridin-3-yl)-but-2-enamide | $^1$H NMR (400 MHz, DMSO-d6) δ ppm, 12.46 (s, 1H), 10.19 (s, 1H), 8.56 (s, 2H), 8.40 (d, J = 2.4 Hz, 1H), 8.23 (d, J = 5.6 Hz, 1H), 7.98 (s, 1H), 7.84 (d, J = 5.2 Hz, 1H), 7.74 (d, J = 7.6 Hz, 1H), 7.59 (s, 1H), 7.53 (m, 1H), 7.45 (m, 1H), 6.76 (m, 1H), 6.31 (d, J = 15.6 Hz, 1H), 3.08 (m, 2H), 2.19 (s, 6H). MS (ES) m/z 416 (M + H). |
| 61 | (E)-N-(5-(3-(2-cyanopyridin-4-yl)-1H-pyrrolo-[2,3-b]pyridin-5-yl)pyridin-3-yl)-4-(dimethylamino)but-2-enamide | $^1$H NMR (400 MHz, DMSO-d6) δ ppm, 12.55 (s, 1H), 10.21 (s, 1H), 8.69 (d, J = 5.2 Hz, 1H), 8.66 (d, J = 1.6 Hz, 1H, 8.56 (d, J = 1.6 Hz, 1H), 8.49 (d, J = 6.8 Hz, 2H), 8.21 (dd, J = 1.6 Hz, 4.0 Hz, 1H), 7.98 (s, 1H), 7.74 (d, J = 8.0 Hz, 1H), 7.47 (m, 2H), 6.77 (m, 1H), 6.30 (d, J = 15.2 Hz, 1H), 3.07 (d, J = 5.6 Hz, 2H), 2.19 (s, 6H). MS (ES) m/z 423 (M + H). |
| 62 | N-(5-(3-(3-(trifluoromethyl)phenyl)-1H-pyrrolo[2,3-b]-pyridin-5-yl)-pyridin-3-yl)-acrylamide | $^1$H NMR (400 MHz, DMSO-d$_6$) δ ppm, 12.27 (s, 1H), 10.49 (s, 1H), 8.86 (s, 1H), 8.73 (s, 1H), 8.59 (s, 1H), 8.51 (s, 1H), 8.40 (s, 1H), 8.18-8.13 (m, 2H), 8.06 (s, 1H), 7.72-7.68 (m, 1H), 7.61 (d, J = 8.61 Hz, 1H), 6.52-6.46 (m, 1H), 6.33 (d, J = 16.82 Hz, 1H), 5.84 (d, J = 11.73 Hz, 1H), MS (ES) m/z 409 (M + H). |
| 63 | N-(3-(3-(3-fluorophenyl)-1H-pyrrolo[2,3-b]-pyridin-5-yl)-5-(trifluoromethyl)phenyl)-acrylamide | $^1$H NMR (400 MHz, DMSO-d$_6$) δ ppm, 12.20 (s, 1H), 10.58 (s, 1H), 8.59 (s, 1H), 8.52 (s, 1H), 8.24 (s, 1H), 8.12 (s, 1H), 8.07 (s, 1H), 7.84 (s, 1H), 7.69-7.61 (m, 2H), 7.53-7.47 (m, 1H), 7.14-7.07 (m, 1H), 6.50-6.43 (m, 1H), 6.34 (d, J = 16.83 Hz, 1H), 5.85 (d, J = 11.74 Hz, 1H). MS (ES) m/z 426 (M + H). |
| 64 | (E)-N-(3-(3-(3-cyanophenyl)-1H-pyrrolo[2,3-b]pyridin-5-yl)-5-methoxyphenyl)-4-dimethylamino)-N-methylbut-2-enamide | $^1$H NMR (400 MHz, DMSO-d$_6$) δ ppm, 12.23 (s, 1H), 8.63 (s, 1H), 8.54 (s, 1H), 8.25 (s, 1H), 8.18 (d, J = 7.82 Hz, 1H), 8.13 (s, 1H), 7.71 (d, J = 7.82 Hz, 1H), 7.67-7.64 (m, 1H), 7.39 (s, 1H), 7.38 (s, 1H), 6.94 (s, 1H), 6.68-6.60 (m, 1H), 6.33-6.29 (m, 1H), 3.87 (s, 3H), 3.79 (br. s, 2H), 3.35 (s, 3H), 2.66 (s, 6H). MS (ES) m/z 466 (M + H). |

TABLE 2-continued

Compound Examples

| Ex. # | Structure | Name | Spectral Data |
|---|---|---|---|
| 65 | 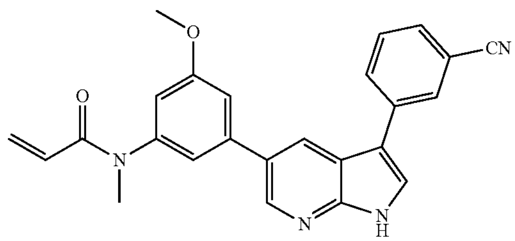 [SMILES: C=CC(=O)N(C)c1cc(OC)cc(-c2cnc3[nH]cc(-c4cccc(C#N)c4)c3c2)c1] | N-(3-(3-(3-cyanophenyl)-1H-pyrrolo[2,3-b]pyridin-5-yl)-5-methoxyphenyl)-N-methylacrylamide | $^1$H NMR (400 MHz, DMSO-d$_6$) δ ppm, 12.22 (s, 1H), 8.62 (s, 1H), 8.54 (s, 1H), 8.26 (s, 1H), 8.19 (d, J = 7.82 Hz, 1H), 8.12 (s, 1H), 7.70 (d, J = 7.83 Hz, 1H), 7.67-7.63 (m, 1H), 7.35 (s, 1H), 7.32 (s, 1H), 6.90 (s, 1H), 6.24-6.16 (m, 2H), 5.62-5.59 (m, 1H), 3.87 (s, 3H), 3.33 (s, 3H). MS (ES) m/z 409 (M + H). |
| 66 | 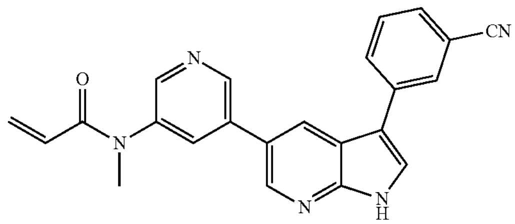 [SMILES: C=CC(=O)N(C)c1cncc(-c2cnc3[nH]cc(-c4cccc(C#N)c4)c3c2)c1] | N-(5-(3-(3-cyanophenyl)-1H-pyrrolo[2,3-b]pyridin-5-yl)-pyridin-3-yl)-N-methylacrylamide | $^1$H NMR (400 MHz, DMSO-d$_6$) δ ppm, 12.29 (s, 1H), 9.04 (s, 1H), 8.69 (s, 1H), 8.68 (s, 1H), 8.16 (s, 1H), 8.28 (s, 2H), 8.22 (d, J = 7.82 Hz, 1H), 8.16 (s, 1H), 7.71 (d, J = 7.83 Hz, 1H), 7.67-7.63 (m, 1H), 6.21 (br. s, 2H), 5.68-5.64 (m, 1H), 3.38 (s, 3H). MS (ES) m/z 380 (M + H). |
| 67 | 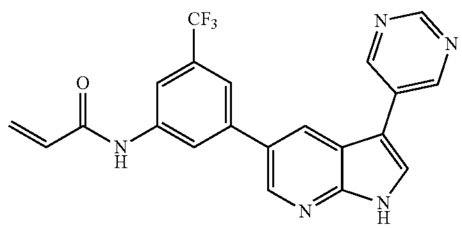 [SMILES: C=CC(=O)Nc1cc(-c2cnc3[nH]cc(-c4cncnc4)c3c2)cc(C(F)(F)F)c1] | N-(3-(3-(pyrimidin-5-yl)-1H-pyrrolo-[2,3-b]pyridin-5-yl)-5-(trifluoromethyl)phenyl)-acrylamide | $^1$H NMR (400 MHz, DMSO-d$_6$) δ ppm, 12.40 (s, 1H), 10.59 (s, 1H), 9.31 (s, 2H), 9.10 (s, 1H), 8.65 (s, 1H), 8.64 (s, 1H), 8.26 (s, 1H), 8.22 (s, 1H), 8.16 (s, 1H), 7.92 (s, 1H), 6.51-6.44 (m, 1H), 6.34 (d, J = 16.82 Hz, 1H), 5.85 (d, J = 10.17 Hz, 1H). MS (ES) m/z 410 (M + H). |
| 68 | 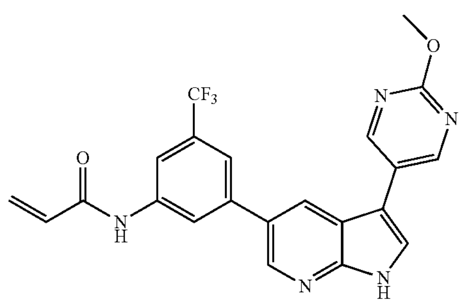 [SMILES: C=CC(=O)Nc1cc(-c2cnc3[nH]cc(-c4cnc(OC)nc4)c3c2)cc(C(F)(F)F)c1] | N-(3-(3-(2-methoxypyrimidin-5-yl)-1H-pyrrolo[2,3-b]pyridin-5-yl)-5-(trifluoromethyl)-phenyl)acrylamide | $^1$H NMR (400 MHz, DMSO-d$_6$) δ ppm, 12.52 (s, 1H), 10.60 (s, 1H), 9.08 (s, 2H), 8.62 (s, 1H), 8.56 (s, 1H), 8.22 (s, 1H), 8.16 (s, 1H), 8.08 (s, 1H), 7.91 (s, 1H), 6.50-6.44 (m, 1H), 6.33 (d, J = 17.21 Hz, 1H), 5.85 (d, J = 9.39 Hz, 1H), 3.98 (s, 3H). MS (ES) m/z 440 (M + H). |
| 69 | 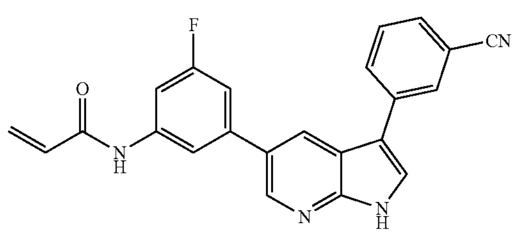 [SMILES: C=CC(=O)Nc1cc(F)cc(-c2cnc3[nH]cc(-c4cccc(C#N)c4)c3c2)c1] | N-(3-(3-(3-cyanophenyl)-1H-pyrrolo[2,3-b]pyridin-5-yl)-5-fluorophenyl)-acrylamide | $^1$H NMR (400 MHz, DMSO-d6) δ ppm, 12.25 (s, 1H), 10.47 (s, 1H), 8.55 (d, J = 10.96 Hz, 2H), 8.26 (s, 1H), 8.19-8.14 (m, 2H), 7.76-7.63 (m, 4H), 7.43 (d, J = 9.39 Hz, 1H), 6.48-6.42 (m, 1H), 6.33-6.29 (m, 1H), 5.82 (d, J = 10.18 Hz, 1H). MS (ES) m/z 383 (M + H). |
| 70 | 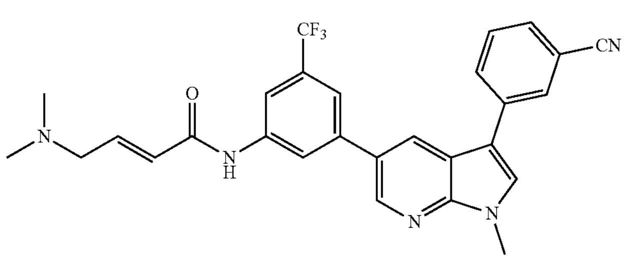 [SMILES: CN(C)C/C=C/C(=O)Nc1cc(-c2cnc3c(c2)c(-c2cccc(C#N)c2)cn3C)cc(C(F)(F)F)c1] | (E)-N-(3-(3-(3-cyanophenyl)-1-methyl-1H-pyrrolo[2,3-b]pyridin-5-yl)-5-(trifluoromethyl)phenyl)-4-dimethylamino)-but-2-enamide | $^1$H NMR (400 MHz, DMSO-d$_6$) δ ppm, 10.97 (s, 1H), 8.64 (s, 1H), 8.61 (s, 1H), 8.27 (s, 1H), 8.24 (s, 1H), 8.22 (s, 1H), 8.17-8.15 (m, 2H), 7.87 (s, 1H), 7.74-7.65 (m, 2H), 6.89-6.85 (m, 1H), 6.55-6.51 (m, 1H), 3.94 (s, 3H), 3.09-3.06 (m, 2H), 2.77 (s, 3H). MS (ES) m/z 504 (M + H). |

TABLE 2-continued

Compound Examples

| Ex. # | Structure | Name | Spectral Data |
|---|---|---|---|
| 71 | 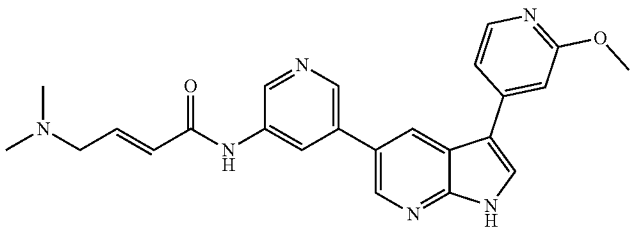 | (E)-4-(dimethylamino)-N-(5-(3-(2-methoxypyridin-4-yl)-1H-pyrrolo[2,3-b]pyridin-5-yl)-pyridin-3-yl)but-2-enamide | $^1$H NMR (400 MHz, DMSO-d6) δ ppm, 10.14 (s, 1H), 8.86 (d, J = 2.4 Hz, 1H), 8.73 (d, J = 2.0 Hz, 1H), 8.57 (dd, J = 12.4 Hz, 2.0 Hz, 2H), 8.39 (t, J = 2.0 Hz, 1H), 8.28 (s, 1H), 8.18 (d, J = 5.6 Hz, 1H), 7.48 (dd, J = 4.0 Hz, 1.6 Hz, 1H), 7.23 (d, J = 0.8 Hz, 1H), 6.83-6.79 (m, 1H), 6.33 (d, J = 15.6 Hz, 1H), 3.90 (s, 3H). MS (ES) m/z 429 (M + H). |
| 72 | 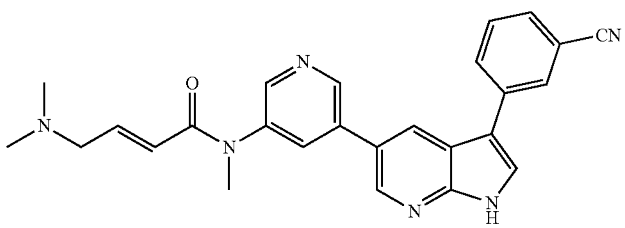 | (E)-N-(5-(3-(3-cyanophenyl)-1H-pyrrolo[2,3-b]-pyridin-5-yl)-pyridin-3-yl)-4-(dimethylamino)-N-methylbut-2-enamide | $^1$H NMR (400 MHz, DMSO-d$_6$) δ ppm, 12.29 (s, 1H), 9.09 (s, 1H), 8.71 (s, 1H), 8.69 (s, 1H), 8.55 (s, 1H), 8.34 (s, 1H), 8.27 (s, 1H), 8.20 (d, J = 7.04 Hz, 1H), 8.17 (s, 1H), 7.74-7.71 (m, 1H), 7.68-7.64 (m, 1H), 6.71-6.63 (m, 1H), 6.26 (br. s, 1H), 3.80 (br. s, 2H), 3.39 (s, 3H), 2.67 (s, 6H). MS (ES) m/z 437 (M + H). |
| 73 | 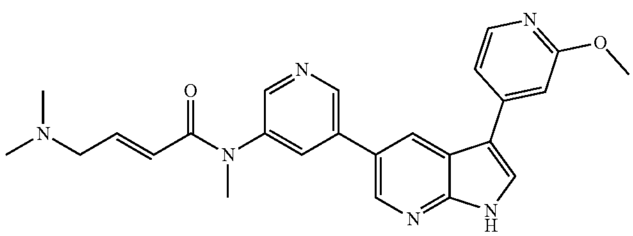 | (E)-4-(dimethylamino)-N-(5-(3-(2-methoxypyridin-4-yl)-1H-pyrrolo-[2,3-b]pyridin-5-yl)pyridin-3-yl)-N-methylbut-2-enamide | $^1$H NMR (400 MHz, DMSO-d$_6$) δ ppm, 12.40 (s, 1H), 9.08 (s, 1H), 8.71 (s, 2H), 8.55 (s, 1H), 8.38 (s, 1H), 8.29 (s, 1H), 8.19 (s, 1H), 7.52 (s, 1H), 6.72-6.63 (m, 1H), 6.25 (br. s, 1H), 3.91 (s, 3H), 3.80 (br. s, 2H), 3.40 (s, 3H), 2.68 (s, 6H). MS (ES) m/z 443 (M + H). |
| 74 | 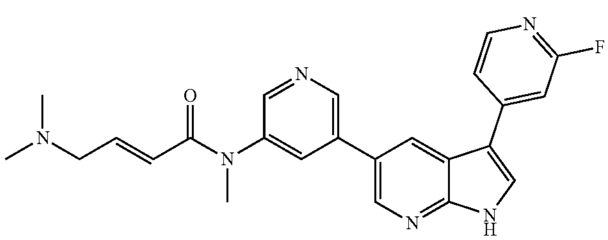 [SMILES: CN(C)C/C=C/C(=O)N(C)c1cncc(-c2cnc3[nH]cc(-c4ccnc(F)c4)c3c2)c1] | (E)-4-(dimethylamino)-N-(5-(3-(2-fluoropyridin-4-yl)-1H-pyrrolo[2,3-b]pyridin-5-yl)pyridin-3-yl)-N-methylbut-2-enamide | $^1$H NMR (400 MHz, DMSO-d$_6$) δ ppm, 12.55 (s, 1H), 9.11 (s, 1H), 8.75 (d, J = 4.07 Hz, 2H), 8.57 (d, J = 1.96 Hz, 1H), 8.44 (d, J = 2.74 Hz, 1H), 8.38 (s, 1H), 7.88 (d, J = 4.07 Hz, 1H), 7.65 (s, 1H), 6.73-6.66 (m, 1H), 6.30 (br. s, 1H), 3.80 (br. s, 2H), 3.40 (s, 3H), 2.69 (s, 6H). MS (ES) m/z 431 (M + H). |
| 75 | 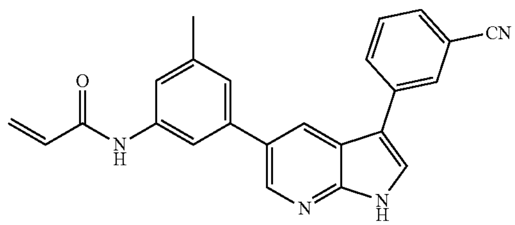 [SMILES: C=CC(=O)Nc1cc(C)cc(-c2cnc3[nH]cc(-c4cccc(C#N)c4)c3c2)c1] | N-(3-(3-(3-cyanophenyl)-1H-pyrrolo[2,3-b]-pyridin-5-yl)-5-methylphenyl)-acrylamide | $^1$H NMR (400 MHz, DMSO-d$_6$) δ ppm, 12.20 (s, 1H), 10.18 (s, 1H), 8.52 (s, 1H), 8.46 (s, 1H), 8.23 (s, 1H), 8.16 (d, J = 8.21 Hz, 1H), 8.12 (s, 1H), 7.75 (s, 1H), 7.72-7.64 (m, 2H), 7.59 (s, 1H), 7.32 (s, 1H), 6.50-6.43 (m, 1H), 6.27 (d, J = 14.87 Hz, 1H), 5.77 (d, J = 11.74 Hz, 1H), 2.40 (s, 3H). MS (ES) m/z 379 (M + H). |
| 76 | 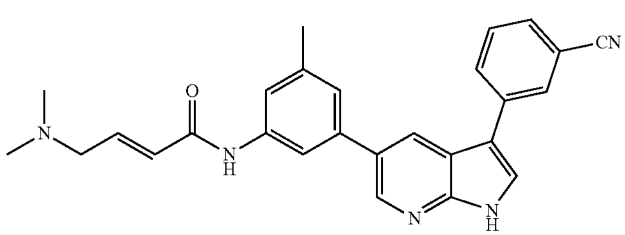 [SMILES: Cc1cc(NC(=O)/C=C/CN(C)C)cc(-c2cnc3[nH]cc(-c4cccc(C#N)c4)c3c2)c1] | (E)-N-(3-(3-(3-cyanophenyl)-1H-pyrrolo[2,3-b]-pyridin-5-yl)-5-methylphenyl)-4-(dimethylamino)but-2-enamide | $^1$H NMR (400 MHz, DMSO-d$_6$) δ ppm, 12.35 (s, 1H), 10.26 (s, 1H), 8.50 (s, 1H), 8.44 (s, 1H), 8.22 (s, 1H), 8.16 (d, J = 7.05 Hz, 1H), 8.11 (s, 1H), 7.77 (s, 1H), 7.70-7.63 (m, 2H), 7.58 (s, 1H), 7.29 (s, 1H), 6.77-6.70 (m, 1H), 6.31 (d, J = 15.65 Hz, 1H), 3.06 (d, J = 5.87 Hz, 1H), 2.38 (s, 3H), 2.12 (s, 6H). MS (ES) m/z 436 (M + H). |

TABLE 2-continued

Compound Examples

| Ex. # | Structure | Name | Spectral Data |
|---|---|---|---|
| 77 | 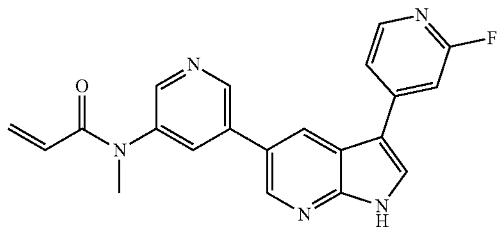 [SMILES: C=CC(=O)N(C)c1cncc(-c2cnc3[nH]cc(-c4ccnc(F)c4)c3c2)c1] | N-(5-(3-(2-fluoro-pyridin-4-yl)-1H-pyrrolo[2,3-b]-pyridin-5-yl)-pyridin-3-yl)-N-methylacrylamide | ¹H NMR (400 MHz, DMSO-d₆) δ ppm, 12.52 (s, 1H), 9.06 (s, 1H), 8.76 (s, 1H), 8.73 (s, 1H), 8.52 (d, J = 2.35 Hz, 1H), 8.43 (s, 1H), 8.33 (s, 1H), 8.23 (d, J = 5.09 Hz, 1H), 7.88 (d, J = 5.47 Hz, 1H), 7.65 (s, 1H), 6.21 (br. s, 2H), 5.66 (br. s, 1H), 3.39 (s, 3H). MS (ES) m/z 374 (M + H). |
| 78 | 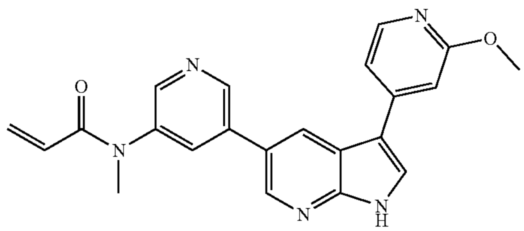 [SMILES: C=CC(=O)N(C)c1cncc(-c2cnc3[nH]cc(-c4ccnc(OC)c4)c3c2)c1] | N-(5-(3-(2-methoxypyridin-4-yl)-1H-pyrrolo[2,3-b]pyridin-5-yl)pyridin-3-yl)-N-methylacrylamide | ¹H NMR (400 MHz, DMSO-d₆) δ ppm, 12.39 (s, 1H), 9.03 (s, 1H), 8.70 (s, 1H), 8.67 (s, 1H), 8.52 (d, J = 1.96 Hz, 1H), 8.32 (s, 1H), 8.28 (s, 1H), 8.18 (d, J = 5.47 Hz, 1H), 7.51 (d, J = 5.48 Hz, 1H), 7.27 (s, 1H), 6.20 (br. s, 2H), 5.66 (br. s, 1H), 3.89 (s, 3H), 3.38 (s, 3H). MS (ES) m/z 386 (M + H). |
| 79 | 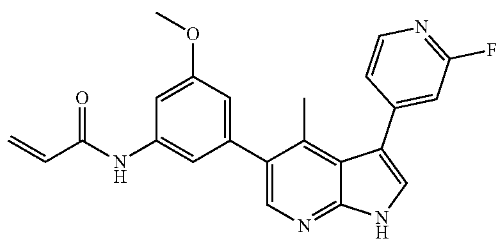 [SMILES: C=CC(=O)Nc1cc(OC)cc(-c2cnc3[nH]cc(-c4ccnc(F)c4)c3c2C)c1] | N-(3-(3-(2-fluoro-pyridin-4-yl)-4-methyl-1H-pyrrolo[2,3-b]pyridin-5-yl)-5-methoxyphenyl)acrylamide | ¹H NMR (400 MHz, DMSO-d₆) δ ppm, 12.23 (s, 1H), 10.23 (s, 1H), 8.23 (d, J = 5.48 Hz, 1H), 8.15 (s, 1H), 7.80 (s, 1H), 7.51 (d, J = 5.48 Hz, 1H), 7.39 (s, 1H), 7.31 (s, 1H), 7.27 (s, 1H), 6.72 (s, 1H), 6.47-6.41 (m, 1H), 6.27 (d, J = 16.83 Hz, 1H), 5.77 (d, J = 11.73 Hz, 1H), 3.79 (s, 3H), 2.30 (s, 3H). MS (ES) m/z 403 (M + H). |
| 80 | 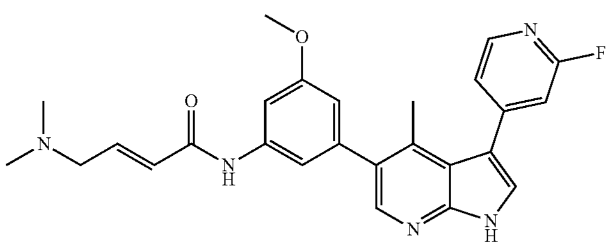 [SMILES: COc1cc(NC(=O)/C=C/CN(C)C)cc(-c2cnc3[nH]cc(-c4ccnc(F)c4)c3c2C)c1] | (E)-4-(dimethyl-amino)-N-(3-(3-(2-fluoropyridin-4-yl)-4-methyl-1H-pyrrolo[2,3-b]pyridin-5-yl)-5-methoxyphenyl)-but-2-enamide | ¹H NMR (400 MHz, DMSO-d₆) δ ppm, 12.23 (s, 1H), 10.13 (s, 1H), 8.23 (d, J = 5.09 Hz, 1H), 8.14 (s, 1H), 7.80 (s, 2H), 7.51 (d, J = 5.08 Hz, 1H), 7.39 (s, 1H), 7.31 (s, 1H), 7.25 (s, 1H), 6.70 (br. s, 1H), 6.27 (d, J = 15.65 Hz, 1H), 3.79 (s, 3H), 3.06 (d, J = 6.26 Hz, 2H), 2.30 (s, 3H), 2.17 (s, 6H). MS (ES) m/z 460 (M + H). |
| 81 | 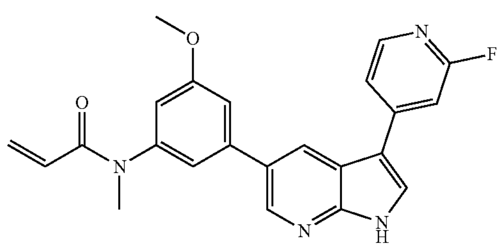 [SMILES: C=CC(=O)N(C)c1cc(OC)cc(-c2cnc3[nH]cc(-c4ccnc(F)c4)c3c2)c1] | N-(3-(3-(2-fluoro-pyridin-4-yl)-1H-pyrrolo[2,3-b]-pyridin-5-yl)-5-methoxyphenyl)-N-methylacrylamide | MS (ES) m/z 404 (M + H). |
| 82 | 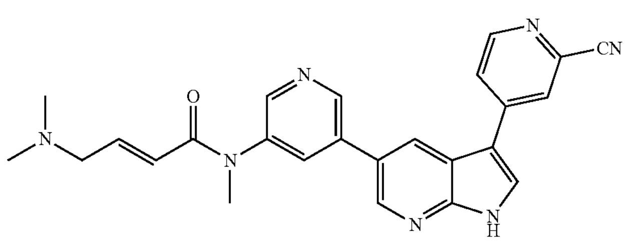 [SMILES: CN(C)C/C=C/C(=O)N(C)c1cncc(-c2cnc3[nH]cc(-c4ccnc(C#N)c4)c3c2)c1] | (E)-N-(5-(3-(2-cyanopyridin-4-yl)-1H-pyrrolo[2,3-b]pyridin-5-yl)pyridin-3-yl)-4-(dimethyl-amino)-N-methyl-but-2-enamide | ¹H NMR (400 MHz, DMSO-d₆) δ 12.65 (d, J = 2.4 Hz, 1H), 9.83 (s, 1H), 9.14 (s, 1H), 8.84 (d, J = 1.8 Hz, 1H), 8.76 (d, J = 1.9 Hz, 1H), 8.72 (d, J = 5.3 Hz, 1H), 8.59 (d, J = 2.2 Hz, 1H), 8.52 (narrow m, 2H), 8.38 (br s, 1H), 8.25 (dd, J = 5.3, 1.8 Hz, 1H), 6.74-6.66 (m, 1H), 6.29 (br s, 1H), 3.81 (br s, 2H), 3.41 (s, 3H), 2.69 (s, 6H). MS (ES) m/z = 438 (M + H). |

TABLE 2-continued

Compound Examples

| Ex. # | Structure | Name | Spectral Data |
|---|---|---|---|
| 83 | 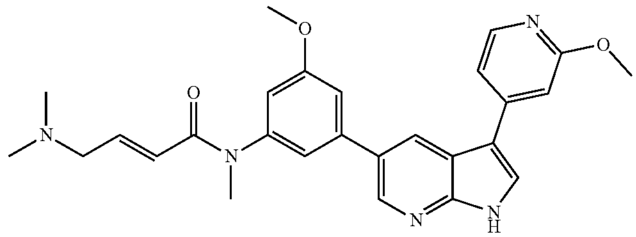 | (E)-4-(dimethylamino)-N-(3-methoxy-5-(3-(2-methoxypyridin-4-yl)-1H-pyrrolo[2,3-b]pyridin-5-yl)phenyl)-N-methylbut-2-enamide | $^1$H NMR (400 MHz, DMSO-d$_6$) δ 12.38 (s, 1H), 9.76 (s, 1H), 8.65 (d, J = 2.0 Hz, 1H), 8.54 (d, J = 1.9 Hz, 1H), 8.28 (d, J = 2.8 Hz, 1H), 8.19 (d, J = 5.5 Hz, 1H), 7.50 (dd, J = 5.5, 1.3 Hz, 1H), 7.40 (br d, J = 6.6 Hz, 2H), 7.26 (s, 1H), 6.95 (apparent t, J = 2.0 Hz, 1H), 6.70-6.60 (m, 1H), 6.35-6.25 (m, 1H), 3.91 (s, 3H), 3.88 (s, 3H), 3.85-3.75 (m, 2H), 3.35 (s, 3H), 2.67 (br s, 3H), 2.66 (br s, 3H). MS (ES) m/z 458 (M + H). |
| 84 | 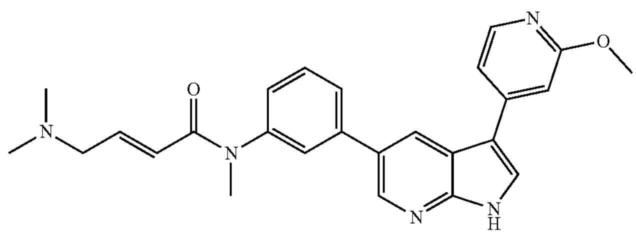 | (E)-4-(dimethylamino)-N-(3-(3-(2-methoxypyridin-4-yl)-1H-pyrrolo[2,3-b]pyridin-5-yl)phenyl)-N-methylbut-2-enamide | $^1$H NMR (400 MHz, DMSO-d$_6$) δ 12.38 (s, 1H), 9.68 (br s, 1H), 8.65 (d, J = 2.0 Hz, 1H), 8.57 (d, J = 1.8 Hz, 1H), 8.29 (d, J = 2.8 Hz, 1H), 8.19 (d, J = 5.4 Hz, 1H), 7.85 (d, J = 1.9 Hz, 2H), 7.59 (dd, J = 10.1, 6.0 Hz, 1H), 7.51 (dd, J = 5.5, 1.4 Hz, 1H), 7.33 (d, J = 7.8 Hz, 1H), 7.26 (s, 1H), 6.69-6.61 (m, 1H), 6.28-6.23 (m, 1H), 3.91 (s, 3H), 3.78 (m, 2H), 3.36 (s, 3H), 2.66 (s, 3H), 2.65 (s, 3H). MS (ES) m/z = 442 (M + H). |
| 85 | 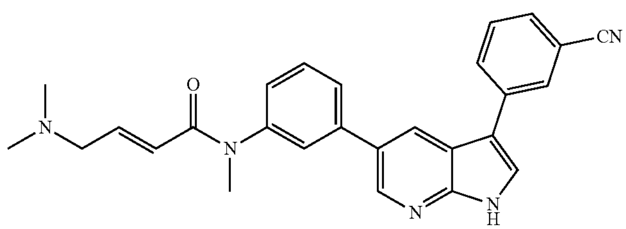 [SMILES: CN(C)C/C=C/C(=O)N(C)c1cccc(-c2cnc3[nH]cc(-c4cccc(C#N)c4)c3c2)c1] | (E)-N-(3-(3-(3-cyanophenyl)-1H-pyrrolo[2,3-b]pyridin-5-yl)phenyl)-4-dimethylamino)-N-methylbut-2-enamide | $^1$H NMR (400 MHz, DMSO-d$_6$) δ 12.25 (s, 1H), 9.65 (br s, 1H), 8.64 (d, J = 2.0 Hz, 1H), 8.57 (d, J = 1.8 Hz, 1H), 8.26 (br s, 1H), 8.21-8.16 (m, 1H), 8.14 (d, J = 2.7 Hz, 1H), 7.91-7.79 (m, 2H), 7.72 (d, J = 7.7 Hz, 1H), 7.66 (apparent t, J = 7.7 Hz, 1H), 7.60 (apparent t, J = 7.8 Hz, 1H), 7.34-7.31 (m, 1H), 6.70-6.61 (m, 1H), 6.26 (br d, J = 14.3 Hz, 1H), 3.78 (narrow m, 2H), 3.37 (s, 3H), 2.67 (s, 3H), 2.66 (d, 3H). MS (ES) m/z = 436 (M + H) |
| 86 | 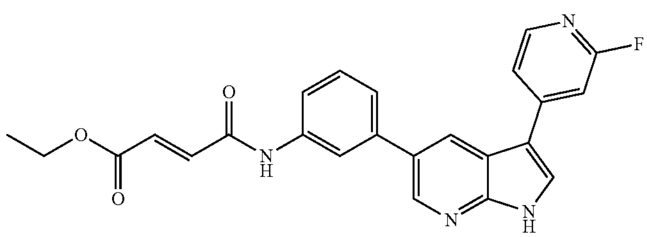 [SMILES: CCOC(=O)/C=C/C(=O)Nc1cccc(-c2cnc3[nH]cc(-c4ccnc(F)c4)c3c2)c1] | ethyl (E)-4-((3-(3-(2-fluoropyridin-4-yl)-1H-pyrrolo[2,3-b]pyridin-5-yl)phenyl)amino)-4-oxobut-2-enoate | $^1$H NMR (400 MHz, DMSO-d$_6$) δ 12.49 (d, J = 2.5 Hz, 1H), 10.71 (s, 1H), 8.58 (narrow m, 2H), 8.41 (d, J = 2.8 Hz, 1H), 8.23 (d, J = 5.3 Hz, 1H), 8.01 (s, 1H), 7.85-7.83 (m, 1H), 7.76 (d, J = 7.3 Hz, 1H), 7.60-7.57 (narrow m, 2H), 7.50 (apparent t, J = 7.9 Hz, 1H), 7.26 (d, J = 15.4 Hz, 1H), 6.74 (d, J = 15.4 Hz, 1H), 4.23 (q, J = 7.1 Hz, 2H), 3.19-3.12 (m, 1H), 1.63-1.50 (m, 1H), 1.28 (t, J = 7.1 Hz, 3H). MS (ES) m/z = 431 (M + H). |
| 87 | 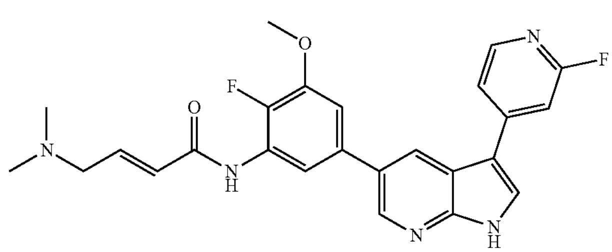 [SMILES: COc1cc(-c2cnc3[nH]cc(-c4ccnc(F)c4)c3c2)cc(NC(=O)/C=C/CN(C)C)c1F] | (E)-4-(dimethylamino)-N-(2-fluoro-5-(3-(2-fluoropyridin-4-yl)-1H-pyrrolo[2,3-b]pyridin-5-yl)-3-methoxyphenyl)but-2-enamide | $^1$H NMR (400 MHz, DMSO-d$_6$) δ 12.48 (s, 1H), 10.25 (s, 1H), 9.84 (br s, 1H), 8.60-8.56 (m, 2H), 8.40 (d, J = 2.8 Hz, 1H), 8.23 (d, J = 5.3 Hz, 1H),7.85-7.82 (m, 2H), 7.60 (s, 1H), 7.39 (d, J = 5.8 Hz, 1H), 6.78-6.76 (m, 1H), 6.65 (d, J = 15.3 Hz, 1H), 3.99 (s, 3H), 4.00-3.94 (m, 2H), 2.82 (s, 6H). MS (ES) m/z = 464 (M + H). |

TABLE 2-continued

Compound Examples

| Ex. # | Structure | Name | Spectral Data |
|---|---|---|---|
| 88 | 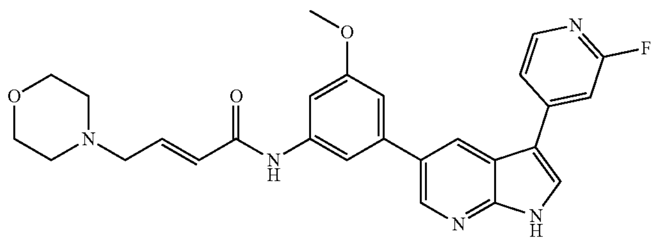 [SMILES: COc1cc(NC(=O)/C=C/CN2CCOCC2)cc(-c2cnc3[nH]cc(-c4ccnc(F)c4)c3c2)c1] | (E)-N-(3-(3-(2-fluoropyridin-4-yl)-1H-pyrrolo[2,3-b]pyridin-5-yl)-5-methoxyphenyl)-4-morpholinobut-2-enamide | $^1$H NMR (400 MHz, DMSO-d$_6$) δ 12.48 (s, 1H), 10.49 (s, 1H), 8.58-8.54 (m, 2H), 8.39 (d, J = 2.8 Hz, 1H), 8.22 (d, J = 5.3 Hz, 1H), 7.84-7.81 (m, 1H), 7.58 (s, 1H), 7.51 (s, 1H), (s, 1H), 7.11 (narrow m, 1H), 6.80-6.74 (m, 1H), 6.50 (d, J = 15.2 Hz, 1H), 4.10-3.50 (m, 6H), 3.86 (s, 3H), 3.45-2.95 (m, 4H). MS (ES) m/z = 488 (M + H). |
| 89 | 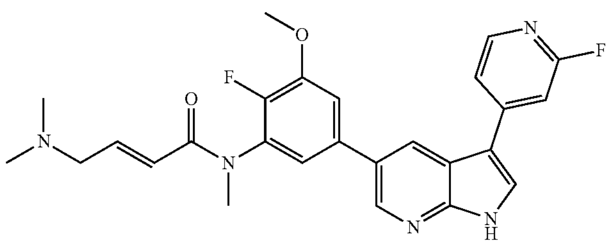 [SMILES: COc1cc(-c2cnc3[nH]cc(-c4ccnc(F)c4)c3c2)cc(N(C)C(=O)/C=C/CN(C)C)c1F] | (E)-4-(dimethylamino)-N-(2-fluoro-5-(3-(2-fluoropyridin-4-yl)-1H-pyrrolo[2,3-b]pyridin-5-yl)-3-methoxyphenyl)-N-methylbut-2-enamide | $^1$H NMR (400 MHz, DMSO-d$_6$) δ 12.50 (d, J = 2.1 Hz, 1H), 9.67 (br s, 1H), 8.71 (narrow m, 1H), 8.64 (narrow m, 1H), 8.41 (d, J = 2.8 Hz, 1H), 8.24 (d, J = 5.3 Hz, 1H), 7.85 (d, J = 5.3 Hz, 1H), 7.65 (d, J = 7.4 Hz, 1H), 7.62 (s, 1H), 7.57 (d, J = 4.5 Hz, 1H), 6.75-6.66 (m, 1H), 6.28 (d, J = 15.3 Hz, 1H), 4.03 (s, 3H), 3.81 (s, 2H), 3.30 (s, 3H), 2.68 (s, 3H), 2.67 (s, 3H). MS (ES) m/z = 478 (M + H). |
| 90 | 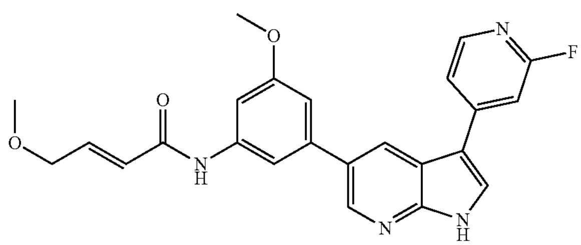 [SMILES: COC/C=C/C(=O)Nc1cc(OC)cc(-c2cnc3[nH]cc(-c4ccnc(F)c4)c3c2)c1] | (E)-N-(3-(3-(2-fluoropyridin-4-yl)-1H-pyrrolo[2,3-b]-pyridin-5-yl)-5-methoxyphenyl)-4-methoxybut-2-enamide | $^1$H NMR (400 MHz, DMSO-d$_6$) δ 12.47 (s, 1H), 10.22 (s, 1H), 8.57-8.55 (m, 2H), 8.40 (d, J = 2.8 Hz, 1H), 8.23 (d, J = 5.3 Hz, 1H), 7.85-7.82 (m, 1H), 7.60 (s, 1H), 7.52-7.46 (m, 2H), 7.12-7.02 (m, 1H), 6.82 (apparent dt, J = 15.4, 4.1 Hz, 1H), 6.38-6.32 (m, 1H), 4.12 (dd, J = 4.0, 1.9 Hz, 2H), 3.85 (s, 3H), 3.35 (s, 3H). MS (ES) m/z = 433 (M + H). |
| 91 | 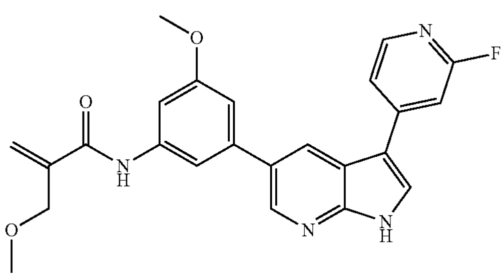 [SMILES: C=C(COC)C(=O)Nc1cc(OC)cc(-c2cnc3[nH]cc(-c4ccnc(F)c4)c3c2)c1] | N-(3-(3-(2-fluoropyridin-4-yl)-1H-pyrrolo[2,3-b]-pyridin-5-yl)-5-methoxyphenyl)-2-(methoxymethyl)acrylamide | $^1$H NMR (400 MHz, DMSO-d$_6$) δ 12.48 (s, 1H), 10.00 (s, 1H), 8.60-8.55 (m, 2H), 8.39 (d, J = 2.9 Hz, 1H), 8.23 (d, J = 5.3 Hz, 1H), 7.83 (d, J = 5.2 Hz, 1H), 7.60 (s, 2H), 7.53-7.48 (m, 1H), 7.12-7.07 (m, 1H), 6.00 (s, 1H), 5,73 (s, 1H), 4.18 (s, 2H), 3.85 (s, 3H), 3.32 (s, 3H). MS (ES) m/z = 433 (M + H). |
| 92 | 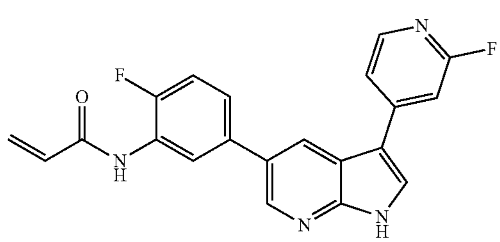 [SMILES: C=CC(=O)Nc1cc(-c2cnc3[nH]cc(-c4ccnc(F)c4)c3c2)ccc1F] | N-(2-fluoro-5-(3-(2-fluoropyridin-4-yl)-1H-pyrrolo[2,3-b]pyridin-5-yl)phenyl)acrylamide | $^1$H NMR (400 MHz, DMSO-d$_6$) δ 12.48 (s, 1H), 10.10 (s, 1H), 8.58-8.54 (m, 2H), 8.40 (d, J = 2.8 Hz, 1H), 8.38-8.28 (m, 1H), 8.23 (d, J = 5.3 Hz, 1H), 7.86-7.83 (m, 1H), 7.72-7.60 (m, 2H), 7.42 (dd, J = 10.7, 8.6 Hz, 1H), 6.65 (dd, J = 17.0, 10.3 Hz, 1H), 6.30 (dd, J = 17.0, 1.9 Hz, 1H), 5.81 (dd, J = 10.2, 1.8 Hz, 1H). MS (ES) m/z = 377 (M + H). |

TABLE 2-continued

Compound Examples

| Ex. # | Structure | Name | Spectral Data |
|---|---|---|---|
| 93 | 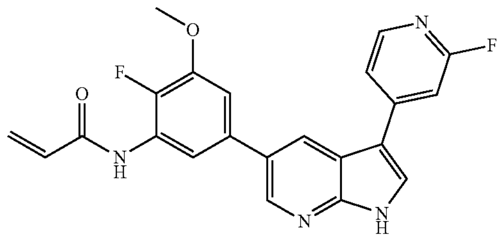 [SMILES: C=CC(=O)Nc1cc(-c2cnc3[nH]cc(-c4ccnc(F)c4)c3c2)cc(OC)c1F] | N-(2-fluoro-5-(3-(2-fluoropyridin-4-yl)-1H-pyrrolo-[2,3-b]pyridin-5-yl)-3-methoxy-phenyl)acrylamide | $^1$H NMR (400 MHz, DMSO-d$_6$) δ 12.48 (br s, 1H), 9.99 (s, 1H), 8.60-8.55 (m, 1H), 8.39 (d, J = 2.8 Hz, 1H), 8.23 (d, J = 5.3 Hz, 1H), 7.86-7.83 (m, 1H), 7.60 (s, 1H), 7.35 (dd, J = 7.4, 1.8 Hz, 1H), 6.64 (dd, J = 17.0, 10.2 Hz, 1H), 6.29 (dd, J = 17.0, 1.8 Hz, 1H), 5.80 (dd, J = 10.2, 1.8 Hz, 1H), 3.99 (s, 3H); MS (ES) m/z = 407 (M + H). |
| 94 | 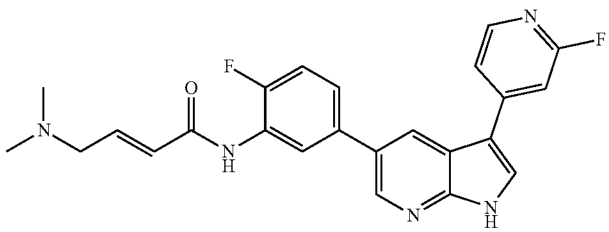 [SMILES: CN(C)C/C=C/C(=O)Nc1cc(-c2cnc3[nH]cc(-c4ccnc(F)c4)c3c2)ccc1F] | (E)-4-(dimethyl-amino)-N-(2-fluoro-5-(3-(2-fluoropyridin-4-yl)-1H-pyrrolo-[2,3-b]pyridin-5-yl)phenyl)but-2-enamide | $^1$H NMR (400 MHz, DMSO-d$_6$) δ 12.46 (s, 1H), 9.99 (s, 1H), 8.58-8.54 (m, 2H), 8.40 (s, 1H), 8.32 (br d, J = 7.3 Hz, 1H), 8.22 (d, J = 5.4 Hz, 1H), 7.86-7.82 (m, 1H), 7.65-7.57 (m, 2H), 7.40 (dd, J = 10.6, 8.6 Hz, 1H), 6.78 (apparent dt, J = 15.4, 5.9 Hz, 1H), 6.48 (d, J = 15.5 Hz, 1H), 3.09-3.06 (m, 2H), 2.19 (s, 6H). MS (ES) m/z = 433 (M + H). |
| 95 | 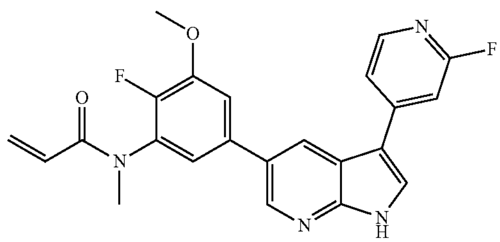 [SMILES: C=CC(=O)N(C)c1cc(-c2cnc3[nH]cc(-c4ccnc(F)c4)c3c2)cc(OC)c1F] | N-(2-fluoro-5-(3-(2-fluoropyridin-4-yl)-1H-pyrrolo-[2,3-b]pyridin-5-yl)-3-methoxy-phenyl)-N-methyl-acrylamide | $^1$H NMR (400 MHz, DMSO-d$_6$) δ 12.49 (s, 1H), 8.69-8.64 (m, 2H), 8.39 (d, J = 2.8 Hz, 1H), 8.23 (d, J = 5.3 Hz, 1H), 7.88-7.86 (m, 1H), 7.63-7.61 (m, 2H), 7.54-7.53 (m, 1H), 6.21-6.16 (m, 2H), 5.66-5.63 (m, 1H), 4.02 (s, 3H), 3.29 (s, 3H). MS (ES) m/z = 421 (M + H). |
| 96 | 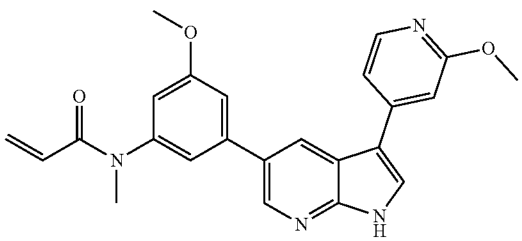 [SMILES: C=CC(=O)N(C)c1cc(OC)cc(-c2cnc3[nH]cc(-c4ccnc(OC)c4)c3c2)c1] | N-(3-methoxy-5-(3-(2-methoxy-pyridin-4-yl)-1H-pyrrolo-[2,3-b]pyridin-5-yl)phenyl)-N-methylacrylamide | |
| 97 | 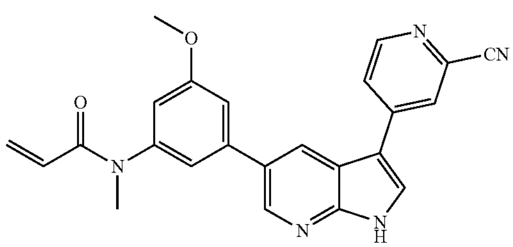 [SMILES: C=CC(=O)N(C)c1cc(OC)cc(-c2cnc3[nH]cc(-c4ccnc(C#N)c4)c3c2)c1] | N-(3-(3-(2-cyano-pyridin-4-yl)-1H-pyrrolo[2,3-b]-pyridin-5-yl)-5-methoxyphenyl)-N-methyl-acrylamide | |
| 98 | 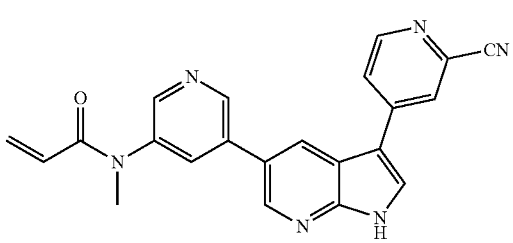 [SMILES: C=CC(=O)N(C)c1cncc(-c2cnc3[nH]cc(-c4ccnc(C#N)c4)c3c2)c1] | N-(5-(3-(2-cyano-pyridin-4-yl)-1H-pyrrolo[2,3-b]-pyridin-5-yl)-pyridin-3-yl)-N-methylacrylamide | |

TABLE 2-continued

Compound Examples

| Ex. # | Structure | Name | Spectral Data |
|---|---|---|---|
| 99 | 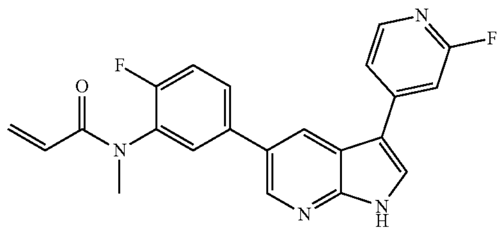 [SMILES: C=CC(=O)N(C)c1cc(-c2cnc3[nH]cc(-c4ccnc(F)c4)c3c2)ccc1F] | N-(2-fluoro-5-(3-(2-fluoropyridin-4-yl)-1H-pyrrolo-[2,3-b]pyridin-5-yl)phenyl)-N-methylacrylamide | |
| 100 | 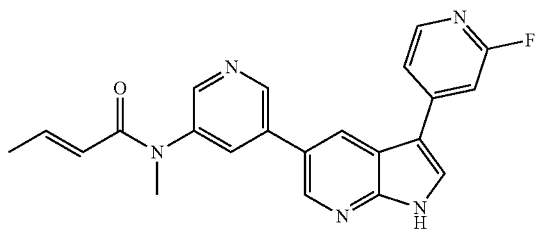 [SMILES: C/C=C/C(=O)N(C)c1cncc(-c2cnc3[nH]cc(-c4ccnc(F)c4)c3c2)c1] | (E)-N-(5-(3-(2-fluoropyridin-4-yl)-1H-pyrrolo-[2,3-b]pyridin-5-yl)pyridin-3-yl)-N-methylbut-2-enamide | |
| 101 | 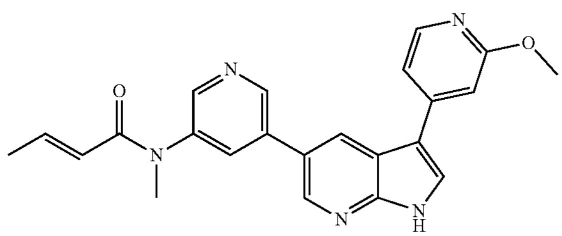 [SMILES: C/C=C/C(=O)N(C)c1cncc(-c2cnc3[nH]cc(-c4ccnc(OC)c4)c3c2)c1] | (E)-N-(5-(3-(2-methoxypyridin-4-yl)-1H-pyrrolo-[2,3-b]pyridin-5-yl)pyridin-3-yl)-N-methylbut-2-enamide | |
| 102 | 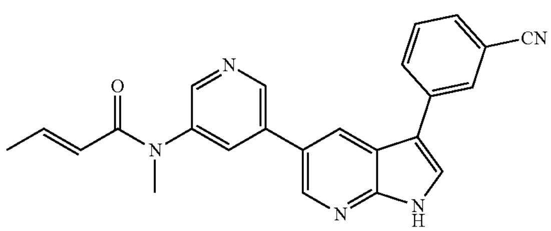 [SMILES: C/C=C/C(=O)N(C)c1cncc(-c2cnc3[nH]cc(-c4cccc(C#N)c4)c3c2)c1] | (E)-N-(5-(3-(3-cyanophenyl)-1H-pyrrolo[2,3-b]-pyridin-5-yl)-pyridin-3-yl)-N-methylbut-2-enamide | |
| 103 | 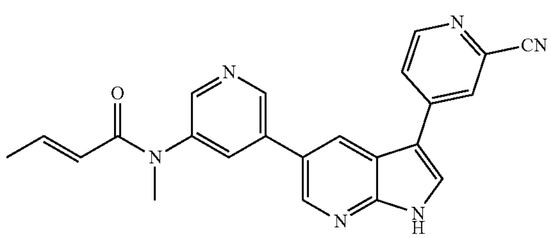 [SMILES: C/C=C/C(=O)N(C)c1cncc(-c2cnc3[nH]cc(-c4ccnc(C#N)c4)c3c2)c1] | (E)-N-(5-(3-(2-cyanopyridin-4-yl)-1H-pyrrolo-[2,3-b]pyridin-5-yl)pyridin-3-yl)-N-methylbut-2-enamide | |
| 104 | 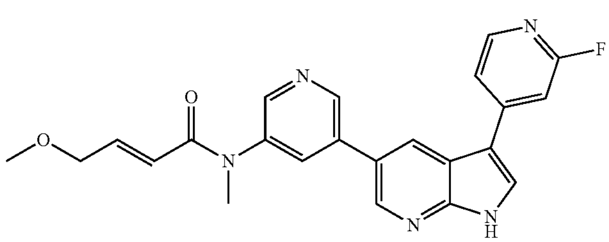 [SMILES: COC/C=C/C(=O)N(C)c1cncc(-c2cnc3[nH]cc(-c4ccnc(F)c4)c3c2)c1] | (E)-N-(5-(3-(2-fluoropyridin-4-yl)-1H-pyrrolo-[2,3-b]pyridin-5-yl)pyridin-3-yl)-4-methoxy-N-methylbut-2-enamide | |

TABLE 2-continued

Compound Examples

| Ex. # | Structure | Name | Spectral Data |
|---|---|---|---|
| 105 | 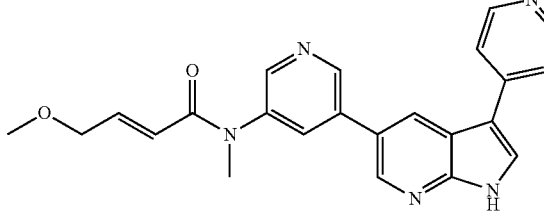 | (E)-4-methoxy-N-(5-(3-(2-methoxy-pyridin-4-yl)-1H-pyrrolo[2,3-b]-pyridin-5-yl)-pyridin-3-yl)-N-methylbut-2-enamide | |
| 106 | 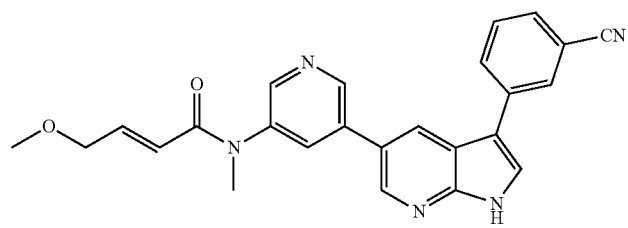 [SMILES: COC/C=C/C(=O)N(C)c1cncc(-c2cnc3[nH]cc(-c4cccc(C#N)c4)c3c2)c1] | (E)-N-(5-(3-(3-cyanophenyl)-1H-pyrrolo[2,3-b]-pyridin-5-yl)-pyridin-3-yl)-4-methoxy-N-methylbut-2-enamide | |
| 107 | 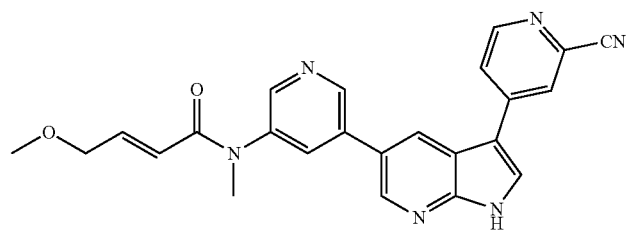 [SMILES: COC/C=C/C(=O)N(C)c1cncc(-c2cnc3[nH]cc(-c4ccnc(C#N)c4)c3c2)c1] | (E)-N-(5-(3-(2-cyanopyridin-4-yl)-1H-pyrrolo-[2,3-b]pyridin-5-yl)pyridin-3-yl)-4-methoxy-N-methylbut-2-enamide | |
| 108 | 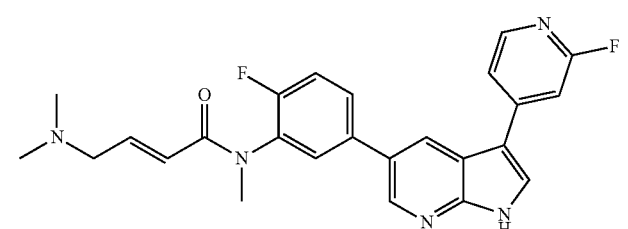 | (E)-4-(dimethyl-amino)-N-(2-fluoro-5-(3-(2-fluoropyridin-4-yl)-1H-pyrrolo-[2,3-b]pyridin-5-yl)phenyl)-N-methylbut-2-enamide | |
| 109 | 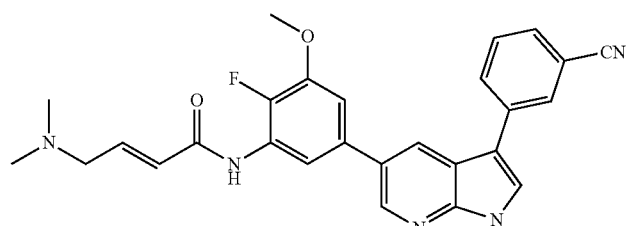 | (E)-N-(5-(3-(3-cyanophenyl)-1H-pyrrolo[2,3-b]pyridin-5-yl)-2-fluoro-3-methoxyphenyl)-4-(dimethyl-amino)but-2-enamide | |
| 110 | 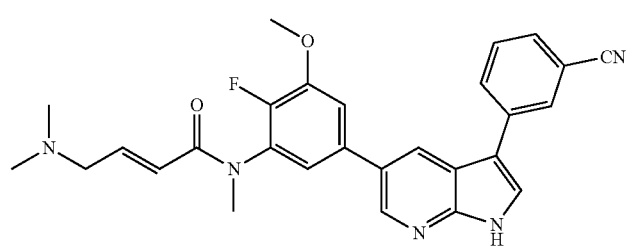 [SMILES: COc1cc(-c2cnc3[nH]cc(-c4cccc(C#N)c4)c3c2)cc(N(C)C(=O)/C=C/CN(C)C)c1F] | (E)-N-(5-(3-(3-cyanophenyl)-1H-pyrrolo[2,3-b]-pyridin-5-yl)-2-fluoro-3-methoxy-phenyl)-4-dimethylamino)-N-methylbut-2-enamide | |

TABLE 2-continued

Compound Examples

| Ex. # | Structure | Name | Spectral Data |
|---|---|---|---|
| 111 | 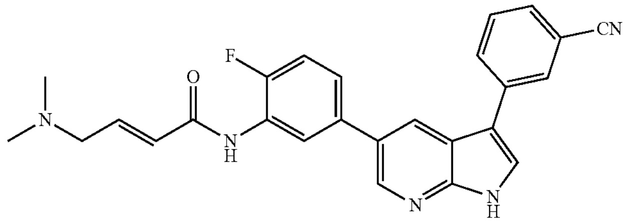 [SMILES: CN(C)C/C=C/C(=O)Nc1cc(-c2cnc3[nH]cc(-c4cccc(C#N)c4)c3c2)ccc1F] | (E)-N-(5-(3-(3-cyanophenyl)-1H-pyrrolo[2,3-b]-pyridin-5-yl)-2-fluorophenyl)-4-(dimethylamino)but-2-enamide | |
| 112 | 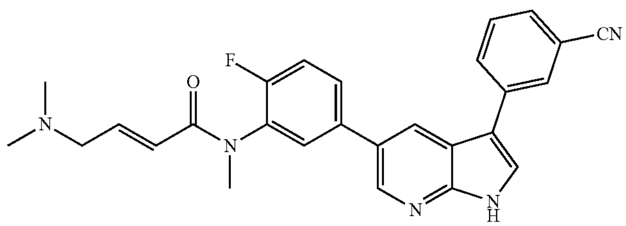 [SMILES: CN(C)C/C=C/C(=O)N(C)c1cc(-c2cnc3[nH]cc(-c4cccc(C#N)c4)c3c2)ccc1F] | (E)-N-(5-(3-(3-cyanophenyl)-1H-pyrrolo[2,3-b]-pyridin-5-yl)-2-fluorophenyl)-4-(dimethylamino)-N-methylbut-2-enamide | |
| 113 | 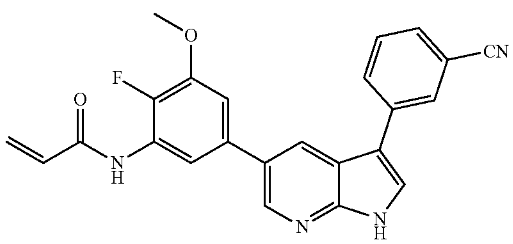 [SMILES: C=CC(=O)Nc1cc(-c2cnc3[nH]cc(-c4cccc(C#N)c4)c3c2)cc(OC)c1F] | N-(5-(3-(3-cyanophenyl)-1H-pyrrolo[2,3-b]-pyridin-5-yl)-2-fluoro-3-methoxyphenyl)-acrylamide | |
| 114 | 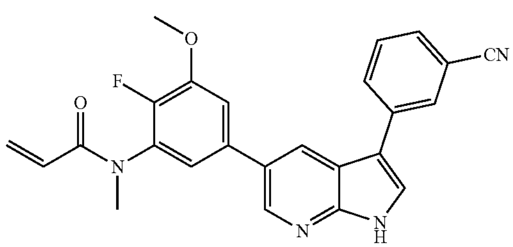 [SMILES: C=CC(=O)N(C)c1cc(-c2cnc3[nH]cc(-c4cccc(C#N)c4)c3c2)cc(OC)c1F] | N-(5-(3-(3-cyanophenyl)-1H-pyrrolo[2,3-b]-pyridin-5-yl)-2-fluoro-3-methoxyphenyl)-N-methyl-acrylamide | |
| 115 | 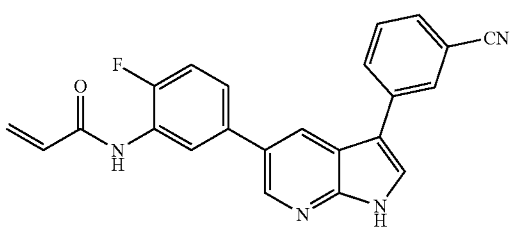 [SMILES: C=CC(=O)Nc1cc(-c2cnc3[nH]cc(-c4cccc(C#N)c4)c3c2)ccc1F] | N-(5-(3-(3-cyanophenyl)-1H-pyrrolo[2,3-b]-pyridin-5-yl)-2-fluorophenyl)-acrylamide | |
| 116 | 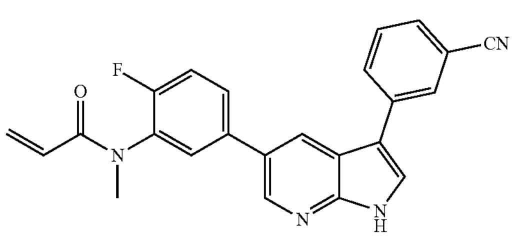 [SMILES: C=CC(=O)N(C)c1cc(-c2cnc3[nH]cc(-c4cccc(C#N)c4)c3c2)ccc1F] | N-(5-(3-(3-cyanophenyl)-1H-pyrrolo[2,3-b]-pyridin-5-yl)-2-fluorophenyl)-N-methylacrylamide | |

TABLE 2-continued

Compound Examples

| Ex. # | Structure | Name | Spectral Data |
|---|---|---|---|
| 117 | 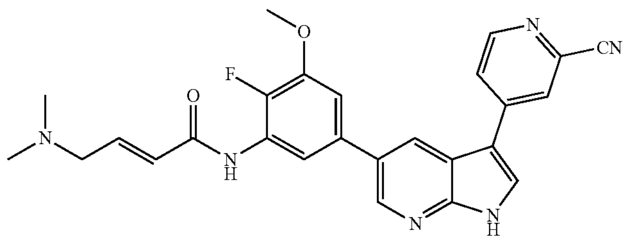 [SMILES: COc1cc(-c2cnc3[nH]cc(-c4ccnc(C#N)c4)c3c2)cc(NC(=O)/C=C/CN(C)C)c1F] | (E)-N-(5-(3-(2-cyanopyridin-4-yl)-1H-pyrrolo-[2,3-b]pyridin-5-yl)-2-fluoro-3-methoxyphenyl)-4-(dimethylamino)but-2-enamide | |
| 118 | 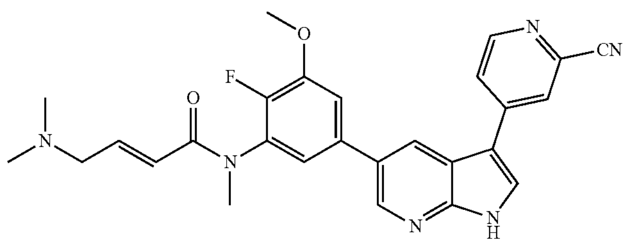 [SMILES: COc1cc(-c2cnc3[nH]cc(-c4ccnc(C#N)c4)c3c2)cc(N(C)C(=O)/C=C/CN(C)C)c1F] | (E)-N-(5-(3-(2-cyanopyridin-4-yl)-1H-pyrrolo-[2,3-b]pyridin-5-yl)-2-fluoro-3-methoxyphenyl)-4-(dimethylamino)-N-methylbut-2-enamide | |
| 119 | 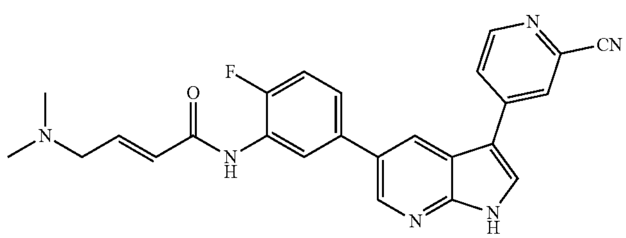 [SMILES: CN(C)C/C=C/C(=O)Nc1cc(-c2cnc3[nH]cc(-c4ccnc(C#N)c4)c3c2)ccc1F] | (E)-N-(5-(3-(2-cyanopyridin-4-yl)-1H-pyrrolo-[2,3-b]pyridin-5-yl)-2-fluorophenyl)-4-(dimethylamino)-but-2-enamide | |
| 120 | 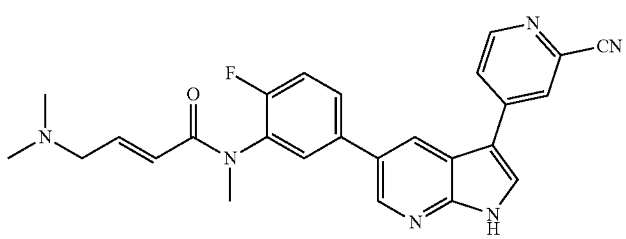 [SMILES: CN(C)C/C=C/C(=O)N(C)c1cc(-c2cnc3[nH]cc(-c4ccnc(C#N)c4)c3c2)ccc1F] | (E)-N-(5-(3-(2-cyanopyridin-4-yl)-1H-pyrrolo-[2,3-b]pyridin-5-yl)-2-fluorophenyl)-4-(dimethylamino)-N-methylbut-2-enamide | |
| 121 | 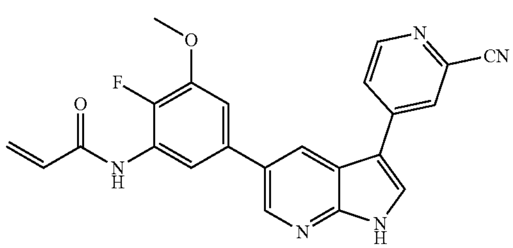 [SMILES: C=CC(=O)Nc1cc(-c2cnc3[nH]cc(-c4ccnc(C#N)c4)c3c2)cc(OC)c1F] | N-(5-(3-(2-cyanopyridin-4-yl)-1H-pyrrolo[2,3-b]-pyridin-5-yl)-2-fluoro-3-methoxyphenyl)acrylamide | |
| 122 | 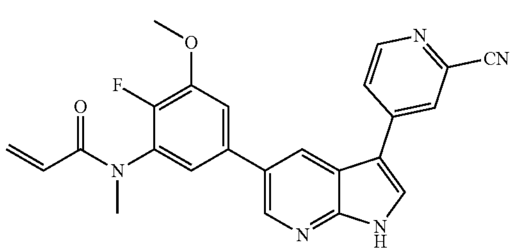 [SMILES: C=CC(=O)N(C)c1cc(-c2cnc3[nH]cc(-c4ccnc(C#N)c4)c3c2)cc(OC)c1F] | N-(5-(3-(2-cyanopyridin-4-yl)-1H-pyrrolo[2,3-b]-pyridin-5-yl)-2-fluoro-3-methoxyphenyl)-N-methylacrylamide | |

TABLE 2-continued

Compound Examples

| Ex. # | Structure | Name | Spectral Data |
|---|---|---|---|
| 123 | 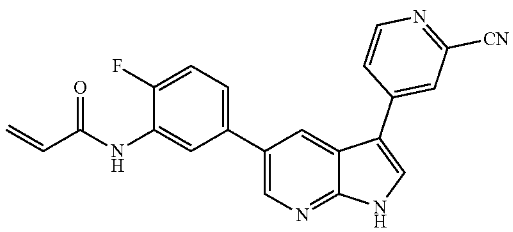 [SMILES: C=CC(=O)Nc1cc(-c2cnc3[nH]cc(-c4ccnc(C#N)c4)c3c2)ccc1F] | N-(5-(3-(2-cyano-pyridin-4-yl)-1H-pyrrolo[2,3-b]-pyridin-5-yl)-2-fluorophenyl)-acrylamide | |
| 124 | 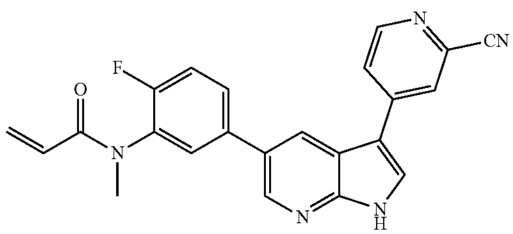 [SMILES: C=CC(=O)N(C)c1cc(-c2cnc3[nH]cc(-c4ccnc(C#N)c4)c3c2)ccc1F] | N-(5-(3-(2-cyano-pyridin-4-yl)-1H-pyrrolo[2,3-b]-pyridin-5-yl)-2-fluorophenyl)-N-methylacrylamide | |
| 125 | 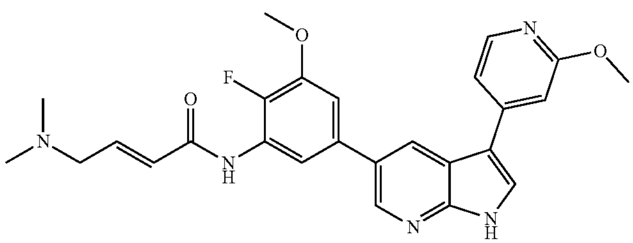 | (E)-4-(dimethyl-amino)-N-(2-fluoro-3-methoxy-5-(3-(2-methoxy-pyridin-4-yl)-1H-pyrrolo[2,3-b]-pyridin-5-yl)-phenyl)but-2-enamide | |
| 126 | 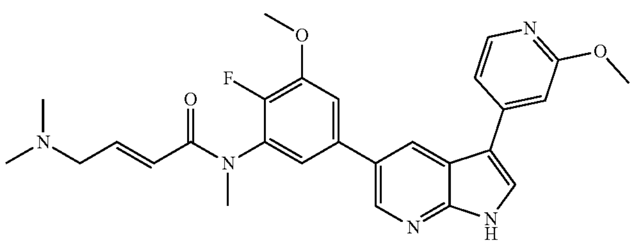 | (E)-4-(dimethyl-amino)-N-(2-fluoro-3-methoxy-5-(3-(2-methoxy-pyridin-4-yl)-1H-pyrrolo[2,3-b]-pyridin-5-yl)-phenyl)-N-methyl-but-2-enamide | |
| 127 | 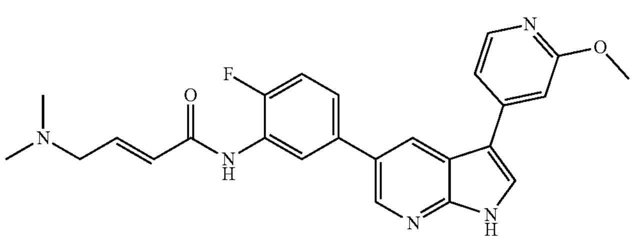 | (E)-4-(dimethyl-amino)-N-(2-fluoro-5-(3-(2-methoxypyridin-4-yl)-1H-pyrrolo-[2,3-b]pyridin-5-yl)phenyl)but-2-enamide | |
| 128 | 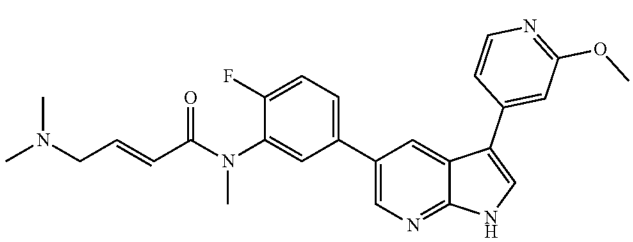 | (E)-4-(dimethyl-amino)-N-(2-fluoro-5-(3-(2-methoxypyridin-4-yl)-1H-pyrrolo-[2,3-b]pyridin-5-yl)phenyl)-N-methylbut-2-enamide | |

TABLE 2-continued

Compound Examples

| Ex. # | Structure | Name | Spectral Data |
|---|---|---|---|
| 129 | 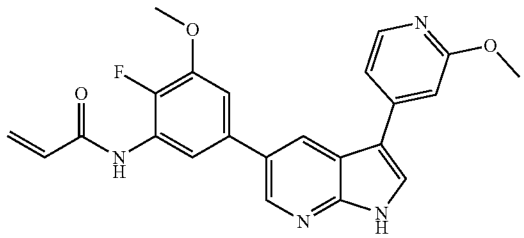 | N-(2-fluoro-3-methoxy-5-(3-(2-methoxypyridin-4-yl)-1H-pyrrolo-[2,3-b]pyridin-5-yl)phenyl)acrylamide | |
| 130 | 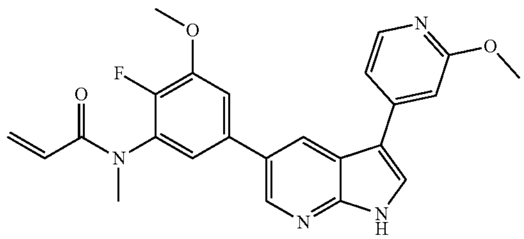 [SMILES: C=CC(=O)N(C)c1cc(-c2cnc3[nH]cc(-c4ccnc(OC)c4)c3c2)cc(OC)c1F] | N-(2-fluoro-3-methoxy-5-(3-(2-methoxypyridin-4-yl)-1H-pyrrolo-[2,3-b]pyridin-5-yl)phenyl)-N-methylacrylamide | |
| 131 | 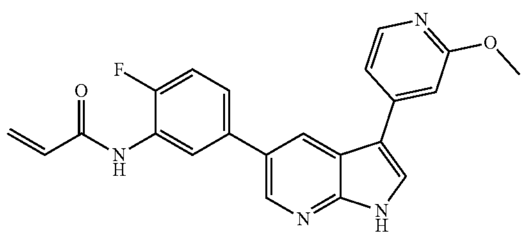 [SMILES: C=CC(=O)Nc1cc(-c2cnc3[nH]cc(-c4ccnc(OC)c4)c3c2)ccc1F] | N-(2-fluoro-5-(3-(2-methoxy-pyridin-4-yl)-1H-pyrrolo[2,3-b]-pyridin-5-yl)-phenyl)acrylamide | |
| 132 | 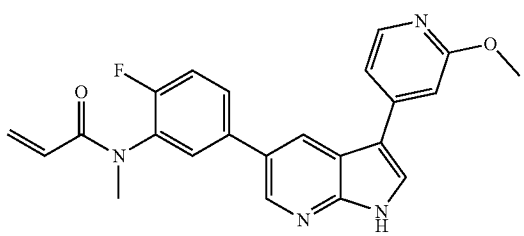 [SMILES: C=CC(=O)N(C)c1cc(-c2cnc3[nH]cc(-c4ccnc(OC)c4)c3c2)ccc1F] | N-(2-fluoro-5-(3-(2-methoxy-pyridin-4-yl)-1H-pyrrolo[2,3-b]-pyridin-5-yl)-phenyl)-N-methyl-crylamide | |
| 133 | 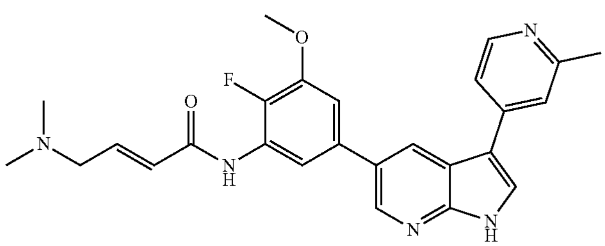 | (E)-4-(dimethyl-amino)-N-(2-fluoro-3-methoxy-5-(3-(2-methyl-pyridin-4-yl)-1H-pyrrolo[2,3-b]-pyridin-5-yl)-phenyl)but-2-enamide | |
| 134 | 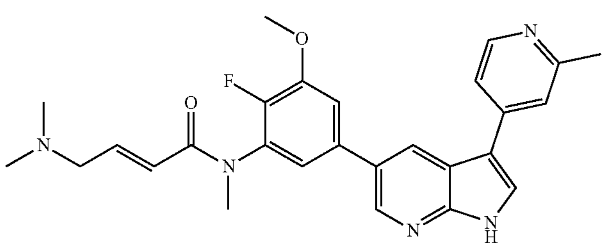 | (E)-4-(dimethyl-amino)-N-(2-fluoro-3-methoxy-5-(3-(2-methyl-pyridin-4-yl)-1H-pyrrolo[2,3-b]-pyridin-5-yl)-phenyl)-N-methyl-but-2-enamide | |

TABLE 2-continued

Compound Examples

| Ex. # | Structure | Name | Spectral Data |
|---|---|---|---|
| 135 | 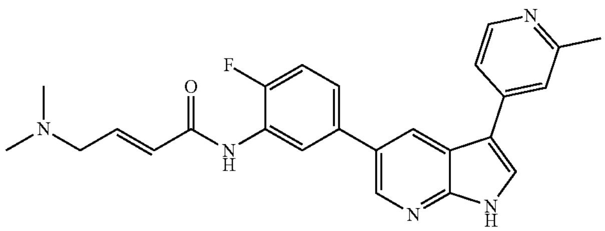 | (E)-4-(dimethyl-amino)-N-(2-fluoro-5-(3-(2-methylpyridin-4-yl)-1H-pyrrolo-[2,3-b]pyridin-5-yl)phenyl)-but-2-enamide | |
| 136 | 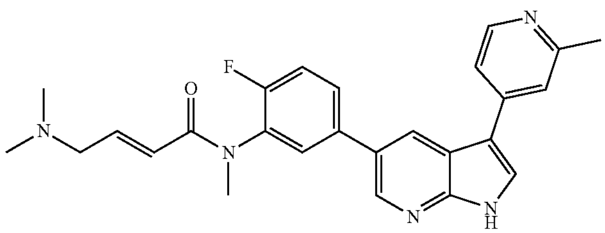 | (E)-4-(dimethyl-amino)-N-(2-fluoro-5-(3-(2-methylpyridin-4-yl)-1H-pyrrolo-[2,3-b]pyridin-5-yl)phenyl)-N-methylbut-2-enamide | |
| 137 | 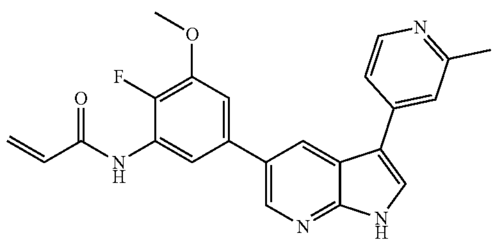 [SMILES: C=CC(=O)Nc1cc(-c2cnc3[nH]cc(-c4ccnc(C)c4)c3c2)cc(OC)c1F] | N-(2-fluoro-3-methoxy-5-(3-(2-methylpyridin-4-yl)-1H-pyrrolo-[2,3-b]pyridin-5-yl)phenyl)acryl-amide | |
| 138 | 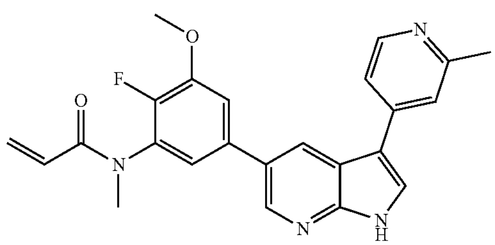 [SMILES: C=CC(=O)N(C)c1cc(-c2cnc3[nH]cc(-c4ccnc(C)c4)c3c2)cc(OC)c1F] | N-(2-fluoro-3-methoxy-5-(3-(2-methylpyridin-4-yl)-1H-pyrrolo-[2,3-b]pyridin-5-yl)phenyl)-N-methylacrylamide | |
| 139 | 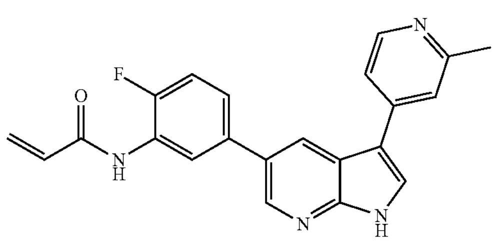 [SMILES: C=CC(=O)Nc1cc(-c2cnc3[nH]cc(-c4ccnc(C)c4)c3c2)ccc1F] | N-(2-fluoro-5-(3-(2-methylpyridin-4-yl)-1H-pyrrolo-[2,3-b]pyridin-5-yl)phenyl)acryl-amide | |
| 140 | 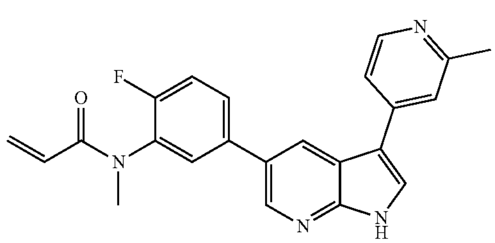 [SMILES: C=CC(=O)N(C)c1cc(-c2cnc3[nH]cc(-c4ccnc(C)c4)c3c2)ccc1F] | N-(2-fluoro-5-(3-(2-methylpyridin-4-yl)-1H-pyrrolo-[2,3-b]pyridin-5-yl)phenyl)-N-methylacrylamide | |

The following compounds can generally be made using the methods described above. It is expected that these compounds when made will have activity similar to those that have been prepared. In embodiments, the compound may be selected from:

N-(3-(3-(3-cyanophenyl)-1H-pyrrolo[2,3-b]pyridin-5-yl)phenyl)-N-methyl acrylamide N-(3-(3-(3-cyanophenyl)-1H-pyrrolo[2,3-b]pyridin-5-yl)-5-(trifluoromethyl)phenyl)-N-methylacrylamide (E)-N-(3-(3-(3-cyanophenyl)-1H-pyrrolo[2,3-b]pyridin-5-yl)-5-(trifluoromethyl)phenyl)-4-(dimethylamino)-N-methylbut-2-enamide N-(3-(3-(2-fluoropyridin-4-yl)-1H-pyrrolo[2,3-b]pyridin-5-yl)phenyl)-N-methylacrylamide N-(3-(3-(2-fluoropyridin-4-yl)-1H-pyrrolo[2,3-b]pyridin-5-yl)-5-(trifluoromethyl)phenyl)-N-methylacrylamide (E)-4-(dimethylamino)-N-(3-(3-(2-fluoropyridin-4-yl)-1H-pyrrolo[2,3-b]pyridin-5-yl)phenyl)-N-methylbut-2-enamide (E)-4-(dimethylamino)-N-(3-(3-(2-fluoropyridin-4-yl)-1H-pyrrolo[2,3-b]pyridin-5-yl)-5-methoxyphenyl)-N-methylbut-2-enamide (E)-4-(dimethylamino)-N-(3-(3-(2-fluoropyridin-4-yl)-1H-pyrrolo[2,3-b]pyridin-5-yl)-5-(trifluoromethyl)phenyl)-N-methylbut-2-enamide N-(3-(3-(2-cyanopyridin-4-yl)-1H-pyrrolo[2,3-b]pyridin-5-yl)phenyl)-N-methylacrylamide N-(3-(3-(2-cyanopyridin-4-yl)-1H-pyrrolo[2,3-b]pyridin-5-yl)-5-(trifluoromethyl)phenyl)-N-methylacrylamide (E)-N-(3-(3-(2-cyanopyridin-4-yl)-1H-pyrrolo[2,3-b]pyridin-5-yl)phenyl)-4-(dimethylamino)-N-methylbut-2-enamide (E)-N-(3-(3-(2-cyanopyridin-4-yl)-1H-pyrrolo[2,3-b]pyridin-5-yl)-5-methoxyphenyl)-4-(dimethylamino)-N-methylbut-2-enamide (E)-N-(3-(3-(2-cyanopyridin-4-yl)-1H-pyrrolo[2,3-b]pyridin-5-yl)-5-(trifluoromethyl)phenyl)-4-(dimethylamino)-N-methylbut-2-enamide N-(3-(3-(2-methoxypyridin-4-yl)-1H-pyrrolo[2,3-b]pyridin-5-yl)-5-(trifluoromethyl)phenyl)-N-methylacrylamide (E)-4-(dimethylamino)-N-(3-(3-(2-methoxypyridin-4-yl)-1H-pyrrolo[23-b]pyridin-5-yl)-5-(trifluoromethyl)phenyl)-N-methylbut-2-enamide N-(2-methoxy-5-(3-(2-methoxypyridin-4-yl)-1H-pyrrolo[2,3-b]pyridin-5-yl)pyridin-3-yl)acrylamide N-(2-ethoxy-5-(3-(2-methoxypyridin-4-yl)-1H-pyrrolo[2,3-b]pyridin-5-yl)pyridin-3-yl)acrylamide N-(2-cyclobutoxy-5-(3-(2-methoxypyridin-4-yl)-1H-pyrrolo[2,3-b]pyridin-5-yl)pyridin-3-yl)acrylamide N-(5-(3-(2-methoxypyridin-4-yl)-1H-pyrrolo[2,3-b]pyridin-5-yl)-2-(oxetan-3-yloxy)pyridin-3-yl)acrylamide N-(5-(3-(2-methoxypyridin-4-yl)-1H-pyrrolo[2,3-b]pyridin-5-yl)-2-((tetrahydrofuran-3-yl)oxy)pyridin-3-yl)acrylamide (E)-4-(dimethylamino)-N-(2-methoxy-5-(3-(2-methoxypyridin-4-yl)-1H-pyrrolo[2,3-b]pyridin-5-yl)pyridin-3-yl)but-2-enamide (E)-4-(dimethylamino)-N-(2-ethoxy-5-(3-(2-methoxypyridin-4-yl)-1H-pyrrolo[2,3-b]pyridin-5-yl)pyridin-3-yl)but-2-enamide (E)-N-(2-cyclobutoxy-5-(3-(2-methoxypyridin-4-yl)-1H-pyrrolo[2,3-b]pyridin-5-yl)pyridin-3-yl)-4-(dimethylamino)but-2-enamide (E)-4-(dimethylamino)-N-(5-(3-(2-methoxypyridin-4-yl)-1H-pyrrolo[2,3-b]pyridin-5-yl)-2-(oxetan-3-yloxy)pyridin-3-yl)but-2-enamide (E)-4-(dimethylamino)-N-(5-(3-(2-methoxypyridin-4-yl)-1H-pyrrolo[2,3-b]pyridin-5-yl)-2-((tetrahydrofuran-3-yl)oxy)pyridin-3-yl)but-2-enamide N-(5-(3-(2-fluoropyridin-4-yl)-1H-pyrrolo[2,3-b]pyridin-5-yl)-2-methoxypyridin-3-yl)acrylamide N-(2-ethoxy-5-(3-(2-fluoropyridin-4-yl)-1H-pyrrolo[2,3-b]pyridin-5-yl)pyridin-3-yl)acrylamide N-(2-cyclobutoxy-5-(3-(2-fluoropyridin-4-yl)-1H-pyrrolo[2,3-b]pyridin-5-yl)pyridin-3-yl)acrylamide N-(5-(3-(2-fluoropyridin-4-yl)-1H-pyrrolo[2,3-b]pyridin-5-yl)-2-(oxetan-3-yloxy)pyridin-3-yl)acrylamide N-(5-(3-(2-fluoropyridin-4-yl)-1H-pyrrolo[2,3-b]pyridin-5-yl)-2-((tetrahydrofuran-3-yl)oxy)pyridin-3-yl)acrylamide (E)-4-(dimethylamino)-N-(5-(3-(2-fluoropyridin-4-yl)-1H-pyrrolo[2,3-b]pyridin-5-yl)-2-methoxypyridin-3-yl)but-2-enamide (E)-4-(dimethylamino)-N-(2-ethoxy-5-(3-(2-fluoropyridin-4-yl)-1H-pyrrolo[2,3-b]pyridin-5-yl)pyridin-3-yl)but-2-enamide (E)-N-(2-cyclobutoxy-5-(3-(2-fluoropyridin-4-yl)-1H-pyrrolo[2,3-b]pyridin-5-yl)pyridin-3-yl)-4-(dimethylamino)but-2-enamide (E)-4-(dimethylamino)-N-(5-(3-(2-fluoropyridin-4-yl)-1H-pyrrolo[2,3-b]pyridin-5-yl)-2-(oxetan-3-yloxy)pyridin-3-yl)but-2-enamide (E)-4-(dimethylamino)-N-(5-(3-(2-fluoropyridin-4-yl)-1H-pyrrolo[2,3-b]pyridin-5-yl)-2-((tetrahydrofuran-3-yl)oxy)pyridin-3-yl)but-2-enamide N-(5-(3-(2-cyanopyridin-4-yl)-1H-pyrrolo[2,3-b]pyridin-5-yl)-2-methoxypyridin-3-yl)acrylamide N-(5-(3-(2-cyanopyridin-4-yl)-1H-pyrrolo[2,3-b]pyridin-5-yl)-2-ethoxypyridin-3-yl)acrylamide N-(5-(3-(2-cyanopyridin-4-yl)-1H-pyrrolo[2,3-b]pyridin-5-yl)-2-cyclobutoxypyridin-3-yl)acrylamide N-(5-(3-(2-cyanopyridin-4-yl)-1H-pyrrolo[2,3-b]pyridin-5-yl)-2-(oxetan-3-yloxy)pyridin-3-yl)acrylamide N-(5-(3-(2-cyanopyridin-4-yl)-1H-pyrrolo[2,3-b]pyridin-5-yl)-2-((tetrahydrofuran-3-yl)oxy)pyridin-3-yl)acrylamide (E)-N-(5-(3-(2-cyanopyridin-4-yl)-1H-pyrrolo[2,3-b]pyridin-5-yl)-2-methoxypyridin-3-yl)-4-(dimethylamino)but-2-enamide (E)-N-(5-(3-(2-cyanopyridin-4-yl)-1H-pyrrolo[2,3-b]pyridin-5-yl)-2-ethoxypyridin-3-yl)-4-(dimethylamino)but-2-enamide (E)-N-(5-(3-(2-cyanopyridin-4-yl)-1H-pyrrolo[2,3-b]pyridin-5-yl)-2-cyclobutoxypyridin-3-yl)-4-(dimethylamino)but-2-enamide (E)-N-(5-(3-(2-cyanopyridin-4-yl)-1H-pyrrolo[2,3-b]pyridin-5-yl)-2-(oxetan-3-yloxy)pyridin-3-yl)-4-(dimethylamino)but-2-enamide (E)-N-(5-(3-(2-cyanopyridin-4-yl)-1H-pyrrolo[2,3-b]pyridin-5-yl)-2-((tetrahydrofuran-3-yl)oxy)pyridin-3-yl)-4-(dimethylamino)but-2-enamide N-(5-(3-(3-cyanophenyl)-1H-pyrrolo[2,3-b]pyridin-5-yl)-2-methoxypyridin-3-yl)acrylamide N-(5-(3-(3-cyanophenyl)-1H-pyrrolo[2,3-b]pyridin-5-yl)-2-ethoxypyridin-3-yl)acrylamide N-(5-(3-(3-cyanophenyl)-1H-pyrrolo[2,3-b]pyridin-5-yl)-2-cyclobutoxypyridin-3-yl)acrylamide N-(5-(3-(3-cyanophenyl)-1H-pyrrolo[2,3-b]pyridin-5-yl)-2-(oxetan-3-yloxy)pyridin-3-yl)acrylamide N-(5-(3-(3-cyanophenyl)-1H-pyrrolo[2,3-b]pyridin-5-yl)-2-((tetrahydrofuran-3-yl)oxy)pyridin-3-yl)acrylamide (E)-N-(5-(3-(3-cyanophenyl)-1H-pyrrolo[2,3-b]pyridin-5-yl)-2-methoxypyridin-3-yl)-4-(dimethylamino)but-2-enamide (E)-N-(5-(3-(3-cyanophenyl)-1H-pyrrolo[2,3-b]pyridin-5-yl)-2-ethoxypyridin-3-yl)-4-(dimethylamino)but-2-enamide (E)-N-(5-(3-(3-cyanophenyl)-1H-pyrrolo[2,3-b]pyridin-5-yl)-2-cyclobutoxypyridin-3-yl)-4-(dimethylamino)but-2-enamide (E)-N-(5-(3-(3-cyanophenyl)-1H-pyrrolo[2,3-b]pyridin-5-yl)-2-(oxetan-3-yloxy)pyridin-3-yl)-4-(dimethylamino)but-2-enamide (E)-N-(5-(3-(3-cyanophenyl)-1H-pyrrolo[2,3-b]pyridin-5-yl)-2-((tetrahydrofuran-3-yl)oxy)pyridin-3-yl)-4-(dimethylamino)but-2-enamide N-(3-(3-(2-methoxypyridin-4-yl)-1-methyl-1H-pyrrolo[2,3-b]pyridin-5-yl)phenyl)acrylamide N-(3-methoxy-5-(3-(2-methoxypyridin-4-yl)-1-methyl-1H-pyrrolo[2,3-b]pyridin-5-yl)phenyl)acrylamide (E)-4-(dimethylamino)-N-(3-(3-(2-methoxypyridin-4-yl)-1-methyl-1H-pyrrolo[2,3-b]pyridin-5-yl)phenyl)but-2-enamide (E)-4-(dimethylamino)-N-(3-methoxy-5-(3-(2-methoxypyridin-4-yl)-1-methyl-1H-pyrrolo[2,3-b]pyridin-5-yl)phenyl)but-2-enamide N-(5-(3-(2-methoxypyridin-4-yl)-1-methyl-1H-pyrrolo[2,3-b]pyridin-5-yl)pyridin-3-yl)acrylamide (E)-4-(dimethylamino)-N-(5-(3-(2-methoxypyridin-4-yl)-1-methyl-1H-pyrrolo[2,3-b]pyridin-5-yl)pyridin-3-yl)but-2-enamide (5-(3-acrylamidophenyl)-3-(2-methoxypyridin-4-yl)-1H-pyrrolo[2,3-b]pyridin-1-yl)methyl dihydrogen phosphate (5-(3-acrylamido-5-methoxyphenyl)-3-(2-methoxypyridin-4-yl)-1H-pyrrolo[2,3-b]pyridin-1-yl)methyl dihydrogen phosphate (E)-(5-(3-(4-(dimethylamino)but-2-enamido)phenyl)-3-(2-methoxypyridin-4-yl)-1H-pyrrolo[2,3-b]pyridin-1-yl)methyl dihydrogen phosphate (E)-(5-(3-(4-(dimethylamino)but-2-enamido)-5-methoxyphenyl)-3-(2-methoxypyridin-4-yl)-1H-pyrrolo[2,3-b]pyridin-1-yl)methyl dihydrogen phosphate (5-(5-acrylamidopyridin-3-yl)-3-(2-methoxypyridin-4-yl)-1H-pyrrolo[2,3-b]pyridin-1-yl)methyl dihydrogen phosphate (E)-(5-(5-(4-(dimethylamino)but-2-enamido)pyridin-3-yl)-3-(2-methoxypyridin-4-yl)-1H-pyrrolo[2,3-b]pyridin-1-yl)methyl dihydrogen phosphate N-(3-(3-(2-fluoropyridin-4-yl)-1-methyl-1H-pyrrolo[2,3-b]pyridin-5-yl)phenyl)acrylamide N-(3-(3-(2-fluoropyridin-4-yl)-1-methyl-1H-pyrrolo[2,3-b]pyridin-5-yl)-5-methoxyphenyl)acrylamide (E)-4-(dimethylamino)-N-(3-(3-(2-fluoropyridin-4-yl)-1-methyl-1H-pyrrolo[2,3-b]pyridin-5-yl)phenyl)but-2-enamide (E)-4-(dimethylamino)-N-(3-(3-(2-fluoropyridin-4-yl)-1-methyl-1H-pyrrolo[2,3-b]pyridin-5-yl)-5-methoxyphenyl)but-2-enamide N-(5-(3-(2-fluoropyridin-4-yl)-1-methyl-1H-pyrrolo[2,3-b]pyridin-5-yl)pyridin-3-yl)acrylamide (E)-4-(dimethylamino)-N-(5-(3-(2-fluoropyridin-4-yl)-1-methyl-1H-pyrrolo[2,3-b]pyridin-5-yl)pyridin-3-yl)but-2-enamide (5-(3-acrylamidophenyl)-3-(2-fluoropyridin-4-yl)-1H-pyrrolo[2,3-b]pyridin-1-yl)methyl dihydrogen phosphate (5-(3-acrylamido-5-methoxyphenyl)-3-(2-fluoropyridin-4-yl)-1H-pyrrolo[2,3-b]pyridin-1-yl)methyl dihydrogen phosphate (E)-(5-(3-(4-(dimethylamino)but-2-enamido)phenyl)-3-(2-fluoropyridin-4-yl)-1H-pyrrolo[2,3-b]pyridin-1-yl)methyl dihydrogen phosphate (E)-(5-(3-(4-(dimethylamino)but-2-enamido)-5-methoxyphenyl)-3-(2-fluoropyridin-4-yl)-1H-pyrrolo[2,3-b]pyridin-1-yl)methyl dihydrogen phosphate (5-(5-acrylamidopyridin-3-yl)-3-(2-fluoropyridin-4-yl)-1H-pyrrolo[2,3-b]pyridin-1-yl)methyl dihydrogen phosphate (E)-(5-(5-(4-(dimethylamino)but-2-enamido)pyridin-3-yl)-3-(2-fluoropyridin-4-yl)-1H-pyrrolo[2,3-b]pyridin-1-yl)methyl dihydrogen phosphate N-(3-(3-(2-cyanopyridin-4-yl)-1-methyl-1H-pyrrolo[2,3-b]pyridin-5-yl)phenyl)acrylamide N-(3-(3-(2-cyanopyridin-4-yl)-1-methyl-1H-pyrrolo[2,3-b]pyridin-5-yl)-5-methoxyphenyl)acrylamide (E)-N-(3-(3-(2-cyanopyridin-4-yl)-1-methyl-1H-pyrrolo[2,3-b]pyridin-5-yl)phenyl)-4-(dimethylamino)but-2-enamide (E)-N-(3-(3-(2-cyanopyridin-4-yl)-1-methyl-1H-pyrrolo[2,3-b]pyridin-5-yl)-5-methoxyphenyl)-4-(dimethylamino)but-2-enamide N-(5-(3-(2-cyanopyridin-4-yl)-1-methyl-1H-pyrrolo[2,3-b]pyridin-5-yl)pyridin-3-yl)acrylamide (E)-N-(5-(3-(2-cyanopyridin-4-yl)-1-methyl-1H-pyrrolo[2,3-b]pyridin-5-yl)pyridin-3-yl)-4-(dimethylamino)but-2-enamide (5-(3-acrylamidophenyl)-3-(2-cyanopyridin-4-yl)-1H-pyrrolo[2,3-b]pyridin-1-yl)methyl dihydrogen phosphate (5-(3-acrylamido-5-methoxyphenyl)-3-(2-cyanopyridin-4-yl)-1H-pyrrolo[2,3-b]pyridin-1-yl)methyl dihydrogen phosphate (E)-(3-(2-cyanopyridin-4-yl)-5-(3-(4-(dimethylamino)but-2-enamido)phenyl)-1H-pyrrolo[2,3-b]pyridin-1-yl)methyl dihydrogen phosphate (E)-(3-(2-cyanopyridin-4-yl)-5-(3-(4-(dimethylamino)but-2-enamido)-5-methoxyphenyl)-1H-pyrrolo[2,3-h]pyridin-1-yl)methyl dihydrogen phosphate (5-(5-acrylamidopyridin-3-yl)-3-(2-cyanopyridin-4-yl)-1H-pyrrolo[2,3-b]pyridin-1-yl)methyl dihydrogen phosphate (E)-(3-(2-cyanopyridin-4-yl)-5-(5-(4-(dimethylamino)but-2-enamido)pyridin-3-yl)-1H-pyrrolo[2,3-h]pyridin-1-yl)methyl dihydrogen phosphate N-(3-(3-(3-cyanophenyl)-1-methyl-1H-pyrrolo[2,3-b]pyridin-5-yl)phenyl)acrylamide N-(3-(3-(3-cyanophenyl)-1-methyl-1H-pyrrolo[2,3-b]pyridin-5-yl)-5-methoxyphenyl)acrylamide (E)-N-(3-(3-(3-cyanophenyl)-1-methyl-1H-pyrrol o[2,3-b]pyridin-5-yl)phenyl)-4-(dimethylamino)but-2-enamide (E)-N-(3-(3-(3-cyanophenyl)-1-methyl-1H-pyrrolo[2,3-b]pyridin-5-yl)-5-methoxyphenyl)-4-(dimethylamino)but-2-enamide N-(5-(3-(3-cyanophenyl)-1-methyl-1H-pyrrolo[2,3-b]pyridin-5-yl)pyridin-3-yl)acrylamide (E)-N-(5-(3-(3-cyanophenyl)-1-methyl-1H-pyrrolo[2,3-b]pyridin-5-yl)pyridin-3-yl)-4-(dimethylamino)but-2-enamide (5-(3-acrylamidophenyl)-3-(3-cyanophenyl)-1H-pyrrolo[2,3-b]pyridin-1-yl)methyl dihydrogen phosphate (5-(3-acrylamido-5-methoxyphenyl)-3-(3-cyanophenyl)-H-pyrrolo[2,3-b]pyridin-1-yl)methyl dihydrogen phosphate (E)-(3-(3-cyanophenyl)-5-(3-(4-(dimethylamino)but-2-enamido)phenyl)-1H-pyrrolo[2,3-b]pyridin-1-yl)methyl dihydrogen phosphate (E)-(3-(3-cyanophenyl)-5-(3-(4-(dimethylamino)but-2-enamido)-5-methoxyphenyl)-1H-pyrrolo[2,3-b]pyridin-1-yl)methyl dihydrogen phosphate (5-(5-acrylamidopyridin-3-yl)-3-(3-cyanophenyl)-1H-pyrrolo[2,3-b]pyridin-1-yl)methyl dihydrogen phosphate (E)-(3-(3-cyanophenyl)-5-(5-(4-(dimethylamino)but-2-enamido)pyridin-3-yl)-1H-pyrrolo[2,3-b]pyridin-1-yl)methyl dihydrogen phosphate
N-(3-(3-(2-methoxypyridin-4-yl)-1-methyl-1H-pyrrolo[2,3-b]pyridin-5-yl)phenyl)-N-methylacrylamide
N-(3-methoxy-5-(3-(2-methoxypyridin-4-yl)-1-methyl-1H-pyrrolo[2,3-b]pyridin-5-yl)phenyl)-N-methylacrylamide
(E)-4-(dimethylamino)-N-(3-(3-(2-methoxypyridin-4-yl)-1-methyl-1H-pyrrolo[2,3-b]pyridin-5-yl)phenyl)-N-methylbut-2-enamide
(E)-4-(dimethylamino)-N-(3-methoxy-5-(3-(2-methoxypyridin-4-yl)-1-methyl-1H-pyrrolo[2,3-b]pyridin-5-yl)phenyl)-N-methylbut-2-enamide
N-(5-(3-(2-methoxypyridin-4-yl)-1-methyl-1H-pyrrolo[2,3-b]pyridin-5-yl)pyridin-3-yl)-N-methylacrylamide
(E)-4-(dimethylamino)-N-(5-(3-(2-methoxypyridin-4-yl)-1-methyl-1H-pyrrolo[2,3-b]pyridin-5-yl)pyridin-3-yl)-N-methylbut-2-enamide
(3-(2-methoxypyridin-4-yl)-5-(3-(N-methylacrylamido)phenyl)-1H-pyrrolo[2,3-b]pyridin-1-yl)methyl dihydrogen phosphate
(5-(3-methoxy-5-(N-methylacrylamido)phenyl)-3-(2-methoxypyridin-4-yl)-1H-pyrrolo[2,3-b]pyridin-1-yl)methyl dihydrogen phosphate
(E)-(5-(3-(4-(dimethylamino)-N-methylbut-2-enamido)phenyl)-3-(2-methoxypyridin-4-yl)-1H-pyrrolo[2,3-b]pyridin-1-yl)methyl dihydrogen phosphate
(E)-(5-(3-(4-(dimethylamino)-N-methylbut-2-enamido)-5-methoxyphenyl)-3-(2-methoxypyridin-4-yl)-1H-pyrrolo[2,3-b]pyridin-1-yl)methyl dihydrogen phosphate
(3-(2-methoxypyridin-4-yl)-5-(5-(N-methylacrylamido)pyridin-3-yl)-1H-pyrrolo[2,3-b]pyridin-1-yl)methyl dihydrogen phosphate
(E)-(5-(5-(4-(dimethylamino)-N-methylbut-2-enamido)pyridin-3-yl)-3-(2-methoxypyridin-4-yl)-1H-pyrrolo[2,3-b]pyridin-1-yl)methyl dihydrogen phosphate
N-(3-(3-(2-fluoropyridin-4-yl)-1-methyl-1H-pyrrolo[2,3-b]pyridin-5-yl)phenyl)-N-methylacrylamide
N-(3-(3-(2-fluoropyridin-4-yl)-1-methyl-1H-pyrrolo[2,3-b]pyridin-5-yl)-5-methoxyphenyl)-N-methylacrylamide
(E)-4-(dimethylamino)-N-(3-(3-(2-fluoropyridin-4-yl)-1-methyl-1H-pyrrolo[2,3-b]pyridin-5-yl)phenyl)-N-methylbut-2-enamide
(E)-4-(dimethylamino)-N-(3-(3-(2-fluoropyridin-4-yl)-1-methyl-1H-pyrrolo[2,3-b]pyridin-5-yl)-5-methoxyphenyl)-N-methylbut-2-enamide
N-(5-(3-(2-fluoropyridin-4-yl)-1-methyl-1H-pyrrolo[2,3-b]pyridin-5-yl)pyridin-3-yl)-N-methylacrylamide
(E)-4-(dimethylamino)-N-(5-(3-(2-fluoropyridin-4-yl)-1-methyl-H-pyrrolo[2,3-b]pyridin-5-yl)pyridin-3-yl)-N-methylbut-2-enamide
(3-(2-fluoropyridin-4-yl)-5-(3-(N-methylacrylamido)phenyl) )-1H-pyrrolo[2,3]pyridin-1-yl)methyl dihydrogen phosphate
(3-(2-fluoropyridin-4-yl)-5-(3-methoxy-5-(N-methylacrylamido)phenyl)-1H-pyrrolo[2,3-b]pyridin-1-yl)methyl dihydrogen phosphate
(E)-(5-(3-(4-(dimethylamino)-N-methylbut-2-enamido)phenyl)-3-(2-fluoropyridin-4-yl)-1H-pyrrolo[2,3-b]pyridin-1-yl)methyl dihydrogen phosphate
(E)-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)methyl dihydrogen phosphate
(3-(2-fluoropyridin-4-yl)-5-(5-(N-methylacrylamido)pyridin-3-yl)-1H-pyrrolo[2,3-b]pyridin-1-yl)methyl dihydrogen phosphate
(E)-(5-(5-(4-(dimethylamino)-N-methylbut-2-enamido)pyridin-3-yl)-3-(2-fluoropyridin-4-yl)-1H-pyrrolo[2,3-b]pyridin-1-yl)methyl dihydrogen phosphate
(5-(3-acrylamidophenyl)-3-(2-methoxypyridin-4-yl)-1H-pyrrolo[2,3-b]pyridin-1-yl)methyl diethyl phosphate
(5-(3-acrylamido-5-methoxyphenyl)-3-(2-methoxypyridin-4-yl)-1H-pyrrolo[2,3-b]pyridin-1-yl)methyl diethyl phosphate
(E)-(5-(3-(4-(dimethylamino)but-2-enamido)phenyl)-3-(2-methoxypyridin-4-yl)-1H-pyrrolo[2,3-b]pyridin-1-yl)methyl diethyl phosphate
(E)-(5-(3-(4-(dimethylamino)but-2-enamido)-5-methoxyphenyl)-3-(2-methoxypyridin-4-yl)-1H-pyrrolo[2,3-b]pyridin-1-yl)methyl diethyl phosphate
(5-(5-acrylamidopyridin-3-yl)-3-(2-methoxypyridin-4-yl)-1H-pyrrolo[2,3-b]pyridin-1-yl)methyl diethyl phosphate
(E)-(5-(5-(4-(dimethylamino)but-2-enamido)pyridin-3-yl)-3-(2-methoxypyridin-4-yl)-1H-pyrrolo[2,3-b]pyridin-1-yl)methyl diethyl phosphate
(5-(3-acrylamidophenyl)-3-(2-fluoropyridin-4-yl)-1H-pyrrolo[2,3-b]pyridin-1-yl)methyl diethyl phosphate
(5-(3-acrylamido-5-methoxyphenyl)-3-(2-fluoropyridin-4-yl)-1H-pyrrolo[2,3-b]pyridin-1-yl)methyl diethyl phosphate
(E)-(5-(3-(4-(dimethylamino)but-2-enamido)phenyl)-3-(2-fluoropyridin-4-yl)-1H-pyrrolo[2,3-b]pyridin-1-yl)methyl diethyl phosphate
(E)-(5-(3-(4-(dimethylamino)but-2-enamido)-5-methoxyphenyl)-3-(2-fluoropyridin-4-yl)-1H-pyrrolo[2,3-b]pyridin-1-yl)methyl diethyl phosphate
(5-(5-acrylamidopyridin-3-yl)-3-(2-fluoropyridin-4-yl)-1H-pyrrolo[2,3-b]pyridin-1-yl)methyl diethyl phosphate
(E)-(5-(5-(4-(dimethylamino)but-2-enamido)pyridin-3-yl)-3-(2-fluoropyridin-4-yl)-1H-pyrrolo[2,3-b]pyridin-1-yl)methyl diethyl phosphate
(5-(3-acrylamidophenyl)-3-(2-cyanopyridin-4-yl)-1H-pyrrolo[2,3-b]pyridin-1-yl)methyl diethyl phosphate
(5-(3-acrylamido-5-methoxyphenyl)-3-(2-cyanopyridin-4-yl)-1H-pyrrolo[2,3-b]pyridin-1-yl)methyl diethyl phosphate
(E)-(3-(2-cyanopyridin-4-yl)-5-(3-(4-(dimethylamino)but-2-enamido)phenyl)-1H-pyrrolo[2,3-b]pyridin-1-yl)methyl diethyl phosphate
(E)-(3-(2-cyanopyridin-4-yl)-5-(3-(4-(dimethylamino)but-2-enamido)-5-methoxyphenyl)-1H-pyrrolo[2,3-b]pyridin-1-yl)methyl diethyl phosphate
(5-(5-acrylamidopyridin-3-yl)-3-(2-cyanopyridin-4-yl)-1H-pyrrolo[2,3-b]pyridin-1-yl)methyl diethyl phosphate
(E)-(3-(2-cyanopyridin-4-yl)-5-(5-(4-(dimethylamino)but-2-enamido)pyridin-3-yl)-1H-pyrrolo[2,3-b]pyridin-1-yl)methyl diethyl phosphate
(5-(3-acrylamidophenyl)-3-(3-cyanophenyl)-1H-pyrrolo[2,3-b]pyridin-1-yl)methyl diethyl phosphate
(5-(3-acrylamido-5-methoxyphenyl)-3-(3-cyanophenyl)-1H-pyrrolo[2,3-b]pyridin-1-yl)methyl diethyl phosphate
(E)-(3-(3-cyanophenyl)-5-(3-(4-(dimethylamino)but-2-enamido)phenyl)-1H-pyrrolo[2,3-b]pyridin-1-yl)methyl diethyl phosphate
(E)-(3-(3-cyanophenyl)-5-(3-(4-(dimethylamino)but-2-enamido)-5-methoxyphenyl)-1H-pyrrolo[2,3-b]pyridin-1-yl)methyl diethyl phosphate
(5-(5-acrylamidopyridin-3-yl)-3-(3-cyanophenyl)-1H-pyrrolo[2,3-b]pyridin-1-yl)methyl diethyl phosphate
(E)-(3-(3-cyanophenyl)-5-(5-(4-(dimethylamino)but-2-enamido)pyridin-3-yl)-1H-pyrrolo[2,3-b]pyridin-1-yl)methyl diethyl phosphate diethyl ((3-(2-methoxypyridin-4-yl)-5-(3-(N-methylacrylamido)phenyl)-1H-pyrrolo[2,3-b]pyridin-1-yl)methyl) phosphate
diethyl ((5-(3-methoxy-5-(N-methylacrylamido)phenyl)-3-(2-methoxypyridin-4-yl)-1H-pyrrolo[2,3-b]pyridin-1-yl)methyl) phosphate
(E)-(5-(3-(4-(dimethylamino)-N-methylbut-2-enamido)phenyl)-3-(2-methoxypyridin-4-yl)-1H-pyrrolo[2,3-b]pyridin-1-yl)methyl diethyl phosphate
(E)-(5-(3-(4-(dimethylamino)-N-methylbut-2-enamido)-5-methoxyphenyl)-3-(2-methoxypyridin-4-yl)-1H-pyrrolo[2,3-b]pyridin-1-yl)methyl diethyl phosphate
diethyl ((3-(2-methoxypyridin-4-yl)-5-(5-(N-methylacrylamido)pyridin-3-yl)-1H-pyrrolo[2,3-b]pyridin-1-yl)methyl) phosphate
(E)-(5-(5-(4-(dimethylamino)-N-methylbut-2-enamido)pyridin-3-yl)-3-(2-methoxypyridin-4-yl)-1H-pyrrolo[2,3-b]pyridin-1-yl)methyl diethyl phosphate
diethyl ((3-(2-fluoropyridin-4-yl)-5-(3-(N-methylacrylamido)phenyl)-1H-pyrrolo[2,3-b]pyridin-1-yl)methyl) phosphate
diethyl ((3-(2-fluoropyridin-4-yl)-5-(3-methoxy-5-(N-methylacrylamido)phenyl)-1H-pyrrolo[2,3-b]pyridin-1-yl)methyl) phosphate
(E)-(5-(3-(4-(dimethylamino)-N-methylbut-2-enamido)phenyl)-3-(2-fluoropyridin-4-yl)-1H-pyrrolo[2,3-b]pyridin-1-yl)methyl diethyl phosphate
(E)-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)methyl diethyl phosphate
diethyl ((3-(2-fluoropyridin-4-yl)-5-(5-(N-methylacrylamido)pyridin-3-yl)-1H-pyrrolo[2,3-b]pyridin-1-yl)methyl) phosphate
(E)-(5-(5-(4-(dimethylamino)-N-methylbut-2-enamido)pyridin-3-yl)-3-(2-fluoropyridin-4-yl)-1H-pyrrolo[2,3-b]pyridin-1-yl)methyl diethyl phosphate
(3-(2-cyanopyridin-4-yl)-5-(3-(N-methylacrylamido)phenyl)-1H-pyrrolo[2,3-b]pyridin-1-yl)methyl diethyl phosphate
(3-(2-cyanopyridin-4-yl)-5-(3-methoxy-5-(N-methylacrylamido)phenyl)-1H-pyrrolo[2,3-b]pyridin-1-yl)methyl diethyl phosphate
(E)-(3-(2-cyanopyridin-4-yl)-5-(3-(4-(dimethylamino)-N-methylbut-2-enamido)phenyl)-1H-pyrrolo[2,3-b]pyridin-1-yl)methyl diethyl phosphate
(E)-(3-(2-cyanopyridin-4-yl)-5-(3-(4-(dimethylamino)-N-methylbut-2-enamido)-5-methoxyphenyl)-1H-pyrrolo[2,3-b]pyridin-1-yl)methyl diethyl phosphate
(3-(2-cyanopyridin-4-yl)-5-(5-(N-methylacrylamido)pyridin-3-yl)-1H-pyrrolo[2,3-b]pyridin-1-yl)methyl diethyl phosphate
(E)-(3-(2-cyanopyridin-4-yl)-5-(5-(4-(dimethylamino)-N-methylbut-2-enamido)pyridin-3-yl)-1H-pyrrolo[2,3-b]pyridin-1-yl)methyl diethyl phosphate
(3-(3-cyanophenyl)-5-(3-(N-methylacrylamido)phenyl)-1H-pyrrolo[2,3-b]pyridin-1-yl)methyl diethyl phosphate
(3-(3-cyanophenyl)-5-(3-methoxy-5-(N-methylacrylamido)phenyl)-1H-pyrrolo[2,3-b]pyridin-1-yl)methyl diethyl phosphate
(E)-(3-(3-cyanophenyl)-5-(3-(4-(dimethylamino)-N-methylbut-2-enamido)phenyl)-1H-pyrrolo[2,3-b]pyridin-1-yl)methyl diethyl phosphate
(E)-(3-(3-cyanophenyl)-5-(3-(4-(dimethylamino)-N-methylbut-2-enamido)-5-methoxyphenyl)-1H-pyrrolo[2,3-b]pyridin-1-yl)methyl diethyl phosphate
(3-(3-cyanophenyl)-5-(5-(N-methylacrylamido)pyridin-3-yl)-1H-pyrrolo[2,3-b]pyridin-1-yl)methyl diethyl phosphate
(E)-(3-(3-cyanophenyl)-5-(5-(4-(dimethylamino)-N-methylbut-2-enamido)pyridin-3-yl)-1H-pyrrolo[2,3-b]pyridin-1-yl)methyl diethyl phosphate
(5-(3-acrylamidophenyl)-3-(2-methoxypyridin-4-yl)-1H-pyrrolo[2,3-b]pyridin-1-yl)methyl di-tert-butyl phosphate
(5-(3-acrylamido-5-methoxyphenyl)-3-(2-methoxypyridin-4-yl)-1H-pyrrolo[2,3-b]pyridin-1-yl)methyl di-tert-butyl phosphate
(E)-di-tert-butyl ((5-(3-(4-(dimethylamino)but-2-enamido)phenyl)-3-(2-methoxypyridin-4-yl)-1H-pyrrolo[2,3-b]pyridin-1-yl)methyl) phosphate
(E)-di-tert-butyl ((5-(3-(4-(dimethylamino)but-2-enamido)-5-methoxyphenyl)-3-(2-methoxypyridin-4-yl)-1H-pyrrolo[2,3-b]pyridin-1-yl)methyl) phosphate
(5-(5-acrylamidopyridin-3-yl)-3-(2-methoxypyridin-4-yl)-1H-pyrrolo[2,3-b]pyridin-1-yl)methyl di-tert-butyl phosphate
(E)-di-tert-butyl ((5-(5-(4-(dimethylamino)but-2-enamido)pyridin-3-yl)-3-(2-methoxypyridin-4-yl)-1H-pyrrolo[2,3-b]pyridin-1-yl)methyl) phosphate
(5-(3-acrylamidophenyl)-3-(2-fluoropyridin-4-yl)-1H-pyrrolo[2,3-b]pyridin-1-yl)methyl di-tert-butyl phosphate
(5-(3-acrylamido-5-methoxyphenyl)-3-(2-fluoropyridin-4-yl)-1H-pyrrolo[2,3-b]pyridin-1-yl)methyl di-tert-butyl phosphate
(E)-di-tert-butyl ((5-(3-(4-(dimethylamino)but-2-enamido)phenyl)-3-(2-fluoropyridin-4-yl)-1H-pyrrolo[2,3-b]pyridin-1-yl)methyl) phosphate
(E)-di-tert-butyl ((5-(3-(4-(dimethylamino)but-2-enamido)-5-methoxyphenyl)-3-(2-fluoropyridin-4-yl)-1H-pyrrolo[2,3-b]pyridin-1-yl)methyl) phosphate
(5-(5-acrylamidopyridin-3-yl)-3-(2-fluoropyridin-4-yl)-1H-pyrrolo[2,3-b]pyridin-1-yl)methyl di-tert-butyl phosphate
(E)-di-tert-butyl ((5-(5-(4-(dimethylamino)but-2-enamido)pyridin-3-yl)-3-(2-fluoropyridin-4-yl)-1H-pyrrolo[2,3-b]pyridin-1-yl)methyl) phosphate
(5-(3-acrylamidophenyl)-3-(2-cyanopyridin-4-yl)-1H-pyrrolo[2,3-b]pyridin-1-yl)methyl di-tert-butyl phosphate
(5-(3-acrylamido-5-methoxyphenyl)-3-(2-cyanopyridin-4-yl)-1H-pyrrolo[2,3-b]pyridin-1-yl)methyl di-tert-butyl phosphate
(E)-di-tert-butyl ((3-(2-cyanopyridin-4-yl)-5-(3-(4-(dimethylamino)but-2-enamido)phenyl)-1H-pyrrolo[2,3-b]pyridin-1-yl)methyl) phosphate
(E)-di-tert-butyl ((3-(2-cyanopyridin-4-yl)-5-(3-(4-(dimethylamino)but-2-enamido)-5-methoxyphenyl)-1H-pyrrolo[2,3-b]pyridin-1-yl)methyl) phosphate
(5-(5-acrylamidopyridin-3-yl)-3-(2-cyanopyridin-4-yl)-1H-pyrrolo[2,3-b]pyridin-1-yl)methyl di-tert-butyl phosphate
(E)-di-tert-butyl ((3-(2-cyanopyridin-4-yl)-5-(5-(4-(dimethylamino)but-2-enamido)pyridin-3-yl)-1H-pyrrolo[2,3-b]pyridin-1-yl)methyl) phosphate
(5-(3-acrylamidophenyl)-3-(3-cyanophenyl)-1H-pyrrolo[2,3-b]pyridin-1-yl)methyl di-tert-butyl phosphate
(5-(3-acrylamido-5-methoxyphenyl)-3-(3-cyanophenyl)-H-pyrrolo[2,3-b]pyridin-1-yl)methyl di-tert-butyl phosphate
(E)-di-tert-butyl ((3-(3-cyanophenyl)-5-(3-(4-(dimethylamino)but-2-enamido)phenyl)-1H-pyrrolo[2,3-b]pyridin-1-yl)methyl) phosphate
(E)-di-tert-butyl ((3-(3-cyanophenyl)-5-(3-(4-(dimethylamino)but-2-enamido)-5-methoxyphenyl)-1H-pyrrolo[2,3-b]pyridin-1-yl)methyl) phosphate
(5-(5-acrylamidopyridin-3-yl)-3-(3-cyanophenyl)-1H-pyrrolo[2,3-b]pyridin-1-yl)methyl di-tert-butyl phosphate (E)-di-tert-butyl ((3-(3-cyanophenyl)-5-(5-(4-(dimethylamino)but-2-enamido)pyridin-3-yl)-1H-pyrrolo[2,3-b]pyridin-1-yl)methyl) phosphate
N-(3-(3-(2-cyanopyridin-4-yl)-1-methyl-1H-pyrrolo[2,3-b]pyridin-5-yl)phenyl)-N-methylacrylamide
N-(3-(3-(2-cyanopyridin-4-yl)-1-methyl-1H-pyrrolo[2,3-b]pyridin-5-yl)-5-methoxyphenyl)-N-methylacrylamide
(E)-N-(3-(3-(2-cyanopyridin-4-yl)-1-methyl-1H-pyrrolo[2,3-b]pyridin-5-yl)phenyl)-4-(dimethylamino)-N-methylbut-2-enamide
(E)-N-(3-(3-(2-cyanopyridin-4-yl)-1-methyl-1H-pyrrolo[2,3-b]pyridin-5-yl)-5-methoxyphenyl)-4-(dimethylamino)-N-methylbut-2-enamide
N-(5-(3-(2-cyanopyridin-4-yl)-1-methyl-1H-pyrrolo[2,3-b]pyridin-5-yl)pyridin-3-yl)-N-methylacrylamide
(E)-N-(5-(3-(2-cyanopyridin-4-yl)-1-methyl-1H-pyrrolo[2,3-b]pyridin-5-yl)pyridin-3-yl)-4-(dimethylamino)-N-methylbut-2-enamide
(3-(2-cyanopyridin-4-yl)-5-(3-(N-methylacrylamido)phenyl)-1H-pyrrolo[2,3-b]pyridin-1-yl)methyl dihydrogen phosphate
(3-(2-cyanopyridin-4-yl)-5-(3-methoxy-5-(N-methylacrylamido)phenyl)-1H-pyrrolo[2,3-b]pyridin-1-yl)methyl dihydrogen phosphate
(E)-(3-(2-cyanopyridin-4-yl)-5-(3-(4-(dimethylamino)-N-methylbut-2-enamido)phenyl)-1H-pyrrolo[2,3-b]pyridin-1-yl)methyl dihydrogen phosphate
(E)-(3-(2-cyanopyridin-4-yl)-5-(3-(4-(dimethylamino)-N-methylbut-2-enamido)-5-methoxyphenyl)-1H-pyrrolo[2,3-b]pyridin-1-yl)methyl dihydrogen phosphate
(3-(2-cyanopyridin-4-yl)-5-(5-(N-methylacrylamido)pyridin-3-yl)-1H-pyrrolo[2,3-b]pyridin-1-yl)methyl dihydrogen phosphate
(E)-(3-(2-cyanopyridin-4-yl)-5-(5-(4-(dimethylamino)-N-methylbut-2-enamido)pyridin-3-yl)-1H-pyrrolo[2,3-b]pyridin-1-yl)methyl dihydrogen phosphate
N-(3-(3-(3-cyanophenyl)-1-methyl-1H-pyrrolo[2,3-b]pyridin-5-yl)phenyl)-N-methylacrylamide
N-(3-(3-(3-cyanophenyl)-1-methyl-1H-pyrrolo[2,3-b]pyridin-5-yl)-5-methoxyphenyl)-N-methylacrylamide
(E)-N-(3-(3-(3-cyanophenyl)-1-methyl-1H-pyrrolo[2,3-b]pyridin-5-yl)phenyl)-4-(dimethylamino)-N-methylbut-2-enamide
(E)-N-(3-(3-(3-cyanophenyl)-1-methyl-1H-pyrrolo[2,3-b]pyridin-5-yl)-5-methoxyphenyl)-4-(dimethylamino)-N-methylbut-2-enamide
N-(5-(3-(3-cyanophenyl)-1-methyl-1H-pyrrolo[2,3-b]pyridin-5-yl)pyridin-3-yl)-N-methylacrylamide
(E)-N-(5-(3-(3-cyanophenyl)-1-methyl-1H-pyrrolo[2,3-b]pyridin-5-yl)pyridin-3-yl)-4-(dimethylamino)-N-methylbut-2-enamide
(3-(3-cyanophenyl)-5-(3-(N-methylacrylamido)phenyl)-1H-pyrrolo[2,3-b]pyridin-1-yl)methyl dihydrogen phosphate
(3-(3-cyanophenyl)-5-(3-methoxy-5-(N-methylacrylamido)phenyl)-1H-pyrrolo[2,3-b]pyridin-1-yl)methyl dihydrogen phosphate
(E)-(3-(3-cyanophenyl)-5-(3-(4-(dimethylamino)-N-methylbut-2-enamido)phenyl)-1H-pyrrolo[2,3-b]pyridin-1-yl)methyl dihydrogen phosphate
(E)-(3-(3-cyanophenyl)-5-(3-(4-(dimethylamino)-N-methylbut-2-enamido)-5-methoxyphenyl)-1H-pyrrolo[2,3-b]pyridin-1-yl)methyl dihydrogen phosphate
(3-(3-cyanophenyl)-5-(5-(N-methylacrylamido)pyridin-3-yl)-1H-pyrrolo[2,3-b]pyridin-1-yl)methyl dihydrogen phosphate
(E)-(3-(3-cyanophenyl)-5-(5-(4-(dimethylamino)-N-methylbut-2-enamido)pyridin-3-yl)-1H-pyrrolo[2,3-b]pyridin-1-yl)methyl dihydrogen phosphate
(5-(3-acrylamidophenyl)-3-(2-methoxypyridin-4-yl)-1H-pyrrolo[2,3-b]pyridin-1-yl)methyl acetate
(5-(3-acrylamido-5-methoxyphenyl)-3-(2-methoxypyridin-4-yl)-1H-pyrrolo[2,3-b]pyridin-1-yl)methyl acetate
(E)-(5-(3-(4-(dimethylamino)but-2-enamido)phenyl)-3-(2-methoxypyridin-4-yl)-1H-pyrrolo[2,3-b]pyridin-1-yl)methyl acetate
(E)-(5-(3-(4-(dimethylamino)but-2-enamido)-5-methoxyphenyl)-3-(2-methoxypyridin-4-yl)-1H-pyrrolo[2,3-b]pyridin-1-yl)methyl acetate
(5-(5-acrylamidopyridin-3-yl)-3-(2-methoxypyridin-4-yl)-1H-pyrrolo[2,3-b]pyridin-1-yl)methyl acetate
(E)-(5-(5-(4-(dimethylamino)but-2-enamido)pyridin-3-yl)-3-(2-methoxypyridin-4-yl)-1H-pyrrolo[2,3-b]pyridin-1-yl)methyl acetate
(5-(3-acrylamidophenyl)-3-(2-fluoropyridin-4-yl)-1H-pyrrolo[2,3-b]pyridin-1-yl)methyl acetate
(5-(3-acrylamido-5-methoxyphenyl)-3-(2-fluoropyridin-4-yl)-1H-pyrrolo[2,3-b]pyridin-1-yl)methyl acetate
(E)-(5-(3-(4-(dimethylamino)but-2-enamido)phenyl)-3-(2-fluoropyridin-4-yl)-1H-pyrrolo[2,3-b]pyridin-1-yl)methyl acetate
(E)-(5-(3-(4-(dimethylamino)but-2-enamido)-5-methoxyphenyl)-3-(2-fluoropyridin-4-yl)-1H-pyrrolo[2,3-b]pyridin-1-yl)methyl acetate
(5-(5-acrylamidopyridin-3-yl)-3-(2-fluoropyridin-4-yl)-1H-pyrrolo[2,3-b]pyridin-1-yl)methyl acetate
(E)-(5-(5-(4-(dimethylamino)but-2-enamido)pyridin-3-yl)-3-(2-fluoropyridin-4-yl)-1H-pyrrolo[2,3-b]pyridin-1-yl)methyl acetate
(5-(3-acrylamidophenyl)-3-(2-cyanopyridin-4-yl)-1H-pyrrolo[2,3-b]pyridin-1-yl)methyl acetate
(5-(3-acrylamido-5-methoxyphenyl)-3-(2-cyanopyridin-4-yl)-1H-pyrrolo[2,3-b]pyridin-1-yl)methyl acetate
(E)-(3-(2-cyanopyridin-4-yl)-5-(3-(4-(dimethylamino)but-2-enamido)phenyl)-1H-pyrrolo[2,3-b]pyridin-1-yl)methyl acetate
(E)-(3-(2-cyanopyridin-4-yl)-5-(3-(4-(dimethylamino)but-2-enamido)-5-methoxyphenyl)-1H-pyrrolo[2,3-b]pyridin-1-yl)methyl acetate
(5-(5-acrylamidopyridin-3-yl)-3-(2-cyanopyridin-4-yl)-1H-pyrrolo[2,3-b]pyridin-1-yl)methyl acetate
(E)-(3-(2-cyanopyridin-4-yl)-5-(5-(4-(dimethylamino)but-2-enamido)pyridin-3-yl)-1H-pyrrolo[2,3-b]pyridin-1-yl)methyl acetate
(5-(3-acrylamidophenyl)-3-(3-cyanophenyl)-1H-pyrrolo[2,3-b]pyridin-1-yl)methyl acetate
(5-(3-acrylamido-5-methoxyphenyl)-3-(3-cyanophenyl)-1H-pyrrolo[2,3-b]pyridin-1-yl)methyl acetate
(E)-(3-(3-cyanophenyl)-5-(3-(4-(dimethylamino)but-2-enamido)phenyl)-1H-pyrrolo[2,3-b]pyridin-1-yl)methyl acetate
(E)-(3-(3-cyanophenyl)-5-(3-(4-(dimethylamino)but-2-enamido)-5-methoxyphenyl)-1H-pyrrolo[2,3-b]pyridin-1-yl)methyl acetate
(5-(5-acrylamidopyridin-3-yl)-3-(3-cyanophenyl)-1H-pyrrolo[2,3-b]pyridin-1-yl)methyl acetate
(E)-(3-(3-cyanophenyl)-5-(5-(4-(dimethylamino)but-2-enamido)pyridin-3-yl)-1H-pyrrolo[2,3-b]pyridin-1-yl)methyl acetate
(5-(3-acrylamidophenyl)-3-(2-methoxypyridin-4-yl)-1H-pyrrolo[2,3-b]pyridin-1-yl)methyl pivalate
(5-(3-acrylamido-5-methoxyphenyl)-3-(2-methoxypyridin-4-yl)-1H-pyrrolo[2,3-b]pyridin-1-yl)methyl pivalate (E)-(5-(3-(4-(dimethylamino)but-2-enamido)phenyl)-3-(2-methoxypyridin-4-yl)-1H-pyrrolo[2,3-b]pyridin-1-yl)methyl pivalate (E)-(5-(3-(4-(dimethylamino)but-2-enamido)-5-methoxyphenyl)-3-(2-methoxypyridin-4-yl)-1H-pyrrolo[2,3-b]pyridin-1-yl)methyl pivalate (5-(5-acrylamidopyridin-3-yl)-3-(2-methoxypyridin-4-yl)-1H-pyrrolo[2,3-b]pyridin-1-yl)methyl pivalate (E)-(5-(5-(4-(dimethylamino)but-2-enamido)pyridin-3-yl)-3-(2-methoxypyridin-4-yl)-1H-pyrrolo[2,3-b]pyridin-1-yl)methyl pivalate (5-(3-acrylamidophenyl)-3-(2-fluoropyridin-4-yl)-1H-pyrrolo[2,3-b]pyridin-1-yl)methyl pivalate (5-(3-acrylamido-5-methoxyphenyl)-3-(2-fluoropyridin-4-yl)-1H-pyrrolo[2,3-b]pyridin-1-yl)methyl pivalate (E)-(5-(3-(4-(dimethylamino)but-2-enamido)phenyl)-3-(2-fluoropyridin-4-yl)-1H-pyrrolo[2,3-b]pyridin-1-yl)methyl pivalate (E)-(5-(3-(4-(dimethylamino)but-2-enamido)-5-methoxyphenyl)-3-(2-fluoropyridin-4-yl)-1H-pyrrolo[2,3-b]pyridin-1-yl)methyl pivalate (5-(5-acrylamidopyridin-3-yl)-3-(2-fluoropyridin-4-yl)-1H-pyrrolo[2,3-b]pyridin-1-yl)methyl pivalate (E)-(5-(5-(4-(dimethylamino)but-2-enamido)pyridin-3-yl)-3-(2-fluoropyridin-4-yl)-1H-pyrrolo[2,3-b]pyridin-1-yl)methyl pivalate (5-(3-acrylamidophenyl)-3-(2-cyanopyridin-4-yl)-1H-pyrrolo[2,3-b]pyridin-1-yl)methyl pivalate (5-(3-acrylamido-5-methoxyphenyl)-3-(2-cyanopyridin-4-yl)-1H-pyrrolo[2,3-b]pyridin-1-yl)methyl pivalate (E)-(3-(2-cyanopyridin-4-yl)-5-(3-(4-(dimethylamino)but-2-enamido)phenyl)-1H-pyrrolo[2,3-b]pyridin-1-yl)methyl pivalate (E)-(3-(2-cyanopyridin-4-yl)-5-(3-(4-(dimethylamino)but-2-enamido)-5-methoxyphenyl)-1H-pyrrolo[2,3-b]pyridin-1-yl)methyl pivalate (5-(5-acrylamidopyridin-3-yl)-3-(2-cyanopyridin-4-yl)-1H-pyrrolo[2,3-b]pyridin-1-yl)methyl pivalate (E)-(3-(2-cyanopyridin-4-yl)-5-(5-(4-(dimethylamino)but-2-enamido)pyridin-3-yl)-1H-pyrrolo[2,3-b]pyridin-1-yl)methyl pivalate (5-(3-acrylamidophenyl)-3-(3-cyanophenyl)-1H-pyrrolo[2,3-b]pyridin-1-yl)methyl pivalate (5-(3-acrylamido-5-methoxyphenyl)-3-(3-cyanophenyl)-1H-pyrrolo[2,3-b]pyridin-1-yl)methyl pivalate (E)-(3-(3-cyanophenyl)-5-(3-(4-(dimethylamino)but-2-enamido)phenyl)-1H-pyrrolo[2,3-b]pyridin-1-yl)methyl pivalate (E)-(3-(3-cyanophenyl)-5-(3-(4-(dimethylamino)but-2-enamido)-5-methoxyphenyl)-1H-pyrrolo[2,3-b]pyridin-1-yl)methyl pivalate (5-(5-acrylamidopyridin-3-yl)-3-(3-cyanophenyl)-1H-pyrrolo[2,3-b]pyridin-1-yl)methyl pivalate (E)-(3-(3-cyanophenyl)-5-(5-(4-(dimethylamino)but-2-enamido)pyridin-3-yl)-1H-pyrrolo[2,3-b]pyridin-1-yl)methyl pivalate (2S,3S)-(5-(3-acrylamidophenyl)-3-(2-methoxypyridin-4-yl)-1H-pyrrolo[2,3-b]pyridin-1-yl)methyl 2-amino-3-methylpentanoate (2S,3S)-(5-(3-acrylamido-5-methoxyphenyl)-3-(2-methoxypyridin-4-yl)-1H-pyrrolo[2,3-b]pyridin-1-yl)methyl 2-amino-3-methyl pentanoate (2S,3S)-(5-(3-((E)-4-(dimethylamino)but-2-enamido)phenyl)-3-(2-methoxypyridin-4-yl)-1H-pyrrolo[2,3-b]pyridin-1-yl)methyl 2-amino-3-methylpentanoate (2S,3S)-(5-(3-((E)-4-(dimethylamino)but-2-enamido)-5-methoxyphenyl)-3-(2-methoxypyridin-4-yl)-1H-pyrrolo[2,3-b]pyridin-1-yl)methyl 2-amino-3-methylpentanoate (2S,3S)-(5-(5-acrylamidopyridin-3-yl)-3-(2-methoxypyridin-4-yl)-1H-pyrrolo[2,3-b]pyridin-1-yl)methyl 2-amino-3-methylpentanoate (2S,3S)-(5-(5-((E)-4-(dimethylamino)but-2-enamido)pyridin-3-yl)-3-(2-methoxypyridin-4-yl)-1H-pyrrolo[2,3-b]pyridin-1-yl)methyl 2-amino-3-methylpentanoate (2S,3S)-(5-(3-acrylamidophenyl)-3-(2-fluoropyridin-4-yl)-1H-pyrrolo[2,3-b]pyridin-1-yl)methyl 2-amino-3-methyl pentanoate (2S,3S)-(5-(3-acrylamido-5-methoxyphenyl)-3-(2-fluoropyridin-4-yl)-1H-pyrrolo[2,3-b]pyridin-1-yl)methyl 2-amino-3-methylpentanoate (2S,3S)-(5-(3-((E)-4-(dimethylamino)but-2-enamido)phenyl)-3-(2-fluoropyridin-4-yl)-1H-pyrrolo[2,3-b]pyridin-1-yl)methyl 2-amino-3-methylpentanoate (2S,3S)-(5-(3-((E)-4-(dimethylamino)but-2-enamido)-5-methoxyphenyl)-3-(2-fluoropyridin-4-yl)-1H-pyrrolo[2,3-b]pyridin-1-yl)methyl 2-amino-3-methylpentanoate (2S,3S)-(5-(5-acrylamidopyridin-3-yl)-3-(2-fluoropyridin-4-yl)-1H-pyrrolo[2,3-b]pyridin-1-yl)methyl 2-amino-3-methylpentanoate (2S,3S)-(5-(5-((E)-4-(dimethylamino)but-2-enamido)pyridin-3-yl)-3-(2-fluoropyridin-4-yl)-1H-pyrrolo[2,3-b]pyridin-1-yl)methyl 2-amino-3-methylpentanoate (2S,3S)-(5-(3-acrylamidophenyl)-3-(2-cyanopyridin-4-yl)-1H-pyrrolo[2,3-b]pyridin-1-yl)methyl 2-amino-3-methylpentanoate (2S,3S)-(5-(3-acrylamido-5-methoxyphenyl)-3-(2-cyanopyridin-4-yl)-1H-pyrrolo[2,3-b]pyridin-1-yl)methyl 2-amino-3-methylpentanoate (2S,3S)-3-(2-cyanopyridin-4-yl)-5-(3-((E)-4-(dimethylamino)but-2-enamido)phenyl)-1H-pyrrolo[2,3-b]pyridin-1-yl)methyl 2-amino-3-methylpentanoate (2S,3S)-3-(2-cyanopyridin-4-yl)-5-(3-((E)-4-(dimethylamino)but-2-enamido)-5-methoxyphenyl)-1H-pyrrolo[2,3-b]pyridin-1-yl)methyl 2-amino-3-methylpentanoate (2S,3S)-(5-(5-acrylamidopyridin-3-yl)-3-(2-cyanopyridin-4-yl)-1H-pyrrolo[2,3-b]pyridin-1-yl)methyl 2-amino-3-methylpentanoate (2S,3S)-3-(2-cyanopyridin-4-yl)-5-(5-((E)-4-(dimethylamino)but-2-enamido)pyridin-3-yl)-1H-pyrrolo[2,3-b]pyridin-1-yl)methyl 2-amino-3-methylpentanoate (2S,3S)-(5-(3-acrylamidophenyl)-3-(3-cyanophenyl)-1H-pyrrolo[2,3-b]pyridin-1-yl)methyl 2-amino-3-methylpentanoate (2S,3S)-(5-(3-acrylamido-5-methoxyphenyl)-3-(3-cyanophenyl)-1H-pyrrolo[2,3-b]pyridin-1-yl)methyl 2-amino-3-methylpentanoate (2S,3S)-(3-(3-cyanophenyl)-5-(3-((E)-4-(dimethylamino)but-2-enamido)phenyl)-1H-pyrrolo[2,3-b]pyridin-1-yl)methyl 2-amino-3-methylpentanoate (2S,3S)-(3-(3-cyanophenyl)-5-(3-((E)-4-(dimethylamino)but-2-enamido)-5-methoxyphenyl)-1H-pyrrolo[2,3-b]pyridin-1-yl)methyl 2-amino-3-methylpentanoate (2S,3S)-(5-(5-acrylamidopyridin-3-yl)-3-(3-cyanophenyl)-1H-pyrrolo[2,3-b]pyridin-1-yl)methyl 2-amino-3-methylpentanoate (2S,3S)-(3-(3-cyanophenyl)-5-(5-((E)-4-(dimethylamino)but-2-enamido)pyridin-3-yl)-1H-pyrrolo[2,3-b]pyridin-1-yl)methyl 2-amino-3-methylpentanoate (S)-(5-(3-acrylamidophenyl)-3-(2-methoxypyridin-4-yl)-1H-pyrrolo[2,3-b]pyridin-1-yl)methyl 2-amino-4-methylpentanoate (S)-(5-(3-acrylamido-5-methoxyphenyl)-3-(2-methoxypyridin-4-yl)-1H-pyrrolo[2,3-b]pyridin-1-yl)methyl 2-amino-4-methylpentanoate (S,E)-(5-(3-(4-(dimethylamino)but-2-enamido)phenyl)-3-(2-methoxypyridin-4-yl)-1H-pyrrolo[2,3-b]pyridin-1-yl)methyl 2-amino-4-methylpentanoate (S,E)-(5-(3-(4-(dimethylamino)but-2-enamido)-5-methoxyphenyl)-3-(2-methoxypyridin-4-yl)-1H-pyrrolo[2,3-b]pyridin-1-yl)methyl 2-amino-4-methylpentanoate (S)-(5-(5-acrylamidopyridin-3-yl)-3-(2-methoxypyridin-4-yl)-1H-pyrrolo[2,3-b]pyridin-1-yl)methyl 2-amino-4-methylpentanoate (S,E)-(5-(5-(4-(dimethylamino)but-2-enamido)pyridin-3-yl)-3-(2-methoxypyridin-4-yl)-1H-pyrrolo[2,3-b]pyridin-1-yl)methyl 2-amino-4-methylpentanoate (S)-(5-(3-acrylamidophenyl)-3-(2-fluoropyridin-4-yl)-1H-pyrrolo[2,3-b]pyridin-1-yl)methyl 2-amino-4-methylpentanoate (S)-(5-(3-acrylamido-5-methoxyphenyl)-3-(2-fluoropyridin-4-yl)-1H-pyrrolo[2,3-b]pyridin-1-yl)methyl 2-amino-4-methylpentanoate (S,E)-(5-(3-(4-(dimethylamino)but-2-enamido)phenyl)-3-(2-fluoropyridin-4-yl)-1H-pyrrolo[2,3-b]pyridin-1-yl)methyl 2-amino-4-methylpentanoate (S,E)-(5-(3-(4-(dimethylamino)but-2-enamido)-5-methoxyphenyl)-3-(2-fluoropyridin-4-yl)-1H-pyrrolo[2,3-b]pyridin-1-yl)methyl 2-amino-4-methylpentanoate (S)-(5-(5-acrylamidopyridin-3-yl)-3-(2-fluoropyridin-4-yl)-1H-pyrrolo[2,3-b]pyridin-1-yl)methyl 2-amino-4-methylpentanoate (S,E)-(5-(5-(4-(dimethylamino)but-2-enamido)pyridin-3-yl)-3-(2-fluoropyridin-4-yl)-1H-pyrrolo[2,3-b]pyridin-1-yl)methyl 2-amino-4-methylpentanoate (S)-(5-(3-acrylamidophenyl)-3-(2-cyanopyridin-4-yl)-1H-pyrrolo[2,3-b]pyridin-1-yl)methyl 2-amino-4-methylpentanoate (S)-(5-(3-acrylamido-5-methoxyphenyl)-3-(2-cyanopyridin-4-yl)-1H-pyrrolo[2,3-b]pyridin-1-yl)methyl 2-amino-4-methylpentanoate (S,E)-(3-(2-cyanopyridin-4-yl)-5-(3-(4-(dimethylamino)but-2-enamido)phenyl)-1H-pyrrolo[2,3-b]pyridin-1-yl)methyl 2-amino-4-methylpentanoate (S,E)-(3-(2-cyanopyridin-4-yl)-5-(3-(4-(dimethylamino)but-2-enamido)-5-methoxyphenyl)-1H-pyrrolo[2,3-b]pyridin-1-yl)methyl 2-amino-4-methylpentanoate (S)-(5-(5-acrylamidopyridin-3-yl)-3-(2-cyanopyridin-4-yl)-1H-pyrrolo[2,3-b]pyridin-1-yl)methyl 2-amino-4-methylpentanoate (S,E)-(3-(2-cyanopyridin-4-yl)-5-(5-(4-(dimethylamino)but-2-enamido)pyridin-3-yl)-1H-pyrrolo[2,3-b]pyridin-1-yl)methyl 2-amino-4-methylpentanoate (S)-(5-(3-acrylamidophenyl)-3-(3-cyanophenyl)-1H-pyrrolo[2,3-b]pyridin-1-yl)methyl 2-amino-4-methylpentanoate (S)-(5-(3-acrylamido-5-methoxyphenyl)-3-(3-cyanophenyl)-1H-pyrrolo[2,3-b]pyridin-1-yl)methyl 2-amino-4-methylpentanoate (S,E)-(3-(3-cyanophenyl)-5-(3-(4-(dimethylamino)but-2-enamido)phenyl)-1H-pyrrolo[2,3-b]pyridin-1-yl)methyl 2-amino-4-methylpentanoate (S,E)-(3-(3-cyanophenyl)-5-(3-(4-(dimethylamino)but-2-enamido)-5-methoxyphenyl)-1H-pyrrolo[2,3-b]pyridin-1-yl)methyl 2-amino-4-methylpentanoate (S)-(5-(5-acrylamidopyridin-3-yl)-3-(3-cyanophenyl)-1H-pyrrolo[2,3-b]pyridin-1-yl)methyl 2-amino-4-methylpentanoate (S,E)-(3-(3-cyanophenyl)-5-(5-(4-(dimethylamino)but-2-enamido)pyridin-3-yl)-1H-pyrrolo[2,3-b]pyridin-1-yl)methyl 2-amino-4-methylpentanoate 1-(5-(3-acrylamidophenyl)-3-(3-cyanophenyl)-1H-pyrrolo[2,3-b]pyridin-1-yl)ethyl dihydrogen phosphate 1-(5-(3-acrylamido-5-methoxyphenyl)-3-(3-cyanophenyl)-1H-pyrrolo[2,3-b]pyridin-1-yl)ethyl dihydrogen phosphate (E)-1-(3-(3-cyanophenyl)-5-(3-(4-(dimethylamino)but-2-enamido)phenyl)-1H-pyrrolo[2,3-b]pyridin-1-yl)ethyl dihydrogen phosphate (E)-1-(3-(3-cyanophenyl)-5-(3-(4-(dimethylamino)but-2-enamido)-5-methoxyphenyl)-1H-pyrrolo[2,3-b]pyridin-1-yl)ethyl dihydrogen phosphate 1-(5-(5-acrylamidopyridin-3-yl)-3-(3-cyanophenyl)-1H-pyrrolo[2,3-b]pyridin-1-yl)ethyl dihydrogen phosphate (E)-1-(3-(3-cyanophenyl)-5-(5-(4-(dimethylamino)but-2-enamido)pyridin-3-yl)-1H-pyrrolo[2,3-b]pyridin-1-yl)ethyl dihydrogen phosphate 1-(3-(3-cyanophenyl)-5-(3-(N-methylacrylamido)phenyl)-1H-pyrrolo[2,3-b]pyridin-1-yl)ethyl dihydrogen phosphate 1-(3-(3-cyanophenyl)-5-(3-methoxy-5-(N-methylacrylamido)phenyl)-1H-pyrrolo[2,3-b]pyridin-1-yl)ethyl dihydrogen phosphate (E)-1-(3-(3-cyanophenyl)-5-(3-(4-(dimethylamino)-N-methylbut-2-enamido)phenyl)-1H-pyrrolo[2,3-b]pyridin-1-yl)ethyl dihydrogen phosphate (E)-1-(3-(3-cyanophenyl)-5-(3-(4-(dimethylamino)-N-methylbut-2-enamido)-5-methoxyphenyl)-1H-pyrrolo[2,3-b]pyridin-1-yl)ethyl dihydrogen phosphate 1-(3-(3-cyanophenyl)-5-(5-(N-methylacrylamido)pyridin-3-yl)-1H-pyrrolo[2,3-b]pyridin-1-yl)ethyl dihydrogen phosphate (E)-1-(3-(3-cyanophenyl)-5-(5-(4-(dimethylamino)-N-methylbut-2-enamido)pyridin-3-yl)-1H-pyrrolo[2,3-b]pyridin-1-yl)ethyl dihydrogen phosphate 1-(5-(3-acrylamidophenyl)-3-(2-fluoropyridin-4-yl)-1H-pyrrolo[2,3-b]pyridin-1-yl)ethyl dihydrogen phosphate 1-(5-(3-acrylamido-5-methoxyphenyl)-3-(2-fluoropyridin-4-yl)-1H-pyrrolo[2,3-b]pyridin-1-yl)ethyl dihydrogen phosphate (E)-1-(5-(3-(4-(dimethylamino)but-2-enamido)phenyl)-3-(2-fluoropyridin-4-yl)-1H-pyrrolo[2,3-b]pyridin-1-yl)ethyl dihydrogen phosphate (E)-1-(5-(3-(4-(dimethylamino)but-2-enamido)-5-methoxyphenyl)-3-(2-fluoropyridin-4-yl)-1H-pyrrolo[2,3-b]pyridin-1-yl)ethyl dihydrogen phosphate 1-(5-(5-acrylamidopyridin-3-yl)-3-(2-fluoropyridin-4-yl)-1H-pyrrolo[2,3-b]pyridin-1-yl)ethyl dihydrogen phosphate (E)-1-(5-(5-(4-(dimethylamino)but-2-enamido)pyridin-3-yl)-3-(2-fluoropyridin-4-yl)-1H-pyrrolo[2,3-b]pyridin-1-yl)ethyl dihydrogen phosphate 1-(3-(2-fluoropyridin-4-yl)-5-(3-(N-methylacrylamido)phenyl)-1H-pyrrolo[2,3-b]pyridin-1-yl)ethyl dihydrogen phosphate 1-(3-(2-fluoropyridin-4-yl)-5-(3-methoxy-5-(N-methylacrylamido)phenyl)-1H-pyrrolo[2,3-b]pyridin-1-yl)ethyl dihydrogen phosphate (E)-1-(5-(3-(4-(dimethylamino)-N-methylbut-2-enamido)phenyl)-3-(2-fluoropyridin-4-yl)-1H-pyrrolo[2,3-b]pyridin-1-yl)ethyl dihydrogen phosphate (E)-1-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)ethyl dihydrogen phosphate 1-(3-(2-fluoropyridin-4-yl)-5-(5-(N-methylacrylamido) pyridin-3-yl)-1H-pyrrolo[2,3-b]pyridin-1-yl)ethyl dihydrogen phosphate (E)-1-(5-(5-(4-(dimethylamino)-N-methylbut-2-enamido) pyridin-3-yl)-3-(2-fluoropyridin-4-yl)-1H-pyrrolo[2,3-b] pyridin-1-yl)ethyl dihydrogen phosphate 1-(5-(3-acrylamidophenyl)-3-(2-fluoropyridin-4-yl)-1H-pyrrolo[2,3-b]pyridin-1-yl)ethyl diethyl phosphate 1-(5-(3-acrylamido-5-methoxyphenyl)-3-(2-fluoropyridin-4-yl)-1H-pyrrolo[2,3-b]pyridin-1-yl)ethyl diethyl phosphate (E)-1-(5-(3-(4-(dimethylamino)but-2-enamido)phenyl)-3-(2-fluoropyridin-4-yl)-1H-pyrrolo[2,3-b]pyridin-1-yl) ethyl diethyl phosphate (E)-1-(5-(3-(4-(dimethylamino)but-2-enamido)-5-methoxyphenyl)-3-(2-fluoropyridin-4-yl)-1H-pyrrolo[2,3-b]pyridin-1-yl)ethyl diethyl phosphate 1-(5-(5-acrylamidopyridin-3-yl)-3-(2-fluoropyridin-4-yl)-1H-pyrrolo[2,3-b]pyridin-1-yl)ethyl diethyl phosphate (E)-1-(5-(5-(4-(dimethylamino)but-2-enamido)pyridin-3-yl)-3-(2-fluoropyridin-4-yl)-1H-pyrrolo[2,3-b]pyridin-1-yl)ethyl diethyl phosphate diethyl (1-(3-(2-fluoropyridin-4-yl)-5-(3-(N-methylacrylamido)phenyl)-1H-pyrrolo[2,3-b]pyridin-1-yl)ethyl) phosphate diethyl (1-(3-(2-fluoropyridin-4-yl)-5-(3-methoxy-5-(N-methylacrylamido)phenyl)-1H-pyrrolo[2,3-b]pyridin-1-yl)ethyl) phosphate (E)-1-(5-(3-(4-(dimethylamino)-N-methylbut-2-enamido) phenyl)-3-(2-fluoropyridin-4-yl)-1H-pyrrolo[2,3-b]pyridin-1-yl)ethyl diethyl phosphate (E)-1-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)ethyl diethyl phosphate diethyl (1-(3-(2-fluoropyridin-4-yl)-5-(5-(N-methylacrylamido)pyridin-3-yl)-1H-pyrrolo[2,3-b]pyridin-1-yl) ethyl) phosphate (E)-1-(5-(5-(4-(dimethylamino)-N-methylbut-2-enamido) pyridin-3-yl)-3-(2-fluoropyridin-4-yl)-1H-pyrrolo[2,3-b] pyridin-1-yl)ethyl diethyl phosphate 1-(5-(3-acrylamidophenyl)-3-(3-cyanophenyl)-1H-pyrrolo [2,3-b]pyridin-1-yl)ethyl diethyl phosphate 1-(5-(3-acrylamido-5-methoxyphenyl)-3-(3-cyanophenyl)-1H-pyrrolo[2,3-b]pyridin-1-yl)ethyl diethyl phosphate (E)-1-(3-(3-cyanophenyl)-5-(3-(4-(dimethylamino)but-2-enamido)phenyl)-1H-pyrrolo[2,3-b]pyridin-1-yl)ethyl diethyl phosphate (E)-1-(3-(3-cyanophenyl)-5-(3-(4-(dimethylamino)but-2-enamido)-5-methoxyphenyl)-1H-pyrrolo[2,3-b]pyridin-1-yl)ethyl diethyl phosphate 1-(5-(5-acrylamidopyridin-3-yl)-3-(3-cyanophenyl)-1H-pyrrolo[2,3-b]pyridin-1-yl)ethyl diethyl phosphate (E)-1-(3-(3-cyanophenyl)-5-(5-(4-(dimethylamino)but-2-enamido)pyridin-3-yl)-1H-pyrrolo[2,3-b]pyridin-1-yl) ethyl diethyl phosphate 1-(3-(3-cyanophenyl)-5-(3-(N-methylacrylamido)phenyl)-1H-pyrrolo[2,3-b]pyridin-1-yl)ethyl diethyl phosphate 1-(3-(3-cyanophenyl)-5-(3-methoxy-5-(N-methylacrylamido)phenyl)-1H-pyrrolo[2,3-b]pyridin-1-yl)ethyl diethyl phosphate (E)-1-(3-(3-cyanophenyl)-5-(3-(4-(dimethylamino)-N-methylbut-2-enamido)phenyl)-1H-pyrrolo[2,3-b]pyridin-1-yl)ethyl diethyl phosphate (E)-1-(3-(3-cyanophenyl)-5-(3-(4-(dimethylamino)-N-methylbut-2-enamido)-5-methoxyphenyl)-1H-pyrrolo[2,3-b]pyridin-1-yl)ethyl diethyl phosphate 1-(3-(3-cyanophenyl)-5-(5-(N-methylacrylamido)pyridin-3-yl)-1H-pyrrolo[2,3-b]pyridin-1-yl)ethyl diethyl phosphate (E)-1-(3-(3-cyanophenyl)-5-(5-(4-(dimethylamino)-N-methylbut-2-enamido)pyridin-3-yl)-1H-pyrrolo[2,3-b] pyridin-1-yl)ethyl diethyl phosphate 1-(5-(3-acrylamidophenyl)-3-(2-fluoropyridin-4-yl)-1H-pyrrolo[2,3-b]pyridin-1-yl)ethyl di-tert-butyl phosphate 1-(5-(3-acrylamido-5-methoxyphenyl)-3-(2-fluoropyridin-4-yl)-1H-pyrrolo[2,3-b]pyridin-1-yl)ethyl di-tert-butyl phosphate (E)-di-tert-butyl (1-(5-(3-(4-(dimethylamino)but-2-enamido)phenyl)-3-(2-fluoropyridin-4-yl)-1H-pyrrolo[2,3-b] pyridin-1-yl)ethyl) phosphate (E)-di-tert-butyl (1-(5-(3-(4-(dimethylamino)but-2-enamido)-5-methoxyphenyl)-3-(2-fluoropyridin-4-yl)-1H-pyrrolo[2,3-b]pyridin-1-yl)ethyl) phosphate 1-(5-(5-acrylamidopyridin-3-yl)-3-(2-fluoropyridin-4-yl)-1H-pyrrolo[2,3-b]pyridin-1-yl)ethyl di-tert-butyl phosphate (E)-di-tert-butyl (1-(5-(5-(4-(dimethylamino)but-2-enamido)pyridin-3-yl)-3-(2-fluoropyridin-4-yl)-1H-pyrrolo [2,3-b]pyridin-1-yl)ethyl) phosphate di-tert-butyl (1-(3-(2-fluoropyridin-4-yl)-5-(3-(N-methylacrylamido)phenyl)-1H-pyrrolo[2,3-b]pyridin-1-yl)ethyl) phosphate di-tert-butyl (1-(3-(2-fluoropyridin-4-yl)-5-(3-methoxy-5-(N-methylacrylamido)phenyl)-1H-pyrrolo[2,3-b]pyridin-1-yl)ethyl) phosphate (E)-di-tert-butyl (1-(5-(3-(4-(dimethylamino)-N-methylbut-2-enamido)phenyl)-3-(2-fluoropyridin-4-yl)-1H-pyrrolo [2,3-b]pyridin-1-yl)ethyl) phosphate (E)-di-tert-butyl (1-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)ethyl) phosphate di-tert-butyl (1-(3-(2-fluoropyridin-4-yl)-5-(5-(N-methylacrylamido)pyridin-3-yl)-1H-pyrrolo[2,3-b]pyridin-1-yl) ethyl) phosphate (E)-di-tert-butyl (1-(5-(5-(4-(dimethylamino)-N-methylbut-2-enamido)pyridin-3-yl)-3-(2-fluoropyridin-4-yl)-1H-pyrrolo[2,3-b]pyridin-1-yl)ethyl) phosphate 1-(5-(3-acrylamidophenyl)-3-(3-cyanophenyl)-1H-pyrrolo [2,3-b]pyridin-1-yl)ethyl di-tert-butyl phosphate 1-(5-(3-acrylamido-5-methoxyphenyl)-3-(3-cyanophenyl)-1H-pyrrolo[2,3-b]pyridin-1-yl)ethyl di-tert-butyl phosphate (E)-di-tert-butyl (1-(3-(3-cyanophenyl)-5-(3-(4-(dimethylamino)but-2-enamido)phenyl)-1H-pyrrolo[2,3-b]pyridin-1-yl)ethyl) phosphate (E)-di-tert-butyl (1-(3-(3-cyanophenyl)-5-(3-(4-(dimethylamino)but-2-enamido)-5-methoxyphenyl)-1H-pyrrolo[2,3-b]pyridin-1-yl)ethyl) phosphate 1-(5-(5-acrylamidopyridin-3-yl)-3-(3-cyanophenyl)-1H-pyrrolo[2,3-b]pyridin-1-yl)ethyl di-tert-butyl phosphate (E)-di-tert-butyl (1-(3-(3-cyanophenyl)-5-(5-(4-(dimethylamino)but-2-enamido)pyridin-3-yl)-1H-pyrrolo[2,3-b] pyridin-1-yl)ethyl) phosphate di-tert-butyl (1-(3-(3-cyanophenyl)-5-(3-(N-methylacrylamido)phenyl)-1H-pyrrolo[2,3-b]pyridin-1-yl)ethyl) phosphate di-tert-butyl (1-(3-(3-cyanophenyl)-5-(3-methoxy-5-(N-methylacrylamido)phenyl)-1H-pyrrolo[2,3-b]pyridin-1-yl)ethyl) phosphate (E)-di-tert-butyl (1-(3-(3-cyanophenyl)-5-(3-(4-(dimethylamino)-N-methylbut-2-enamido)phenyl)-1H-pyrrolo[2,3-b]pyridin-1-yl)ethyl) phosphate (E)-di-tert-butyl (1-(3-(3-cyanophenyl)-5-(3-(4-(dimethylamino)-N-methylbut-2-enamido)-5-methoxyphenyl)-1H-pyrrolo[2,3-b]pyridin-1-yl)ethyl) phosphate
di-tert-butyl (1-(3-(3-cyanophenyl)-5-(5-(N-methylacrylamido)pyridin-3-yl)-1H-pyrrolo[2,3-b]pyridin-1-yl)ethyl) phosphate
(E)-di-tert-butyl (1-(3-(3-cyanophenyl)-5-(5-(4-(dimethylamino)-N-methylbut-2-enamido)pyridin-3-yl)-1H-pyrrolo[2,3-b]pyridin-1-yl)ethyl) phosphate
1-(5-(3-acrylamidophenyl)-3-(2-fluoropyridin-4-yl)-1H-pyrrolo[2,3-b]pyridin-1-yl)ethyl acetate
1-(5-(3-acrylamido-5-methoxyphenyl)-3-(2-fluoropyridin-4-yl)-1H-pyrrolo[2,3-b]pyridin-1-yl)ethyl acetate
(E)-1-(5-(3-(4-(dimethylamino)but-2-enamido)phenyl)-3-(2-fluoropyridin-4-yl)-1H-pyrrolo[2,3-b]pyridin-1-yl)ethyl acetate
(E)-1-(5-(3-(4-(dimethylamino)but-2-enamido)-5-methoxyphenyl)-3-(2-fluoropyridin-4-yl)-1H-pyrrolo[2,3-b]pyridin-1-yl)ethyl acetate
1-(5-(5-acrylamidopyridin-3-yl)-3-(2-fluoropyridin-4-yl)-1H-pyrrolo[2,3-b]pyridin-1-yl)ethyl acetate
(E)-1-(5-(5-(4-(dimethylamino)but-2-enamido)pyridin-3-yl)-3-(2-fluoropyridin-4-yl)-1H-pyrrolo[2,3-b]pyridin-1-yl)ethyl acetate
1-(3-(2-fluoropyridin-4-yl)-5-(3-(N-methylacrylamido)phenyl)-1H-pyrrolo[2,3-b]pyridin-1-yl)ethyl acetate
1-(3-(2-fluoropyridin-4-yl)-5-(3-methoxy-5-(N-methylacrylamido)phenyl)-1H-pyrrolo[2,3-b]pyridin-1-yl)ethyl acetate
(E)-1-(5-(3-(4-(dimethylamino)-N-methylbut-2-enamido)phenyl)-3-(2-fluoropyridin-4-yl)-1H-pyrrolo[2,3-b]pyridin-1-yl)ethyl acetate
(E)-1-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)ethyl acetate
1-(3-(2-fluoropyridin-4-yl)-5-(5-(N-methylacrylamido)pyridin-3-yl)-1H-pyrrolo[2,3-b]pyridin-1-yl)ethyl acetate
(E)-1-(5-(5-(4-(dimethylamino)-N-methylbut-2-enamido)pyridin-3-yl)-3-(2-fluoropyridin-4-yl)-1H-pyrrolo[2,3-b]pyridin-1-yl)ethyl acetate
1-(5-(3-acrylamidophenyl)-3-(3-cyanophenyl)-1H-pyrrolo[2,3-b]pyridin-1-yl)ethyl acetate
1-(5-(3-acrylamido-5-methoxyphenyl)-3-(3-cyanophenyl)-1H-pyrrolo[2,3-b]pyridin-1-yl)ethyl acetate
(E)-1-(3-(3-cyanophenyl)-5-(3-(4-(dimethylamino)but-2-enamido)phenyl)-1H-pyrrolo[2,3-b]pyridin-1-yl)ethyl acetate
(E)-1-(3-(3-cyanophenyl)-5-(3-(4-(dimethylamino)but-2-enamido)-5-methoxyphenyl)-1H-pyrrolo[2,3-b]pyridin-1-yl)ethyl acetate
1-(5-(5-acrylamidopyridin-3-yl)-3-(3-cyanophenyl)-1H-pyrrolo[2,3-b]pyridin-1-yl)ethyl acetate
(E)-1-(3-(3-cyanophenyl)-5-(5-(4-(dimethylamino)but-2-enamido)pyridin-3-yl)-1H-pyrrolo[2,3-b]pyridin-1-yl)ethyl acetate
1-(3-(3-cyanophenyl)-5-(3-(N-methylacrylamido)phenyl)-1H-pyrrolo[2,3-b]pyridin-1-yl)ethyl acetate
1-(3-(3-cyanophenyl)-5-(3-methoxy-5-(N-methylacrylamido)phenyl)-1H-pyrrolo[2,3-b]pyridin-1-yl)ethyl acetate
(E)-1-(3-(3-cyanophenyl)-5-(3-(4-(dimethylamino)-N-methylbut-2-enamido)phenyl)-1H-pyrrolo[2,3-b]pyridin-1-yl)ethyl acetate
(E)-1-(3-(3-cyanophenyl)-5-(3-(4-(dimethylamino)-N-methylbut-2-enamido)-5-methoxyphenyl)-1H-pyrrolo[2,3-b]pyridin-1-yl)ethyl acetate
1-(3-(3-cyanophenyl)-5-(5-(N-methylacrylamido)pyridin-3-yl)-1H-pyrrolo[2,3-b]pyridin-1-yl)ethyl acetate
(E)-1-(3-(3-cyanophenyl)-5-(5-(4-(dimethylamino)-N-methylbut-2-enamido)pyridin-3-yl)-1H-pyrrolo[2,3-b]pyridin-1-yl)ethyl acetate
1-(5-(3-acrylamidophenyl)-3-(2-fluoropyridin-4-yl)-1H-pyrrolo[2,3-b]pyridin-1-yl)ethyl pivalate
1-(5-(3-acrylamido-5-methoxyphenyl)-3-(2-fluoropyridin-4-yl)-1H-pyrrolo[2,3-b]pyridin-1-yl)ethyl pivalate
(E)-1-(5-(3-(4-(dimethylamino)but-2-enamido)phenyl)-3-(2-fluoropyridin-4-yl)-1H-pyrrolo[2,3-b]pyridin-1-yl)ethyl pivalate
(E)-1-(5-(3-(4-(dimethylamino)but-2-enamido)-5-methoxyphenyl)-3-(2-fluoropyridin-4-yl)-1H-pyrrolo[2,3-b]pyridin-1-yl)ethyl pivalate
1-(5-(5-acrylamidopyridin-3-yl)-3-(2-fluoropyridin-4-yl)-1H-pyrrolo[2,3-b]pyridin-1-yl)ethyl pivalate
(E)-1-(5-(5-(4-(dimethylamino)but-2-enamido)pyridin-3-yl)-3-(2-fluoropyridin-4-yl)-1H-pyrrolo[2,3-b]pyridin-1-yl)ethyl pivalate
1-(3-(2-fluoropyridin-4-yl)-5-(3-(N-methylacrylamido)phenyl)-1H-pyrrolo[2,3-b]pyridin-1-yl)ethyl pivalate
1-(3-(2-fluoropyridin-4-yl)-5-(3-methoxy-5-(N-methylacrylamido)phenyl)-1H-pyrrolo[2,3-b]pyridin-1-yl)ethyl pivalate
(E)-1-(5-(3-(4-(dimethylamino)-N-methylbut-2-enamido)phenyl)-3-(2-fluoropyridin-4-yl)-1H-pyrrolo[2,3-b]pyridin-1-yl)ethyl pivalate
(E)-1-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)ethyl pivalate
1-(3-(2-fluoropyridin-4-yl)-5-(5-(N-methyl acrylamido)pyridin-3-yl)-1H-pyrrolo[2,3-b]pyridin-1-yl)ethyl pivalate
(E)-1-(5-(5-(4-(dimethylamino)-N-methylbut-2-enamido)pyridin-3-yl)-3-(2-fluoropyridin-4-yl)-1H-pyrrolo[2,3-b]pyridin-1-yl)ethyl pivalate
1-(5-(3-acrylamidophenyl)-3-(3-cyanophenyl)-1H-pyrrolo[2,3-b]pyridin-1-yl)ethyl pivalate
1-(5-(3-acrylamido-5-methoxyphenyl)-3-(3-cyanophenyl)-1H-pyrrolo[2,3-b]pyridin-1-yl)ethyl pivalate
(E)-1-(3-(3-cyanophenyl)-5-(3-(4-(dimethylamino)but-2-enamido)phenyl)-1H-pyrrolo[2,3-b]pyridin-1H-yl)ethyl pivalate
(E)-1-(3-(3-cyanophenyl)-5-(3-(4-(dimethylamino)but-2-enamido)-5-methoxyphenyl)-1H-pyrrolo[2,3-b]pyridin-1-yl)ethyl pivalate
1-(5-(5-acrylamidopyridin-3-yl)-3-(3-cyanophenyl)-1H-pyrrolo[2,3-b]pyridin-1-yl)ethyl pivalate
(E)-1-(3-(3-cyanophenyl)-5-(5-(4-(dimethylamino)but-2-enamido)pyridin-3-yl)-1H-pyrrolo[2,3-b]pyridin-1-yl)ethyl pivalate
1-(3-(3-cyanophenyl)-5-(3-(N-methylacrylamido)phenyl)-1H-pyrrolo[2,3-b]pyridin-1-yl)ethyl pivalate
1-(3-(3-cyanophenyl)-5-(3-methoxy-5-(N-methylacrylamido)phenyl)-1H-pyrrolo[2,3-b]pyridin-1-yl)ethyl pivalate
(E)-1-(3-(3-cyanophenyl)-5-(3-(4-(dimethylamino)-N-methylbut-2-enamido)phenyl)-1H-pyrrolo[2,3-b]pyridin-1-yl)ethyl pivalate
(E)-1-(3-(3-cyanophenyl)-5-(3-(4-(dimethylamino)-N-methylbut-2-enamido)-5-methoxyphenyl)-1H-pyrrolo[2,3-b]pyridin-1-yl)ethyl pivalate
1-(3-(3-cyanophenyl)-5-(5-(N-methylacrylamido)pyridin-3-yl)-1H-pyrrolo[2,3-b]pyridin-1-yl)ethyl pivalate (E)-1-(3-(3-cyanophenyl)-5-(5-(4-(dimethylamino)-N-methylbut-2-enamido)pyridin-3-yl)-1H-pyrrolo[2,3-b]pyridin-1-yl)ethyl pivalate (2S,3S)-1-(5-(3-acrylamidophenyl)-3-(2-fluoropyridin-4-yl)-1H-pyrrolo[2,3-b]pyridin-1-yl)ethyl 2-amino-3-methylpentanoate (2S,3S)-1-(5-(3-acrylamido-5-methoxyphenyl)-3-(2-fluoropyridin-4-yl)-1H-pyrrolo[2,3-b]pyridin-1-yl)ethyl 2-amino-3-methylpentanoate (2S,3S)-1-(5-(3-((E)-4-(dimethylamino)but-2-enamido)phenyl)-3-(2-fluoropyridin-4-yl)-1H-pyrrolo[2,3-b]pyridin-1-yl)ethyl 2-amino-3-methylpentanoate (2S,3S)-1-(5-(3-((E)-4-(dimethylamino)but-2-enamido)-5-methoxyphenyl)-3-(2-fluoropyridin-4-yl)-1H-pyrrolo[2,3-b]pyridin-1-yl)ethyl 2-amino-3-methylpentanoate (2S,3S)-1-(5-(5-acrylamidopyridin-3-yl)-3-(2-fluoropyridin-4-yl)-1H-pyrrolo[2,3-b]pyridin-1-yl)ethyl 2-amino-3-methylpentanoate (2S,3S)-1-(5-(5-((E)-4-(dimethylamino)but-2-enamido)pyridin-3-yl)-3-(2-fluoropyridin-4-yl)-1H-pyrrolo[2,3-b]pyridin-1-yl)ethyl 2-amino-3-methylpentanoate (2S,3S)-1-(3-(2-fluoropyridin-4-yl)-5-(3-(N-methylacrylamido)phenyl)-1H-pyrrolo[2,3-b]pyridin-1-yl)ethyl 2-amino-3-methylpentanoate (2S,3S)-1-(3-(2-fluoropyridin-4-yl)-5-(3-methoxy-5-(N-methylacrylamido)phenyl)-1H-pyrrolo[2,3-b]pyridin-1-yl)ethyl 2-amino-3-methylpentanoate (2S,3S)-1-(5-(3-((E)-4-(dimethylamino)-N-methylbut-2-enamido)phenyl)-3-(2-fluoropyridin-4-yl)-1H-pyrrolo[2,3-b]pyridin-1-yl)ethyl 2-amino-3-methylpentanoate (2S,3S)-1-(5-(3-((E)-4-(dimethylamino)-N-methylbut-2-enamido)-5-methoxyphenyl)-3-(2-fluoropyridin-4-yl)-1H-pyrrolo[2,3-b]pyridin-1-yl)ethyl 2-amino-3-methylpentanoate (2S,3S)-1-(3-(2-fluoropyridin-4-yl)-5-(5-(N-methylacrylamido)pyridin-3-yl)-1H-pyrrolo[2,3-b]pyridin-1-yl)ethyl 2-amino-3-methylpentanoate (2S,3S)-1-(5-(5-((E)-4-(dimethylamino)-N-methylbut-2-enamido)pyridin-3-yl)-3-(2-fluoropyridin-4-yl)-1H-pyrrolo[2,3-b]pyridin-1-yl)ethyl 2-amino-3-methylpentanoate (2S,3S)-1-(5-(3-acrylamidophenyl)-3-(3-cyanophenyl)-1H-pyrrolo[2,3-b]pyridin-1-yl)ethyl 2-amino-3-methylpentanoate (2S,3S)-1-(5-(3-acrylamido-5-methoxyphenyl)-3-(3-cyanophenyl)-1H-pyrrolo[2,3-b]pyridin-1-yl)ethyl 2-amino-3-methylpentanoate (2S,3S)-1-(3-(3-cyanophenyl)-5-(3-((E)-4-(dimethylamino)but-2-enamido)phenyl)-1H-pyrrolo[2,3-b]pyridin-1-yl)ethyl 2-amino-3-methylpentanoate (2S,3S)-1-(3-(3-cyanophenyl)-5-(3-((E)-4-(dimethylamino)but-2-enamido)-5-methoxyphenyl)-1H-pyrrolo[2,3-b]pyridin-1-yl)ethyl 2-amino-3-methylpentanoate (2S,3S)-1-(5-(5-acrylamidopyridin-3-yl)-3-(3-cyanophenyl)-1H-pyrrolo[2,3-b]pyridin-1-yl)ethyl 2-amino-3-methyl pentanoate (2S,3S)-1-(3-(3-cyanophenyl)-5-(5-((E)-4-(dimethylamino)but-2-enamido)pyridin-3-yl)-1H-pyrrolo[2,3-b]pyridin-1-yl)ethyl 2-amino-3-methylpentanoate (2S,3S)-1-(3-(3-cyanophenyl)-5-(3-(N-methylacrylamido)phenyl)-1H-pyrrolo[2,3-b]pyridin-1-yl)ethyl 2-amino-3-methylpentanoate (2S,3S)-1-(3-(3-cyanophenyl)-5-(3-methoxy-5-(N-methylacrylamido)phenyl)-1H-pyrrolo[2,3-b]pyridin-1-yl)ethyl 2-amino-3-methylpentanoate (2S,3S)-1-(3-(3-cyanophenyl)-5-(3-((E)-4-(dimethylamino)-N-methylbut-2-enamido)phenyl)-1H-pyrrolo[2,3-b]pyridin-1-yl)ethyl 2-amino-3-methylpentanoate (2S,3S)-1-(3-(3-cyanophenyl)-5-(3-((E)-4-(dimethylamino)-N-methylbut-2-enamido)-5-methoxyphenyl)-1H-pyrrolo[2,3-b]pyridin-1-yl)ethyl 2-amino-3-methylpentanoate (2S,3S)-1-(3-(3-cyanophenyl)-5-(5-(N-methylacrylamido)pyridin-3-yl)-1H-pyrrolo[2,3-b]pyridin-1-yl)ethyl 2-amino-3-methylpentanoate (2S,3S)-1-(3-(3-cyanophenyl)-5-(5-((E)-4-(dimethylamino)-N-methylbut-2-enamido)pyridin-3-yl)-1H-pyrrolo[2,3-b]pyridin-1-yl)ethyl 2-amino-3-methylpentanoate (2S)-1-(5-(3-acrylamidophenyl)-3-(2-fluoropyridin-4-yl)-1H-pyrrolo[2,3-b]pyridin-1-yl)ethyl 2-amino-4-methylpentanoate (2S)-1-(5-(3-acrylamido-5-methoxyphenyl)-3-(2-fluoropyridin-4-yl)-1H-pyrrolo[2,3-b]pyridin-1-yl)ethyl 2-amino-4-methyl pentanoate (2S)-1-(5-(3-((E)-4-(dimethylamino)but-2-enamido)phenyl)-3-(2-fluoropyridin-4-yl)-1H-pyrrolo[2,3-b]pyridin-1-yl)ethyl 2-amino-4-methylpentanoate (2S)-1-(5-(3-((E)-4-(dimethylamino)but-2-enamido)-5-methoxyphenyl)-3-(2-fluoropyridin-4-yl)-1H-pyrrolo[2,3-b]pyridin-1-yl)ethyl 2-amino-4-methylpentanoate (2S)-1-(5-(5-acrylamidopyridin-3-yl)-3-(2-fluoropyridin-4-yl)-1H-pyrrolo[2,3-b]pyridin-1-yl)ethyl 2-amino-4-methylpentanoate (2S)-1-(5-(5-((E)-4-(dimethylamino)but-2-enamido)pyridin-3-yl)-3-(2-fluoropyridin-4-yl)-1H-pyrrolo[2,3-b]pyridin-1-yl)ethyl 2-amino-4-methylpentanoate (2S)-1-(3-(2-fluoropyridin-4-yl)-5-(3-(N-methylacrylamido)phenyl)-1H-pyrrolo[2,3-b]pyridin-1-yl)ethyl 2-amino-4-methylpentanoate (2S)-1-(3-(2-fluoropyridin-4-yl)-5-(3-methoxy-5-(N-methylacrylamido)phenyl)-1H-pyrrolo[2,3-b]pyridin-1-yl)ethyl 2-amino-4-methylpentanoate (2S)-1-(5-(3-((E)-4-(dimethylamino)-N-methylbut-2-enamido)phenyl)-3-(2-fluoropyridin-4-yl)-1H-pyrrolo[2,3-b]pyridin-1-yl)ethyl 2-amino-4-methylpentanoate (2S)-1-(5-(3-((E)-4-(dimethylamino)-N-methylbut-2-enamido)-5-methoxyphenyl)-3-(2-fluoropyridin-4-yl)-1H-pyrrolo[2,3-b]pyridin-1-yl)ethyl 2-amino-4-methylpentanoate (2S)-1-(3-(2-fluoropyridin-4-yl)-5-(5-(N-methylacrylamido)pyridin-3-yl)-1H-pyrrolo[2,3-b]pyridin-1-yl)ethyl 2-amino-4-methylpentanoate (2S)-1-(5-(5-((E)-4-(dimethylamino)-N-methylbut-2-enamido)pyridin-3-yl)-3-(2-fluoropyridin-4-yl)-1H-pyrrolo[2,3-b]pyridin-1-yl)ethyl 2-amino-4-methylpentanoate (2S)-1-(5-(3-acrylamidophenyl)-3-(3-cyanophenyl)-1H-pyrrolo[2,3-b]pyridin-1-yl)ethyl 2-amino-4-methylpentanoate (2S)-1-(5-(3-acrylamido-5-methoxyphenyl)-3-(3-cyanophenyl)-1H-pyrrolo[2,3-b]pyridin-1-yl)ethyl 2-amino-4-methylpentanoate (2S)-1-(3-(3-cyanophenyl)-5-(3-((E)-4-(dimethylamino)but-2-enamido)phenyl)-1H-pyrrolo[2,3-b]pyridin-1-yl)ethyl 2-amino-4-methylpentanoate (2S)-1-(3-(3-cyanophenyl)-5-(3-((E)-4-(dimethylamino)but-2-enamido)-5-methoxyphenyl)-1H-pyrrolo[2,3-b]pyridin-1-yl)ethyl 2-amino-4-methylpentanoate (2S)-1-(5-(5-acrylamidopyridin-3-yl)-3-(3-cyanophenyl)-1H-pyrrolo[2,3-b]pyridin-1-yl)ethyl 2-amino-4-methylpentanoate (2S)-1-(3-(3-cyanophenyl)-5-(5-((E)-4-(dimethylamino) but-2-enamido)pyridin-3-yl)-1H-pyrrolo[2,3-b]pyridin-1-yl)ethyl 2-amino-4-methylpentanoate
(2S)-1-(3-(3-cyanophenyl)-5-(3-(N-methylacrylamido)phenyl)-1H-pyrrolo[2,3-b]pyridin-1-yl)ethyl 2-amino-4-methylpentanoate
(2S)-1-(3-(3-cyanophenyl)-5-(3-methoxy-5-(N-methylacrylamido)phenyl)-1H-pyrrolo[2,3-b]pyridin-1-yl)ethyl 2-amino-4-methylpentanoate
(2S)-1-(3-(3-cyanophenyl)-5-(3-((E)-4-(dimethylamino)-N-methylbut-2-enamido)phenyl)-1H-pyrrolo[2,3-b]pyridin-1-yl)ethyl 2-amino-4-methylpentanoate
(2S)-1-(3-(3-cyanophenyl)-5-(3-((E)-4-(dimethylamino)-N-methylbut-2-enamido)-5-methoxyphenyl)-1H-pyrrolo[2,3-b]pyridin-1-yl)ethyl 2-amino-4-methylpentanoate
(2S)-1-(3-(3-cyanophenyl)-5-(5-(N-methylacrylamido)pyridin-3-yl)-1H-pyrrolo[2,3-b]pyridin-1-yl)ethyl 2-amino-4-methylpentanoate
(2S)-1-(3-(3-cyanophenyl)-5-(5-((E)-4-(dimethylamino)-N-methylbut-2-enamido)pyridin-3-yl)-1H-pyrrolo[2,3-b]pyridin-1-yl)ethyl 2-amino-4-methylpentanoate
(5-(3-acrylamidophenyl)-3-(2-methoxypyridin-4-yl)-1H-pyrrolo[2,3-b]pyridin-1-yl)methyl ethyl hydrogen phosphate
(5-(3-acrylamido-5-methoxyphenyl)-3-(2-methoxypyridin-4-yl)-1H-pyrrolo[2,3-b]pyridin-1-yl)methyl ethyl hydrogen phosphate
(E)-(5-(3-(4-(dimethylamino)but-2-enamido)phenyl)-3-(2-methoxypyridin-4-yl)-1H-pyrrolo[2,3-b]pyridin-1-yl)methyl ethyl hydrogen phosphate
(E)-(5-(3-(4-(dimethylamino)but-2-enamido)-5-methoxyphenyl)-3-(2-methoxypyridin-4-yl)-1H-pyrrolo[2,3-b]pyridin-1-yl)methyl ethyl hydrogen phosphate
(5-(5-acrylamidopyridin-3-yl)-3-(2-methoxypyridin-4-yl)-1H-pyrrolo[2,3-b]pyridin-1-yl)methyl ethyl hydrogen phosphate
(E)-(5-(5-(4-(dimethylamino)but-2-enamido)pyridin-3-yl)-3-(2-methoxypyridin-4-yl)-1H-pyrrolo[2,3-b]pyridin-1-yl)methyl ethyl hydrogen phosphate
(5-(3-acrylamidophenyl)-3-(2-fluoropyridin-4-yl)-1H-pyrrolo[2,3-b]pyridin-1-yl)methyl ethyl hydrogen phosphate
(5-(3-acrylamido-5-methoxyphenyl)-3-(2-fluoropyridin-4-yl)-1H-pyrrolo[2,3-b]pyridin-1-yl)methyl ethyl hydrogen phosphate
(E)-(5-(3-(4-(dimethylamino)but-2-enamido)phenyl)-3-(2-fluoropyridin-4-yl)-1H-pyrrolo[2,3-b]pyridin-1-yl)methyl ethyl hydrogen phosphate
(E)-(5-(3-(4-(dimethylamino)but-2-enamido)-5-methoxyphenyl)-3-(2-fluoropyridin-4-yl)-1H-pyrrolo[2,3-b]pyridin-1-yl)methyl ethyl hydrogen phosphate
(5-(5-acrylamidopyridin-3-yl)-3-(2-fluoropyridin-4-yl)-1H-pyrrolo[2,3-b]pyridin-1-yl)methyl ethyl hydrogen phosphate
(E)-(5-(5-(4-(dimethylamino)but-2-enamido)pyridin-3-yl)-3-(2-fluoropyridin-4-yl)-1H-pyrrolo[2,3-b]pyridin-1-yl)methyl ethyl hydrogen phosphate
(5-(3-acrylamidophenyl)-3-(2-cyanopyridin-4-yl)-1H-pyrrolo[2,3-b]pyridin-1-yl)methyl ethyl hydrogen phosphate
(5-(3-acrylamido-5-methoxyphenyl)-3-(2-cyanopyridin-4-yl)-1H-pyrrolo[2,3-b]pyridin-1-yl)methyl ethyl hydrogen phosphate
(E)-(3-(2-cyanopyridin-4-yl)-5-(3-(4-(dimethylamino)but-2-enamido)phenyl)-1H-pyrrolo[2,3-b]pyridin-1-yl)methyl ethyl hydrogen phosphate
(E)-(3-(2-cyanopyridin-4-yl)-5-(3-(4-(dimethylamino)but-2-enamido)-5-methoxyphenyl)-1H-pyrrolo[2,3-b]pyridin-1-yl)methyl ethyl hydrogen phosphate
(5-(5-acrylamidopyridin-3-yl)-3-(2-cyanopyridin-4-yl)-1H-pyrrolo[2,3-b]pyridin-1-yl)methyl ethyl hydrogen phosphate
(E)-(3-(2-cyanopyridin-4-yl)-5-(5-(4-(dimethylamino)but-2-enamido)pyridin-3-yl)-1H-pyrrolo[2,3-b]pyridin-1-yl)methyl ethyl hydrogen phosphate
(5-(3-acrylamidophenyl)-3-(3-cyanophenyl)-1H-pyrrolo[2,3-b]pyridin-1-yl)methyl ethyl hydrogen phosphate
(5-(3-acrylamido-5-methoxyphenyl)-3-(3-cyanophenyl)-H-pyrrolo[2,3-b]pyridin-1-yl)methyl ethyl hydrogen phosphate
(E)-(3-(3-cyanophenyl)-5-(3-(4-(dimethylamino)but-2-enamido)phenyl)-1H-pyrrolo[2,3-b]pyridin-1-yl)methyl ethyl hydrogen phosphate
(E)-(3-(3-cyanophenyl)-5-(3-(4-(dimethylamino)but-2-enamido)-5-methoxyphenyl)-1H-pyrrolo[2,3-b]pyridin-1-yl) methyl ethyl hydrogen phosphate
(5-(5-acrylamidopyridin-3-yl)-3-(3-cyanophenyl)-1H-pyrrolo[2,3-b]pyridin-1-yl)methyl ethyl hydrogen phosphate
(E)-(3-(3-cyanophenyl)-5-(5-(4-(dimethylamino)but-2-enamido)pyridin-3-yl)-1H-pyrrolo[2,3-b]pyridin-1-yl) methyl ethyl hydrogen phosphate
ethyl ((3-(2-methoxypyridin-4-yl)-5-(3-(N-methylacrylamido)phenyl)-1H-pyrrolo[2,3-b]pyridin-1-yl)methyl) hydrogen phosphate
ethyl ((5-(3-methoxy-5-(N-methylacrylamido)phenyl)-3-(2-methoxypyridin-4-yl)-1H-pyrrolo[2,3-b]pyridin-1-yl) methyl) hydrogen phosphate
(E)-(5-(3-(4-(dimethylamino)-N-methylbut-2-enamido)phenyl)-3-(2-methoxypyridin-4-yl)-1H-pyrrolo[2,3-b]pyridin-1-yl)methyl ethyl hydrogen phosphate
(E)-(5-(3-(4-(dimethylamino)-N-methylbut-2-enamido)-5-methoxyphenyl)-3-(2-methoxypyridin-4-yl)-1H-pyrrolo[2,3-b]pyridin-1-yl)methyl ethyl hydrogen phosphate
ethyl ((3-(2-methoxypyridin-4-yl)-5-(5-(N-methylacrylamido)pyridin-3-yl)-1H-pyrrolo[2,3-b]pyridin-1-yl) methyl) hydrogen phosphate
(E)-(5-(5-(4-(dimethylamino)-N-methylbut-2-enamido) pyridin-3-yl)-3-(2-methoxypyridin-4-yl)-1H-pyrrolo[2,3-b]pyridin-1-yl)methyl ethyl hydrogen phosphate
ethyl ((3-(22-fluoropyridin-4-yl)-5-(3-(N-methylacrylamido)phenyl)-H-pyrrolo[2,3-b]pyridin-1-yl)methyl) hydrogen phosphate
ethyl ((3-(2-fluoropyridin-4-yl)-5-(3-methoxy-5-(N-methylacrylamido)phenyl)-1H-pyrrolo[2,3-b]pyridin-1-yl) methyl) hydrogen phosphate
(E)-(5-(3-(4-(dimethylamino)-N-methylbut-2-enamido)phenyl)-3-(2-fluoropyridin-4-yl)-1H-pyrrolo[2,3-b]pyridin-1-yl)methyl ethyl hydrogen phosphate
(E)-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)methyl ethyl hydrogen phosphate
ethyl ((3-(2-fluoropyridin-4-yl)-5-(5-(N-methylacrylamido) pyridin-3-yl)-1H-pyrrolo[2,3-b]pyridin-1-yl)methyl) hydrogen phosphate
(E)-(5-(5-(4-(dimethylamino)-N-methylbut-2-enamido) pyridin-3-yl)-3-(2-fluoropyridin-4-yl)-1H-pyrrolo[2,3-b] pyridin-1-yl)methyl ethyl hydrogen phosphate
(3-(2-cyanopyridin-4-yl)-5-(3-(N-methylacrylamido)phenyl)-1H-pyrrolo[2,3-b]pyridin-1-yl)methyl ethyl hydrogen phosphate
(3-(2-cyanopyridin-4-yl)-5-(3-methoxy-5-(N-methylacrylamido)phenyl)-1H-pyrrolo[2,3-b]pyridin-1-yl)methyl ethyl hydrogen phosphate
(E)-(3-(2-cyanopyridin-4-yl)-5-(3-(4-(dimethylamino)-N-methylbut-2-enamido)phenyl)-1H-pyrrolo[2,3-b]pyridin-1-yl)methyl ethyl hydrogen phosphate (E)-(3-(2-cyanopyridin-4-yl)-5-(3-(4-(dimethylamino)-N-methylbut-2-enamido)-5-methoxyphenyl)-1H-pyrrolo[2,3-b]pyridin-1-yl)methyl ethyl hydrogen phosphate (3-(2-cyanopyridin-4-yl)-5-(5-(N-methylacrylamido)pyridin-3-yl)-1H-pyrrolo[2,3-b]pyridin-1-yl)methyl ethyl hydrogen phosphate (E)-(3-(2-cyanopyridin-4-yl)-5-(5-(4-(dimethylamino)-N-methylbut-2-enamido)pyridin-3-yl)-1H-pyrrolo[2,3-b]pyridin-1-yl)methyl ethyl hydrogen phosphate (3-(3-cyanophenyl)-5-(3-(N-methylacrylamido)phenyl)-1H-pyrrolo[2,3-b]pyridin-1-yl)methyl ethyl hydrogen phosphate (3-(3-cyanophenyl)-5-(3-methoxy-5-(N-methylacrylamido)phenyl)-1H-pyrrolo[2,3-b]pyridin-1-yl)methyl ethyl hydrogen phosphate (E)-(3-(3-cyanophenyl)-5-(3-(4-(dimethylamino)-N-methylbut-2-enamido)phenyl)-1H-pyrrolo[2,3-b]pyridin-1-yl)methyl ethyl hydrogen phosphate (E)-(3-(3-cyanophenyl)-5-(3-(4-(dimethylamino)-N-methylbut-2-enamido)-5-methoxyphenyl)-1H-pyrrolo[2,3-b]pyridin-1-yl)methyl ethyl hydrogen phosphate (3-(3-cyanophenyl)-5-(5-(N-methylacrylamido)pyridin-3-yl)-1H-pyrrolo[2,3-b]pyridin-1-yl)methyl ethyl hydrogen phosphate (E)-(3-(3-cyanophenyl)-5-(5-(4-(dimethylamino)-N-methylbut-2-enamido)pyridin-3-yl)-1H-pyrrolo[2,3-b]pyridin-1-yl)methyl ethyl hydrogen phosphate ethyl (1-(3-(2-methoxypyridin-4-yl)-5-(3-(N-methylacrylamido)phenyl)-1H-pyrrolo[2,3-b]pyridin-1-yl)ethyl) hydrogen phosphate ethyl (1-(5-(3-methoxy-5-(N-methylacrylamido)phenyl)-3-(2-methoxypyridin-4-yl)-1H-pyrrolo[2,3-b]pyridin-1-yl)ethyl) hydrogen phosphate (E)-1-(5-(3-(4-(dimethylamino)-N-methylbut-2-enamido)phenyl)-3-(2-methoxypyridin-4-yl)-1H-pyrrolo[2,3-b]pyridin-1-yl)ethyl ethyl hydrogen phosphate (E)-1-(5-(3-(4-(dimethylamino)-N-methylbut-2-enamido)-5-methoxyphenyl)-3-(2-methoxypyridin-4-yl)-1H-pyrrolo[2,3-b]pyridin-1-yl)ethyl ethyl hydrogen phosphate ethyl (1-(3-(2-methoxypyridin-4-yl)-5-(5-(N-methylacrylamido)pyridin-3-yl)-1H-pyrrolo[2,3-b]pyridin-1-yl)ethyl) hydrogen phosphate (E)-1-(5-(5-(4-(dimethylamino)-N-methylbut-2-enamido)pyridin-3-yl)-3-(2-methoxypyridin-4-yl)-1H-pyrrolo[2,3-b]pyridin-1-yl)ethyl ethyl hydrogen phosphate ethyl (1-(3-(2-fluoropyridin-4-yl)-5-(3-(N-methylacrylamido)phenyl)-1H-pyrrolo[2,3-b]pyridin-1-yl)ethyl) hydrogen phosphate ethyl (1-(3-(2-fluoropyridin-4-yl)-5-(3-methoxy-5-(N-methylacrylamido)phenyl)-1H-pyrrolo[2,3-b]pyridin-1-yl)ethyl) hydrogen phosphate (E)-1-(5-(3-(4-(dimethylamino)-N-methylbut-2-enamido)phenyl)-3-(2-fluoropyridin-4-yl)-1H-pyrrolo[2,3-b]pyridin-1-yl)ethyl ethyl hydrogen phosphate (E)-1-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)ethyl ethyl hydrogen phosphate ethyl (1-(3-(2-fluoropyridin-4-yl)-5-(5-(N-methylacrylamido)pyridin-3-yl)-1H-pyrrolo[2,3-b]pyridin-1-yl)ethyl) hydrogen phosphate (E)-1-(5-(5-(4-(dimethylamino)-N-methylbut-2-enamido)pyridin-3-yl)-3-(2-fluoropyridin-4-yl)-1H-pyrrolo[2,3-b]pyridin-1-yl)ethyl ethyl hydrogen phosphate 1-(3-(2-cyanopyridin-4-yl)-5-(3-(N-methylacrylamido)phenyl)-1H-pyrrolo[2,3-b]pyridin-1-yl)ethyl ethyl hydrogen phosphate 1-(3-(2-cyanopyridin-4-yl)-5-(3-methoxy-5-(N-methylacrylamido)phenyl)-1H-pyrrolo[2,3-b]pyridin-1-yl)ethyl ethyl hydrogen phosphate (E)-1-(3-(2-cyanopyridin-4-yl)-5-(3-(4-(dimethylamino)-N-methylbut-2-enamido)phenyl)-1H-pyrrolo[2,3-b]pyridin-1-yl)ethyl ethyl hydrogen phosphate (E)-1-(3-(2-cyanopyridin-4-yl)-5-(3-(4-(dimethylamino)-N-methylbut-2-enamido)-5-methoxyphenyl)-1H-pyrrolo[2,3-b]pyridin-1-yl)ethyl ethyl hydrogen phosphate 1-(3-(2-cyanopyridin-4-yl)-5-(5-(N-methylacrylamido)pyridin-3-yl)-1H-pyrrolo[2,3-b]pyridin-1-yl)ethyl ethyl hydrogen phosphate (E)-1-(3-(2-cyanopyridin-4-yl)-5-(5-(4-(dimethylamino)-N-methylbut-2-enamido)pyridin-3-yl)-1H-pyrrolo[2,3-b]pyridin-1-yl)ethyl ethyl hydrogen phosphate 1-(3-(3-cyanophenyl)-5-(3-(N-methylacrylamido)phenyl)-1H-pyrrolo[2,3-b]pyridin-1-yl)ethyl ethyl hydrogen phosphate 1-(3-(3-cyanophenyl)-5-(3-methoxy-5-(N-methylacrylamido)phenyl)-1H-pyrrolo[2,3-b]pyridin-1-yl)ethyl ethyl hydrogen phosphate (E)-1-(3-(3-cyanophenyl)-5-(3-(4-(dimethylamino)-N-methylbut-2-enamido)phenyl)-1H-pyrrolo[2,3-b]pyridin-1-yl)ethyl ethyl hydrogen phosphate (E)-1-(3-(3-cyanophenyl)-5-(3-(4-(dimethylamino)-N-methylbut-2-enamido)-5-methoxyphenyl)-1H-pyrrolo[2,3-b]pyridin-1-yl)ethyl ethyl hydrogen phosphate 1-(3-(3-cyanophenyl)-5-(5-(N-methylacrylamido)pyridin-3-yl)-1H-pyrrolo[2,3-b]pyridin-1-yl)ethyl ethyl hydrogen phosphate (E)-1-(3-(3-cyanophenyl)-5-(5-(4-(dimethylamino)-N-methylbut-2-enamido)pyridin-3-yl)-1H-pyrrolo[2,3-b]pyridin-1-yl)ethyl ethyl hydrogen phosphate 1-(5-(3-acrylamidophenyl)-3-(2-methoxypyridin-4-yl)-1H-pyrrolo[2,3-b]pyridin-1-yl)ethyl ethyl hydrogen phosphate 1-(5-(3-acrylamido-5-methoxyphenyl)-3-(2-methoxypyridin-4-yl)-1H-pyrrolo[2,3-b]pyridin-1-yl)ethyl ethyl hydrogen phosphate (E)-1-(5-(3-(4-(dimethylamino)but-2-enamido)phenyl)-3-(2-methoxypyridin-4-yl)-1H-pyrrolo[2,3-b]pyridin-1-yl)ethyl ethyl hydrogen phosphate (E)-1-(5-(3-(4-(dimethylamino)but-2-enamido)-5-methoxyphenyl)-3-(2-methoxypyridin-4-yl)-1H-pyrrolo[2,3-b]pyridin-1-yl)ethyl ethyl hydrogen phosphate 1-(5-(5-acrylamidopyridin-3-yl)-3-(2-methoxypyridin-4-yl)-1H-pyrrolo[2,3-b]pyridin-1-yl)ethyl ethyl hydrogen phosphate (E)-1-(5-(5-(4-(dimethylamino)but-2-enamido)pyridin-3-yl)-3-(2-methoxypyridin-4-yl)-1H-pyrrolo[2,3-b]pyridin-1-yl)ethyl ethyl hydrogen phosphate 1-(5-(3-acrylamidophenyl)-3-(2-fluoropyridin-4-yl)-1H-pyrrolo[2,3-b]pyridin-1-yl)ethyl ethyl hydrogen phosphate 1-(5-(3-acrylamido-5-methoxyphenyl)-3-(2-fluoropyridin-4-yl)-1H-pyrrolo[2,3-b]pyridin-1-yl)ethyl ethyl hydrogen phosphate (E)-1-(5-(3-(4-(dimethylamino)but-2-enamido)phenyl)-3-(2-fluoropyridin-4-yl)-1H-pyrrolo[2,3-b]pyridin-1-yl)ethyl ethyl hydrogen phosphate (E)-1-(5-(3-(4-(dimethylamino)but-2-enamido)-5-methoxyphenyl)-3-(2-fluoropyridin-4-yl)-1H-pyrrolo[2,3-b]pyridin-1-yl)ethyl ethyl hydrogen phosphate 1-(5-(5-acrylamidopyridin-3-yl)-3-(2-fluoropyridin-4-yl)-1H-pyrrolo[2,3-b]pyridin-1-yl)ethyl ethyl hydrogen phosphate (E)-1-(5-(5-(4-(dimethylamino)but-2-enamido)pyridin-3-yl)-3-(2-fluoropyridin-4-yl)-1H-pyrrolo[2,3-b]pyridin-1-yl)ethyl ethyl hydrogen phosphate 1-(5-(3-acrylamidophenyl)-3-(2-cyanopyridin-4-yl)-1H-pyrrolo[2,3-b]pyridin-1-yl)ethyl ethyl hydrogen phosphate 1-(5-(3-acrylamido-5-methoxyphenyl)-3-(2-cyanopyridin-4-yl)-1H-pyrrolo[2,3-b]pyridin-1-yl)ethyl ethyl hydrogen phosphate (E)-1-(3-(2-cyanopyridin-4-yl)-5-(3-(4-(dimethylamino)but-2-enamido)phenyl)-1H-pyrrolo[2,3-b]pyridin-1-yl)ethyl ethyl hydrogen phosphate (E)-1-(3-(2-cyanopyridin-4-yl)-5-(3-(4-(dimethylamino)but-2-enamido)-5-methoxyphenyl)-1H-pyrrolo[2,3-b]pyridin-1-yl)ethyl ethyl hydrogen phosphate 1-(5-(5-acrylamidopyridin-3-yl)-3-(2-cyanopyridin-4-yl)-1H-pyrrolo[2,3-b]pyridin-1-yl)ethyl ethyl hydrogen phosphate (E)-1-(3-(2-cyanopyridin-4-yl)-5-(5-(4-(dimethylamino)but-2-enamido)pyridin-3-yl)-1H-pyrrolo[2,3-b]pyridin-1-yl)ethyl ethyl hydrogen phosphate 1-(5-(3-acrylamidophenyl)-3-(3-cyanophenyl)-1H-pyrrolo[2,3-b]pyridin-1-yl)ethyl ethyl hydrogen phosphate 1-(5-(3-acrylamido-5-methoxyphenyl)-3-(3-cyanophenyl)-1H-pyrrolo[2,3-b]pyridin-1-yl)ethyl ethyl hydrogen phosphate (E)-1-(3-(3-cyanophenyl)-5-(3-(4-(dimethylamino)but-2-enamido)phenyl)-1H-pyrrolo[2,3-b]pyridin-1-yl)ethyl ethyl hydrogen phosphate (E)-1-(3-(3-cyanophenyl)-5-(3-(4-(dimethylamino)but-2-enamido)-5-methoxyphenyl)-1H-pyrrolo[2,3-b]pyridin-1-yl)ethyl ethyl hydrogen phosphate 1-(5-(5-acrylamidopyridin-3-yl)-3-(3-cyanophenyl)-1H-pyrrolo[2,3-b]pyridin-1-yl)ethyl ethyl hydrogen phosphate (E)-1-(3-(3-cyanophenyl)-5-(5-(4-(dimethylamino)but-2-enamido)pyridin-3-yl)-1H-pyrrolo[2,3-b]pyridin-1-yl)ethyl ethyl hydrogen phosphate (5-(3-acrylamidophenyl)-3-(2-methoxypyridin-4-yl)-1H-pyrrolo[2,3-b]pyridin-1-yl)methyl tert-butyl hydrogen phosphate (5-(3-acrylamido-5-methoxyphenyl)-3-(2-methoxypyridin-4-yl)-1H-pyrrolo[2,3-b]pyridin-1-yl)methyl tert-butyl hydrogen phosphate (E)-tert-butyl ((5-(3-(4-(dimethylamino)but-2-enamido)phenyl)-3-(2-methoxypyridin-4-yl)-1H-pyrrolo[2,3-b]pyridin-1-yl)methyl) hydrogen phosphate (E)-tert-butyl ((5-(3-(4-(dimethylamino)but-2-enamido)-5-methoxyphenyl)-3-(2-methoxypyridin-4-yl)-1H-pyrrolo[2,3-b]pyridin-1-yl)methyl) hydrogen phosphate (5-(5-acrylamidopyridin-3-yl)-3-(2-methoxypyridin-4-yl)-1H-pyrrolo[2,3-b]pyridin-1-yl)methyl tert-butyl hydrogen phosphate (E)-tert-butyl ((5-(5-(4-(dimethylamino)but-2-enamido)pyridin-3-yl)-3-(2-methoxypyridin-4-yl)-1H-pyrrolo[2,3-b]pyridin-1-yl)methyl) hydrogen phosphate (5-(3-acrylamidophenyl)-3-(2-fluoropyridin-4-yl)-1H-pyrrolo[2,3-b]pyridin-1-yl)methyl tert-butyl hydrogen phosphate (5-(3-acrylamido-5-methoxyphenyl)-3-(2-fluoropyridin-4-yl)-1H-pyrrolo[2,3-b]pyridin-1-yl)methyl tert-butyl hydrogen phosphate (E)-tert-butyl ((5-(3-(4-(dimethylamino)but-2-enamido)phenyl)-3-(2-fluoropyridin-4-yl)-1H-pyrrolo[2,3-b]pyridin-1-yl)methyl) hydrogen phosphate (E)-tert-butyl ((5-(3-(4-(dimethylamino)but-2-enamido)-5-methoxyphenyl)-3-(2-fluoropyridin-4-yl)-1H-pyrrolo[2,3-b]pyridin-1-yl)methyl) hydrogen phosphate (5-(5-acrylamidopyridin-3-yl)-3-(2-fluoropyridin-4-yl)-1H-pyrrolo[2,3-b]pyridin-1-yl)methyl tert-butyl hydrogen phosphate (E)-tert-butyl ((5-(5-(4-(dimethylamino)but-2-enamido)pyridin-3-yl)-3-(2-fluoropyridin-4-yl)-1H-pyrrolo[2,3-b]pyridin-1-yl)methyl) hydrogen phosphate (5-(3-acrylamidophenyl)-3-(2-cyanopyridin-4-yl)-1H-pyrrolo[2,3-b]pyridin-1-yl)methyl tert-butyl hydrogen phosphate (5-(3-acrylamido-5-methoxyphenyl)-3-(2-cyanopyridin-4-yl)-1H-pyrrolo[2,3-b]pyridin-1-yl)methyl tert-butyl hydrogen phosphate (E)-tert-butyl ((3-(2-cyanopyridin-4-yl)-5-(3-(4-(dimethylamino)but-2-enamido)phenyl)-1H-pyrrolo[2,3-b]pyridin-1-yl)methyl) hydrogen phosphate (E)-tert-butyl ((3-(2-cyanopyridin-4-yl)-5-(3-(4-(dimethylamino)but-2-enamido)-5-methoxyphenyl)-1H-pyrrolo[2,3-b]pyridin-1-yl)methyl) hydrogen phosphate (5-(5-acrylamidopyridin-3-yl)-3-(2-cyanopyridin-4-yl)-1H-pyrrolo[2,3-b]pyridin-1-yl)methyl tert-butyl hydrogen phosphate (E)-tert-butyl ((3-(2-cyanopyridin-4-yl)-5-(5-(4-(dimethylamino)but-2-enamido)pyridin-3-yl)-1H-pyrrolo[2,3-b]pyridin-1-yl)methyl) hydrogen phosphate (5-(3-acrylamidophenyl)-3-(3-cyanophenyl)-1H-pyrrolo[2,3-b]pyridin-1-yl)methyl tert-butyl hydrogen phosphate (5-(3-acrylamido-5-methoxyphenyl)-3-(3-cyanophenyl)-1H-pyrrolo[2,3-b]pyridin-1-yl)methyl tert-butyl hydrogen phosphate (E)-tert-butyl ((3-(3-cyanophenyl)-5-(3-(4-(dimethylamino)but-2-enamido)phenyl)-1H-pyrrolo[2,3-b]pyridin-1-yl)methyl) hydrogen phosphate (E)-tert-butyl ((3-(3-cyanophenyl)-5-(3-(4-(dimethylamino)but-2-enamido)-5-methoxyphenyl)-1H-pyrrolo[2,3-b]pyridin-1-yl)methyl) hydrogen phosphate (5-(5-acrylamidopyridin-3-yl)-3-(3-cyanophenyl)-1H-pyrrolo[2,3-b]pyridin-1-yl)methyl tert-butyl hydrogen phosphate (E)-tert-butyl ((3-(3-cyanophenyl)-5-(5-(4-(dimethylamino)but-2-enamido)pyridin-3-yl)-1H-pyrrolo[2,3-b]pyridin-1-yl)methyl) hydrogen phosphate tert-butyl ((3-(2-methoxypyridin-4-yl)-5-(3-(N-methylacrylamido)phenyl)-1H-pyrrolo[2,3-b]pyridin-1-yl)methyl) hydrogen phosphate tert-butyl ((5-(3-methoxy-5-(N-methylacrylamido)phenyl)-3-(2-methoxypyridin-4-yl)-1H-pyrrolo[2,3-b]pyridin-1-yl)methyl) hydrogen phosphate (E)-tert-butyl ((5-(3-(4-(dimethylamino)-N-methylbut-2-enamido)phenyl)-3-(2-methoxypyridin-4-yl)-1H-pyrrolo[2,3-b]pyridin-1-yl)methyl) hydrogen phosphate (E)-tert-butyl ((5-(3-(4-(dimethylamino)-N-methylbut-2-enamido)-5-methoxyphenyl)-3-(2-methoxypyridin-4-yl)-1H-pyrrolo[2,3-b]pyridin-1-yl)methyl) hydrogen phosphate tert-butyl ((3-(2-methoxypyridin-4-yl)-5-(5-(N-methylacrylamido)pyridin-3-yl)-1H-pyrrolo[2,3-b]pyridin-1-yl)methyl) hydrogen phosphate (E)-tert-butyl ((5-(5-(4-(dimethylamino)-N-methylbut-2-enamido)pyridin-3-yl)-3-(2-methoxypyridin-4-yl)-1H-pyrrolo[2,3-b]pyridin-1-yl)methyl) hydrogen phosphate tert-butyl ((3-(2-fluoropyridin-4-yl)-5-(3-(N-methylacrylamido)phenyl)-1H-pyrrolo[2,3-b]pyridin-1-yl)methyl) hydrogen phosphate tert-butyl ((3-(2-fluoropyridin-4-yl)-5-(3-methoxy-5-(N-methylacrylamido)phenyl)-1H-pyrrolo[2,3-b]pyridin-1-yl)methyl) hydrogen phosphate
(E)-tert-butyl ((5-(3-(4-(dimethylamino)-N-methylbut-2-enamido)phenyl)-3-(2-fluoropyridin-4-yl)-1H-pyrrolo[2,3-b]pyridin-1-yl)methyl) hydrogen phosphate
(E)-tert-butyl ((5-(3-(4-(dimethylamino)-N-methylbut-2-enamido)-5-methoxyphenyl)-3-(2-fluoropyridin-4-yl)-1H-pyrrolo[2,3-b]pyridin-1-yl)methyl) hydrogen phosphate
tert-butyl ((3-(2-fluoropyridin-4-yl)-5-(5-(N-methylacrylamido)pyridin-3-yl)-1H-pyrrolo[2,3-b]pyridin-1-yl)methyl) hydrogen phosphate
(E)-tert-butyl ((5-(5-(4-(dimethylamino)-N-methylbut-2-enamido)pyridin-3-yl)-3-(2-fluoropyridin-4-yl)-1H-pyrrolo[2,3-b]pyridin-1-yl)methyl) hydrogen phosphate
tert-butyl ((3-(2-cyanopyridin-4-yl)-5-(3-(N-methylacrylamido)phenyl)-1H-pyrrolo[2,3-b]pyridin-1-yl)methyl) hydrogen phosphate
tert-butyl ((3-(2-cyanopyridin-4-yl)-5-(3-methoxy-5-(N-methylacrylamido)phenyl)-1H-pyrrolo[2,3-b]pyridin-1-yl)methyl) hydrogen phosphate
(E)-tert-butyl ((3-(2-cyanopyridin-4-yl)-5-(3-(4-(dimethylamino)-N-methylbut-2-enamido)phenyl)-1H-pyrrolo[2,3-b]pyridin-1-yl)methyl) hydrogen phosphate
(E)-tert-butyl ((3-(2-cyanopyridin-4-yl)-5-(3-(4-(dimethylamino)-N-methylbut-2-enamido)-5-methoxyphenyl)-1H-pyrrolo[2,3-b]pyridin-1-yl)methyl) hydrogen phosphate
tert-butyl ((3-(2-cyanopyridin-4-yl)-5-(5-(N-methylacrylamido)pyridin-3-yl)-1H-pyrrolo[2,3-b]pyridin-1-yl)methyl) hydrogen phosphate
(E)-tert-butyl ((3-(2-cyanopyridin-4-yl)-5-(5-(4-(dimethylamino)-N-methylbut-2-enamido)pyridin-3-yl)-1H-pyrrolo[2,3-b]pyridin-1-yl)methyl) hydrogen phosphate
tert-butyl ((3-(3-cyanophenyl)-5-(3-(N-methylacrylamido)phenyl)-1H-pyrrolo[2,3-b]pyridin-1-yl)methyl) hydrogen phosphate
tert-butyl ((3-(3-cyanophenyl)-5-(3-methoxy-5-(N-methylacrylamido)phenyl)-1H-pyrrolo[2,3-b]pyridin-1-yl)methyl) hydrogen phosphate
(E)-tert-butyl ((3-(3-cyanophenyl)-5-(3-(4-(dimethylamino)-N-methylbut-2-enamido)phenyl)-1H-pyrrolo[2,3-b]pyridin-1-yl)methyl) hydrogen phosphate
(E)-tert-butyl ((3-(3-cyanophenyl)-5-(3-(4-(dimethylamino)-N-methylbut-2-enamido)-5-methoxyphenyl)-1H-pyrrolo[2,3-b]pyridin-1-yl)methyl) hydrogen phosphate
tert-butyl ((3-(3-cyanophenyl)-5-(5-(N-methylacrylamido)pyridin-3-yl)-1H-pyrrolo[2,3-b]pyridin-1-yl)methyl) hydrogen phosphate
(E)-tert-butyl ((3-(3-cyanophenyl)-5-(5-(4-(dimethylamino)-N-methylbut-2-enamido)pyridin-3-yl)-1H-pyrrolo[2,3-b]pyridin-1-yl)methyl) hydrogen phosphate
tert-butyl (1-(3-(2-methoxypyridin-4-yl)-5-(3-(N-methylacrylamido)phenyl)-1H-pyrrolo[2,3-b]pyridin-1-yl)ethyl) hydrogen phosphate
tert-butyl (1-(5-(3-methoxy-5-(N-methylacrylamido)phenyl)-3-(2-methoxypyridin-4-yl)-1H-pyrrolo[2,3-b]pyridin-1-yl)ethyl) hydrogen phosphate
(E)-tert-butyl (1-(5-(3-(4-(dimethylamino)-N-methylbut-2-enamido)phenyl)-3-(2-methoxypyridin-4-yl)-1H-pyrrolo[2,3-b]pyridin-1-yl)ethyl) hydrogen phosphate
(E)-tert-butyl (1-(5-(3-(4-(dimethylamino)-N-methylbut-2-enamido)-5-methoxyphenyl)-3-(2-methoxypyridin-4-yl)-1H-pyrrolo[2,3-b]pyridin-1-yl)ethyl) hydrogen phosphate
tert-butyl (1-(3-(2-methoxypyridin-4-yl)-5-(5-(N-methylacrylamido)pyridin-3-yl)-1H-pyrrolo[2,3-b]pyridin-1-yl)ethyl) hydrogen phosphate
(E)-tert-butyl (1-(5-(5-(4-(dimethylamino)-N-methylbut-2-enamido)pyridin-3-yl)-3-(2-methoxypyridin-4-yl)-1H-pyrrolo[2,3-b]pyridin-1-yl)ethyl) hydrogen phosphate
tert-butyl (1-(3-(2-fluoropyridin-4-yl)-5-(3-(N-methylacrylamido)phenyl)-1H-pyrrolo[2,3-b]pyridin-1-yl)ethyl) hydrogen phosphate
tert-butyl (1-(3-(2-fluoropyridin-4-yl)-5-(3-methoxy-5-(N-methylacrylamido)phenyl)-1H-pyrrolo[2,3-b]pyridin-1-yl)ethyl) hydrogen phosphate
(E)-tert-butyl (1-(5-(3-(4-(dimethylamino)-N-methylbut-2-enamido)phenyl)-3-(2-fluoropyridin-4-yl)-1H-pyrrolo[2,3-b]pyridin-1-yl)ethyl) hydrogen phosphate
(E)-tert-butyl (1-(5-(3-(4-(dimethylamino)-N-methylbut-2-enamido)-5-methoxyphenyl)-3-(2-fluoropyridin-4-yl)-1H-pyrrolo[2,3-b]pyridin-1-yl)ethyl) hydrogen phosphate
tert-butyl (1-(3-(2-fluoropyridin-4-yl)-5-(5-(N-methylacrylamido)pyridin-3-yl)-1H-pyrrolo[2,3-b]pyridin-1-yl)ethyl) hydrogen phosphate
(E)-tert-butyl (1-(5-(5-(4-(dimethylamino)-N-methylbut-2-enamido)pyridin-3-yl)-3-(2-fluoropyridin-4-yl)-1H-pyrrolo[2,3-b]pyridin-1-yl)ethyl) hydrogen phosphate
tert-butyl (1-(3-(2-cyanopyridin-4-yl)-5-(3-(N-methylacrylamido)phenyl)-1H-pyrrolo[2,3-b]pyridin-1-yl)ethyl) hydrogen phosphate
tert-butyl (1-(3-(2-cyanopyridin-4-yl)-5-(3-methoxy-5-(N-methylacrylamido)phenyl)-1H-pyrrolo[2,3-b]pyridin-1-yl)ethyl) hydrogen phosphate
(E)-tert-butyl (1-(3-(2-cyanopyridin-4-yl)-5-(3-(4-(dimethylamino)-N-methylbut-2-enamido)phenyl)-1H-pyrrolo[2,3-b]pyridin-1-yl)ethyl) hydrogen phosphate
(E)-tert-butyl (1-(3-(2-cyanopyridin-4-yl)-5-(3-(4-(dimethylamino)-N-methylbut-2-enamido)-5-methoxyphenyl)-1H-pyrrolo[2,3-b]pyridin-1-yl)ethyl) hydrogen phosphate
tert-butyl (1-(3-(2-cyanopyridin-4-yl)-5-(5-(N-methylacrylamido)pyridin-3-yl)-1H-pyrrolo[2,3-b]pyridin-1-yl)ethyl) hydrogen phosphate
(E)-tert-butyl (1-(3-(2-cyanopyridin-4-yl)-5-(5-(4-(dimethylamino)-N-methylbut-2-enamido)pyridin-3-yl)-1H-pyrrolo[2,3-b]pyridin-1-yl)ethyl) hydrogen phosphate
tert-butyl (1-(3-(3-cyanophenyl)-5-(3-(N-methylacrylamido)phenyl)-1H-pyrrolo[2,3-b]pyridin-1-yl)ethyl) hydrogen phosphate
tert-butyl (1-(3-(3-cyanophenyl)-5-(3-methoxy-5-(N-methylacrylamido)phenyl)-1H-pyrrolo[2,3-b]pyridin-1-yl)ethyl) hydrogen phosphate
(E)-tert-butyl (1-(3-(3-cyanophenyl)-5-(3-(4-(dimethylamino)-N-methylbut-2-enamido)phenyl)-1H-pyrrolo[2,3-b]pyridin-1-yl)ethyl) hydrogen phosphate
(E)-tert-butyl (1-(3-(3-cyanophenyl)-5-(3-(4-(dimethylamino)-N-methylbut-2-enamido)-5-methoxyphenyl)-1H-pyrrolo[2,3-b]pyridin-1-yl)ethyl) hydrogen phosphate
tert-butyl (1-(3-(3-cyanophenyl)-5-(5-(N-methylacrylamido)pyridin-3-yl)-1H-pyrrolo[2,3-b]pyridin-1-yl)ethyl) hydrogen phosphate
(E)-tert-butyl (1-(3-(3-cyanophenyl)-5-(5-(4-(dimethylamino)-N-methylbut-2-enamido)pyridin-3-yl)-1H-pyrrolo[2,3-b]pyridin-1-yl)ethyl) hydrogen phosphate
1-(5-(3-acrylamidophenyl)-3-(2-methoxypyridin-4-yl)-1H-pyrrolo[2,3-b]pyridin-1-yl)ethyl tert-butyl hydrogen phosphate
1-(5-(3-acrylamido-5-methoxyphenyl)-3-(2-methoxypyridin-4-yl)-1H-pyrrolo[2,3-b]pyridin-1-yl)ethyl tert-butyl hydrogen phosphate
(E)-tert-butyl (1-(5-(3-(4-(dimethylamino)but-2-enamido)phenyl)-3-(2-methoxypyridin-4-yl)-1H-pyrrolo[2,3-b]pyridin-1-yl)ethyl) hydrogen phosphate (E)-tert-butyl (1-(5-(3-(4-(dimethylamino)but-2-enamido)-5-methoxyphenyl)-3-(2-methoxypyridin-4-yl)-1H-pyrrolo[2,3-b]pyridin-1-yl)ethyl) hydrogen phosphate 1-(5-(5-acrylamidopyridin-3-yl)-3-(2-methoxypyridin-4-yl)-H-pyrrolo[2,3-b]pyridin-1-yl)ethyl tert-butyl hydrogen phosphate (E)-tert-butyl (1-(5-(5-(4-(dimethylamino)but-2-enamido)pyridin-3-yl)-3-(2-methoxypyridin-4-yl)-1H-pyrrolo[2,3-b]pyridin-1-yl)ethyl) hydrogen phosphate 1-(5-(3-acrylamidophenyl)-3-(2-fluoropyridin-4-yl)-1H-pyrrolo[2,3-b]pyridin-1-yl)ethyl tert-butyl hydrogen phosphate 1-(5-(3-acrylamido-5-methoxyphenyl)-3-(2-fluoropyridin-4-yl)-1H-pyrrolo[2,3-b]pyridin-1-yl)ethyl tert-butyl hydrogen phosphate (E)-tert-butyl (1-(5-(3-(4-(dimethylamino)but-2-enamido)phenyl)-3-(2-fluoropyridin-4-yl)-1H-pyrrolo[2,3-b]pyridin-1-yl)ethyl) hydrogen phosphate (E)-tert-butyl (1-(5-(3-(4-(dimethylamino)but-2-enamido)-5-methoxyphenyl)-3-(2-fluoropyridin-4-yl)-1H-pyrrolo[2,3-b]pyridin-1-yl)ethyl) hydrogen phosphate 1-(5-(5-acrylamidopyridin-3-yl)-3-(2-fluoropyridin-4-yl)-1H-pyrrolo[2,3-b]pyridin-1-yl)ethyl tert-butyl hydrogen phosphate (E)-tert-butyl (1-(5-(5-(4-(dimethylamino)but-2-enamido)pyridin-3-yl)-3-(2-fluoropyridin-4-yl)-1H-pyrrolo[2,3-b]pyridin-1-yl)ethyl) hydrogen phosphate 1-(5-(3-acrylamidophenyl)-3-(2-cyanopyridin-4-yl)-1H-pyrrolo[2,3-b]pyridin-1-yl)ethyl tert-butyl hydrogen phosphate 1-(5-(3-acrylamido-5-methoxyphenyl)-3-(2-cyanopyridin-4-yl)-1H-pyrrolo[2,3-b]pyridin-1-yl)ethyl tert-butyl hydrogen phosphate (E)-tert-butyl (1-(3-(2-cyanopyridin-4-yl)-5-(3-(4-(dimethylamino)but-2-enamido)phenyl)-1H-pyrrolo[2,3-b]pyridin-1-yl)ethyl) hydrogen phosphate (E)-tert-butyl (1-(3-(2-cyanopyridin-4-yl)-5-(3-(4-(dimethylamino)but-2-enamido)-5-methoxyphenyl)-1H-pyrrolo[2,3-b]pyridin-1-yl)ethyl) hydrogen phosphate 1-(5-(5-acrylamidopyridin-3-yl)-3-(2-cyanopyridin-4-yl)-1H-pyrrolo[2,3-b]pyridin-1-yl)ethyl tert-butyl hydrogen phosphate (E)-tert-butyl (1-(3-(2-cyanopyridin-4-yl)-5-(5-(4-(dimethylamino)but-2-enamido)pyridin-3-yl)-1H-pyrrolo[2,3-b]pyridin-1-yl)ethyl) hydrogen phosphate 1-(5-(3-acrylamidophenyl)-3-(3-cyanophenyl)-1H-pyrrolo[2,3-b]pyridin-1-yl)ethyl tert-butyl hydrogen phosphate 1-(5-(3-acrylamido-5-methoxyphenyl)-3-(3-cyanophenyl)-1H-pyrrolo[2,3-b]pyridin-1-yl)ethyl tert-butyl hydrogen phosphate (E)-tert-butyl (1-(3-(3-cyanophenyl)-5-(3-(4-(dimethylamino)but-2-enamido)phenyl)-1H-pyrrolo[2,3-b]pyridin-1-yl)ethyl) hydrogen phosphate (E)-tert-butyl (1-(3-(3-cyanophenyl)-5-(3-(4-(dimethylamino)but-2-enamido)-5-methoxyphenyl)-1H-pyrrolo[2,3-b]pyridin-1-yl)ethyl) hydrogen phosphate 1-(5-(5-acrylamidopyridin-3-yl)-3-(3-cyanophenyl)-1H-pyrrolo[2,3-b]pyridin-1-yl)ethyl tert-butyl hydrogen phosphate (E)-tert-butyl (1-(3-(3-cyanophenyl)-5-(5-(4-(dimethylamino)but-2-enamido)pyridin-3-yl)-1H-pyrrolo[2,3-b]pyridin-1-yl)ethyl) hydrogen phosphate Biological Activity Assay
ITK Inhibitor Binding Potency The ability of candidate compounds to interact with ITK is quantitated by a competitive binding assay using the LanthaScreen technology developed by Life Technologies. This assay is based on the binding of a proprietary, Alexa Fluor™ 647-labeled, ATP-competitive kinase inhibitor (kinase tracer-236) to the ITK expression construct in the presence of a Europium-conjugated antibody, resulting in a FRET (fluorescence resonance energy transfer) signal. Displacement of the kinase tracer by compound results in a lower emission ratio upon excitation of the Europium chelate. Candidate compounds are designed as potential irreversible inhibitors of ITK, capable of ligating to an active site cysteine residue resulting in time dependent covalent binding. The time dependent nature of irreversible inhibition is investigated by performing the binding assay with and without a pre-incubation of compound and ITK. An increase in potency in the pre-incubated assay suggests the candidate compound could be irreversibly modifying ITK or having a slowly reversible mechanism. The inhibitory potency of candidate compounds is measured in 20 mM HEPES pH 7.5, 10 mM $MgCl_2$, 0.01% BSA, 0.0005% Tween-20, and 2% DMSO in the presence of 10 nM ITK, 2 nM Eu-anti-GST antibody, and 50 nM kinase tracer-236 using a 384-well plate format. Background signal is defined in the absence of ITK and uninhibited signal is defined in the presence of vehicle (2% DMSO) alone. Compounds were evaluated in an 11 point dose-response ranging from 20 uM to 0.34 nM. The binding assays are performed under two preincubation conditions to evaluate time dependence of inhibition. For the pre-incubation assay, ITK and Eu-anti-GST antibody are pre-incubated with compound or vehicle for two hours prior to the addition of kinase tracer. The non-preincubated assay is run under conditions where ITK and Eu-anti-GST antibody are added to a mixture of compound and kinase tracer. $IC_{50}$ values of compounds are determined using a 4 parameter logistical fit of emission ratio as a function of the concentration of compound.

ITK Inhibitor Binding Kinetics

To obtain a better understanding of the kinetics of binding by inhibitor compounds to ITK, association and dissociation experiments were performed. Using the same TR-FRET buffer and conditions as described above, the kinetic rate constants for the binding of KT-236 to ITK were initially determined. Once knowing the association (kon) and dissociation (koff) rates of KT-236 binding, the binding kinetics for these candidate compounds could be further elucidated. The dissociation rates were determined by pre-incubating ITK for two hours with various concentrations of the candidate compounds. After this period of time, excess (200 nM final) KT-236 was added to the incubation and the resulting increase in fluorescence followed for approximately four hours. For the association rates, ITK was pre-incubated with KT-236 (50 nM) for 90-120 minutes and then various concentrations of candidate compound added. The resulting decrease in signal was then evaluated for the next two hours. Data from both sets of time course experiments was then analyzed using Dynafit software to obtain the kinetic rate constants (kon, koff, kinact, Ki) utilizing multiple reaction models.

ITK Target Modulation Assay

Target modulation was based upon the ability of a compound to inhibit ITK phosphorylation of its substrate, PLCγ1, at Y783. Human Jurkat T cells were placed in snap-cap polypropylene tubes at 4 million per tube in 800 μL medium (RPMI1640 with 10% heat inactivated serum and 12.3 mM 2-mercaptoethanol and supplemented with glutamine/penicillin/streptomycin). Compounds were added as 100 μL of 10× working stock solutions in medium with 1% DMSO (or medium with 1% DMSO for controls) and placed in a 37° C. incubator for 2 hours. Stimulation was carried out using CD3/CD28 Dynabeads to activate the T cell receptor and mimic antigen presenting cells. Beads were added for 100 sec at a ratio of 1 bead per cell, in 100 μL medium (or medium alone for unstimulated control). Starting at 70 sec, cells and beads were pelleted in a microfuge for 15 sec, the supernatant aspirated, and 50 μL lysis buffer was added per tube and mixed with the pellet at the 100 sec time point. Tubes were placed on a rotator for 30 min at 4° C., and cell debris was pelleted in a microfuge. Supernatant was mixed 1:1 with 2× Sample Buffer and subjected to SDS-polyacrylamide gel electrophoresis. After transfer to nitrocellulose, immunoblotting was done with anti-phospho-Y783 PLCγ1 antibody. Immunoblots were visualized with ECL using horseradish peroxidase conjugated secondary antibody.

ITK IL-2 Release Assay

This assay was based on the ability of a compound to inhibit ITK mediated IL-2 release. Jurkat cells were placed in wells of a 96-well plate at 500,000 per well in 120 μL medium (same as above). Compounds were added as 15 μL per well of 10× working stock solutions in medium with 1% DMSO (or medium with 1% DMSO for controls) and placed in a 37° C. incubator for 2 hours. Stimulation used CD3/CD28 Dynabeads to activate the T cell receptor and mimic antigen presenting cells. Beads were added at a ratio of 1 bead per cell, in 15 μL medium (or medium alone for unstimulated control). After overnight incubation, the plates were centrifuged at 290×g for 5 min, then 100 μL per well of supernatant medium removed for IL-2 cytokine assay. To determine cell viability, to the remaining well contents 50 μL of CellTiter-Glo reagent was added and luminescence determined. The IL-2 cytokine assay utilized an electrochemiluminescence-based ELISA.

TABLE 3

| | Biological Activity | |
|---|---|---|
| Example # | ITK Inhibition IC$_{50}$ uM<br>++ indicates ≤0.1 μM<br>+ indicates ≤1 μM<br>− indicates >1 μM | PLC-γ Inhibition IC$_{50}$ uM<br>++ indicates ≤1 μM<br>+ indicates ≤1-5 μM<br>− indicates >5 μM |
| 1 | ++ | ++ |
| 2 | ++ | + |
| 3 | ++ | ++ |
| 4 | ++ | ++ |
| 5 | ++ | + |
| 6 | ++ | − |
| 7 | + | ++ |
| 8 | ++ | + |
| 9 | ++ | − |
| 10 | ++ | − |
| 11 | ++ | − |
| 12 | ++ | ++ |
| 13 | + | ++ |
| 14 | ++ | ++ |
| 15 | ++ | ++ |
| 16 | ++ | ++ |
| 17 | ++ | ++ |
| 18 | ++ | ++ |
| 19 | ++ | ++ |
| 20 | ++ | ++ |
| 21 | ++ | ++ |
| 22 | ++ | ++ |
| 23 | ++ | ++ |
| 24 | ++ | ++ |
| 25 | + | ++ |
| 26 | ++ | ++ |
| 27 | ++ | + |
| 28 | ++ | ++ |
| 29 | ++ | ++ |
| 30 | ++ | ++ |
| 31 | ++ | ++ |
| 32 | ++ | ++ |
| 33 | ++ | ++ |
| 34 | ++ | ++ |
| 35 | ++ | ++ |
| 36 | ++ | ++ |
| 37 | ++ | ++ |
| 38 | ++ | ++ |
| 39 | ++ | ++ |
| 40 | ++ | ++ |
| 41 | ++ | ++ |
| 42 | ++ | ++ |
| 43 | ++ | ++ |
| 44 | ++ | ++ |
| 45 | ++ | ++ |
| 46 | ++ | + |
| 47 | ++ | + |
| 48 | ++ | ++ |
| 49 | ++ | ++ |
| 50 | ++ | ++ |
| 51 | ++ | − |
| 52 | ++ | + |
| 53 | ++ | ++ |
| 54 | + | + |
| 55 | ++ | ++ |
| 56 | ++ | ++ |
| 57 | ++ | − |
| 58 | + | − |
| 59 | + | − |
| 60 | ++ | ++ |
| 61 | ++ | + |
| 62 | + | − |
| 63 | + | + |
| 64 | ++ | ++ |
| 65 | ++ | ++ |
| 66 | ++ | ++ |
| 67 | ++ | ++ |
| 68 | ++ | ++ |
| 69 | ++ | − |
| 70 | − | − |
| 71 | ++ | ++ |
| 72 | ++ | + |
| 73 | | ++ |
| 74 | ++ | ++ |
| 75 | | + |
| 76 | | + |

Other Anti-inflammatory Assays

Anti-inflammatory Efficacy—Rat Carrageenan Foot Pad Edema: The compounds of the present disclosure will be evaluated for efficacy in vivo in a model of inflammation. Methods to determine efficacy in rat carrageenan foot pad edema are described in U.S. Pat. No. 5,760,068.

Male Sprague Dawley rats are selected for equal average body weight per group. After fasting, with free access to water sixteen hours prior to test, animals are dosed orally (1 mL) with test compounds in a vehicle containing 0.5% methylcellulose and 0.025% surfactant. The control group is dosed with vehicle alone.

One hour after dosing, a subplantar injection of 0.1 mL of 1% solution of carrageenan/sterile 0.9% saline is administered in one foot, to all animals. The volume of the injected foot is measured using a displacement plethysmometer. Foot volume is measured again three hours after carrageenan injection. The three hour foot volume measurement is compared between treated and control groups; the percent inhibition of edema is calculated.

Anti-inflammatory Efficacy—Rat Carrageenan-Induced Analgesia Test: The compounds of the present disclosure will be evaluated for efficacy in vivo in a model of inflammatory analgesia. Methods to determine efficacy in rat carrageenan-induced analgesia test are described in U.S. Pat. No. 5,760,068.

Male Sprague Dawley rats are selected for equal average body weight per group. After fasting, with free access to water sixteen hours prior to test, animals are dosed orally (1 mL) with test compounds in vehicle containing 0.5% methylcellulose and 0.025% surfactant. Control groups are dosed with vehicle alone.

One hour after dosing, a subplantar injection of 0.1 mL of 1% solution of carrageenan/sterile 0.9% saline is administered in one foot, to all animals. Three hours after carrageenan injection, rats are placed in a plexiglass container with a high intensity lamp under the floor. After twenty minutes, thermal stimulation is begun on either the injected or the uninjected foot. Foot withdrawal is determined by a photoelectric cell. The time until foot withdrawal is measured and compared between treated and control groups. The percent inhibition of the hyperalgesic foot withdrawal is calculated.

Efficacy in Collagen-Induced Arthritis: The compounds of the present disclosure will be evaluated in a mouse autoimmune model of rheumatoid arthritis. Methods to determine efficacy in collagen-induced arthritis in the mouse are described by Grimstein, et al. (2011) J. Translational Med. 9, 1-13.

Six week-old male DBA/1J mice are obtained from The Jackson Laboratory. At eight weeks of age, mice are orally administered test compounds daily. Mice are immunized by intradermal injection, at twelve weeks of age, with 0.1 mL of emulsion containing 100 µg of bovine type II collagen (bCII). At 21 days following immunization, mice are boosted with 0.1 mL of bCII (100 µg) emulsified in equal volume of incomplete Freund's Adjuvant (IFA) (Difco, Detroit, Mich.). All mice are monitored three times for the incidence of arthritis and evaluation of a clinical score, ranging from 0-4 was used (0: no swelling or redness; 1: detectable arthritis with erythema; 2: significant swelling and redness; 3: severe swelling and redness from joint to digit; 4: joint stiffness or deformity with ankylosis). The score is calculated from the average cumulative value of all four paws. Severe arthritis is defined as a score >3.

For terminal evaluation of arthritis, mice are euthanized 28 days after initial immunization. The two hind limbs are removed, fixed in formalin, decalcified in RDO solution (Apex Engineering, Aurora, Ill.) for 10-20 min depending on tissue size and examined for pliability. Sections are cut (4 µm thick) and stained with hematoxylin and eosin. Histological evaluation is performed by examining for infiltration of immune cells, hyperplasia, pannus formation and bone deformation for each paw, using a scale ranging from 0-3, according to severity of pathological changes (0: normal, 1: mild, 2: moderate, 3: severe).

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:

1. A compound, of Formula (I):

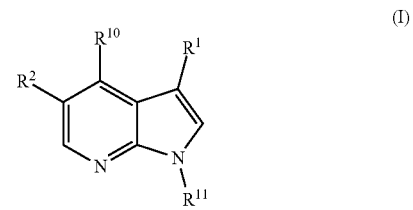

wherein:
$R^1$ is chosen from aryl and heteroaryl, and may be optionally substituted with one $R^3$ substituent;
$R^2$ is chosen from aryl or heteroaryl, and may be optionally substituted with one or more $R^4$ substituents;
$R^3$ is chosen from hydrogen, —$C_{1-4}$alkyl, —$OC_{1-4}$alkyl, —$NHC_{1-4}$alkyl, —$N(C_{1-4}alkyl)_2$, cyano, —C(O)N($R^6$)$_2$, —C(O)$C_{1-4}$alkyl, haloalkyl, oxo, and halo;
each $R^4$ is independently chosen from hydrogen, —$C_{1-4}$alkyl, —$OC_{1-4}$alkyl, —$OC_{1-6}$cycloalkyl, —$OC_{1-6}$heterocycloalkyl, aryl, heteroaryl, haloalkyl, haloalkoxy, halo, —$NR^5R^6$, —$(CH_2)_mCR^7$=$CR^9C(O)$Me, —$(CH_2)_mCR^7$=$CR^9C(O)NR^7_2$, —$(CH_2)_m$ $CR^7$=$CR^9CN$, and wherein if $R^1$ is indolyl then $R^4$ cannot be hydrogen;
$R^5$ is chosen from hydrogen, cyano, —$C(O)CF_3$, —C(O) CH=$CH_2$, —$C(O)CR^7$=$CH_2$, —C(O)CH=$CHR^7$, —$C(O)CR^7$=$CHR^7$, —C(O)CH=$CR^7_2$, —C(O) CH=$CHCH_2R^8$, —C(O)CH=$CHC(O)CH_2R^8$, —COC(CN)=$CHR^6$, —C(O)(C(O)NH$_2$)=$CHR^6$, —$S(O)_2CH$=$CH_2$, —$(CH_2)_mCR^7$=$CR^9C(O)Me$, —$(CH_2)_mCR^7$=$CR^9C(O)NR^7_2$, —$(CH_2)_m$ $CR^7$=$CR^9CN$, and wherein if $R^5$ is —C(O) CH=$CHR^7$ then $R^1$ must have a $R^3$ substituent;
$R^6$ is chosen from hydrogen, —$C_{1-4}$alkyl, and —$(CH_2)_nC_{3-7}$cycloalkyl;
each $R^7$ is independently chosen from hydrogen, —CN, —$C_{1-4}$alkyl, —$C_{3-7}$cycloalkyl, —$C_{3-7}$heterocycle, aryl, and heteroaryl where aryl and heteroaryl may be optionally substituted with one or more $R^9$;
$R^8$ is chosen from hydrogen, —$C_{1-4}$alkyl, —$C_{1-4}$alkylaryl, —$C_{1-4}$alkylheteroaryl, —$C_{3-7}$cycloalkyl, —$C_{3-7}$heterocycle, —OH, —$OC_{1-4}$alkyl, —$C_{1-4}$alkylO$C_{1-4}$alkyl, —$NH_2$, —$NHC_{1-4}$alkyl, —$N(C_{1-4}alkyl)_2$, heterocycle, aryl and heteroaryl;
$R^9$ is chosen from hydrogen, —$C_{1-4}$alkyl, —CN, —$CF_3$, —C(O)Me, —C(O)NH$_2$, and aryl;
$R^{10}$ is chosen from H and —$C_{1-4}$alkyl;
$R^{11}$ is chosen from hydrogen and —$C_{1-4}$alkyl, optionally substituted with —$OPO(OR^{12})_2$, —$OC(O)R^{13}$, or an amino acid;
$R^{12}$ is chosen from hydrogen and —$C_{1-6}$alkyl;
$R^{13}$ is —$C_{1-6}$alkyl;
m is chosen from 1, 2 and 3;

n is chosen from 0, 1, 2, and 3; and
wherein the compound is not

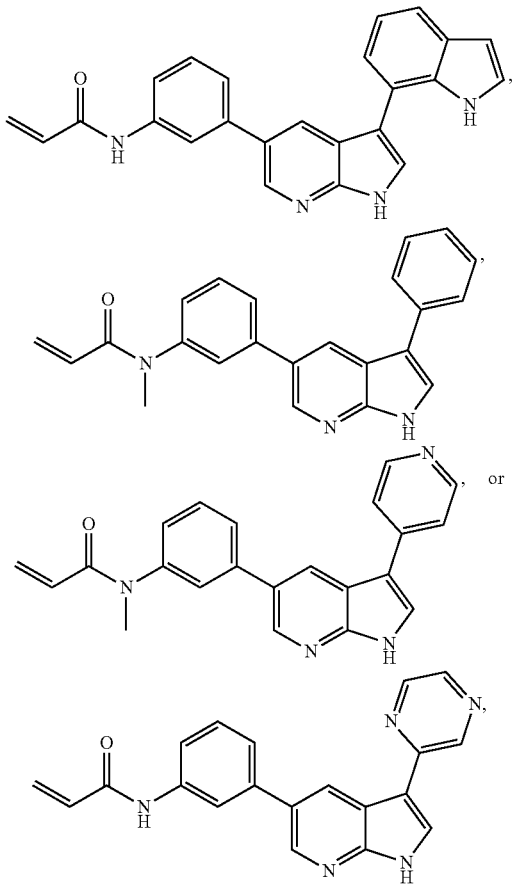

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

2. The compound of claim 1, wherein the compound has structural Formula (II):

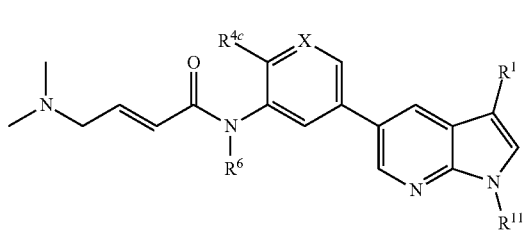

wherein:
R$^1$ is chosen from aryl and heteroaryl, and may be optionally substituted with one R$^3$ substituent;
X is chosen from CR$^{4b}$ and N;
R$^3$ is chosen from hydrogen, —C$_{1-4}$alkyl, —OC$_{1-4}$alkyl, —NHC$_{1-4}$alkyl, —N(C$_{1-4}$alkyl)$_2$, cyano, —C(O)N(R$^6$)$_2$, —C(O)C$_{1-4}$alkyl, haloalkyl, oxo, and halo;
R$^{4b}$ is chosen from hydrogen, —C$_{1-4}$alkyl, —OC$_{1-4}$alkyl, aryl, heteroaryl, haloalkyl, haloalkoxy, and halo;
R$^{4c}$ is chosen from hydrogen, —C$_{1-4}$alkyl, —OC$_{1-4}$alkyl, —OC$_{1-6}$cycloalkyl, and —OC$_{1-6}$heterocycloalkyl;
R$^6$ is chosen from hydrogen and —C$_{1-4}$alkyl;
R$^{11}$ is chosen from hydrogen and —C$_{1-4}$alkyl, optionally substituted with —OPO(OR$^{12}$)$_2$, —OC(O)R$^{13}$, or an amino acid; and
R$^{12}$ is chosen from hydrogen and —C$_{1-6}$alkyl;
R$^{13}$ is —C$_{1-6}$ alkyl.

3. The compound of claim 2, wherein
R$^1$ is phenyl, optionally substituted with one R$^3$ substituent; and
R$^3$ is chosen from hydrogen, cyano, —OC$_{1-4}$alkyl, and halo.

4. The compound of claim 2, wherein
R$^1$ is heteroaryl, and may be optionally substituted with one R$^3$ substituent; and R$^3$ is chosen from hydrogen, cyano, —OC$_{1-4}$alkyl, and halo.

5. The compound of claim 4, wherein R$^1$ is pyridyl.

6. The compound of claim 2, wherein:
R$^{4b}$ is chosen from hydrogen, —C$_{1-4}$alkyl, heteroaryl, —OC$_{1-4}$alkyl, haloalkyl, haloalkoxy, and halo.

7. The compound of claim 2, wherein R$^{4c}$ is hydrogen.

8. The compound of claim 1, wherein the compound has structural Formula (III):

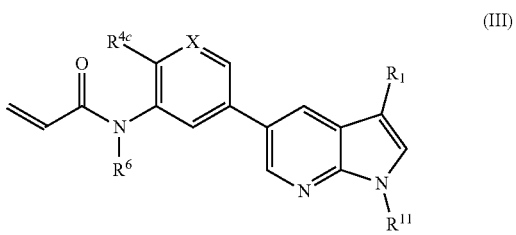

wherein:
R$^1$ is chosen from aryl and heteroaryl, and is substituted with one R$^3$ substituent;
X is chosen from CR$^{4b}$ and N;
R$^3$ is chosen from hydrogen, —C$_{1-4}$alkyl, —OC$_{1-4}$alkyl, —NHC$_{1-4}$alkyl, —N(C$_{1-4}$alkyl)$_2$, cyano, —C(O)N(R$^6$)$_2$, —C(O)C$_{1-4}$alkyl, haloalkyl, oxo, and halo;
R$^{4b}$ is chosen from hydrogen, —C$_{1-4}$alkyl, —OC$_{1-4}$alkyl, aryl, heteroaryl, haloalkyl, haloalkoxy, halo, and wherein if R$^1$ is indolyl then R$^{4b}$ cannot be hydrogen;
R$^{4c}$ is chosen from hydrogen, —C$_{1-4}$alkyl, —OC$_{1-4}$alkyl, —OC$_{1-6}$cycloalkyl, and —OC$_{1-6}$ heterocycloalkyl;
R$^6$ is chosen from hydrogen and —C$_{1-4}$alkyl;
R$^{11}$ is chosen from hydrogen and —C$_{1-4}$alkyl, optionally substituted with —OPO(OR$^{12}$)$_2$, —OC(O)R$^{13}$, or an amino acid;
R$^{12}$ is chosen from hydrogen and —C$_{1-6}$alkyl;
R$^{13}$ is —C$_{1-6}$ alkyl; and wherein the compound is not

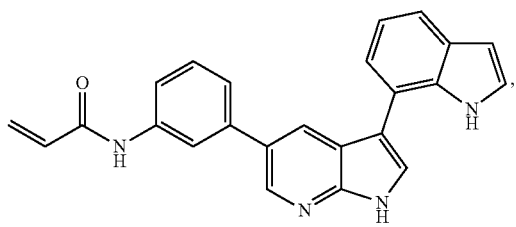

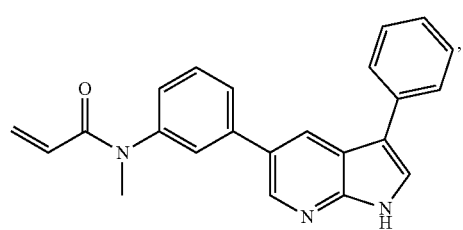

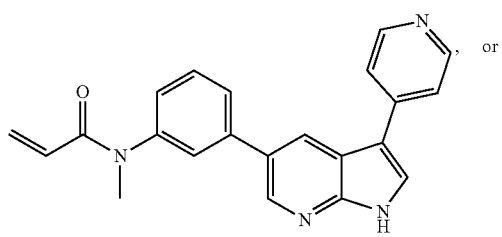, or

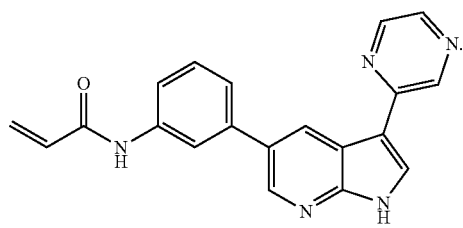

9. The compound of claim 8, wherein
R$^1$ is phenyl, optionally substituted with one R$^3$ substituent; and
R$^3$ is chosen from hydrogen, cyano, —OC$_{1-4}$alkyl, and halo.

10. The compound of claim 8, wherein
R$^1$ is heteroaryl, and may be optionally substituted with one R$^3$ substituent; and
R$^3$ is chosen from hydrogen, cyano, —OC$_{1-4}$alkyl, and halo.

11. The compound of claim 10, wherein R$^1$ is pyridyl.

12. The compound of claim 8, wherein:
R$^{4b}$ is chosen from hydrogen, —C$_{1-4}$alkyl, heteroaryl, —OC$_{1-4}$alkyl, haloalkyl, haloalkoxy, and halo.

13. The compound of claim 8, wherein R$^{4c}$ is hydrogen.

14. The compound of claim 1, wherein the compound has structural Formula (IV):

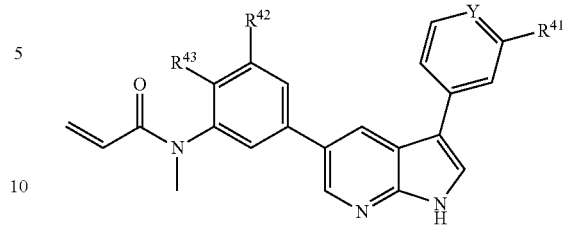

wherein:
Y is chosen from CH and N;
R$^{41}$ is chosen from —C$_{1-4}$alkyl, —OC$_{1-4}$alkyl, cyano, and halo;
R$^{42}$ is chosen from hydrogen and —OC$_{1-4}$alkyl; and
R$^{43}$ is chosen from hydrogen and halo.

15. The compound of claim 1, wherein the compound has structural Formula (V):

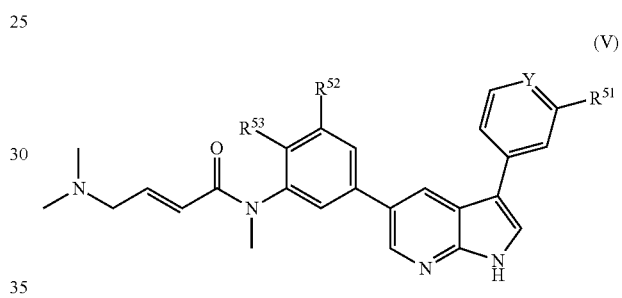

wherein:
Y is chosen from CH and N;
R$^{51}$ is chosen from —C$_{1-4}$alkyl, —OC$_{1-4}$alkyl, cyano, and halo;
R$^{52}$ is chosen from hydrogen and —OC$_{1-4}$alkyl; and
R$^{53}$ is chosen from hydrogen and halo.

16. The compound of claim 1, wherein the compound has structural Formula (VI):

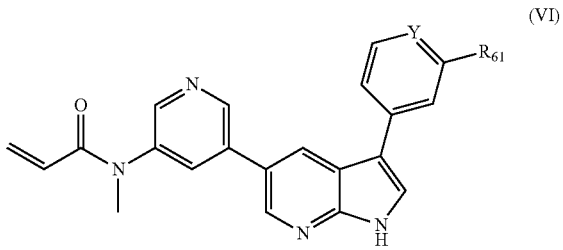

wherein:
Y is chosen from CH and N; and
R$^{61}$ is chosen from —OC$_{1-4}$alkyl, cyano, and halo.

17. The compound of claim 1, wherein the compound has structural Formula (VII):

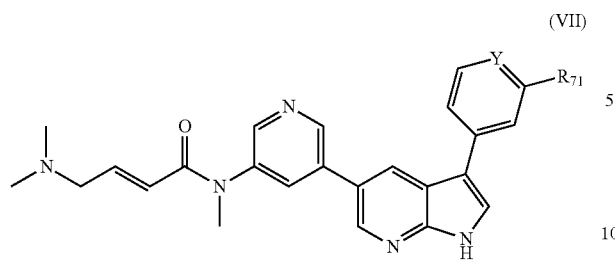

(VII)

wherein:
Y is chosen from CH and N; and
$R^{71}$ is chosen from —$OC_{1-4}$alkyl, cyano, and halo.

18. The compound of claim 1, wherein the compound has structural Formula (VIII):

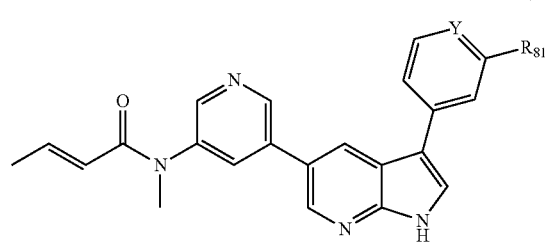

(VIII)

wherein:
Y is chosen from CH and N; and
$R^{81}$ is chosen from —$OC_{1-4}$alkyl, cyano, and halo.

19. The compound of claim 1, wherein the compound has structural Formula (IX):

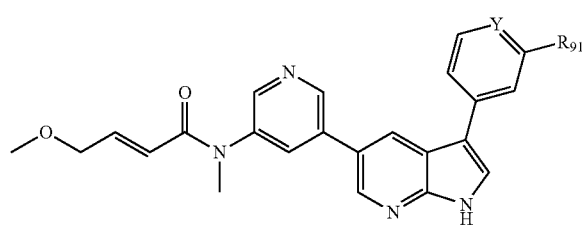

(IX)

wherein:
Y is chosen from CH and N; and
$R^{91}$ is chosen from —$OC_{1-4}$alkyl, cyano, and halo.

20. The compound of claim 1, wherein the compound is selected from

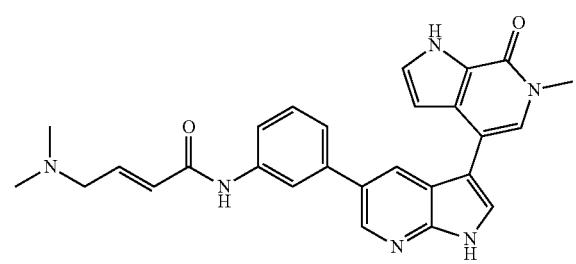

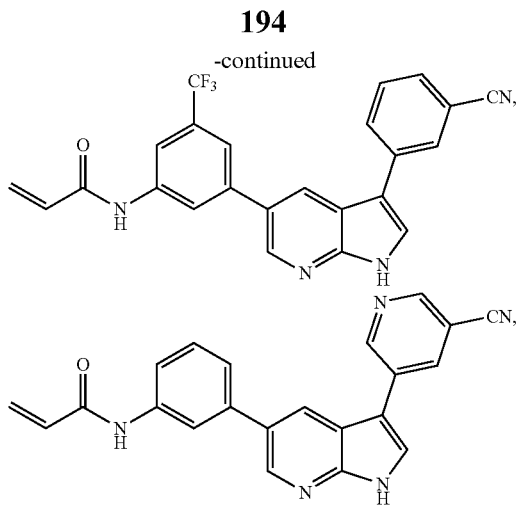

-continued

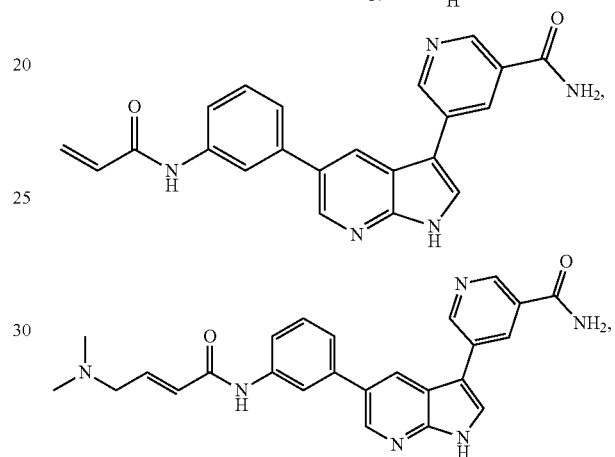

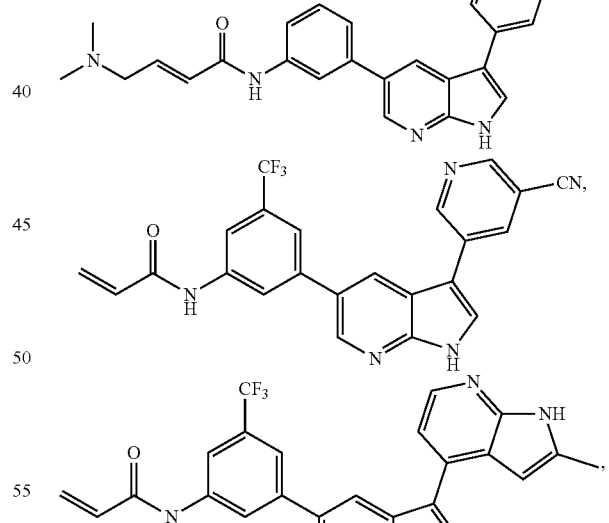

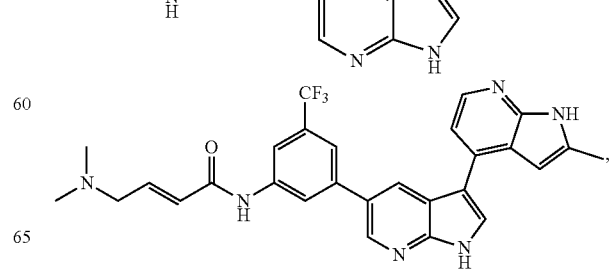

195
-continued
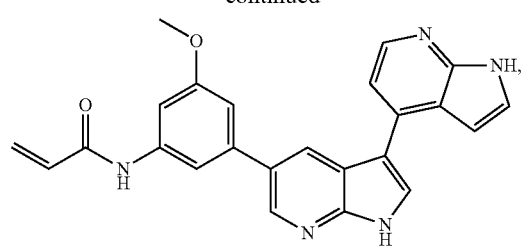
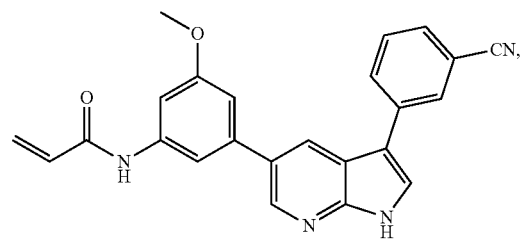
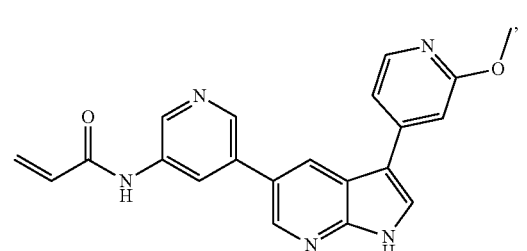
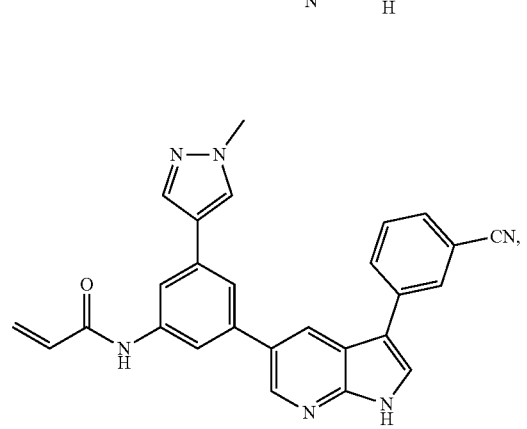
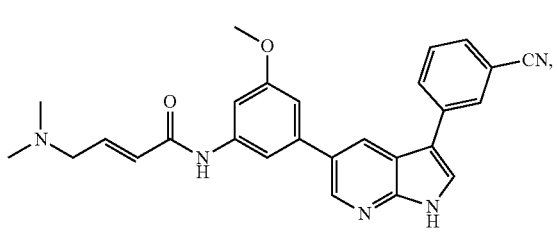
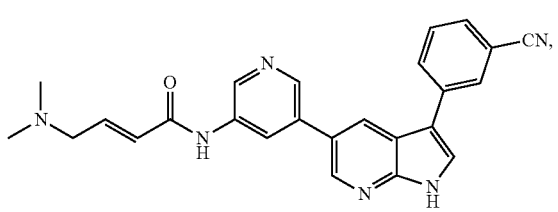
196
-continued
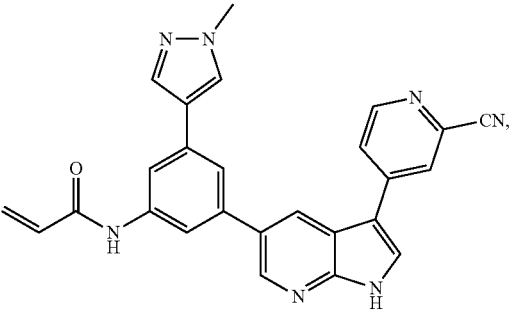
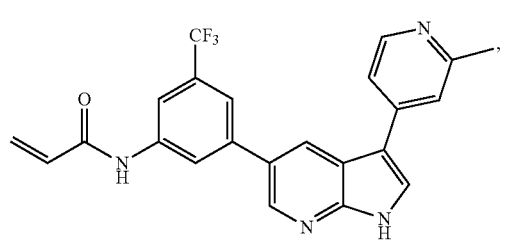
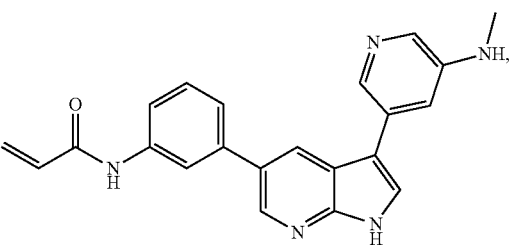
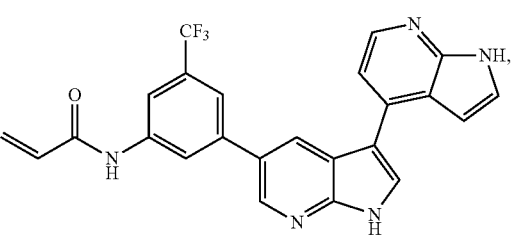
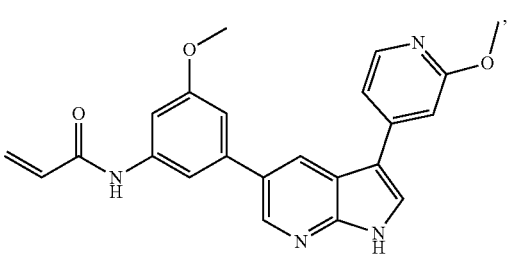
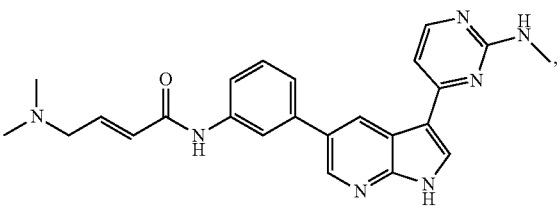

-continued
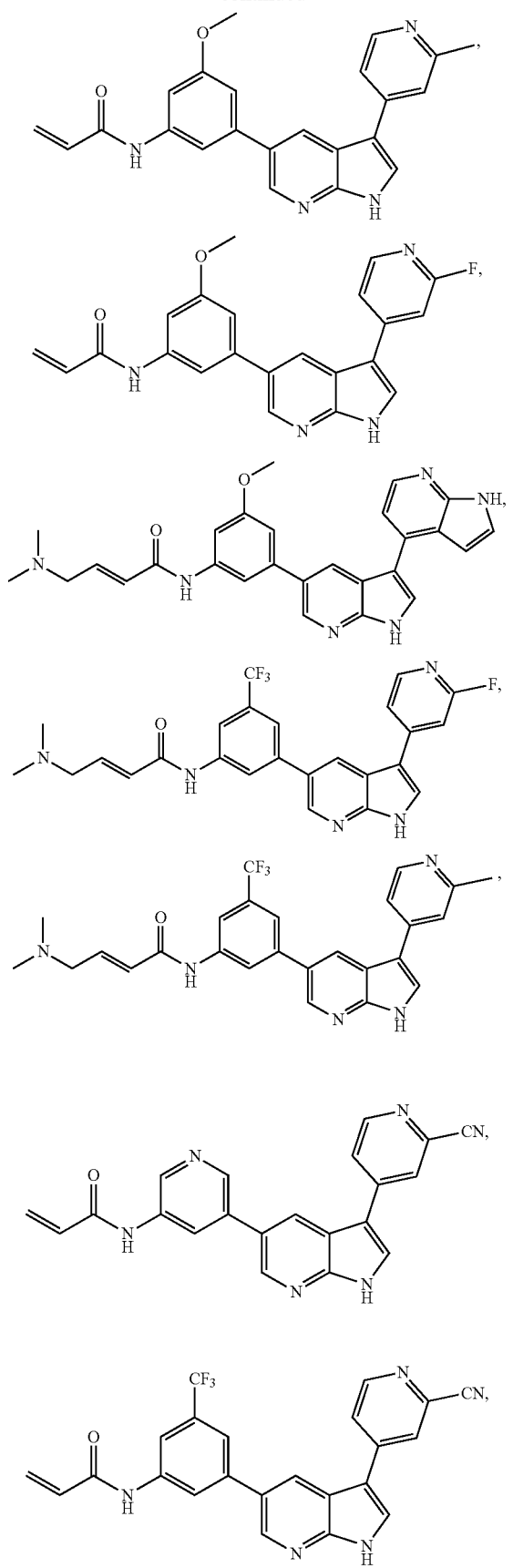
-continued
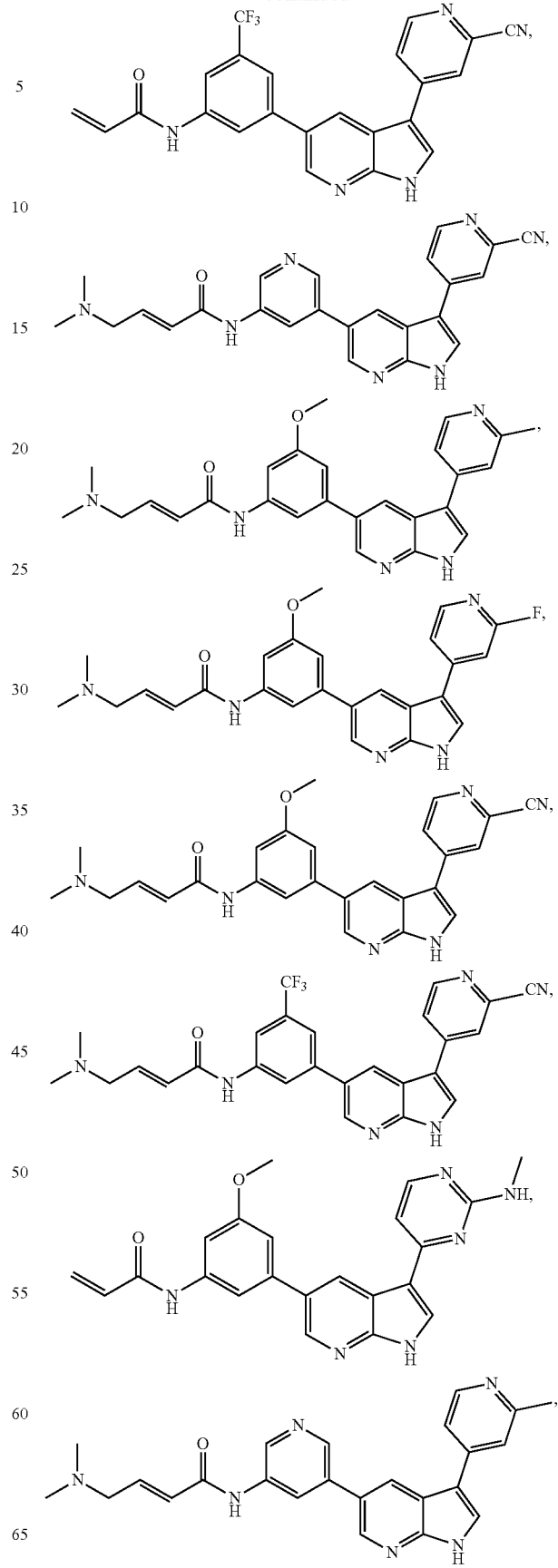

199
-continued
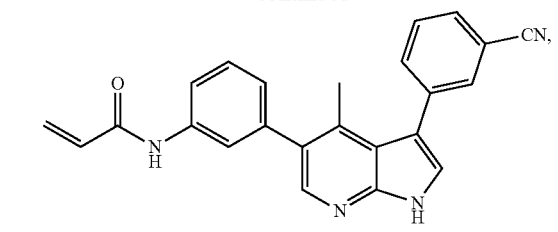
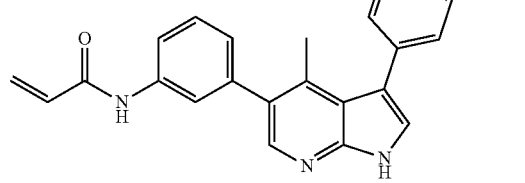
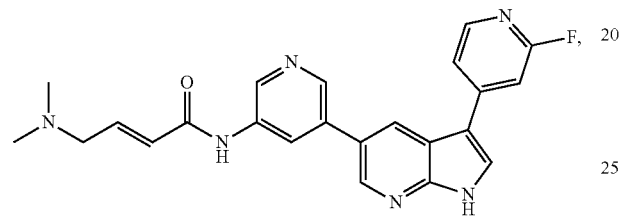
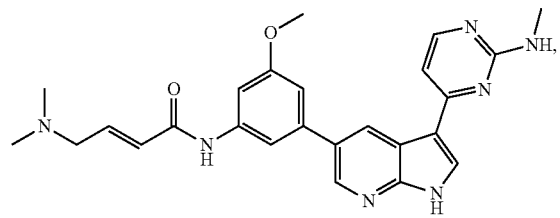
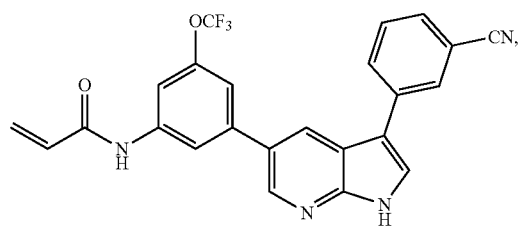
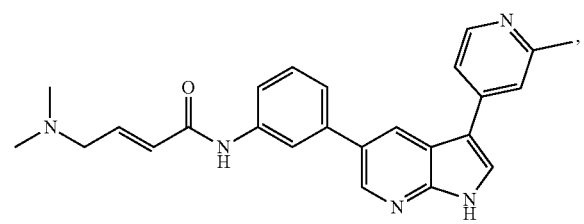
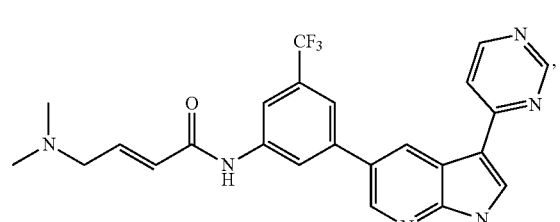
200
-continued
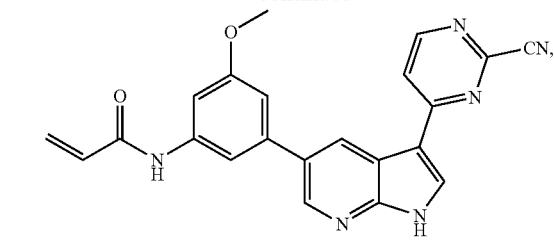
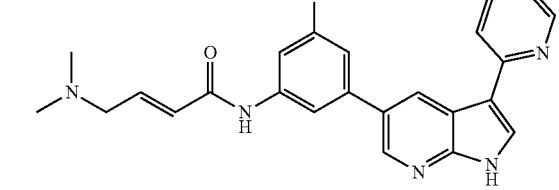
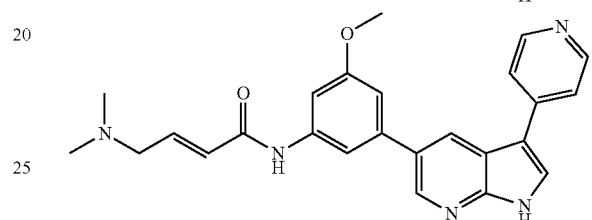
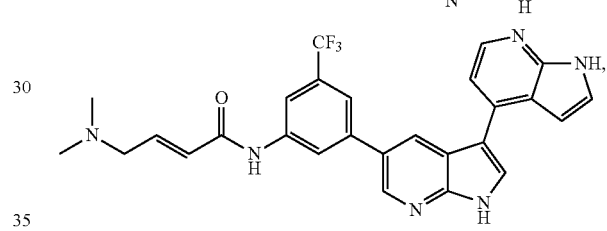
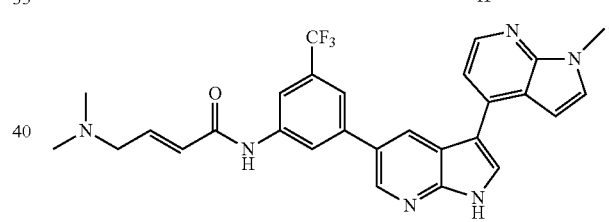
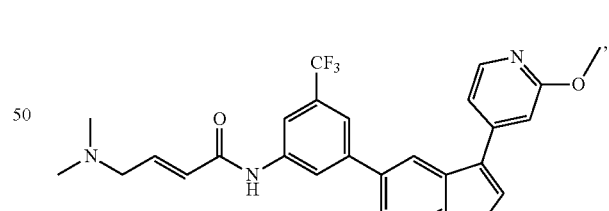
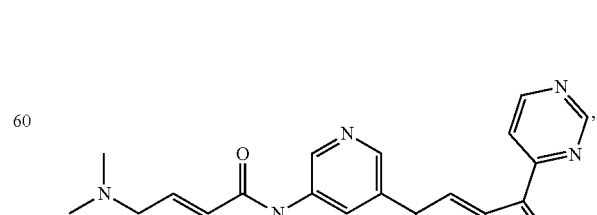

-continued
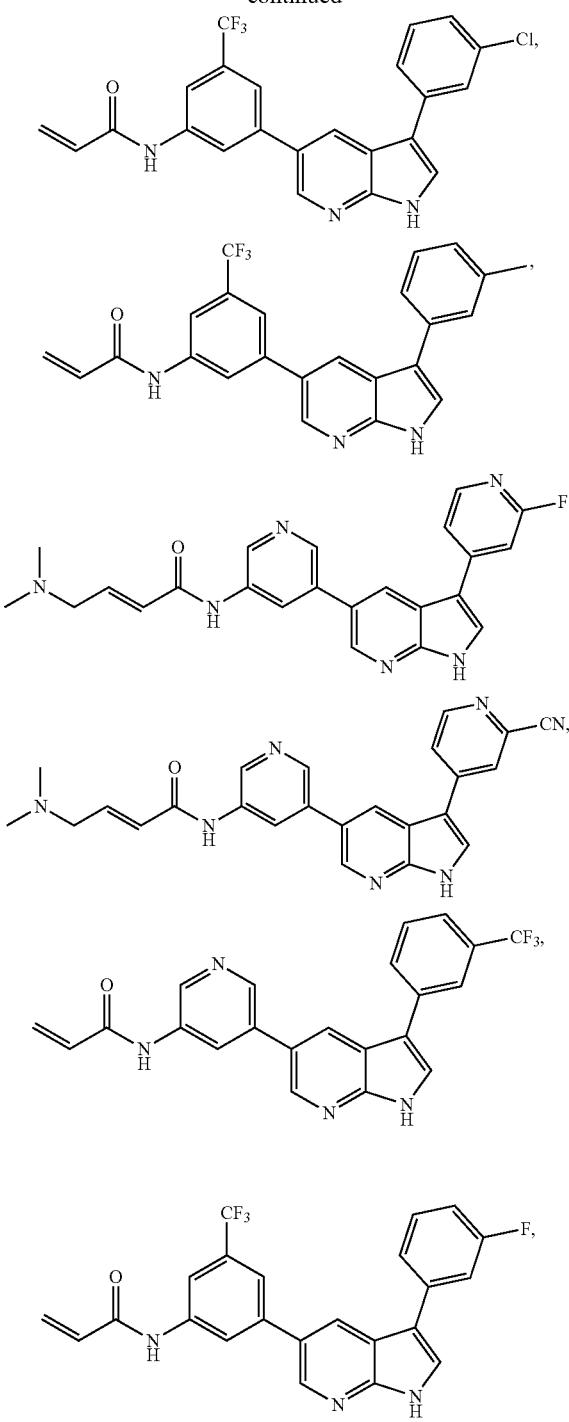
-continued
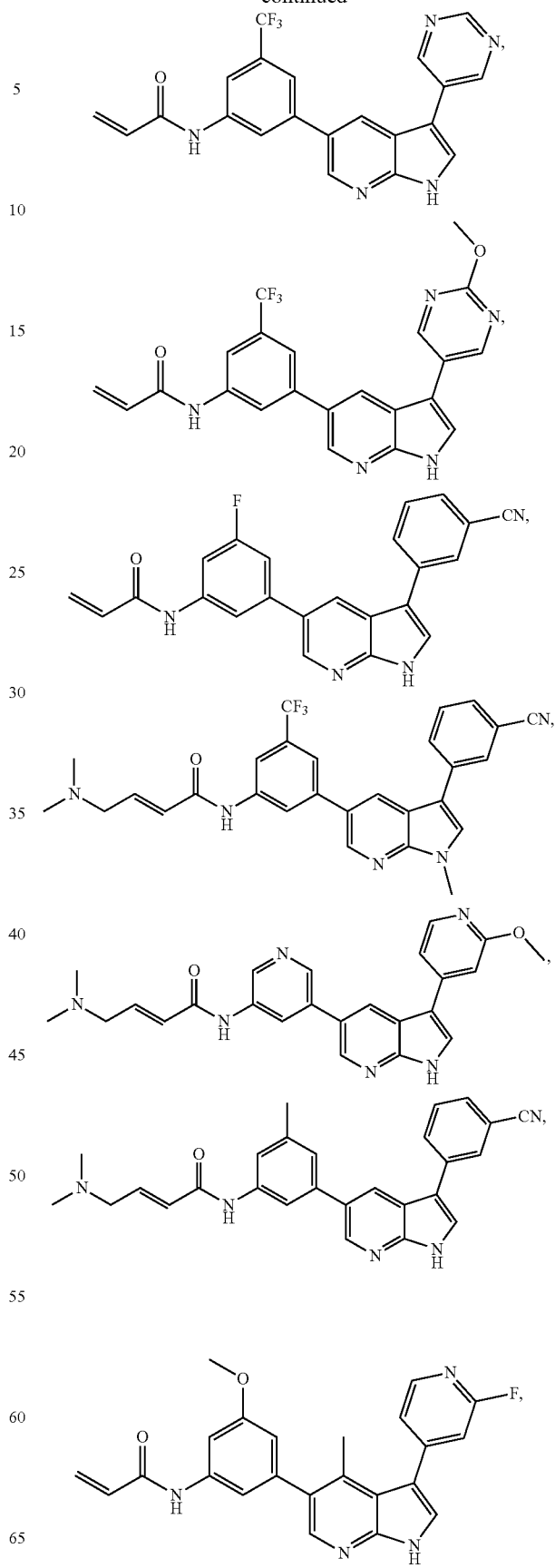

-continued
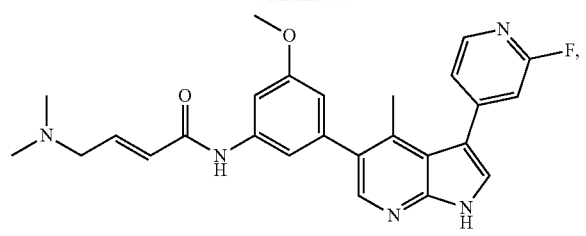
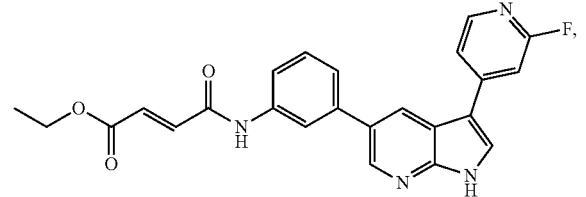
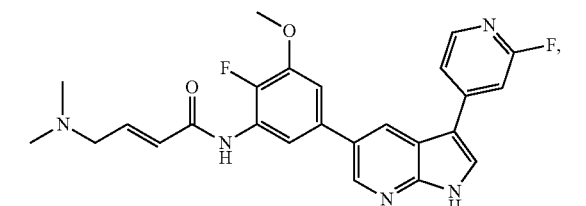
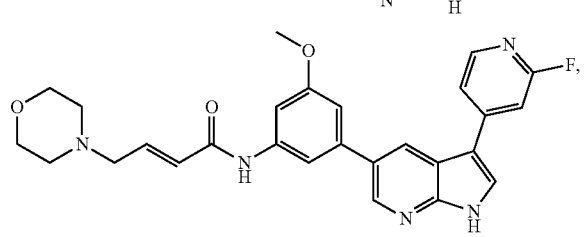
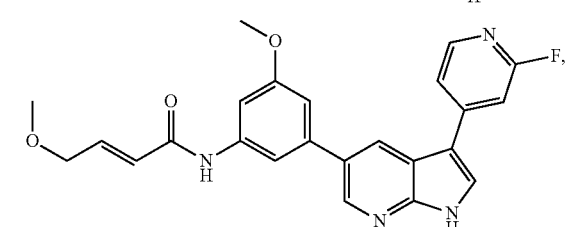
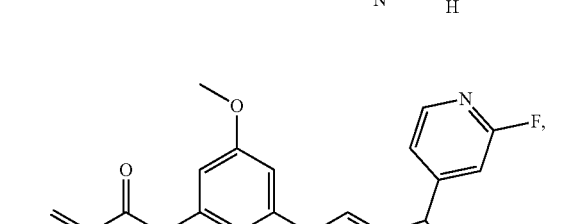
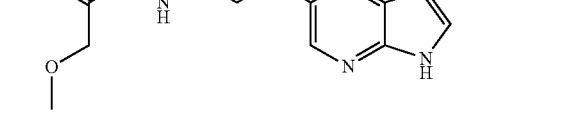
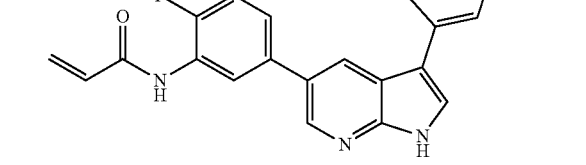
-continued
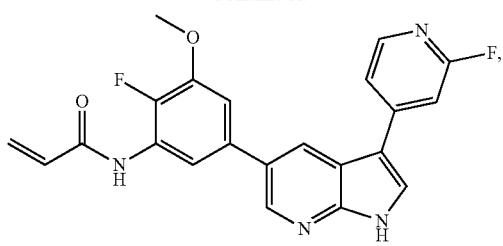
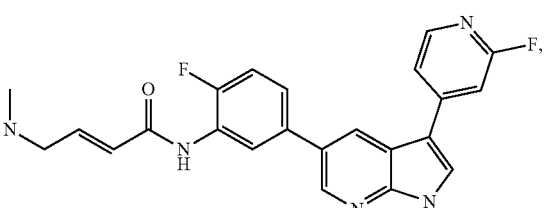
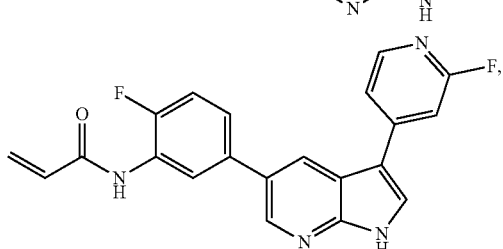
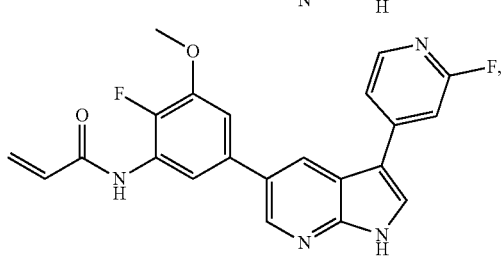
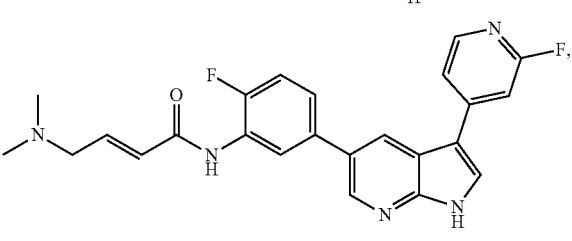
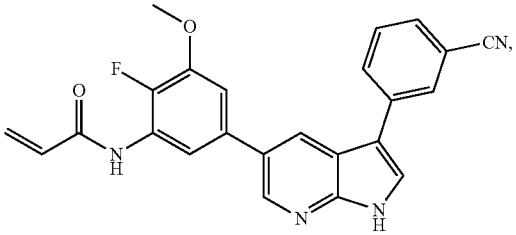
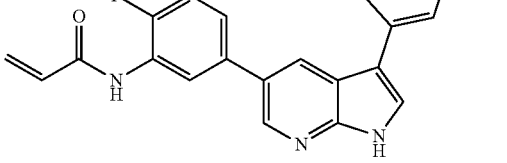

205
-continued

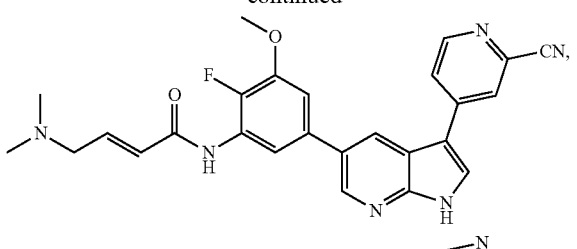

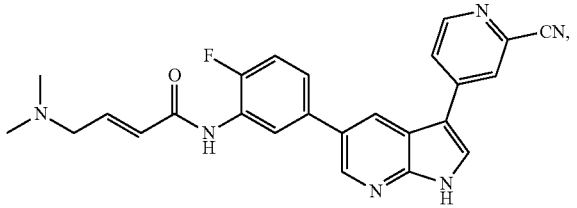

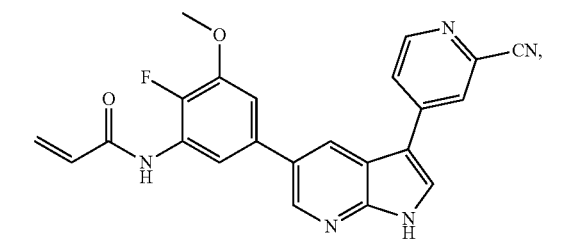

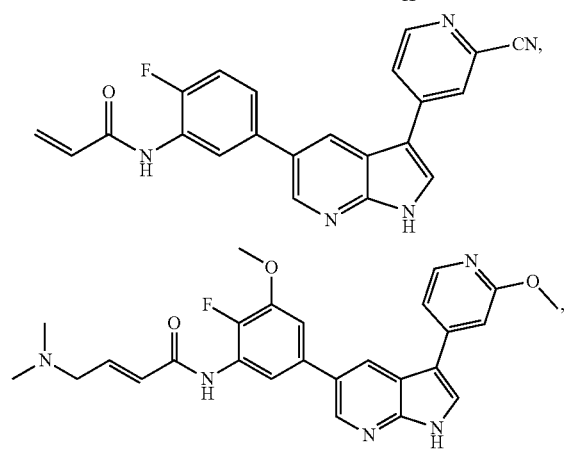

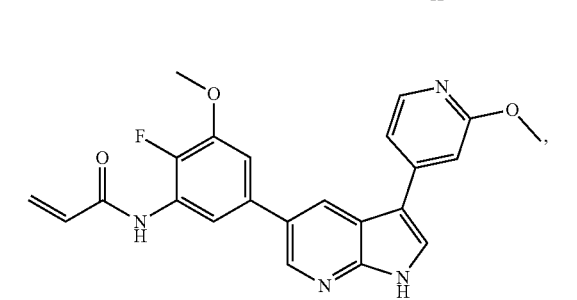

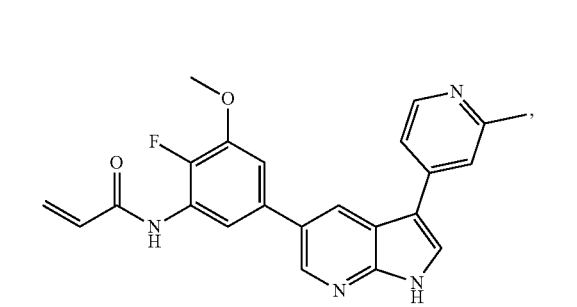

206
-continued

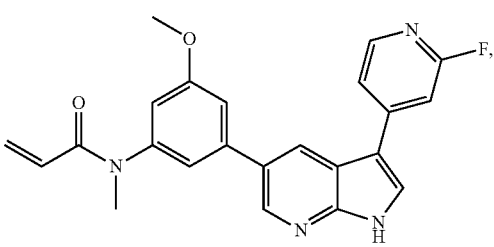

a pharmaceutically acceptable salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

21. The compound of claim 14, wherein the compound is selected from

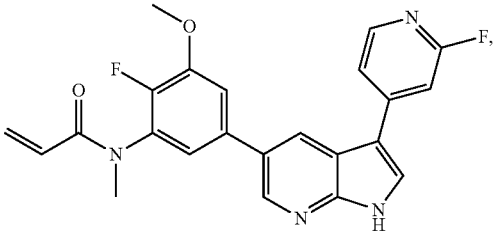

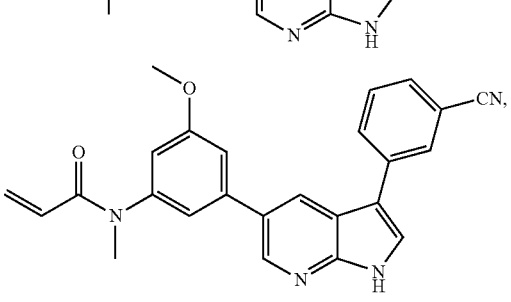

-continued

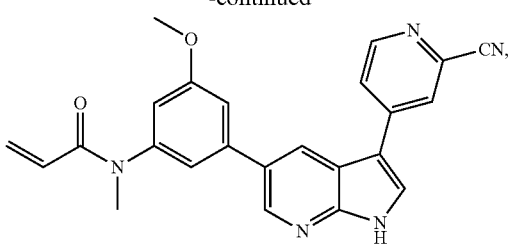
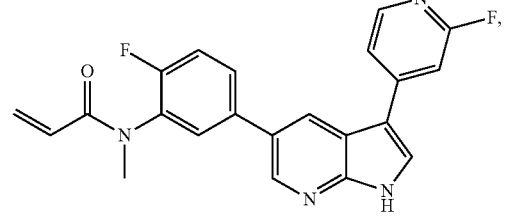
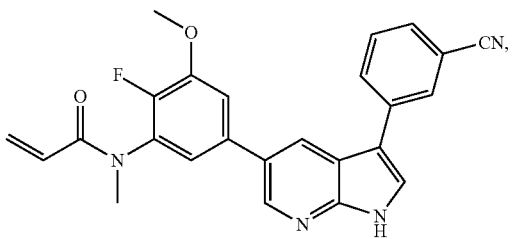
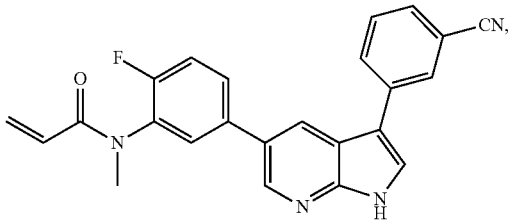
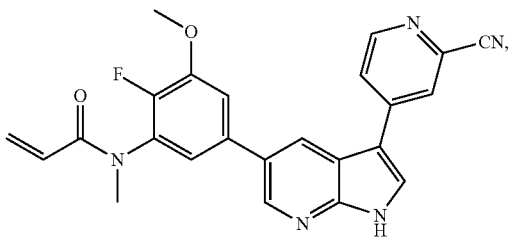
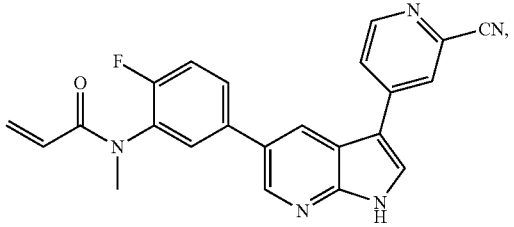
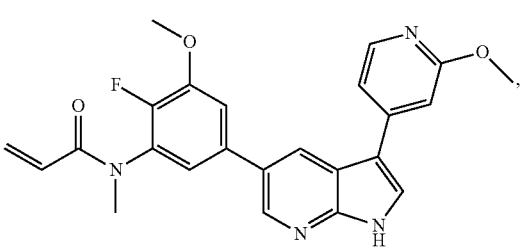

-continued

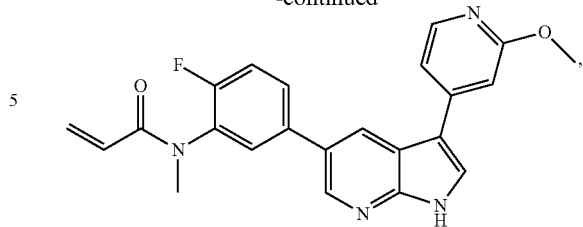
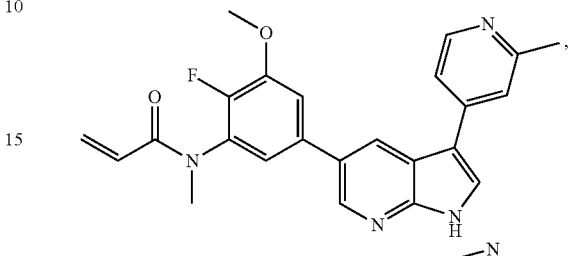
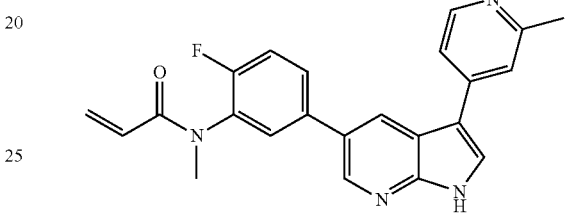

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (eg., tritium, deuterium), or a combination thereof.

22. The compound of claim 15, wherein the compound is selected from

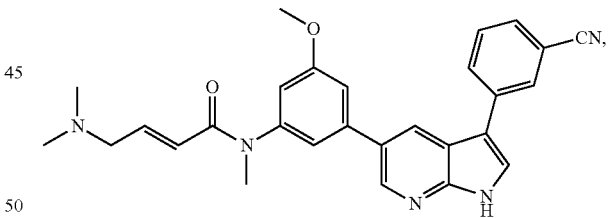
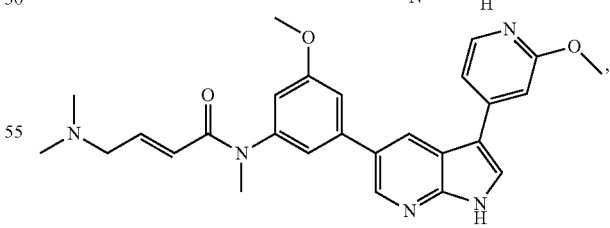
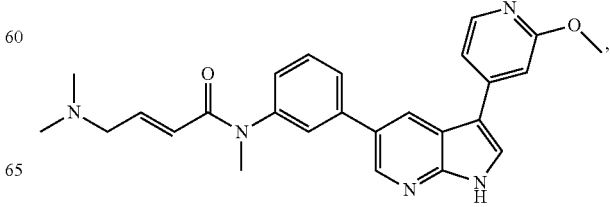

209
-continued

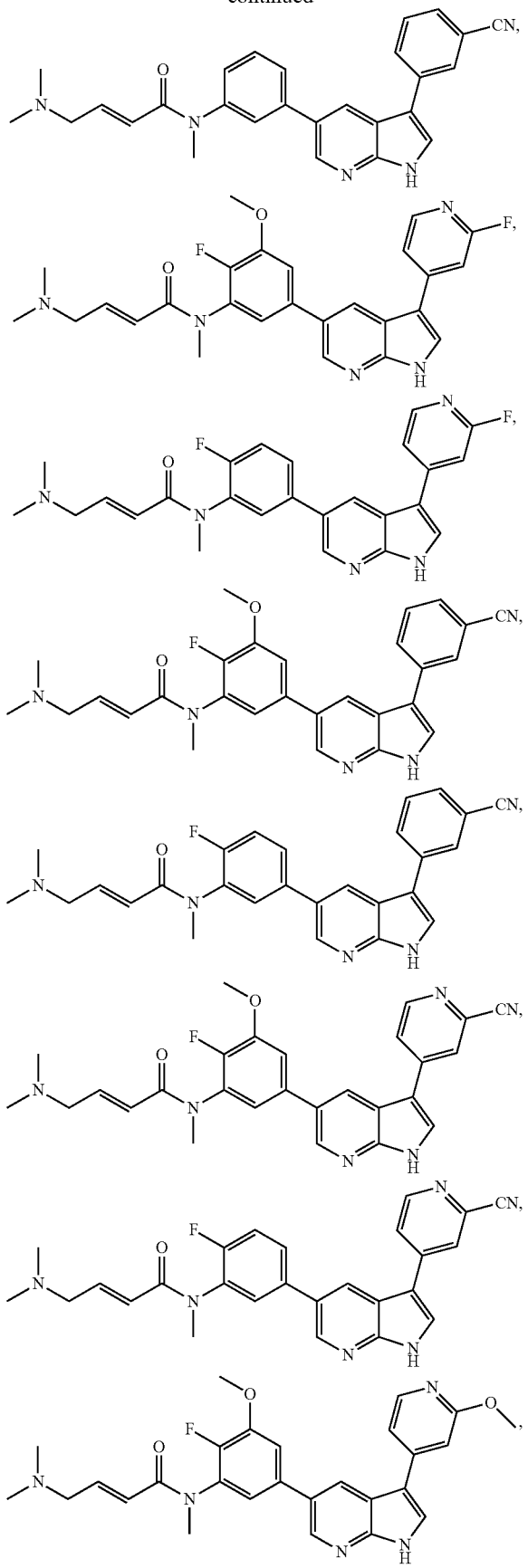

210
-continued

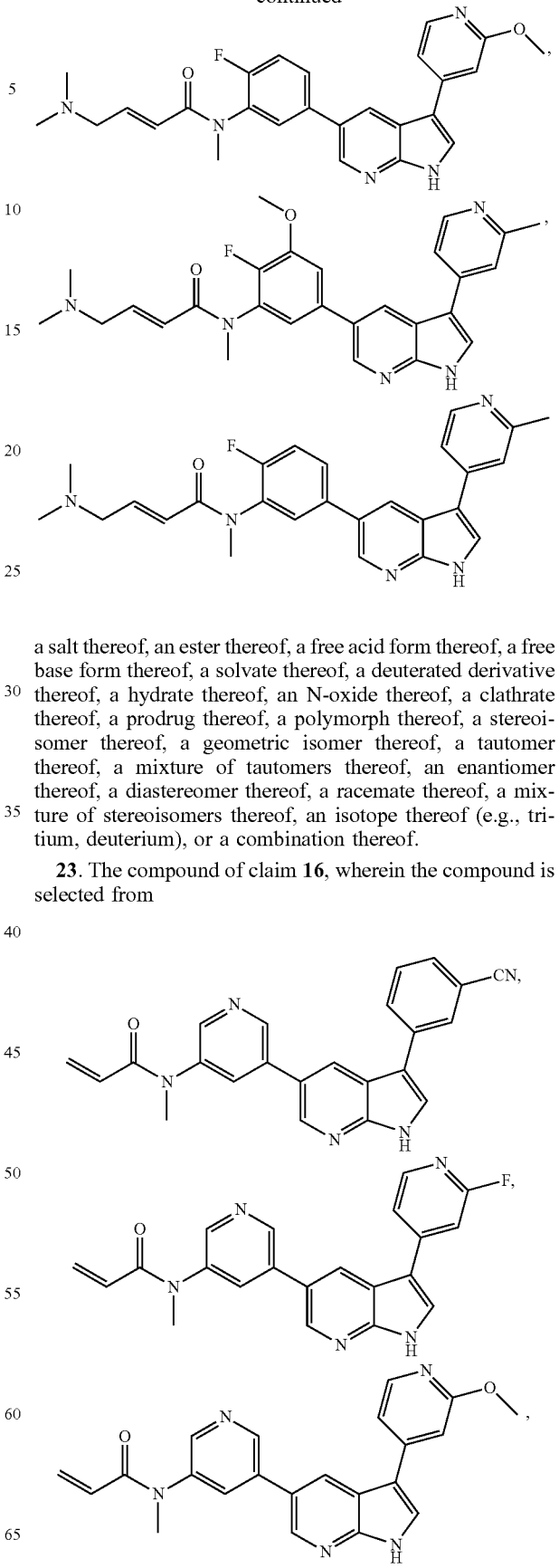

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

23. The compound of claim 16, wherein the compound is selected from

211
-continued

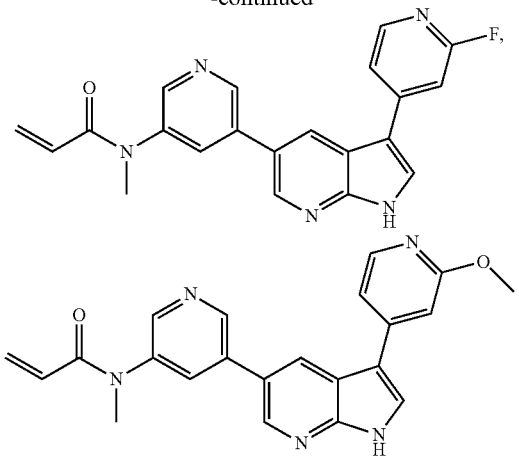

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

24. The compound of claim 17, wherein the compound is selected from

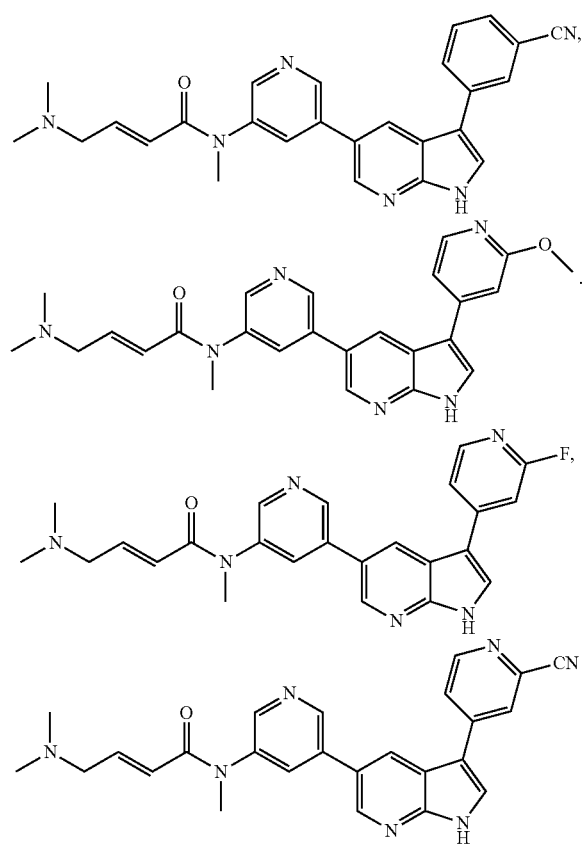

a salt thereof, an ester thereof, a free acid form thereof, a free base form thereof, a solvate thereof, a deuterated derivative

212 thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

25. The compound of claim 18, wherein the compound is selected from

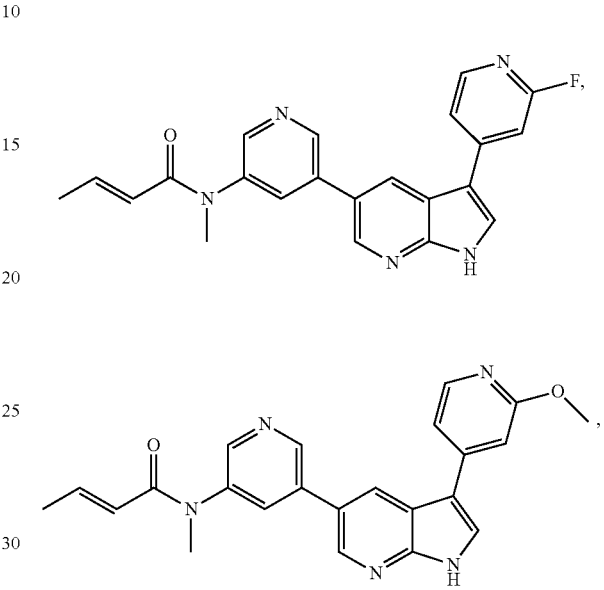

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

26. The compound of claim 19, wherein the compound is selected from

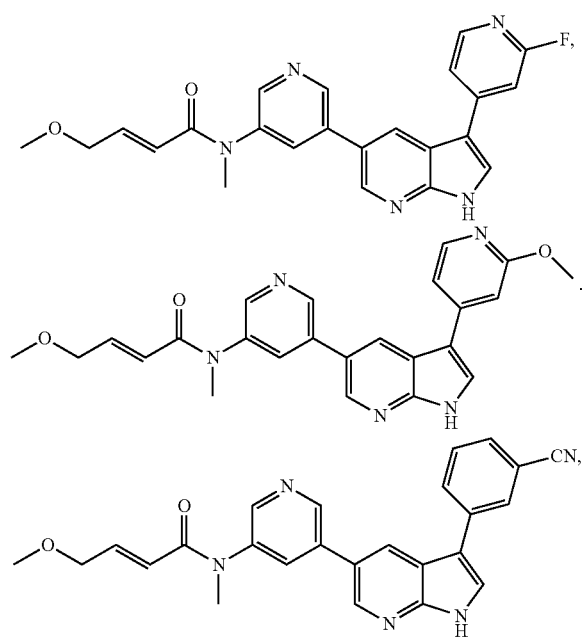

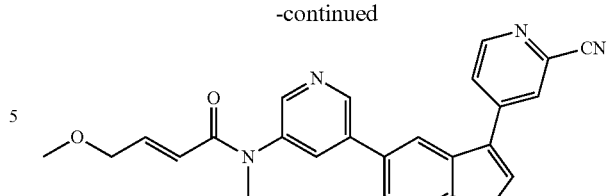

a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

27. A pharmaceutical composition comprising a compound of claim 1 and a pharmaceutically acceptable carrier, adjuvant, or vehicle.

* * * * *